US010059983B2

(12) United States Patent
Jiang et al.

(10) Patent No.: US 10,059,983 B2
(45) Date of Patent: Aug. 28, 2018

(54) MULTIPLEX NUCLEIC ACID ANALYSIS

(75) Inventors: Zhengwen Jiang, Suzhou (CN); Feng Yu, Suzhou (CN); Caihua Li, Suzhou (CN)

(73) Assignee: GENESKY DIAGNOSTICS (SUZHOU) INC., Suzhou, Jiangsu (CN)

( * ) Notice: Subject to any disclaimer, the term of this patent is extended or adjusted under 35 U.S.C. 154(b) by 424 days.

(21) Appl. No.: 14/426,137

(22) PCT Filed: Sep. 10, 2012

(86) PCT No.: PCT/CN2012/081212
§ 371 (c)(1),
(2), (4) Date: Mar. 4, 2015

(87) PCT Pub. No.: WO2014/036743
PCT Pub. Date: Mar. 13, 2014

(65) Prior Publication Data
US 2015/0218626 A1 Aug. 6, 2015

(51) Int. Cl.
C12Q 1/68 (2018.01)
C12Q 1/6827 (2018.01)
C12Q 1/6858 (2018.01)
C12Q 1/6883 (2018.01)
C12Q 1/6862 (2018.01)

(52) U.S. Cl.
CPC ......... *C12Q 1/6827* (2013.01); *C12Q 1/6858* (2013.01); *C12Q 1/6862* (2013.01); *C12Q 1/6883* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,869,252 | A | 2/1999 | Bouma et al. |
|---|---|---|---|
| 6,027,889 | A | 2/2000 | Barany et al. |
| 6,268,148 | B1 | 7/2001 | Barany et al. |
| 6,312,892 | B1 | 11/2001 | Barany et al. |
| 6,506,594 | B1 | 1/2003 | Barany et al. |
| 6,576,453 | B2 | 6/2003 | Barany et al. |
| 6,797,470 | B2 | 9/2004 | Barany et al. |
| 6,852,487 | B1 | 2/2005 | Barany et al. |
| 6,949,370 | B1 | 9/2005 | Barany et al. |
| 6,955,901 | B2 | 10/2005 | Schouten |
| 7,083,917 | B2 | 8/2006 | Barany et al. |
| 7,097,980 | B2 | 8/2006 | Barany et al. |
| 7,166,434 | B2 | 1/2007 | Barany et al. |
| 7,244,831 | B2 | 7/2007 | Barany et al. |
| 7,312,039 | B2 | 12/2007 | Barany et al. |
| 7,320,865 | B2 | 1/2008 | Barany et al. |
| 7,364,858 | B2 | 4/2008 | Barany et al. |
| 7,429,453 | B2 | 9/2008 | Barany et al. |
| 7,556,924 | B2 | 7/2009 | Barany et al. |
| 7,879,579 | B2 | 2/2011 | Barany et al. |
| 7,888,009 | B2 | 2/2011 | Barany et al. |
| 7,892,746 | B2 | 2/2011 | Barany et al. |
| 7,892,747 | B2 | 2/2011 | Barany et al. |
| 7,893,233 | B2 | 2/2011 | Barany et al. |
| 7,914,981 | B2 | 3/2011 | Barany et al. |
| 9,754,616 | B2* | 9/2017 | Biskeborn .............. G11B 5/588 |
| 2007/0092883 | A1 | 4/2007 | Schouten et al. |
| 2010/0105032 | A1 | 4/2010 | Pan et al. |
| 2010/0297630 | A1 | 11/2010 | Reij ans et al. |

FOREIGN PATENT DOCUMENTS

| EP | 1130113 | 9/2001 |
|---|---|---|
| EP | 1319718 | 6/2003 |
| WO | WO97/45559 | 12/1997 |
| WO | WO2007/100243 | 9/2007 |
| WO | WO2010/114599 | 10/2010 |

(Continued)

OTHER PUBLICATIONS

Li et al. (Nature, 2011, vol. 475, 217-223).*
Brownstein et al., Modulation of non-templated nucleotide addition by Taq DNA polymerase primer modifications that facilitate genotyping, BioTechniques, vol. 20, No. 6, (1996) 1004-1010.
Written Opinion for PCT/CN2012/081212.
International Search Report for PCT/CN2012/081212.
Francis Barany, Genetic disease detection and DNA amplification using cloned thermostable ligase, PNAS, 1991, vol. 88, pp. 189-193.
Khanna et al. Multiplex PCR LDR for detection of K-ras mutations in primary colon tumors Oncogene 1999.
McNamara et al. multiplex PCR LDR for diagnosis of infection Journal of Clinical Microbiology 2004.
Schouten et al. Relative quantification of 40 nucleic acid sequences by multiplex ligation-dependent probe amplification, Nucleic Acid Research, 2002, vol. 30, No. 12 e57.

(Continued)

*Primary Examiner* — Stephanie K Mummert
(74) *Attorney, Agent, or Firm* — Lihua Zheng; Zheng & Karg LLP

(57) ABSTRACT

Here provided is a method for multiplex nucleic acid analysis. The method includes steps of hybridizing sets of probes to target nucleic acids in a sample, ligating the hybridized probes, amplifying the ligated probes, and assaying the amplification products to determining the presence, absence, or quantity of the target nucleic acids in the sample. The multiplexity is made available in part by adding detectable moieties and inserting stuffer sequences in primers so that amplification products may be identified on the basis of the detectable moieties and fragment sizes. Also provided is a sensitive method of detecting small copy number changes by measuring the copy number of a plurality of target sites in the nucleic acid in a test sample in comparison to a control sample and then determining the copy number of the nucleic acid based on the measured copy number of the plurality of target sites. Further provided is a kit for multiplex nucleic acid analysis and for small copy number change determination.

45 Claims, 33 Drawing Sheets
(32 of 33 Drawing Sheet(s) Filed in Color)
Specification includes a Sequence Listing.

(56) References Cited

FOREIGN PATENT DOCUMENTS

WO     WO2010114599    * 10/2010   ............... C12Q 1/68
WO     WO2013/009175     1/2013

OTHER PUBLICATIONS

Zhang et al. LDR PCR for polymorphism J Forensic Sci 2009.
Modulation of Non-Templated Nucleotide Addition by TaqDNA Polymerase: Primer Modifications that Facilitate Genotyping Michael J. Brownstein, John D. Carpten and Jeffrey R. Smith. BioTechniques 20:1004-1010 (Jun. 1996).
The study of gene heterogeneity of human chromosome regions 5p15.33 and 8p11 and the lung cancer-related genes in the Han ethnicity. Master Degree Thesis by Xiaobo Zhang. Jun. 2011. [abstract has English translation].
EP search report in the counterpart application EP 12 88 3998 at EPO. dated Mar. 16, 2016.

* cited by examiner

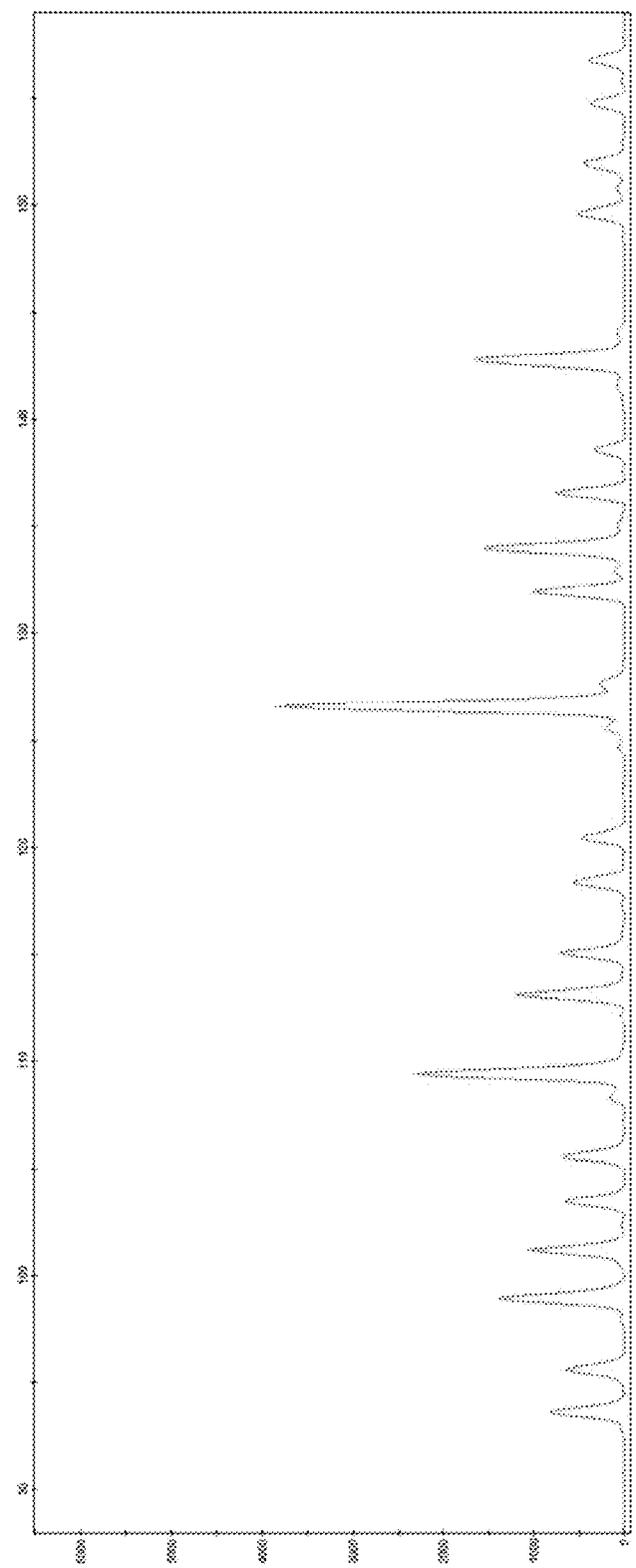

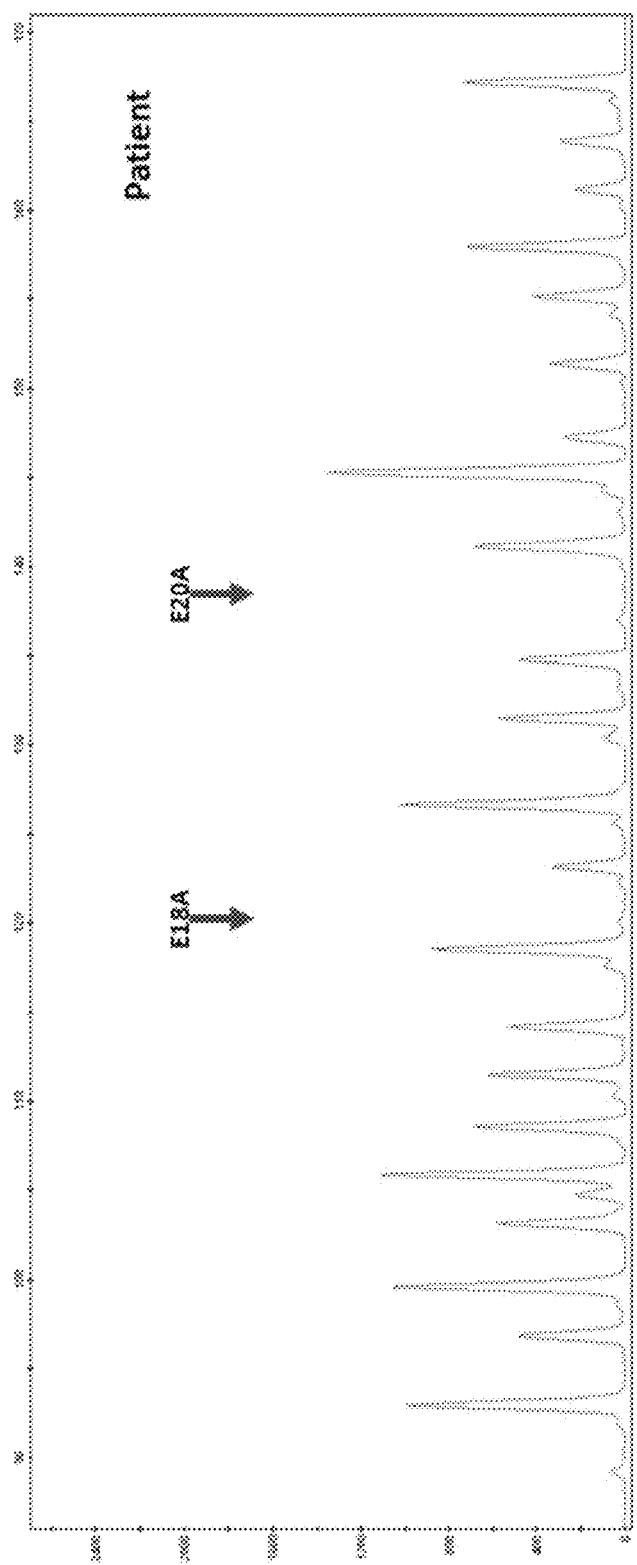

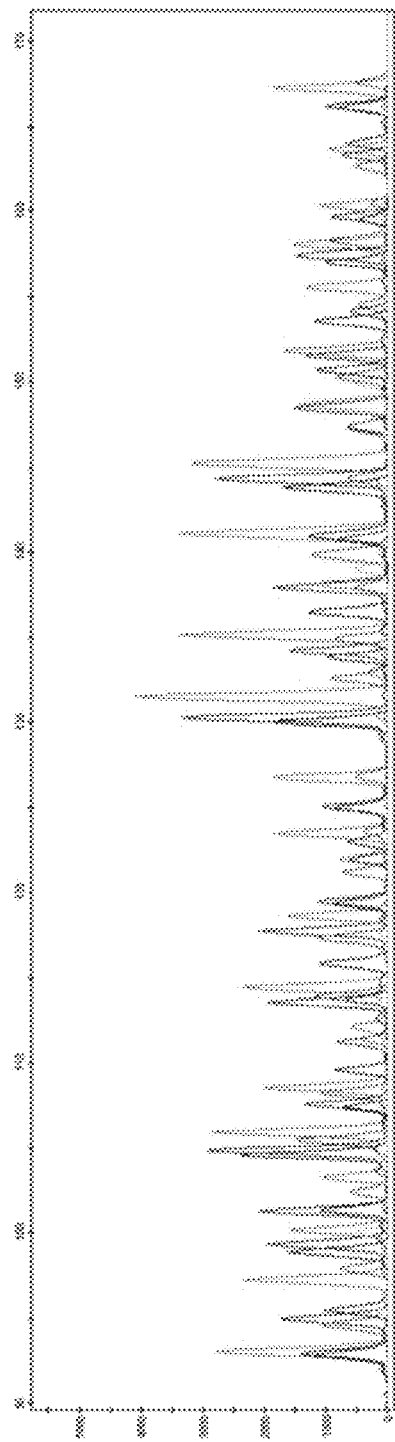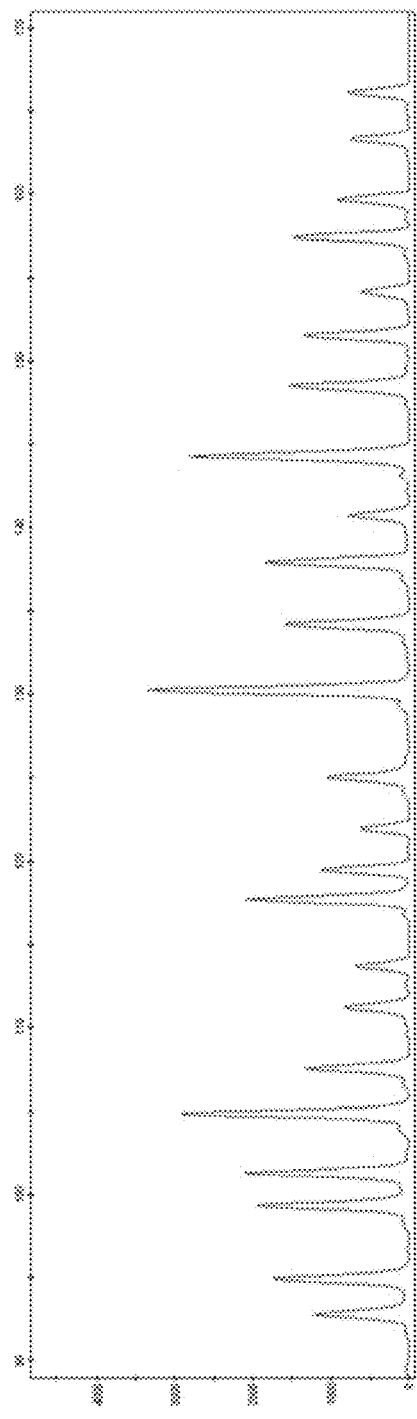

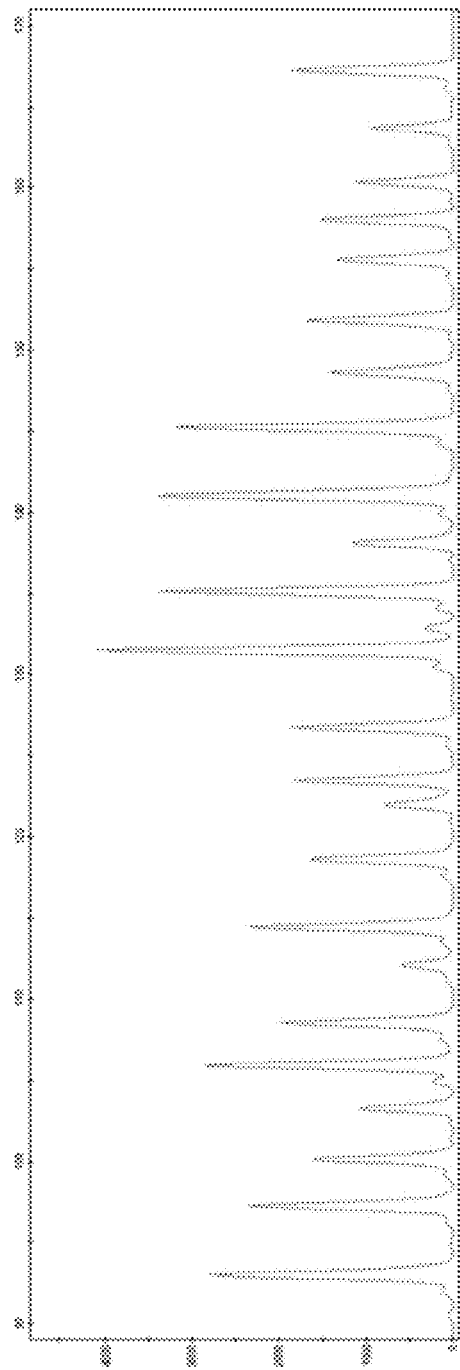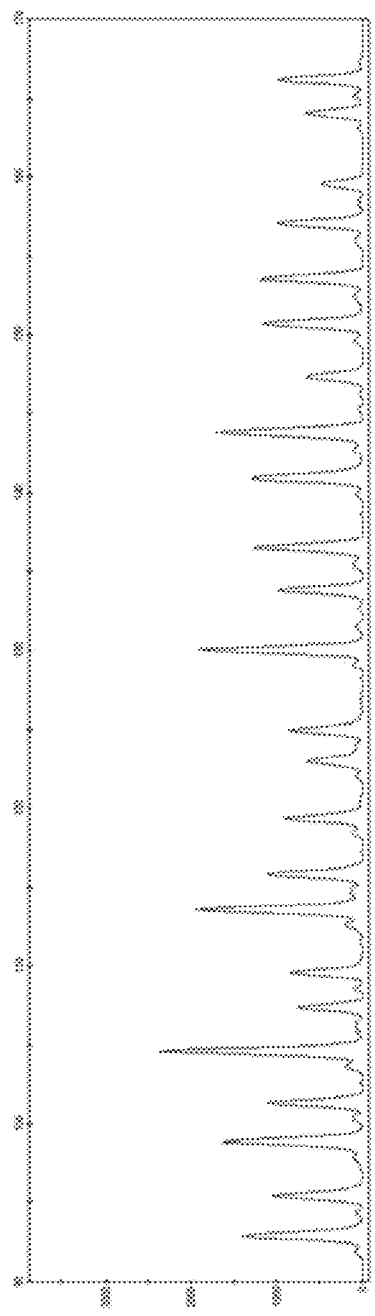

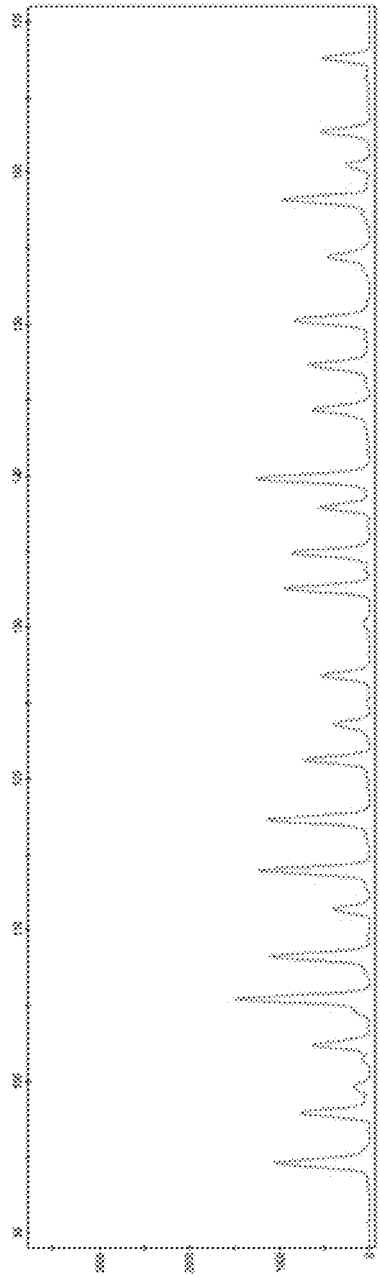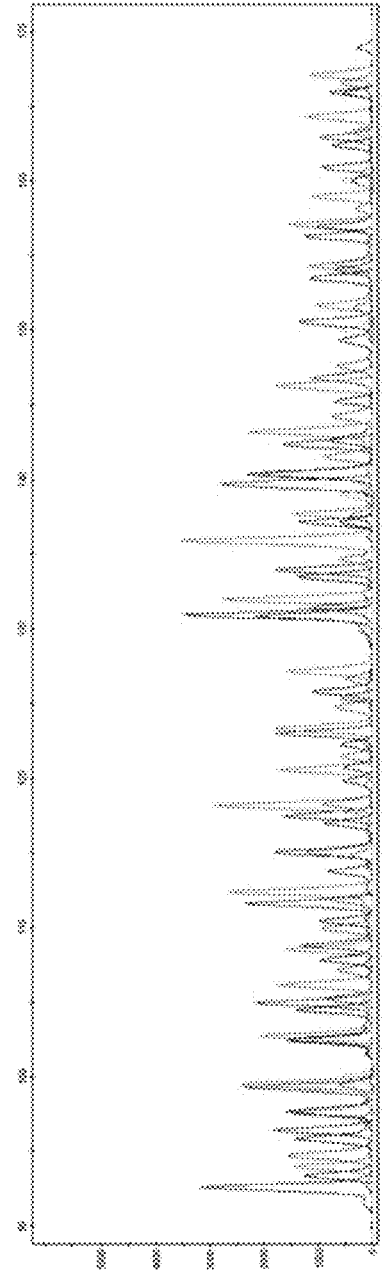

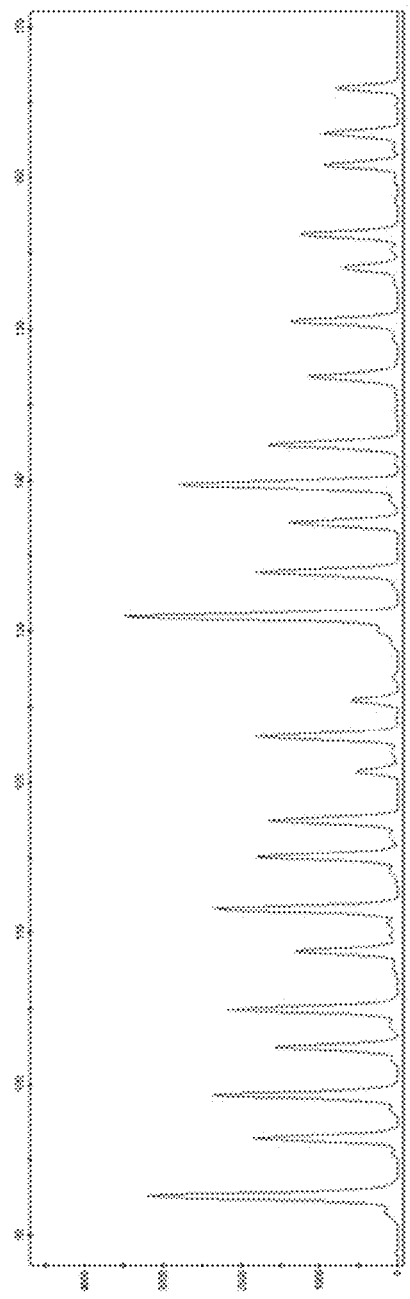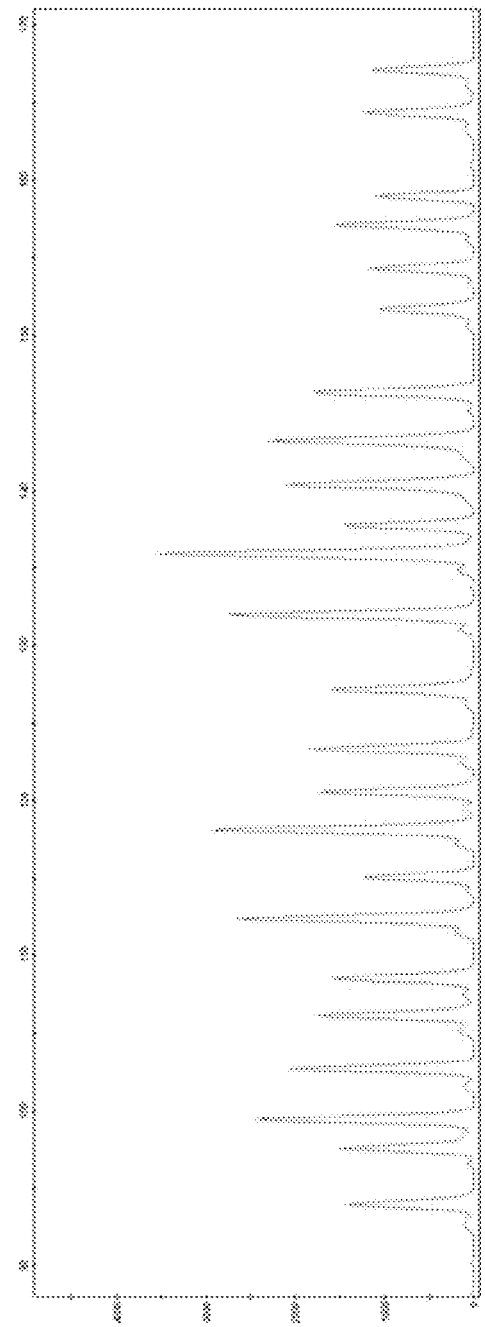

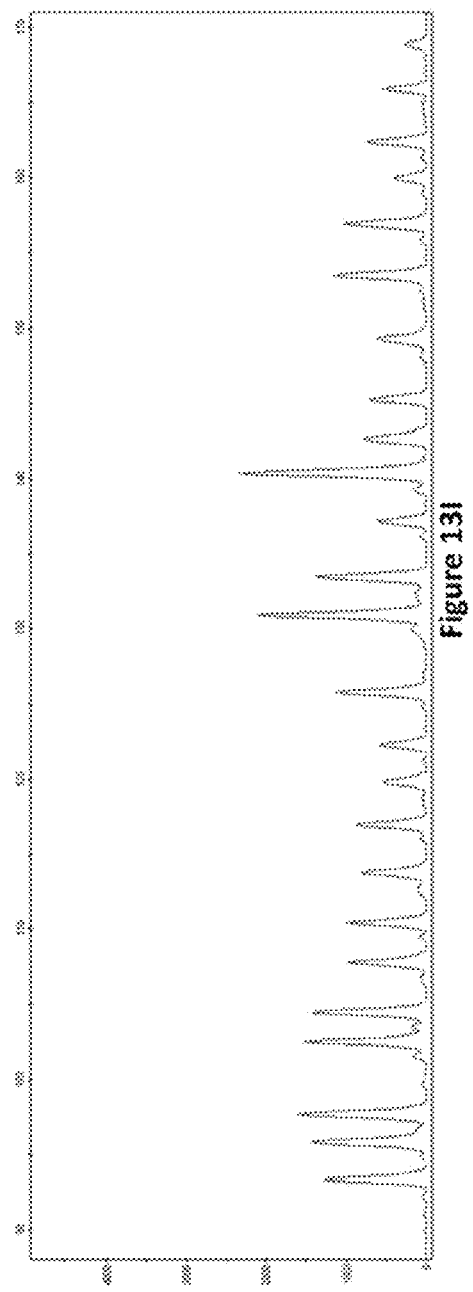
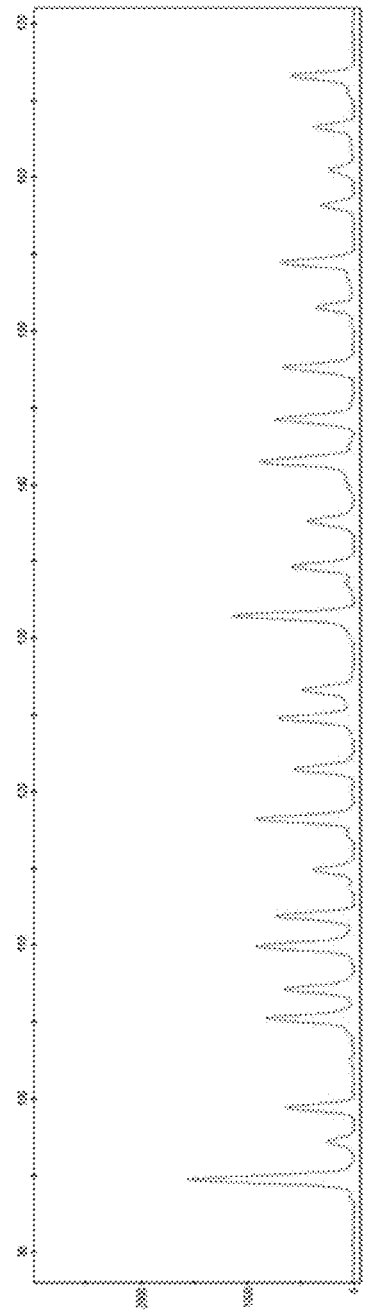
Figure 13I
Figure 13J

MULTIPLEX NUCLEIC ACID ANALYSIS

CROSS REFERENCE TO RELATED APPLICATIONS

This application is a U.S. Continuation under 35 U.S.C. 365(c) of International application No. PCT/CN2012/081212, filed Sep. 10, 2012, the disclosure of which application is incorporated herein by reference.

FIELD OF INVENTION

The present invention relates to the general fields of nucleic acid analysis in a biological sample, particularly the determination of genetic aberrations using a multiplex ligation-dependent method.

BACKGROUND

Nucleic acid analysis in a sample has many applications in both basic research and clinical settings. For example, nucleic acid analysis may be used to identify genetic aberrations in a patient blood sample. Genetic aberrations account for a large number of pathological conditions, including syndromic disorders (e.g., Down's syndrome) and diseases (e.g., breast cancer). Genetic aberrations may be, but is not limited to, single nucleotide polymorphisms (SNPs), gene copy number variants (CNVs), chromosomal rearrangements (e.g., insertions, deletions and duplications), gene mutations (e.g., single nucleotide changes, insertions, and deletions), nucleic acid modifications (e.g., methylation, acetylation and phosphorylations), gene over-expression (e.g., an oncogenes such as RAS), and gene under-expression (e.g., a tumor suppressor gene such as p53). In addition, nucleic acid analysis may be used to identify pathogens and transgenic organisms.

Many techniques have been developed for nucleic acid analysis. For one example, techniques such as oligonucleotide ligation assay (OLA) and ligation chain reaction (LCR) have been used to detect SNPs. See, e.g., Abravaya, et al., 1995, Detection of point mutations with a modified ligase chain reaction (Gap-LCR), Nucleic Acids Res. 23:675-82; Landegren et al., 1988, A ligase-mediated gene detection technique, Science. 241:1077-80; Schwartz et al., 2009, Identification of cystic fibrosis variants by polymerase chain reaction/oligonucleotide ligation assay, J Mol Diagn. 11:211-5. For another example, microarrays and high throughput DNA sequencing may be used to detect chromosome rearrangements and gene copy numbers. See, e.g., Agilent Human Genome CGH Microarray (Agilent Technologies, Inc., Santa Clara, Calif.), and the Illumina HiSeq DNA Sequencing Assays (Illumina, Inc., San Diego, Calif.). However, the nucleic acid analysis using these known techniques are either not easily multiplexed (e.g., the OLA and LCR methods), or time-consuming, expensive and/or inaccurate (e.g., microarrays and high throughput DNA sequencing).

Therefore, it is desirable to have a new technique that makes the nucleic acid analysis easily multiplexed and efficient. An object of the present invention is to provide methods and kits for multiplexed and efficient nucleic acid analysis in a sample. The methods and kits based on the present invention may be suitable for adaptation and incorporation into a compact device or instrument for use in a laboratory or a clinical setting, or in the field.

No reference cited in this background section is to be construed as an "admission" of prior art. Applicant expressly reserves the right to demonstrate, where appropriate, that the references cited herein do not constitute prior art under the applicable statutory provisions.

SUMMARY

This summary briefly introduces a selection of concepts according to the present invention. Detailed descriptions of the concepts are provided in the Detailed Description section. This summary is not intended to identify key or essential features of the claimed subject matter, neither is it intended to be used to limit the scope of the claimed subject matter. Other features, details, utilities, and advantages of the claimed subject matter will be apparent from the whole description of the present invention including the Background, the Summary, the Detailed Description, the Drawings, and the Claims.

In one aspect, the present invention provides methods for multiplex nucleic acids analysis in a sample. In one embodiment, nucleic acids in a sample are assayed by adding a set of probes into the sample to form a mixture; denaturing nucleic acids in the mixture; hybridizing the set of probes to the complementary regions of target nucleic acids; performing a ligation reaction on the hybridized probes to form a third probe; amplifying the third probe with a set of primers to obtain an amplification product; and assaying the presence, absence or quantity of the target nucleic acids in the sample by determining the presence, absence or quantity of the third probe in the amplification product.

In each set of probes, there are at least a first probe having a first portion at least partially complementary to a first region of the target nucleic acid in the sample and a second portion forming a first primer binding site (herein also referred to as primer binding sequence); and a second probe having a first portion at least partially complementary to a second region of the target nucleic acid in the sample and a second portion forming a second primer binding site. The 5' end of the first probe is essentially adjacent to the 3' end of the second probe when both probes are hybridized to the target nucleic acid.

The set of primers used to amplify the ligation product comprises a first primer at least partially complementary to the first primer binding site; and a second primer at least partially complementary to the second primer binding site.

In some embodiments, the method is used to assay multiple target nucleic acids in a multiplexed manner. For example, the presence, absence or quantity of more than about 48, 96, 192, 384 or more target nucleic acids in the sample may be assayed in a multiplexed manner. The probes corresponding to all the target nucleic acids may be added to the sample and a single ligation reaction is performed to obtain ligation products for all the target nucleic acids.

The sample to be assayed may be a sample of a bodily fluid, a biopsy tissue, or a paraffin-embedded tissue from an animal. The bodily fluid may be blood, plasma, serum, urine, sputum, spinal fluid, cerebrospinal fluid, pleural fluid, nipple aspirates, lymph fluid, fluid of the respiratory, intestinal, or genitourinary tracts, tear fluid, saliva, breast milk, fluid from the lymphatic system, semen, cerebrospinal fluid, intra-organ system fluid, ascitic fluid, tumor cyst fluid, amniotic fluid, or combinations thereof from an animal, e.g., a human.

In some embodiments, nucleic acids are extracted from the sample before forming a mixture with the set of probes. The target nucleic acid may be DNA, RNA, or cDNA. The RNA may be reverse transcribed into cDNA before forming a mixture with the set of probes.

In some embodiments, at least one primer of the set of primers is labeled with a detectable moiety, e.g., an oligonucleotide tag or a fluorescent dye. The fluorescent dye may be FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, or Yakima Yellow. In other embodiments, at least one primer of the set of primers includes a stuffer sequence. The stuffer sequence in some primers may have about 10 to about 500 nucleotides. The stuffer sequence in other primers may be about 10 to about 60 nucleotides. In some preferred embodiments, no primer has more than about 125 nucleotides, preferably about 75 nucleotides. In still other embodiments, at least one primer of the set of primers includes an oligonucleotide comprising a sequence GTTTCTT or a functional equivalent variant of the oligonucleotide comprising a sequence GTTTCTT.

In further embodiments, at least one probe of the set of probes includes a stuffer sequence. In some instances, the stuffer sequence may have about 1 to about 200 nucleotides. In other instances, the stuffer sequence has about 1 to about 55 nucleotides. In some preferred embodiments, the third probe has no more than about 250 nucleotides. In other preferred embodiments, the third probe has no more than about 140 nucleotides. In still some preferred embodiments, no probe has more than about 125 nucleotides. In still some other preferred embodiments, no probe has more than about 70 nucleotides. In some further preferred embodiments, no probe has more than about 60 nucleotides.

In some embodiments, the multiplexity of nucleic acid analysis may result from the modifications that at least one primer of the set of primers is labeled with a detectable moiety and that at least one primer of the set of primers includes a stuffer sequence. In other embodiments, the multiplexity of nucleic acid analysis may result from the modifications that at least one primer of the set of primers is labeled with a detectable moiety and that at least one probe of the set of probes includes a stuffer sequence. In still other embodiments, the multiplexity of nucleic acid analysis may result from the modifications that at least one primer of the set of primers includes a stuffer sequence and that at least one probe of the set of probes includes a stuffer sequence. In some preferred embodiments, the multiplexity of nucleic acid analysis may result from the modifications that at least one primer of the set of primers is labeled with a detectable moiety, that at least one primer of the set of primers includes a stuffer sequence, and that at least one probe of the set of probes includes a stuffer sequence. In these embodiments, the determination of the presence, absence or quantity of the third probe in the amplification product may be carried out by measuring the presence, absence or quantity of the third probe in the amplification product on the basis of detectable moieties, fragment sizes, or both. The measurement may be carried out using capillary electrophoresis.

The method according to the present invention may be applied in many nucleic acid assays. For one example, single nucleotide polymorphisms in target nucleic acids may be detected using the method. For this purpose, an allele-specific probe corresponding to the single nucleotide polymorphism may be designed. In addition, a mismatch may be introduced at one or more positions, e.g., the second, third, or fourth nucleotide away from the polymorphic nucleotide in the allele-specific probe so that the specificity of the probe binding is enhanced.

For a second example, copy number variants in target nucleic acids may be detected using the method. In one instance, a deletion of one or more exons in the dystrophin gene may be determined using one or more probe pairs selected from SEQ ID NOs: 158-541.

For a third example, the method may be used to screen for an unknown point mutation, insertion, or deletion of nucleotides. In one instance, a point mutation in the dystrophin gene may be screened using one or more probe pairs selected from SEQ ID NOs: 158-541.

For a fourth example, the method may be used to measure the presence, absence or relative amount of messenger RNA, methylated DNA, a pathogen or a transgenic organism. A pathogen may be a virus or a bacterium. A transgenic organism may be a transgenic plant such as transgenic corn, transgenic rice, transgenic soybean and transgenic cotton, or a transgenic animal such as a transgenic cow, a transgenic pig, a transgenic sheep and a transgenic dog.

In some embodiments, the steps of denaturing, hybridization and ligation may be repeated about 1 to about 100 times. The denaturing step may be carried at about 90° C. to about 99° C. for about 5 seconds to about 30 minutes, and the hybridization and the ligation steps may be carried out simultaneously at about 4° C. to about 70° C. for about 1 minute to about 48 hours. In a preferred embodiment, the denaturing step is carried at about 95° C. for about 30 seconds, and the hybridization and the ligation steps are carried out simultaneously at about 58° C. for about 4 hours, and the steps of denaturing, hybridization and ligation are repeated 4 times.

In another aspect of the present invention, a method is provided for detecting small copy number changes. In one embodiment, for purpose of detecting small copy number changes of a target nucleic acid, two or more sets of probes are used to hybridize to two or more target sites in the same target nucleic acid, with each set of probes hybridizing to a different target site. The small copy number changes may be, for example, a quantitative variation of the target nucleic acid between two samples. In some instances, the quantitative variation of the target nucleic acid is about 0.1% to about 30%.

In some embodiments, for each set of probes hybridizing to each target site in the same target nucleic acid, one or more sets of reference probes are used to hybridize to one or more reference target sites, with each set of reference probes hybridizing to a different reference target site. For example, about 1 to about 100 sets of reference probes are used for an individual target site. In some instances, about 6 sets of reference probes are used for an individual target site.

In some embodiments, the same set of primers is used to amply a group of ligation products (also referred to as the third probes). The ligation products may be formed from one or more sets of probes hybridizing to one or more target sites and from one or more sets of reference probes hybridizing to one or more reference target sites. For example, in one group of ligation products, there may be ligation products formed from about 1 to about 100 sets of probes hybridizing to gene target sites of interest and from about 1 to about 100 sets of reference probes hybridizing to reference target sites.

In other embodiments, about 50 to about 500 sets of probes hybridizing to about 50 to about 500 target sites on a target nucleic acid are used to detect small copy number variation of the target nucleic acid in a sample. In this case, multiple groups of ligation products formed from a plurality of probes for targets site and probes for reference sites may be obtained. For each group of ligation products, the same primer pair may be used to amply the ligation products in that group.

In some preferred embodiments, the target nucleic acids are from human chromosome 21, human chromosome 18, human chromosome 13, human chromosome region 22q11.2, or the pseudoautosomal regions of human chromosomes X or Y. As such, the method according to the present invention may be used to detect fetal aneuploidy for chromosomes 21, 18, 13, X, Y and 22q11.2 in a maternal blood or urine sample. In one instance, the method is used to detect fetal Down's syndrome in a maternal blood or urine sample using one or more probe pairs selected from SEQ ID NOs: 559-942.

In a further aspect of the present invention, a kit for assaying nucleic acids in a sample is provided. In one embodiment, the kit includes one or more sets of probes corresponding to a target nucleic acid; one or more sets of primers for amplifying the third probe; optionally reagents including a ligase, a buffer for a ligation reaction, a DNA polymerase, a buffer for polymerase chain traction or a combination thereof; and optionally a brochure containing instructions of using the kit.

In some embodiments, the set of probes includes a first probe having a first portion at least partially complementary to a first region of a target nucleic acid in the sample and a second portion forming a first primer binding site; and a second probe having a first portion at least partially complementary to a second region of the target nucleic acid in the sample and a second portion forming a second primer binding site. The 5' end of the first probe may be essentially adjacent to the 3' end of the second probe when both probes are hybridized to the target nucleic acid and the first and the second probes may be ligated to form a third probe. In some instances, at least one probe of the set of probes includes a stuffer sequence. The stuffer sequence may have about 1 to about 200 nucleotides.

In other embodiments, the set of primers includes a first primer at least partially complementary to the first primer binding site; and a second primer at least partially complementary to the second primer binding site. In some instances, at least one primer of the set of primers is labeled with a detectable moiety, e.g., an oligonucleotide tag or a fluorescent dye. The fluorescent dye may be FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, or Yakima Yellow. In still other embodiments, at least one primer of the set of primers includes a stuffer sequence. The stuffer sequence has about 10 to about 500 nucleotides.

In some embodiments, the kit is for detecting Duchenne muscular dystrophy and includes one or more sets of probes comprising probe pairs selected from SEQ ID NOs: 158-541. In other embodiments, the kit is for detecting fetal Down's syndrome in a maternal blood sample and includes one or more sets of probes comprising probe pairs selected from SEQ ID NOs: 559-942.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 10A, 10B, 10C, 10D, and 10E are electrophoresis chromatograms depicting the electrophoresis pattern of the amplification products in a multiplexed assay of 48 SNPs.

FIG. 10A is an electrophoresis chromatogram of all 96 amplification products. FIGS. 10B, 10C, 10D and 10E are electrophoresis chromatograms for 24 amplification products produced with primers labeled with blue, green, yellow and red fluorescent dyes, respectively.

FIGS. 11A, 11B, 11C, 11D, 11E, 11F, 11G and 11H are electrophoresis chromatograms depicting the electrophoresis pattern of the amplification products in a multiplexed assay of 192 copy number variants. FIGS. 11A and 11B are electrophoresis chromatograms of all amplification products for the control sample panel A and panel B, respectively. FIGS. 11C and 11D are electrophoresis chromatograms of all amplification products for the patient sample panel A and panel B, respectively. FIGS. 11E and 11F are electrophoresis chromatograms of amplification products labeled with blue fluorescent dyes for the control and the patient samples, respectively. 11G and 11H are electrophoresis chromatograms for amplification products produced with primers labeled with green fluorescent dyes for the control and the patient samples, respectively. The arrows in FIGS. 11F and 11H refer to the missing peaks corresponding to gene target sites.

FIGS. 13A, 13B, 13C, 13D, 13E, 13F, 113G, 13H, 13I, and 13J are electrophoresis chromatograms depicting the electrophoresis pattern of the amplification products for measuring human chromosome 21 copy number in a control DNA sample. FIGS. 13A and 13F are electrophoresis chromatograms of all 96 amplification products for the control sample panel A and panel B, respectively. FIGS. 13B, 13C, 13D, and 13E are electrophoresis chromatograms of the 24 amplification products from the control sample panel A separately labeled with blue, green, yellow and red fluorescent dyes, respectively. FIGS. 13G, 13H, 13I, and 13J are electrophoresis chromatograms of the 24 amplification products from the control sample panel B separately labeled with blue, green, yellow and red fluorescent dyes, respectively.

DETAILED DESCRIPTION OF THE INVENTION

I. Multiplex Nucleic Acid Analysis

Figure 1:
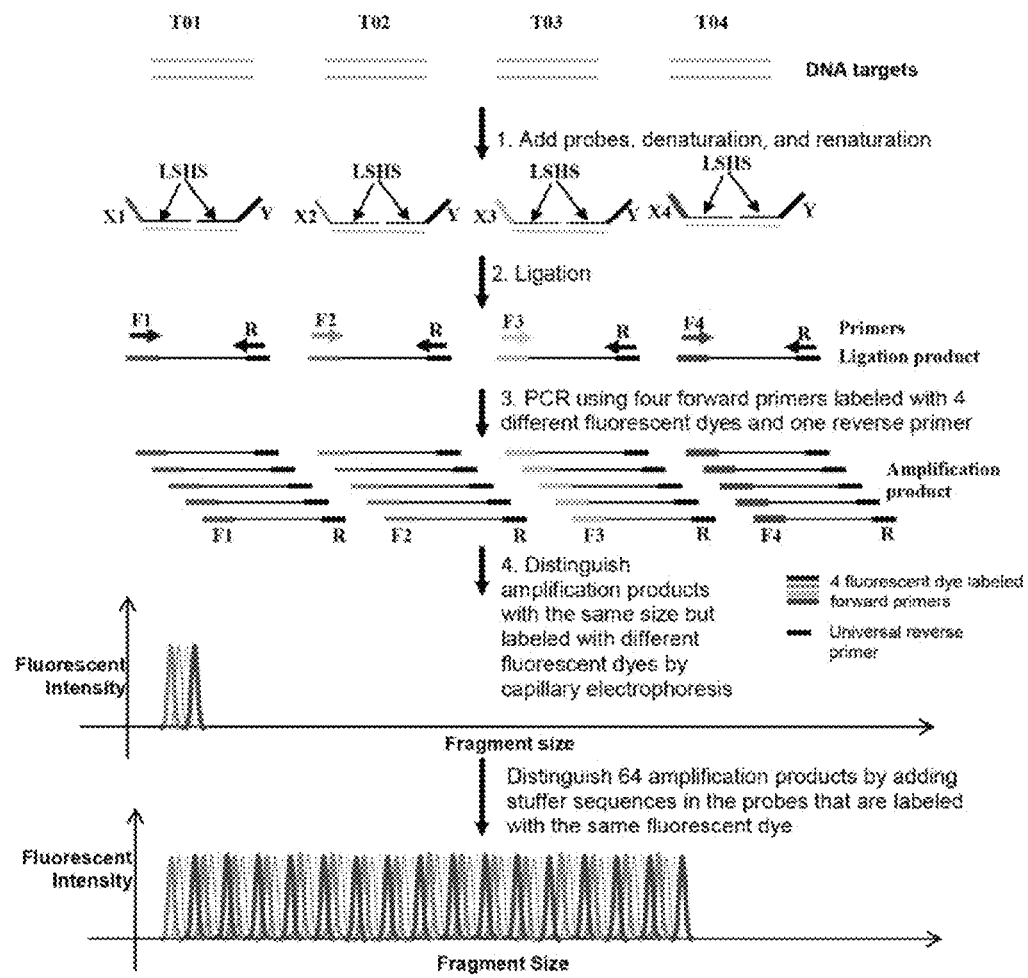
FIG. 1 is a schematic flowchart depicting the method of increasing the multiplexity by employing fluorescent dye labeled primers for amplifying ligation products.

In one aspect, the present invention provides methods for multiplex nucleic acid analysis. In one embodiment, the method for multiplex analysis of target nucleic acids in a sample includes the steps of preparing nucleic acids that are quantitatively and qualitatively correlated to a plurality of target nucleic acids in the sample and determining quantitatively and qualitatively the nucleic acids thus prepared.

As used herein, the phrase "multiplex" or grammatical equivalents refers to the quantitative and qualitative determination of more than one target nucleic acids of interest in a sample. In one embodiment "multiplex" refers to at least about 48 different target sequences. In another embodiment "multiplex" refers to at least about 96 different target sequences. In further embodiment "multiplex" refers to at least about 192 different target sequences. In still further embodiments, "multiplex" refers to at least about 384 different target sequences. In yet still further embodiment "multiplex" refers to at least about 500 to about 100,000 different target sequences.

As used herein, the sample in which target nucleic acids exist may be a sample from a subject, including, but not limited to, bodily fluids (e.g., blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof); environmental samples (e.g., air, agricultural, water and soil samples); biological warfare agent samples; research samples; purified samples, such as purified genomic DNA, RNA, proteins, etc.; and raw samples (bacteria, virus, genomic DNA, etc.).

The term "subject" is intended to include all animals. In particular embodiments, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject", "patient", and "individual" are used interchangeably herein.

In one aspect, the present invention provides methods of preparing nucleic acids that are quantitatively and qualitatively correlated to a plurality of target nucleic acids in a sample. The correlation may be achieved through some mechanisms including, but not limited to, 1) specific hybridizations between complementary nucleic acids and 2) specific enzymatic recognition such as a ligation reaction to connect substantially adjacent nucleotides and a polymerase reaction to add specific nucleotide onto an existing polynucleotide based on a template sequence.

As used herein, "nucleic acid", "polynucleotide", and "oligonucleotide" are interchangeably used to indicate at least two nucleotides covalently linked together. Oligonucleotides may be generated by, e.g., chemical synthesis, restriction endonuclease digestion of plasmids or phage DNA, DNA replication, reverse transcription, or a combination thereof. One or more of the nucleotides can be modified e.g. by addition of a methyl group, a biotin or digoxigenin moiety, a fluorescent tag, or by using radioactive nucleotides.

A nucleic acid used in the present invention may contain phosphodiester bonds, although in some cases nucleic acid analogs are included that may have alternate backbones, including, e.g., phosphoramide, phosphorothioate, phosphorodithioate, O-methylphophoroamidite linkages, and peptide nucleic acid backbones and linkages. See, e.g., Pauwels et al., 1986, Chemica Scripta 26:141-9; U.S. Pat. No. 5,644,048; Briu et al., 1989, J. Am. Chem. Soc. 111:2321;

and Carlsson et al., 1996, Nature 380:207. Other analog nucleic acids include those with positive backbones, non-ionic backbones, and non-ribose backbones. See, e.g., Denpcy et al., 1995, Proc. Natl. Acad. Sci. USA 92:6097; Jeffs et al., 1994, J. Biomolecular NMR 34:17; U.S. Pat. Nos. 5,386,023, 5,235,033 and 5,034,506. All of these references are hereby expressly incorporated by reference. Modifications of the ribose-phosphate backbone may be done to facilitate the addition of labels, or to increase the stability and half-life of such molecules in physiological environments.

In some embodiments, peptide nucleic acids (PNA) may be used for nucleic acids in the present invention. The PNA backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

Nucleic acids may be single stranded or double stranded, as specified, or contain portions of both double stranded or single stranded sequence. Nucleic acids may be DNA, genomic DNA, cDNA, RNA or a hybrid. Nucleic acids may contain any combination of deoxyribo- and ribo-nucleotides, and any combination of bases, including uracil, adenine, thymine, cytosine, guanine, inosine, xanthanine, hypoxanthine, isocytosine, isoguanine, etc. In one embodiment, nucleic acids utilize isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred to herein as a nucleoside.

In some embodiments, the methods according to the present invention are directed to the multiplexed detection of target nucleic acids. The term "target nucleic acid" or grammatical equivalents herein refers to a specific nucleic acid sequence to be detected and/or quantified in the sample to be analyzed. The target nucleic acid may be a portion of a gene, a regulatory sequence, genomic DNA, cDNA, or RNA including mRNA and rRNA.

Complementary nucleic acids are capable of hybridizing to each other under normal hybridization conditions. The term "complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion. As used herein, the pairing of complementary nucleic acids is referred to by the terms "hybridization" or "hybridizing".

Specific enzymatic recognition may be achieved through a ligation reaction to connect substantially adjacent nucleotides or a DNA or RNA polymerase reaction to add specific nucleotide onto an existing polynucleotide based on a template sequence.

Ligases are well known and may be used for specific enzymatic recognition. See, e.g., Lehman, 1974, Science, 186: 790-797; and Engler et al, DNA Ligases, pages 3-30 in Boyer, editor, The Enzymes, Vol. 15B (Academic Press, New York, 1982). Preferred ligases include T3 DNA ligase, T4 DNA ligase, T7 DNA ligase, *E. coli* DNA ligase, Taq DNA ligase, Pfu ligase, and Tth ligase. Protocols for their use are well known. See, e.g., Green and Sambrook, Molecular Cloning: A Laboratory Manual (Fourth Edition): Three-volume set, Cold Spring Harbor Laboratory Press; 4th edition (Jun. 15, 2012) and the like. Generally, ligases require that a 5' phosphate group be present for ligation to the 3' hydroxyl of an adjacent strand.

In some embodiments, the preferred ligase is one which has the least mismatch ligation. The specificity of ligase can be increased by substituting the more specific NAD+-dependant ligases such as *E. coli* ligase and (thermostable) Taq ligase for the less specific T4 DNA ligase. The use of NAD analogues in the ligation reaction further increases specificity of the ligation reaction. See, e.g., U.S. Pat. No. 5,508,179.

DNA or RNA polymerases can extend a nucleic acid sequence by adding nucleotides in the presence of a template. As is well known in the art, there are a wide variety of suitable polymerases. Suitable polymerases include, but are not limited to, DNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., Q beta replicase from bacteriophage, or SP6, T3, T4 and T7 RNA polymerases.

In some embodiments, preferred polymerases are those that are essentially devoid of a 5' to 3' exonuclease activity, so as to assure that the first probe will not be extended past the 5' end of the second probe. Exemplary enzymes lacking a 5' to 3' exonuclease activity include the Klenow fragment of the DNA Polymerase and the Stoffel fragment of DNA Taq Polymerase. (See e.g., Lawyer et al., 1989, J. Biol. Chem., 264:6427-6437; and Lawyer et al., 1993, PCR Meth. Appl., 2:275-287). Other mutant polymerases lacking 5' to 3' exonuclease activity have been generated for polymerases derived from *T. vulgaris*. See U.S. Pat. No. 6,632,645.

In other embodiments, preferred polymerases are those that lack a 3' to 5' exonuclease activity, which is commonly referred to as a proof-reading activity, and which removes bases which are mismatched at the 3' end of a primer-template duplex. Although the presence of 3' to 5' exonuclease activity provides increased fidelity in the strand synthesized, the 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of an oligonucleotide primer used in a primer extension process is critical as it is from this terminus that extension of the nascent strand begins. Degradation of the 3' end leads to a shortened oligonucleotide which may result in a loss of specificity in the PCR reaction.

In still other embodiments, more preferred polymerases are thermostable polymerases. A thermostable enzyme is an enzyme that retains most of its activity after one hour at 40° C. under optimal conditions. Examples of thermostable polymerases which lack both 5' to 3' exonuclease and 3' to 5' exonuclease include Stoffel fragment of Taq DNA polymerase. This polymerase lacks the 5' to 3' exonuclease activity due to genetic manipulation and no 3' to 5' activity is present as Taq polymerase is naturally lacking in 3' to 5' exonuclease activity.

The conditions for performing the addition of one or more nucleotides at the 3' end of a probe will depend on the particular enzyme used, and will generally follow the conditions recommended by the manufacturer of the enzymes used.

In some embodiments, the correlation may be achieved through a combination of different mechanisms, e.g., a combination of both specific hybridizations between complementary nucleic acids and a ligation reaction to connect substantially adjacent nucleotides; or a combination of specific hybridizations between complementary nucleic acids, a ligation reaction to connect substantially adjacent nucleotides, and a polymerase reaction to add specific nucleotide onto an existing polynucleotide based on a template sequence.

In some embodiments, the combination of both specific hybridizations between complementary nucleic acids and a ligation reaction to connect substantially adjacent nucleotides is applied to prepare nucleic acids that are quantitatively and qualitatively correlated with the target nucleic acids in a sample. As such, the method to prepare nucleic acids from a sample include the steps of 1) hybridizing probes to the target nucleic acids in the sample; and 2) ligating the hybridized probes to obtain a preparation of nucleic acids that are quantitatively and qualitatively correlated with the target nucleic acids in the sample.

In other embodiments, the combination of specific hybridizations between complementary nucleic acids, a ligation reaction to connect substantially adjacent nucleotides, and a polymerase reaction to add specific nucleotide onto an existing polynucleotide based on a template sequence is applied to prepare nucleic acids that are quantitatively and qualitatively correlated with the target nucleic acids in a sample. As such, the method to prepare nucleic acids from a sample include the steps of 1) hybridizing probes to the target nucleic acids in the sample; 2) extending one of the probes to close the gap between the probes so that the extended probes may be ligated to an adjacent probe; and 3) ligating the hybridized and extended probes to obtain a preparation of nucleic acids that are quantitatively and qualitatively correlated with the target nucleic acids in the sample.

In some embodiments, the target nucleic acid may be extracted from the sample before being hybridized to probes. Methods known for nucleic acid extraction in the art include the use of phenol/chloroform, the use of salting out procedure, the use of chaotropic salts and silica resins, the use of affinity resins, ion exchange chromatography and the use of magnetic beads. See, for example, U.S. Pat. Nos. 5,057,426 and 4,923,978, EP Patents 0512767, WO 95/13368, WO 97/10331 and WO 96/18731. Conventional techniques of molecular biology, biochemistry, genetics, which are in the skill of the art, are explained fully in the literature. See, for instance, Green and Sambrook, Molecular Cloning: A Laboratory Manual (Fourth Edition): Three-volume set, Cold Spring Harbor Laboratory Press; 4th edition (Jun. 15, 2012); Carson, Miller, and Witherow, Molecular Biology Techniques, Third Edition: A Classroom Laboratory Manual, Academic Press; 3 edition (Nov. 21, 2011); Cheng and Zhang, Molecular Genetic Pathology, Humana Press; 1 edition (Apr. 15, 2008).

In addition, when the target nucleic acids are preferred to be cut into a size that will facilitate handling and hybridization to the probes, particularly for genomic DNA, this may be accomplished by shearing the nucleic acid through mechanical forces (e.g. sonication) or by cleaving the nucleic acid using restriction endonucleases, or any other methods known in the art.

As used herein, "probe" refers to a known sequence of a nucleic acid that is capable of selectively binding to a target nucleic acid. More specifically, "probe" refers to an oligonucleotide designed to be sufficiently complementary to a sequence of one strand of a nucleic acid that is to be probed such that the probe and nucleic acid strand will hybridize under selected stringency conditions. Additionally, "probe" also refers to an end product which is derived by connecting one or more substantially adjacent oligonucleotides hybridized to substantially adjacent segments of a nucleic acid. For example, a "ligated probe" refers to the end product of a ligation reaction between a pair of probes.

As used herein, the term "substantially adjacent" is used in reference to nucleic acid molecules that are in close proximity to one another. The term also refers to a sufficient proximity between two nucleic acid molecules to allow the 5' end of one nucleic acid that is brought into juxtaposition with the 3' end of a second nucleic acid so that they may be ligated by a ligase enzyme. Nucleic acid segments are defined to be substantially adjacent when the 3' end of a first probe and the 5' end of a second probe, with the first probe hybridizing to one segment and the second probe to the other segment, are sufficiently near each other to allow connection of the ends of both probes to one another. Thus, two probes are substantially adjacent, when the ends thereof are sufficiently near each other to allow connection of the ends of both probes to one another.

As such, in some embodiments of the present invention, a set of probes including 2 or more probes are designed to hybridize to a target nucleic acid. The target nucleic acid may contain several target regions; for example, a first target region of the target nucleic acid may hybridize to a first probe or a portion of the first probe, a second target region of the target nucleic acid may hybridize a second probe or a portion of the second probe. In addition, the two target regions may be adjacent or separated. When the two regions are adjacent, e.g., a first probe hybridizing to a first target region and a second probe hybridizing to a second target region, the first and the second hybridized probes may be adjacent so that a ligation reaction may connect the two probes to form a third probe. The third probe may therefore be able to hybridize to both the first region and the second region of the target nucleic acid. When the two regions are separated by one or more nucleotides, the gap between the first and the second hybridized probes may be filled with the use of a polymerase and dNTPs to extend one of the probes so that the extended probe and the other hybridized probe may be substantially adjacent to form a third probe.

The terms "first" and "second" are not meant to confer an orientation of the sequences with respect to the 5'-3' orientation of the target sequence. For example, assuming a 5'-3' orientation of the complementary target nucleic acid, the first target region may be located either 5' to the second region, or 3' to the second region.

As such in one embodiment, the probes of the present invention are designed to be complementary to a target nucleic acid, such that the probes hybridize to the target nucleic acids. This complementarity need not be perfect; there may be any number of base pair mismatches that will interfere with hybridization between the target nucleic acid and the single stranded probe sequence. However, if the number of mismatches is so many so that no hybridization can occur under certain hybridization conditions, the sequence is not a complementary target sequence.

In addition, these probes may take on a variety of configurations and may have a variety of structural components. In some embodiments, a probe may be an allele specific probe or a locus specific probe. An allele specific probe includes an allele-specific hybridization sequence (ASHS) portion that hybridizes to a target nucleic acid and discriminates between alleles, or hybridizes to a target nucleic acid and is modified in an allele specific manner. A locus specific probe includes a locus-specific hybridization sequence (LSHS) portion that hybridizes to a target nucleic acid in a locus specific manner, but does not necessarily discriminate between alleles. A locus specific probe also may be modified, i.e. extended as described below, such that it includes information about a particular allele, but the locus specific primer itself does not discriminate between alleles. The length of the ASHS or LSHS may be designed to confer sufficient specificity for the probe to hybridize to the target nucleic acids. With the general guidance that the longer the ASHS or LSHS sequence, the more specific they binds to the target nucleic acids, a skilled person in the art has the knowledge to varying the length and decide the length of the ASHS or LSHS in order to achieve his/her testing goals as described in detail herein, e.g., in the Examples.

In other embodiments, a probe may include one or more segments in addition to ASHS or LAHS. In some instance, the additional segment of the probe may be a primer binding site, onto which a primer may bind in a polymerase chain reaction. In other instance, the additional segment of the probe may be a stuffer sequence, which may make the ligation product vary in length and thereby be distinguished on the basis of fragment sizes. The length of the primer binding site and the stuffer sequence may be designed by a person skilled in the art to suit his/her testing goals. For example, a primer binding site of the probes may be about 15-20 nucleotides in length, with 18 being especially preferred. For another example, the stuffer sequence of the probes may be about 2-100 nucleotides depending on the needs to distinguish different target nucleic acids. As such, the stuffer sequence is a nucleic acid that is generally not native to the target sequence, but is added or inserted in the probe sequence. Preferred stuffer sequences are those that are not found in a genome, e.g., a human genome, and they do not have undesirable structures, such as hairpin loops.

In some embodiments, double stranded target nucleic acids are denatured to render them single stranded so as to permit hybridization of the target nucleic acids and the probes. The denaturation may be achieved, among other suitable means, by treating the target nucleic acids with heat, alkali, or both heat and alkali. See, e.g., Green and Sambrook, Molecular Cloning: A Laboratory Manual (Fourth Edition): Three-volume set, Cold Spring Harbor Laboratory Press; 4th edition (Jun. 15, 2012). In some embodiments, the denaturing may be carried out at temperature about 90° C. to about 99° C. for about 5 seconds to 30 minutes. In a preferred embodiment, the denaturation may be carried out at about 98° C. for 5 minutes.

The use of different stringency conditions such as variations in hybridization temperature and buffer composition may be used to determine the presence or absence of mismatches between a single stranded target nucleic acid and a probe. With regard to temperature, differences in the number of hydrogen bonds as a function of basepairing between perfect matches and mismatches can be exploited as a result of their different $T_m$s. Under a defined ionic strength, pH and nucleic acid concentration, the $T_m$ is the temperature at which 50% of the probes complementary to the target hybridize to the target sequence at equilibrium. Accordingly, a hybridized nucleic acid comprising perfect complementarity will melt at a higher temperature than one comprising at least one mismatch, with all other parameters being equal. The other parameters include the length of the hybridized nucleic acid, the nature of the backbone (i.e. naturally occurring or nucleic acid analog), the assay solution composition, and the composition of the nucleic acid, e.g., the G-C content.

High stringency conditions are those that result in perfect matches remaining in hybridization complexes, while imperfect matches melt off. On the other hand, low stringency conditions are those that allow the formation of hybridization complexes with both perfect and imperfect matches. Stringent conditions are sequence-dependent and will be different in different circumstances. Longer sequences hybridize specifically at higher temperatures.

A guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at defined ionic strength and pH. Stringent conditions may be those in which the salt concentration is less than about 1.0 M sodium ion, typically about 0.01 to 1.0 M sodium ion concentration (or other salts) at pH 7.0 to 8.3 and the temperature is at least about 3° C. for short probes (e.g. 10 to 50 nucleotides) and at least about 6° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art. See, e.g., Tijssen, supra.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of 40%. Low stringency conditions include NaCl concentrations of 1 M, and high stringency conditions include concentrations of 0.3 M. Furthermore, low stringency conditions include $MgCl_2$ concentrations of 10 mM, moderate stringency as 1-10 mM, and high stringency conditions include concentrations of 1 mM.

Ligase catalyzes the covalent bonding between two nucleotides adjacent to each other. The ligation reaction is facilitated by a complementary strand holding the two nucleotides comprising the 3' and 5' ends of two polynucleotides with no gaps between the two ends in close proximity. In addition, the ligation reaction requires that there is a phosphate group exposed on the 5' end or hydroxyl group exposed on the 3' end.

Ligation can be carried out using any enzyme capable of ligating nucleotides. In some embodiments, Taq DNA ligase is used to ligate the two adjacent oligonucleotide probes hybridized to the target nucleic acid. Taq DNA Ligase catalyzes the formation of a phosphodiester bond between juxtaposed 5' phosphate and 3' hydroxyl termini of two adjacent oligonucleotide probes which are hybridized to a complementary target DNA. The ligation will occur only if the oligonucleotides are perfectly paired to the complementary target DNA and have no gaps between them; therefore, a single-base substitution may be detected if no ligation product is generated.

The condition for the ligation reaction depends on what ligase is used. For a thermal stable ligase, the ligase retains activities at elevated temperatures. For example, Taq DNA ligase remains active at 45-65° C. For a non-thermal stable ligase, the ligase is active at lower temperatures. For example, T4 DNA ligase is active at around 16° C. As such, in one embodiment, the temperature for ligation reaction may be from about 4° C. to about 70° C. depending on which ligase is used.

The amount of the ligase and the duration of the ligation reaction may depend on the amount of probes and target nucleic acids. A person skilled in the art may adjust the amount of the ligase added in a reaction and the duration of the reaction so that a desirable ligation product may be achieved. For example, in some embodiments of the present invention, 40 units of Taq DNA ligase is used for a 20 µl ligation reaction. One unit is defined as the amount of enzyme required to give 50% ligation of the 12-base pair cohesive ends of 1 µg of BstEII-digested λ DNA in a total reaction volume of 50 µl in 15 minutes at 45° C.

In some embodiments, the duration of the ligation reaction is about 1 minute to 48 hours. In other embodiments, the duration of the ligation reaction is about 16 hours. In other embodiments, the steps of denaturation, hybridization, and ligation are repeated several time so that more probes may hybridize to the target nucleic acid or hybridize to the newly ligated probe. For example, the mixture of the probes and the target nucleic acids may be held at about 90° C. to about 99° C. for about 5 second to about 30 seconds for denaturation, and then at about 4° C. to about 58° C. for about 1 minute to 48 hours for hybridization and ligation, and the cycles may be repeated to 100 times. In some preferred embodiments, for example, the mixture of the probes and the target nucleic acids may be held at about 95° C. for about 30 seconds for denaturation, and then at 58° C. for about 4 hours for hybridization and ligation, and the cycles may be repeated 4 times.

In other embodiments, there is a gap between the hybridized probes on the target nucleic acid. In some instances, the gap may be filled by another probe that is complementary to the gap in the target nucleic acid. This gap-filling probe is designed so that when it is hybridized to the nucleic acid, its two ends are substantially adjacent to the other two probes. In other instances, the gap may be filled by extending one of the probes hybridized to the target nucleic acid. This probe extension may be carried out using a DNA polymerase and dNTPs. A description of DNA polymerase is described supra. For both gap filling methods, a ligation reaction is performed to ligate the substantially adjacent gap-filling probe with the other two probes or ligate the substantially adjacent extended probe with the other probe to obtain ligation products. The ligation reaction may be carried out with suitable parameters including, but not limited to, the type of the ligase, the amount of the ligase, and the duration of the ligation reaction as describe above. Supra.

In some embodiments, the ligation products are then analyzed directly to determine the presence, absence, or quantity of target nucleic acids in the sample. In other embodiments, the ligation products are then amplified to obtain amplification products which are analyzed to determine the presence, absence, or quantity of target nucleic acids in the sample.

As used herein, "amplification" refers to the increase in the number of copies of a particular nucleic acid. Copies of a particular nucleic acid made in an amplification reaction are called "amplicons" or "amplification products".

Nucleic acid amplification methods include, without limitation, polymerase chain reaction (PCR) (U.S. Pat. Nos. 4,683,195, 4,683,202, 4,800,159, and 5,219,727) and its variants such as in situ polymerase chain reaction (U.S. Pat. No. 5,538,871), quantitative polymerase chain reaction (U.S. Pat. No. 5,219,727), and nested polymerase chain reaction (U.S. Pat. No. 5,556,773). The foregoing references are incorporated herein for their teachings of these methods.

In some embodiments, the amplification process is achieved through PCR. The PCR amplification process results in the exponential increase of discrete DNA fragments whose length is defined by the 5' ends of the oligonucleotide primers.

In some embodiments, universal primer binding sites are included in the probes and universal primers are used to amplify ligation products for all target nucleic acids. Alternatively, "sets" of universal primer binding sites are included in "sets" of corresponding probes, and "sets" of universal primers are used to amplify "sets" of the ligation products either simultaneously or sequentially to obtain "sets" of amplification products for further analysis.

Accordingly, in some embodiments of the present invention, "sets" of probes are provided for multiplex nucleic acid analysis with each set of probes including a first probe and a second probe. Multiplexity here refers to at least two target nucleic acids, with more than 10 being preferred, depending on the assay, sample and purpose of the test. In some embodiments the multiplexity refers to more than 48, 96, 192, or 384 target nucleic acids.

As used herein, the term "primer" refers to an oligonucleotide, sometimes produced synthetically, which is capable of acting as a point of initiation of nucleic acid sequence synthesis when placed under conditions in which synthesis of a primer extension product which is complementary to a template nucleic acid strand is induced, i.e. in the presence of different nucleotide triphosphates and a polymerase in an appropriate buffer and at a suitable temperature. A primer sequence need not reflect the exact sequence of the template. For example, a non-complementary nucleotide fragment may be attached to the 5' end of the primer, with the remainder of the primer sequence being substantially complementary to the template.

In some embodiments, an oligonucleotide GTTTCTT was included in the 5' portion of a primer sequence. The addition of the oligonucleotide GTTTCTT may help facilitate the non-templated addition of adenosine on the 3' end of PCR products when polymerases such as Taq polymerase are used in the PCR. See, e.g., Brownstein et al., Modulation of Non-Templated Nucleotide Addition by TaqDNA Polymerase: Primer Modifications that Facilitate Genotyping, BioTechniques 20:1004-1010 (June 1996). The consistent addition of adenosine may help to have most or all PCR products consistently have an adenosine end. As such, the genotyping result of these PCR products can be consistent. Without the consistent addition of adenosine, a PCR product may not vary in size by one base pair and the genotyping result of the PCR product may not be consistent. In some embodiments, the reverse primer used for amplifying the ligation products includes oligonucleotide GTTTCTT or its functional equivalents, e.g., GTTTCTTG.

In some embodiments, one or more of the nucleotides of the primer may be modified by adding a detectable moiety, e.g., a methyl group, a biotin or digoxigenin moiety, or a fluorescent tag. For some instances, the moiety is a fluorescent dye and the dye may be, but not limited to, FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, and Yakima Yellow. See, e.g., U.S. Patent Publication No. 20110151459 for fluorescent dyes that may be used to label primers in the present invention and the U.S. Patent Publication No. 20110151459 is here incorporated by reference for the relevant teachings.

In one embodiment, the multiplexy of nucleic acid analysis is increased by adding a detectable moiety to the primers used for amplifying ligation products. In one example, the moieties used for labeling the primers are FAM-blue, VIC-green, NED-yellow and PET-red (Life Technologies, Inc.). As shown in FIG. 1, to analyze target nucleic acids T01, T02, T03, and T04 in a sample according to one embodiment of the present invention, two probes (here referred to as the right probe and the left probe as they appear in the figure) for each target site are designed so that each probe contains a locus specific hybridization sequence (LSHS) and a primer binding site. The right probe contains a primer binding site Y. The primer binding site Y may be shared by the right probes for all target nucleic acids. In contrast, the left probe for each target nucleic acid contains a unique primer binding sequence (X1, X2, X3 and X4). The primer binding sequences are incorporated in the ligation products. To amplify the ligation product, a pair of primers is designed for each ligation product corresponding to each target site. Because the left probes have four unique primer binding sites, four unique forward primers (F1, F2, F3 and F4) are designed corresponding to the four unique primer binding sites, respectively. In the example, the forward primer F1 is labeled with FAM-blue fluorescent dye, F2 with VIC-green, F3 with NED-yellow, and F4 with PET-red. The reverse primer R binds to the primer binding site Y. As such, the amplification product for target T01 is labeled with FAM-blue fluorescent dye. And the amplification products for targets T02, T03, and T04 are labeled with VIC-green, NED-yellow, and PET-red, respectively. The fluorescent labeled amplification products may then be analyzed by capillary electrophoresis on the basis of the different fluorescent dyes that each product is labeled with. The amplification products differentially labeled with fluorescent dyes may be distinguished even if the amplification products for different target nucleic acids are of the same length.

Figure 2:
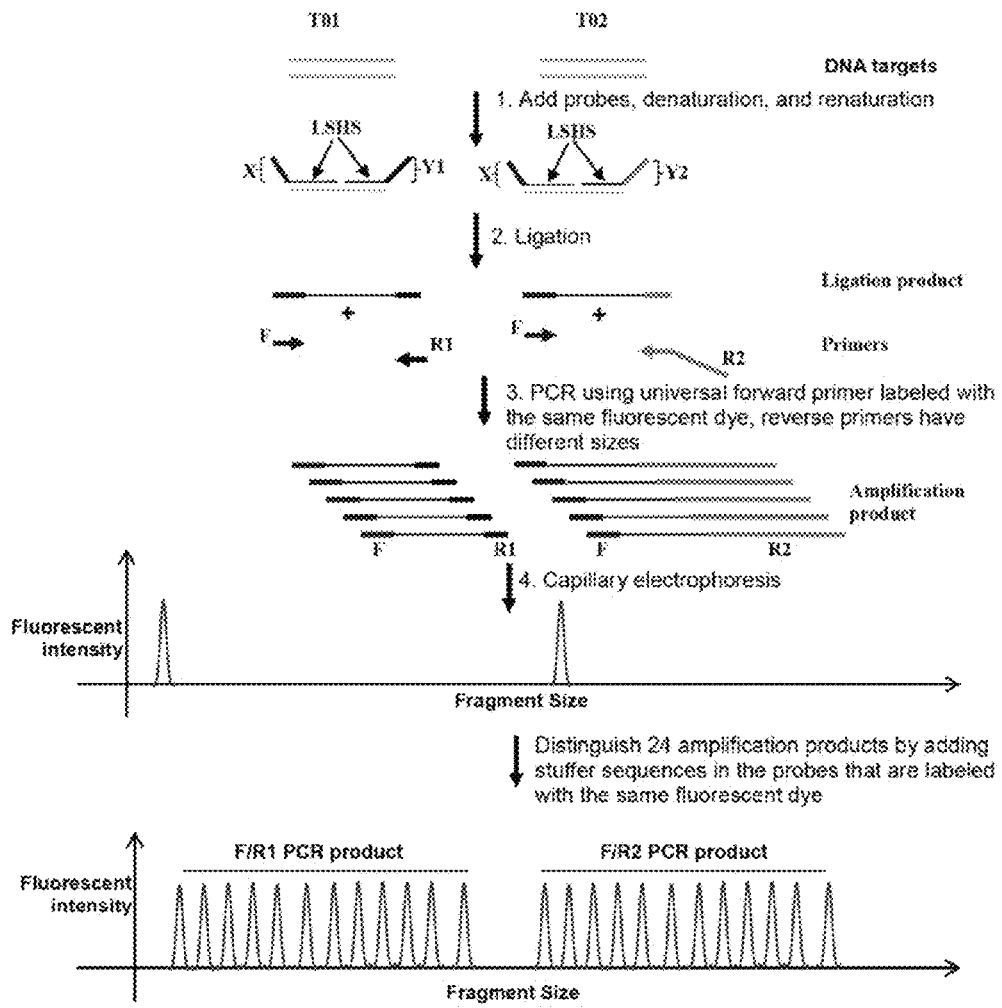
FIG. 2 is a schematic flowchart depicting the method of increasing multiplexity by employing primers with stuffer sequences for amplifying ligation products.

In another embodiment, the multiplexy of nucleic acid analysis is increased by varying the length of primers used for amplifying ligation products. To vary the length of primers, in one example, a stuffer sequence may be inserted into the primers. The stuffer sequence may be incorporated into the amplification product during the PCR reaction; i.e., the primer may be extended to form the amplification product to incorporate the stuffer sequence. As such, the addition of a stuffer sequence may help distinguish the amplification products on the basis of fragment sizes. In one embodiment as illustrated in FIG. 2, a stuffer sequence is inserted in primer R2 so that the amplification product from target T02 has a bigger fragment size than the product from target T01. As shown in FIG. 2, to detect target nucleic acids T01 and T02 in a sample according to one embodiment of the present invention, two probes (here referred to as the right probe and the left probe as they appear in the figure) are designed for each target nucleic acid so that each probe contain a locus specific hybridization sequence and a primer binding sequence. The left probe contains a primer binding sequence X, which is shared by left probes for both target sites. In contrast, the right probe contains a unique primer binding sequence (Y1 or Y2). The primer binding sequences may be incorporated into the ligation products. To amplify the ligation products, a pair of primers is designed for each ligation product corresponding to each target site. The forward primer binds to the primer binding site X shared by the two ligation products. The primers binding to the unique primer binding site Y1 and Y2 are designed to have a stuffer sequence inserted in the 5' portion. In one example, the reverse primer R2 contains a stuffer sequence so that R2 is longer than R1 and the amplification product from F/R2 is longer than from F/R1 if the ligation products for the two target sites are of the same length. In some embodiments, the stuffer sequence may have about 10 to about 500 nucleotides. In other embodiments, the stuffer sequence may have about 10 to about 60 nucleotides. In some preferred embodiments, the length of each and very primer is no more than 125 nucleotides. In other preferred embodiments, the length of each and every primer is no more than 75 nucleotides. The amplification products may then be analyzed by capillary electrophoresis on the basis of the different fragment size. The amplification products thus obtained may be distinguished even if the amplification products are labeled with the same fluorescent dye and the ligation products are of the same length for different target nucleic acids.

Figure 3:
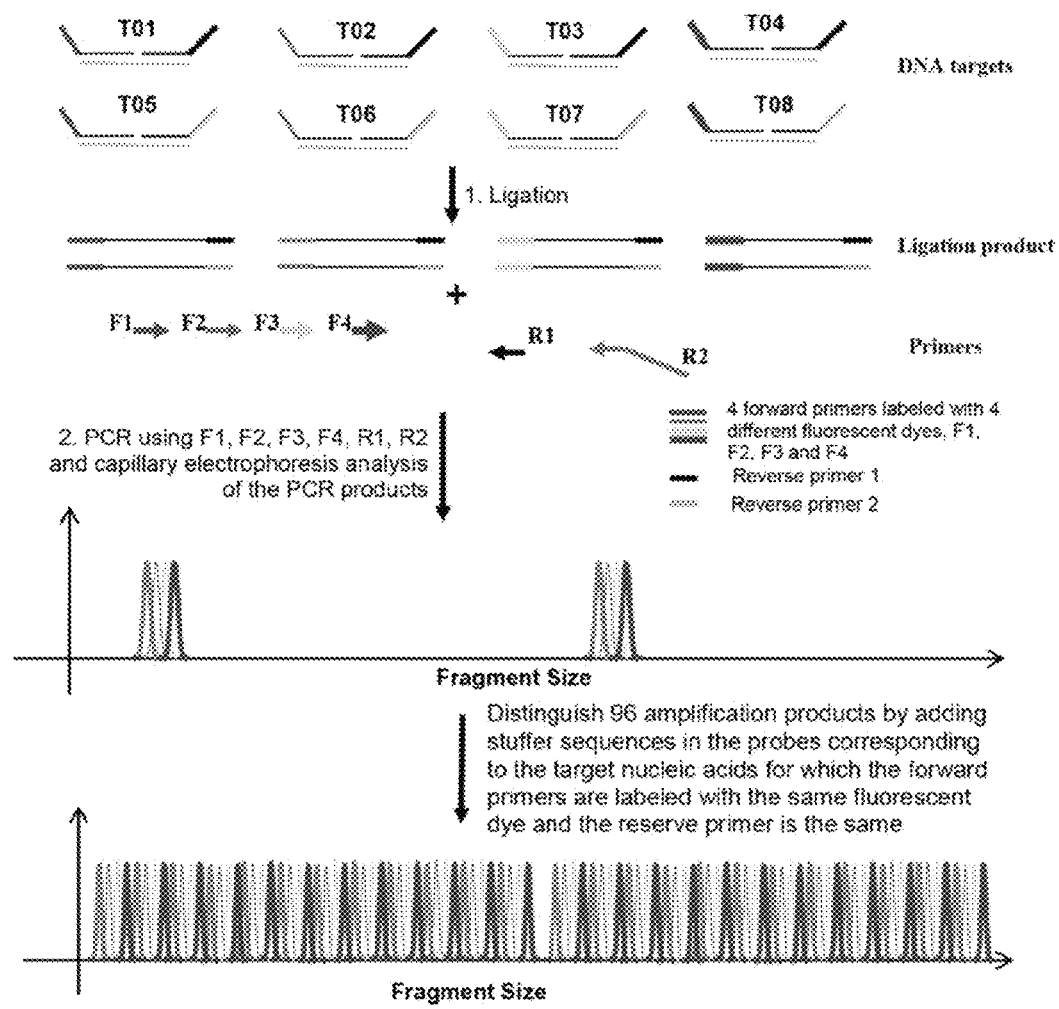
FIG. 3 is a schematic flowchart depicting the method of increasing the fold of multiplexing by employing both fluorescent dye labeled primers and primers with stuffer sequences for amplifying ligation products.

In still other embodiment, the multiplexy of nucleic acid analysis is increased by a combination of the use of primers labeled with fluorescent dyes and primers inserted with stuffer sequences. For example, as illustrated in FIG. 3A, the forward primers are labeled with four fluorescent dyes: F1-FAM-blue, F2-VIC-green, F3, NED-yellow, and F4-PET-red. In addition, the reverse primer R2 contains a stuffer sequence but R1 does not contain a stuffer sequence. As such, the combination may give rise to an eight fold increase in terms of the multiplexy for determining the ligation products; eight ligation product of the same length may be distinguished by determining the corresponding amplification products on the basis of fragment sizes and fluorescent labels.

In still other embodiments, the multiplexy of the nucleic acid analysis according to the present invention may be further increased by inserting stuffer sequences in the probes to be hybridized to target nucleic acids and ligated to form ligation products. The insertion of stuffer sequences in probes may produce ligation products with unique sequence length corresponding to a particular target nucleic acid. For example, to distinguish 16 target nucleic acids T01-T16 in a sample according to one embodiment of the present invention, two locus-specific probes (here referred to as the right probe and the left probe as they appear in the figure) are designed for each target nucleic acid. The left probe contains a locus specific hybridization sequence and a universal primer binding sequence X. The right probe for each target nucleic acid contains locus specific hybridization sequence, a stuffer sequence and a universal primer binding sequence Y. The stuffer sequence for each target nucleic acid may vary in length, e.g., for T01, the right probe has no stuffer sequence; for T02, the right probe has a stuffer sequence of 2 nucleotides; for T03, 4 nucleotides; for T04, 6 nucleotides; for T05, 8 nucleotides; for T06, 10 nucleotides . . . and for T16, 30 nucleotides. Consequently, the ligation product for each target nucleic acid has a unique fragment size because the stuffer sequences in the probes are incorporated into the ligation product. The ligation products are optionally further amplified with a pair of universal primers that binds to the universal primer binding sites X and Y. As such, the fragment sizes of the amplification products match the fragment sizes of the ligation products and therefore may be determined on the basis of fragment sizes. As such, if without the stuffer sequences in the probes, the ligation products are of the same length, the addition of the stuffer sequences in the probes makes it possible to distinguish the ligation product and/or the amplification product for each target nucleic acid on the basis of fragment size. In this example, the multiplexity for target nucleic acid analysis increases 16 folds. Thus, as exemplified in this embodiment, the fold increase of multiplexity may depend on the number of stuffer sequences with different length that are inserted in the locus-specific probes. If 12 stuffer sequences of varying length are inserted in the locus-specific probes for each target nucleic acid, the multiplexity for target nucleic acid analysis may increase 12 fold.

Therefore, according to the present invention, the methods of increasing multiplexity by inserting stuffer sequences in probes may be combined with the method of increasing multiplexity by labeling the primers with detectable moieties and/or inserting stuffer sequences in primers. For example, by both labeling primers with fluorescent dyes and inserting stuffer sequences in probes, 64 amplification products corresponding to 64 target nucleic acids may be distinguished by capillary electrophoresis on the basis of fluorescent dyes and fragment size (see FIG. 1, bottom chart). For another example, by inserting stuffer sequences in both primers and probes, 24 amplification products corresponding to 24 target nucleic acids may be distinguished by capillary electrophoresis on the basis of fragment size (see FIG. 2, bottom chart). For still another example, by labeling primers with fluorescent dyes and inserting stuffer sequences in primers and probes, 96 amplification products corresponding to 96 target nucleic acids may be distinguished by capillary electrophoresis on the basis of fluorescent dyes and fragment size (see FIG. 3, bottom chart).

The analysis of amplification products may be by any method that can separate DNA fragments on the basis of size, mass, fluorescent moieties, or other measurable properties. These methods include, but not limited to, agarose gel electrophoresis followed by capillary electrophoresis (CE), DNA sequencing, ethidium bromide or DNA staining, microarray, and flow cytometry.

For example, capillary electrophoresis may identify DNA fragments on the basis of both fluorescent moieties and fragment sizes. In some embodiments, capillary electrophoresis is performed by injecting the DNA fragments into a capillary, filled with polymer. The DNA is pulled through the tube by the application of an electric field, which separates the fragments such that the smaller fragments travel faster through the capillary. The fragments are then detected on the basis of fluorescent dyes that are attached to the primers used in PCR. This allows multiple fragments to be amplified and run simultaneously in a multiplexed manner. Sizes are assigned using labeled DNA size standards that are added to each sample. In capillary electrophoresis the intensity of signal of an amplification product is the number of relative fluorescence units (rfus) of its corresponding peak. The intensity value correlates with the amount of labeled amplification product.

In some embodiments, capillary electrophoresis is the preferred method for analyzing the amplification products of the present invention. Capillary electrophoresis devices are known in the art. Capillary electrophoresis devices useful according to the invention include, but are not limited to, ABI 3130XL Genetic Analyzer by Applied Biosystems (Foster City, Calif.); MegaBACE 1000 Capillary Array Electrophoresis System by Amersham Pharmacia Biotech (Piscataway, N.J.); CEQ™ 8000 Genetic Analytic System by Beckman Coulter (Fullerton, Calif.); Agilent 2100 Bioanalyzer by Caliper Technologies (Mountain View, Calif.); and iCE280 System by Convergent Bioscience Ltd. (Toronto, Canada).

As is the case throughout this invention disclosure, including the background, the summary, the detailed description and the claims, the designation of the "left" probe and the "right" probe are arbitrary and are interchangeable. For example, the left probe have the features described for the right probe and the right probe may have the features for the left probe. In addition, the designation of the "first" primer and the "second" primer, or the "forward" primer and the "reverse" primer are also arbitrary and interchangeable. Further, when an oligo primer binding to a primer binding site on a template DNA in a PCR amplification reaction, the oligo primer is meant to bind either to the positive strand or to the negative strand of the template DNA. A primer is reversely complementary to a binding site on a single-stranded DNA when the primer is complementary to the opposite strand of the single-stranded DNA. As is well known in the art for a PCR reaction to proceed successfully, the forward primer and the reverse primer do not bind to the same strand of a DNA template. Instead, the forward primer and the reverse primer bind to different strands of a DNA template if an exponential amplification is desired.

II. Applications of Multiplex Nucleic Acid Analysis

Methods of multiplex nucleic acid analysis according to the present invention may be applied to detect various genetic aberrations, including, but not limited to, single nucleotide polymorphisms (SNPs), gene copy number variants (CNVs), chromosomal abnormalities (e.g., insertions, deletions and duplications), gene mutations (e.g., single nucleotide changes, insertions, and deletions), nucleic acid modifications (e.g., methylation, acetylation and phosphorylations), and abnormal gene expression. Some aberrations may be qualitative changes, e.g., the presence or absence of a SNP. Other aberrations may be quantitative, e.g., the change of gene copy number. The quantitative change may be big or small. For example, in a genomic DNA sample from a Down's syndrome patient, the copy number of chromosome 21 increases 50%. In contrast, in a blood sample of a pregnant woman conceiving a Down's syndrome fetus, the copy number of chromosome 21 may increase less than 10%.

The terms "analyzing", "determining," "measuring," "assessing," "assaying," "evaluating," and any grammatical equivalents are used interchangeably to refer to any form of quantitative or qualitative measurement, and include determining if a characteristic, trait, or feature is present or not. An analysis of nucleic acids may be relative or absolute. For example, an increase of copy number of a nucleic acid in a sample may be measured in relative to the copy number of the nucleic acid in a reference sample.

Multiplex SNP Detection.

Recent human genomics research indicates that the genomic makeup between any two humans has over 99.9% similarity. The relatively small number of variations in DNA between individuals gives rise to differences in phenotypic traits, and may be related to many human diseases, susceptibility to various diseases, or response to treatment of disease. Variations in DNA between individuals occur in both coding and non-coding regions, and include changes of a single nucleotide, as well as insertions and deletions of nucleotides. Changes of a single nucleotide in the genome are referred to as single nucleotide polymorphisms, or "SNPs." The occurrences of SNPs in the genome are becoming correlated to the presence of and/or susceptibility to various diseases and conditions. As these correlations and other advances in human genetics are being made, medicine and personal health in general are moving toward a customized approach in which a patient will make appropriate medical and other choices in consideration of his or her genomic information, among other factors. Thus, there is a need to provide individuals and their care-givers with information specific to the individual's personal genome toward providing personalized medical and other decisions.

Figure 4:
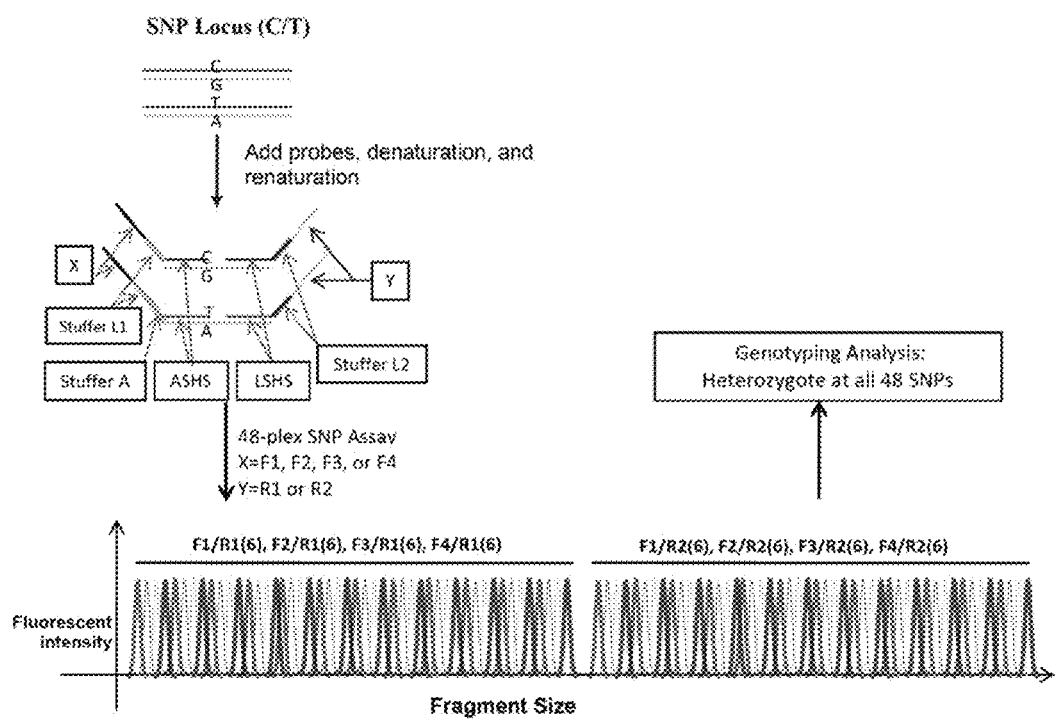
FIG. 4 is a schematic flowchart depicting an exemplary analysis of 48 SNPs in a multiplex assay by employing both fluorescent dye labeled primers and primers with stuffer sequences for amplifying ligation products. X and Y refer to primer binding sites on the probes. LSHS refers to locus-specific hybridization sequences. Stuffer A refers to an allelic-specific stuffer sequence of 2 nucleotides in length. Stuffer L1 and stuffer L2 refer to stuffer sequences used for adjusting the size of the ligated probe. ASHS refers to allele-specific hybridization sequences. F1, F2, F3 and F4 refer to forward primers labeled with blue, green, yellow and red fluorescent dyes, respectively. R1 and R2 refer to reverse primers with different stuffer sequences. F1/R1(6) refers to 12 amplification products using the F1 and R1 primer pair based on 12 ligation products from 6 SNP loci with two SNP alleles per SNP locus. Similar interpretations stand for F2/R1(6), F3/R1(6), F4/R1(6), F1/R2(6), F2/R2(6), F3/R2(6), and F4/R2(6).

A multiplex SNP detection method according to the present invention is illustrated in FIG. 4. In the example, 48 SNP sites are determined in a single assay simultaneously. For illustrative purposes, one SNP has a C or T nucleotide at the polymorphic position. A set of probes (here referred to as the right probe and the left probe as they appear in the figure) are designed. The left probe contains an allele-specific hybridization sequence (ASHS) with the SNP recognition nucleotide "C" or "T" on one end, a primer binding site X, a stuffer A sequence between the ASHS and the primer binding site, and a stuffer L1 sequence between the stuffer A sequence and the primer binding site. The stuffer A sequence helps distinguish the alleles for each SNP site. The right probe contains a locus-specific hybridization sequence (LSHS), a primer binding site Y, and a stuffer L2 sequence between the LSHS and the primer binding site. By varying the length of stuffer L1 and L2 sequences, a six-fold multiplexity may be achieved for the ligation products; ligation products for six SNP sites can be distinguished on the basis of fragment size. In some instances, a mismatch at a position 2, 3, or 4 nucleotides away from the SNP recognition site is introduced into the probe. These mismatches may help increase the specificity of the hybridization of the ASHS to the target site. See, e.g., Luo et al., Improving the fidelity of *Thermus thermophilus* DNA ligase, Nucleic Acids Res. 1996 Aug. 1; 24(15):3071-8, which is herein incorporated by reference.

In addition, by labeling the forward primers with FAM-blue, VIC-green, NED-yellow and PET-red and inserting a stuffer sequence in the reverse primer R2, the multiplexity for the SNP analysis is increased to 96 (=6×2×4×2). As such, the multiplex SNP detection method may analyze 48 SNP sites simultaneously with each SNP site having two alleles. A person skilled in the art may increase the multiplexity for SNP detection by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

Multiplex CNV Detection.

As used herein, CNVs refer to variations in the number of copies of a nucleic acid sequence that contains 2 or more nucleotides in a test sample in comparison with the copy number of the nucleic acid sequence present in a reference sample. CNVs may include deletions, microdeletions, insertions, microinsertions, duplications, multiplications, inversions, translocations and complex multisite variants. CNVs may also encompass chromosomal aneuploidies and partial aneuploidies that may cause many genetic diseases, e.g., Down's syndrome, Turner's syndrome, diGeorge syndrome, Angelman syndrome, Cri-du-chat, Kallmann syndrome, Miller-Dieker syndrome, Prader-Willi syndrome (PWS), Smith-Magenis syndrome, Steroid sulfatase deficiency (X-linked ichthyosis), Williams syndrome, and Wolf-Hirschhorn syndrome.

Figure 5:
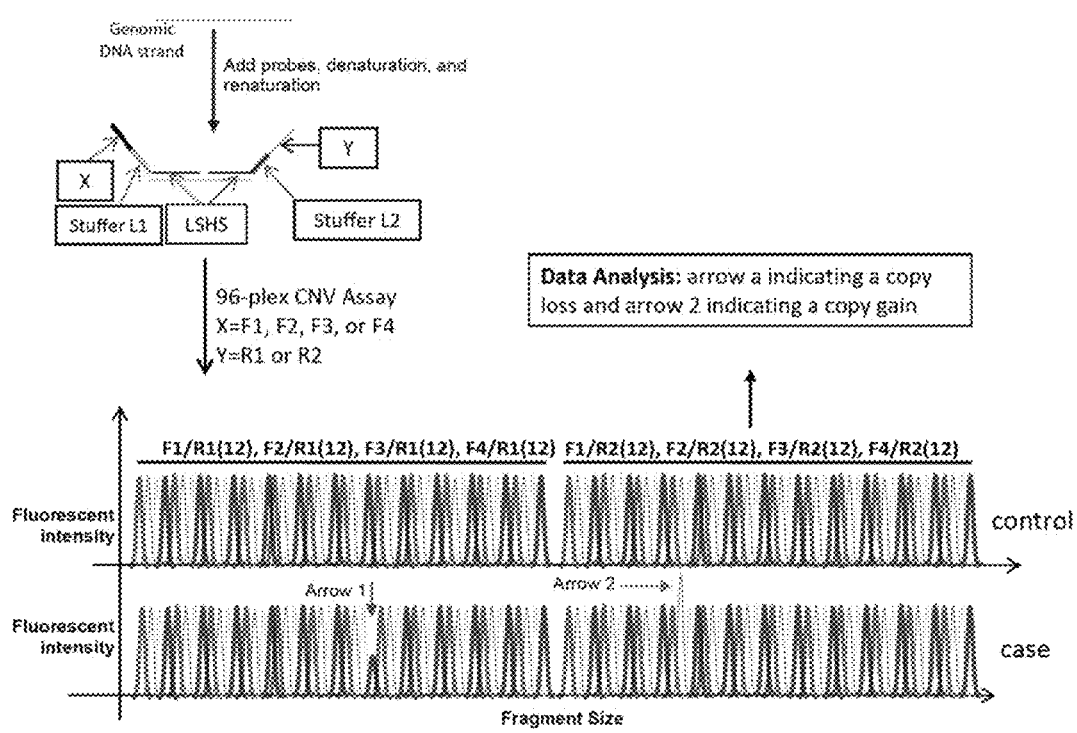
FIG. 5 is a schematic flowchart depicting an exemplary analysis of 96 CNVs in a multiplex assay by employing both fluorescent dye labeled primers and primers with stuffer sequences for amplifying ligation products. X and Y refer to primer binding sites on the probes. LSHS refers to locus-specific hybridization sequences. Stuffer L1 and stuffer L2 refer to stuffer sequences used for adjusting the size of the ligated probe. F1, F2, F3 and F4 refer to forward primers labeled with blue, green, yellow and red fluorescent dyes, respectively. R1 and R2 refer to reverse primers with different stuffer sequences. F1/R1(12) refers to 12 amplification products using the F1 and R1 primer pair based on 12 ligation products from 12 CNVs. Similar interpretations stand for F2/R1(12), F3/R1(12), F4/R1(12), F1/R2(12), F2/R2(12), F3/R2(12), and F4/R2(12).

An exemplary multiplex CNV detection method according to the present invention is illustrated in FIG. 5. In the example, 96 CNVs are measured in a single assay simultaneously. For each CNV, a set of probes (here referred to as the right probe and the left probe as they appear in the figure) are designed. The left probe contains a locus-specific hybridization sequence (LSHS), a primer binding site X, and a stuffer L1 sequence between the LSHS and the primer binding site. The right probe contains a locus-specific hybridization sequence (LSHS), a primer binding site Y, and a stuffer L2 sequence between the LSHS and the primer binding site. By varying the length of stuffer L1 and stuffer L2 sequences, a 12-fold multiplexity may be achieved for the ligation products; ligation products for 12 CNVs can be distinguished on the basis of fragment size. In addition, by labeling the forward primers with FAM-blue, VIC-green, NED-yellow and PET-red and inserting a stuffer sequence in one of the reverse primers R2, the multiplexity for the CNVs analysis may be increased to 96 (=12×4×2). As such, the multiplex CNV detection method may analyze 96 CNVs simultaneously. A person skilled in the art may increase the multiplexity for CNV detection by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

In some embodiments, the fluorescent intensity of each peak was compared to a standard value to determine the copy number of each CNV site. For example, if the intensity decreases in half compared to the standard value, the copy number may be considered as decreased in half. On the other hand, if the intensity increases 50% compared to the standard value, the copy number may be considered as increased 50%. A standard value may be a fluorescent intensity value specific to a testing system. A testing system means the whole experimental system including the reagents, primers, probes, procedures and devices used for the testing the CNVs. One test sample is considered to share the same testing system with another test sample if the whole experimental system is the same except that the initial DNA sample to be tested is different. As such a standard value may be obtained for a specific testing system based on prior testing results of DNA samples for which copy numbers of the CNV sites are known.

In other embodiments, a control sample is used to generate control fluorescent intensity values for the same CNV sites. The copy number for each CNV site is known for the control sample. When the peak intensity for a CNV site in a test sample is compared to the peak intensity for the same CNV site in the control sample, the copy number of the CNV site may be determined. For example, as shown in FIG. 5 bottom chart, arrow 1 points to a CNV site for which the test sample has about 50% copy number of the number in the control sample because the peak intensity decreases about 50% when compared to the peak intensity for the same CNV site in the control sample. For another example, arrow 2 points to a CNV site for which the test sample has about 150% copy number of the number in the control sample because the peak fluorescent intensity in the test sample increases about 50% when compared to the peak for the same CNV site in the control sample.

In other preferred embodiments, the peak values for each CNV site are normalized against peak values for one or more reference target sites. A CNV copy number change may be detected by comparing the normalized peak value for a CNV site in a test sample to the normalized standard value for the same CNV site in the testing system or the normalized peak value for the same CNV site in a control sample. The normalization may correct the variations, e.g., the amount of DNA templates used for probe hybridization, the amount of ligation probes used for probe hybridization, the amount of PCR primers for amplifying ligation products, the ligation efficiency of each set of probes, and the amount of ligation products used for PCR amplification, in obtaining the peak values between different samples and/or between different CNV sites.

To obtain peak values of reference target sites, probes for the reference target sites may be designed in a similar manner and used simultaneously with the probes for the CNV sites in the hybridization and ligation reactions. In addition, probes for the reference target sites and probes for the CNV sites may share the same primer binding sites so that the same set of primers may be used to amplify the ligation products for both the reference sites and the CNV sites.

As such in some instances, peak values for a plurality of reference target sites are obtained in parallel with the peak values for a plurality of CNV sites so that the peak value for each of the plurality of the CNV sites may be normalized against the peak value for each of the plurality of the reference target sites. For example, peak values for 6 reference target sites may be obtained together with the peak values for 6 CNV sites. In this example, 6 sets of probes for the 6 reference target sites and 6 sets of probes for the 6 CNV sites are added to a sample and ligation products are obtained after hybridization and ligation reactions. A single set of primers may be used to amplify the ligation products and peak values are measured by analyzing the amplification products by capillary electrophoresis.

In some embodiments, the normalization of the peak value for a CNV site in a sample is to obtain a ratio (here referred to as R) of the peak value for the CNV site against the peak value for a reference target site. As such, the copy number of a CNV site in a test sample may be measured by comparing the ratio for the CNV site in the test sample (here referred to as $R_{test}$) with the standard ratio for the same CNV site in the testing system (here referred to as $R_{standard}$) or with the ratio for the same CNV site in a control sample (here referred to as $R_{control}$).

In some instances, the copy number of a CNV site in a test sample is measured by comparing the ratio for the CNV site in the test sample ($R_{test}$) with the standard ratio for the same CNV site in the testing system ($R_{standard}$). The copy number of the CNV site in the testing system is known (here referred to as $C_{standard}$). In this case, the copy number of the CNV site in the test sample (here referred to as $C_{test}$) may be calculated as follow: $C_{test}=C_{standard} \times R_{test}/R_{standard}$.

In other instances, the copy number of a CNV site in a test sample may be measured by comparing the ratio for the CNV site in the test sample ($R_{test}$) with the ratio for the same CNV site in a control sample ($R_{control}$). The copy number of the CNV site in the testing system is known (here referred to as $C_{control}$). In this case, the copy number of the CNV site in the test sample ($C_{test}$) may be calculated as follow: $C_{test}=C_{control} \times R_{test}/R_{control}$.

As such, when 6 reference target sites are introduced to normalize the peak value for a CNV site, six copy number measurements ($C_{test}$) for the CNV site may be derived on the basis of the six peak values for the six reference target sites. Based on the six $C_{test}$ measurements, the copy number of the CNV site is obtained according to certain statistical analysis. In one embodiment, the median value of the six $C_{test}$ measurements is deemed the copy number of the CNV site. In another embodiment, the average value of the six $C_{test}$ measurements is deemed the copy number of the CNV site.

In a multiplex CNV analysis method, multiple sets of primers may be used to amply ligation products in a single tube PCR reaction. In this case, each set of primers is used to amplify a group of ligation products from both CNV sites and reference target sites so that peak values of CNV sites may be normalized against peak values of the reference target sites in the same group. Depending on probe designs, the number of CNV sites or reference target sites in each group may vary from 1 to 24. In some embodiments, there are 6 CNV sites and 6 reference target sites in each group. In other embodiments, there are 12 CNV sites and 12 reference target sites in each group. In still other embodiments, there are 9 CNV sites and 3 reference target sites in each group. In further other embodiments, there are 16 CNV sites and 8 reference target sites in each group.

The selection of a reference target site is sometimes based on criteria including, but not limited to, the copy number of each reference target site being stable in different samples and the sequences of the reference target sites being unique and not prone to interfering the reactions of the CNV sites of interest. In addition, when a plurality of reference target sites are used in a group, each reference target site is preferably from a different chromosome. In some embodiments, the quality of detecting copy number changes may be improved by increasing the number of reference target sites.

In some embodiments, when normalization is performed and normalized peak values for each CNV site are obtained for the test sample and the control sample, a comparison of the normalized peak values in the test sample with the values in the control sample may be carried out to determine any change of copy number of each CNV site. For example, if a normalized peak value for a CNV site in the test sample is 1.0 and the normalized peak value for the same CNV site in the control sample (the copy number for the CNV site is known to be 2) is 2.0, the copy number of the CNV site in the test sample is determined to be 1, about half of the copy number in the control sample. For another example, if a normalized peak value for a CNV site in the test sample is 1.0 and the normalized standard peak value for the testing system (the copy number for the CNV site is known to be 2) is 1.0, the copy number of the CNV site in the test sample is determined to be 2, about the same with the copy number in the control sample.

Mutation Screening

DNA mutations refer to nucleotide changes in the genome in comparison to a wild type genome. "Wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, "mutant" refers to a gene or gene-product having at one or more sites a different nucleic acid sequence when compared to the wild-type gene or gene product.

Figure 6:
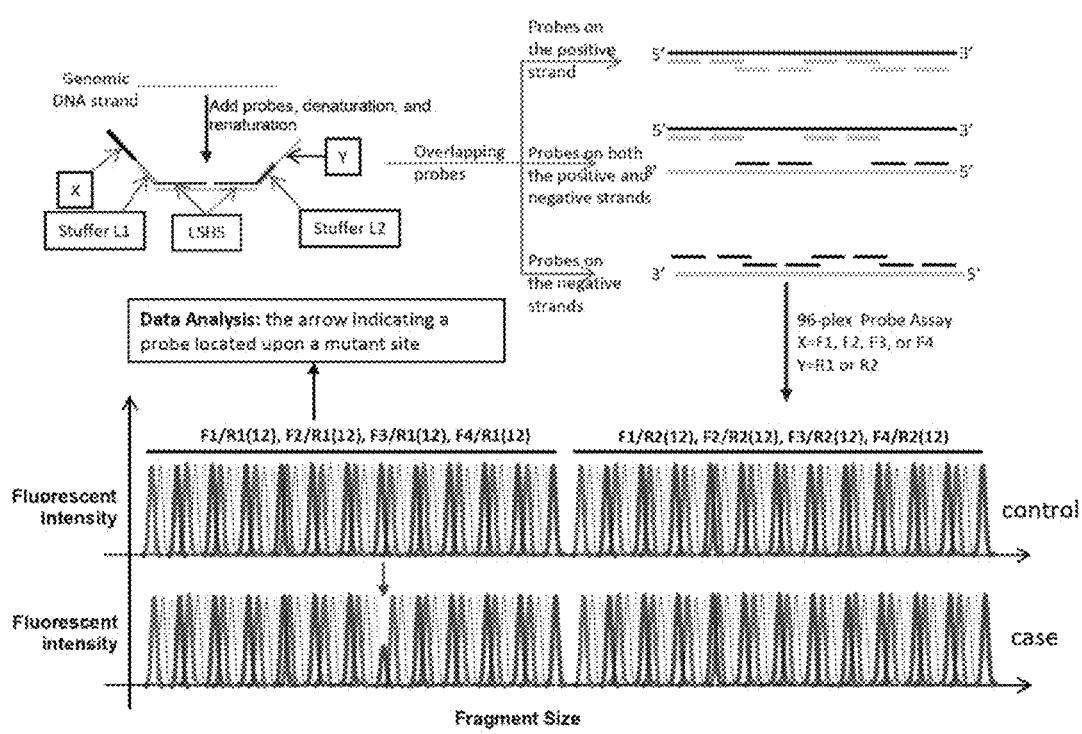
FIG. 6 is a schematic flowchart depicting an exemplary mutations screening analysis of 96 fragments overlapping upon the target region in a multiplexed assay by employing both fluorescent dye labeled primers and primers with stuffer sequences for amplifying ligation products. The labels refer to the similar components as detailed in FIG. 5.

In some embodiments, mutations in a gene may be screened by a method according to the present invention. An exemplary multiplex mutation screening method according to the present invention is illustrated in FIG. 6. In the example, 96 target sites are screened in a single assay simultaneously. For each target site, a set of probes (here referred to as the right probe and the left probe as they appear in the figure) are designed. The left probe contains a locus-specific hybridization sequence (LSHS), a primer binding site X and a stuffer L1 sequence between the LSHS and the primer binding site X. The right probe contains a locus-specific hybridization sequence (LSHS), a primer binding site Y, and a stuffer L2 sequence between the LSHS and the primer binding site Y. By varying the length of stuffer sequences, a 12-fold multiplexity may be achieved for the ligation products; ligation products for 12 target sites can be distinguished on the basis of fragment size. In addition, by labeling the forward primers with FAM-blue, VIC-green, NED-yellow and PET-red and inserting a stuffer sequence in one of the reverse primers R2, the multiplexity for the mutation screening may be increased to 96 (=12×4×2). As such, the multiplex mutation screening method may analyze 96 target sites simultaneously. A person skilled in the art would consider increase the multiplexity for mutation screening by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

As shown in FIG. 6, sets of probes are designed to overlap with each other. The probes may target the positive stand, the negative stand, or both the positive and the negative stands. In all cases, similar to the rationale in FIG. 5, the peak intensity for each target site is compared to a standard value or the peak intensity of the same target site in a control sample. A standard value may be derived in a similar way as described in FIG. 5. As shown in FIG. 6 bottom charts, the arrow points to a peak with about half the intensity of the same target site in the control sample. The decreased peak intensity suggests that the target site may contain a mutation. This is so because the two probes corresponding to the target site covers a mutation and therefore cannot hybridize to the target site to form a proper ligation product and finally result in no amplification product. This exemplary mutation screening method would provide a preliminary result as to the location of a mutation in a target nucleic acid. This may facilitate further sequencing analysis to identify the exact mutation.

Multiplex RNA Analysis

In some embodiments, the target nucleic acids in a sample are RNA and the analysis of the target nucleic acids is to determine the presence, absence, or quantity of the RNA in the sample. In some instances according to the present invention, the RNA is directly used for probe hybridization, probe ligation, ligation product amplification, and amplification product analysis. In other instances, the RNA is reverse-transcribed into complementary DNA (cDNA) before probe hybridization and further steps. As is known in the art, reverse transcription of RNA into cDNA may be accomplished using reverse transcriptase. The analysis of RNA may help determine gene expression levels if the RNA is a transcription product of a gene.

Figure 7:
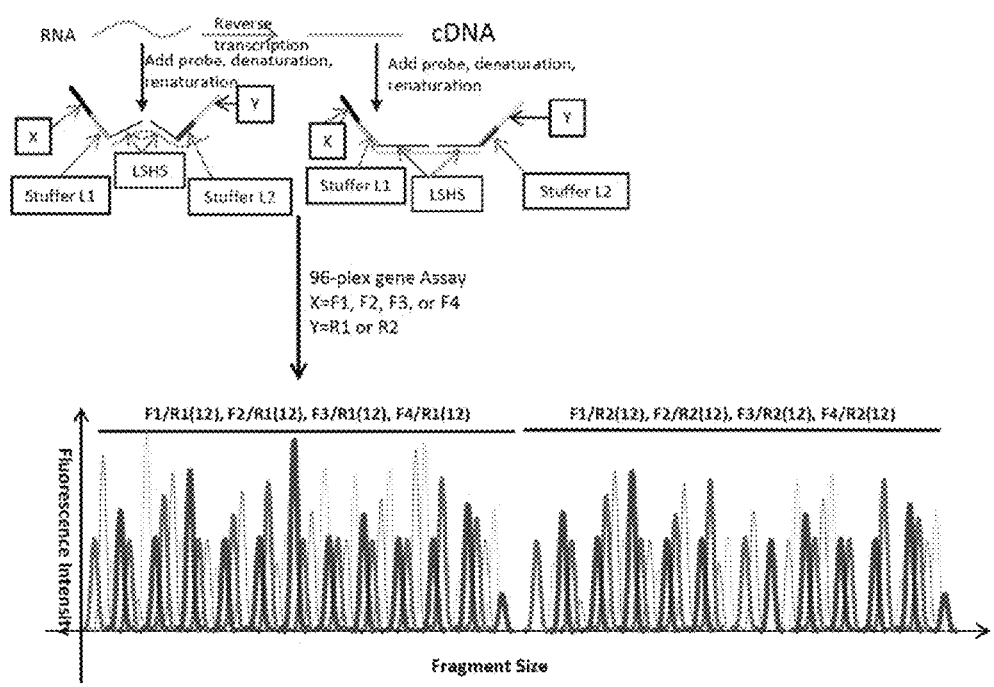
FIG. 7 is a schematic flowchart depicting an exemplary gene expression analysis of 96 mRNAs in a multiplexed assay by employing both fluorescent dye labeled primers and primers with stuffer sequences for amplifying ligation products. The labels refer to the similar components as detailed in FIG. 5.

As such, in some embodiments, target RNAs may be analyzed using a multiplex method according to the present invention. An exemplary multiplex target RNA analysis method according to the present invention is illustrated in FIG. 7. In the example, 96 target RNAs or its reverse transcribed cDNAs are analyzed in a single assay simultaneously. For each target RNA or cDNA, a set of probes (here referred to as the right probe and the left probe as they appear in the figure) are designed. The left probe contains a locus-specific hybridization sequence (LSHS), a primer binding site X, and a stuffer L1 sequence between the LSHS and the primer binding site X. The right probe contains a locus-specific hybridization sequence (LSHS), a primer binding site Y, and a stuffer L2 sequence between the LSHS and the primer binding site Y. By varying the length of stuffer sequences, a 12-fold multiplexity may be achieved for the ligation products; ligation products for 12 target sites can be distinguished on the basis of fragment size. In addition, by labeling the forward primers with FAM-blue, VIC-green, NED-yellow and PET-red and inserting a stuffer sequence in one of the reverse primers R2, the multiplexity for the mutation screening is increased to 96 (=12×4×2). As such, the multiplex gene expression analysis may measure 96 target RNAs simultaneously. A person skilled in the art would consider increase the multiplexity for target RNA analysis by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

In some embodiments, as shown in FIG. 7 and similar to the rationale in FIG. 5, the peak values for each RNA target is normalized against reference target sites before determining the presence, absence or amount of RNA copy number changes between different samples. Reference target sites may be any RNA, for example, RNA of housekeeping genes including, but not limited to, histone, β-actin, glyceraldehyde-β-phosphate dehydrogenase (GAPDH) or hypoxanthine-guanine phosphoribosyltransferase (HPRT) genes. In a multiplex RNA analysis, multiple groups of target RNA and reference target sites may be analyzed simultaneously. The same set of primers is used to amply ligation products for both the target RNA and the reference target sites within each group. The copy number of a target RNA is determined by comparing the normalized peak values for a target RNA in the test sample to the normalized peak values for the target RNA in the control sample. If the value increases 2 times, the copy number of the target RNA increase 2 times. Other aspects of the peak value normalization and copy number measurement methods are similar to those described for the normalization of peak values for CNV sites against reference target sites and therefore are not repeated here.

Multiplex Detection of Pathogens and Transgenic Organism

Multiplex nucleic acid analysis methods according to the present invention may be applied to detect nucleic acids from pathogens and transgenic organisms and thereby identify the pathogens and transgenic organisms. Pathogens, including, but not limited to, a bacterium, a virus, a protozoan, a parasite, a mold, or a fungus, may cause diseases or other conditions in an animal. Traditionally, several methods including bacteriological analysis, virus isolation and culture, histopathology and an enzyme-linked immunosorbent assay (ELISA) (Adams and Thompson, 2008, Rev. Sci. Technol. 27, 197-209) have been developed for the phenotypic characterization and identification of pathogens. Alternatively, molecular diagnosis based on polymerase chain reaction (PCR), RT-PCR, (Dhar et al., 2002, J. Virol. Methods 104, 69-82; Nishizawa et al., 1995, J. Gen. Virol. 76, 1563-1569) or quantitative real-time PCR (DallaValle et al., 2005, Vet. Microbiol. 110, 167-179) using specific primer sets for nucleic acid amplification has been demonstrated for diagnosis of diseases. The development of a new multiplex, rapid, accurate, and sensitive diagnostic methods for the identification of pathogens may help in treating, controlling, or even eradicating many pathogen-related diseases. In addition, transgenic organisms, including transgenic plants, e.g., corn, rise, soybean and cotton and transgenic animals, e.g., cow, peg, sheep and dog may sometimes need to be identified.

One aspect of the present invention provides a multiplex detection of pathogens and transgenic organisms. In some embodiments, target nucleic acids specific to pathogens or transgenic organisms are obtained for multiplex analysis. In some instances, nucleic acids specific to pathogens or transgenic organisms may be DNA unique to the pathogens or the transgenic organisms or unique to the family of the pathogens or the transgenic organisms. The pathogens or transgenic organisms may be from many sources. For example, in screening blood and other bodily fluids and tissues for pathogenic and non-pathogenic bacteria, viruses, parasites, fungi and the like, or transgenic genes, the sources may be blood and other bodily fluid or tissue samples, which may be obtained from living animals or deceased animals. In other instances, nucleic acids specific to a pathogen or transgenic organism may be RNA unique to the pathogens or transgenic organisms or unique to the family of the pathogens or transgenic organisms. For example, RNA viruses such as HIV, HBV, and HCV viruses contain unique RNA molecules and the detection of these unique RNA molecules helps determine the presence, absence or quantity of these RNA viruses.

In some embodiments, the target nucleic acids are amplified before the multiplex analysis. Such amplification is needed when the amount of target nucleic acids obtained from pathogens or transgenic organisms is limited. In other embodiments, when the target nucleic acids are RNA, a reverse transcription step may be optionally performed to convert the RNA into cDNA before the multiplex analysis.

Figure 8:
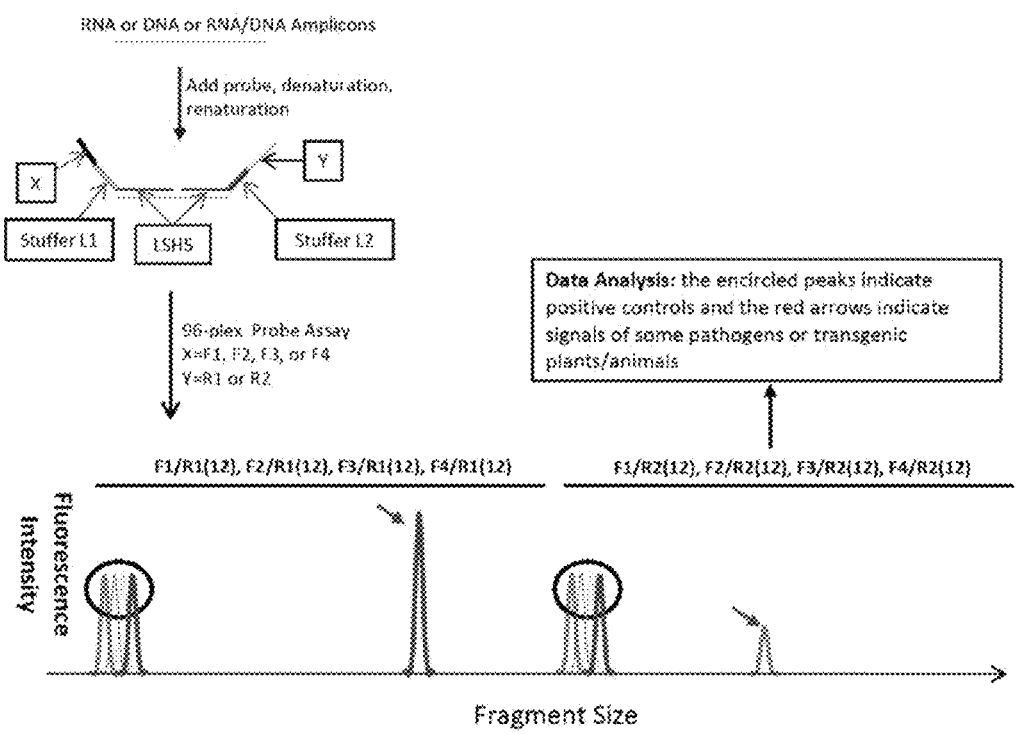
FIG. 8 is a schematic flowchart depicting an exemplary analysis of 96 nucleic acid targets from pathogens or transgenic plants/animals in a multiplexed assay by employing both fluorescent dye labeled primers and primers with stuffer sequences for amplifying ligation products. The labels refer to the similar components as detailed in FIG. 5.

An exemplary multiplex target nucleic acid analysis method for detecting pathogens and transgenic organisms according to the present invention is illustrated in FIG. 8. In the example, 96 target nucleic acids are analyzed in a single assay simultaneously. For each target nucleic acid, a set of probes (here referred to as the right probe and the left probe as they appear in the figure) are designed. The left probe contains a locus-specific hybridization sequence (LSHS), a primer binding site X, and a stuffer L1 sequence between the LSHS and the primer binding site X. The right probe contains a locus-specific hybridization sequence (LSHS), a primer binding site Y, and a stuffer L2 sequence between the LSHS and the primer binding site Y. By varying the length of stuffer sequences, a 12-fold multiplexity may be achieved for the ligation products; ligation products for 12 target nucleic acids can be distinguished on the basis of fragment size. In addition, by labeling the forward primers with FAM-blue, VIC-green, NED-yellow and PET-red and inserting a stuffer sequence in one of the reverse primers R2, the multiplexity for the multiplex pathogen and transgenic organism detection is increased to 96 (=12×4×2). As such, the multiplex pathogen and transgenic organism detection analysis may assay 96 target nucleic acids simultaneously. A person skilled in the art would consider increase the multiplexity for target nucleic acid analysis for detecting pathogens and transgenic organisms by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

As a person skilled in the art understands based on the disclosure of the present invention, the presence of peaks corresponding to target nucleic acids indicates the presence of the corresponding pathogens or transgenic organisms. As shown in FIG. 8 bottom chart, the arrows point to two peaks corresponding to two target nucleic acids, indicating the presence of two corresponding pathogens. The absence of peaks corresponding to the remaining 86 target nucleic acids indicates the absence of the 86 corresponding pathogens. The encircled peaks are positive controls, whose presence indicates the testing system is functional.

In other embodiments, the method according to the present invention may be applied to measure quantitatively the amount of pathogens and transgenic organisms. The rationale behind this application procedure for this purpose are similar to those described for quantitatively measure RNA expression levels in the multiplex RNA analysis section supra except that exogenous nucleic acids may be used as reference target sites. In some embodiments, a certain amount of exogenous DNA or RNA fragments are added into samples and used as reference target sites. For example, in measuring the load of HIV virus in a plasma samples, the same amount of exogenous RNA fragments may be mixed with the same amount of plasma from each sample before RNA extraction. The quantitative evaluation of HIV load may be carried out by quantitatively measuring the HIV RNA level by normalizing the peak values for HIV RNA against the peak values for the exogenous reference RNA fragments.

Multiplex DNA Methylation Analysis

Epigenetic modifications of genomic DNA, e.g., changes in DNA methylation patterns are related to many diseases or other health conditions. Abnormal methylation of normally unmethylated CpG-rich areas, also known as CpG-islands, have been associated with transcriptional inactivation of many disease genes, e.g., tumor suppressor genes, DNA repair genes, metastasis inhibitor genes. See, e.g., Jain P K, Epigenetics: the role of methylation in the mechanism of action of tumor suppressor genes, Ann N Y Acad Sci. 2003 March; 983:71-83. There is a need for a multiplex, quick, and accurate method for detecting DNA methylation patterns, which may aid the diagnosis, prognosis, prediction, and evaluation of treatment plan for underlying diseases or other health conditions.

Figure 9:
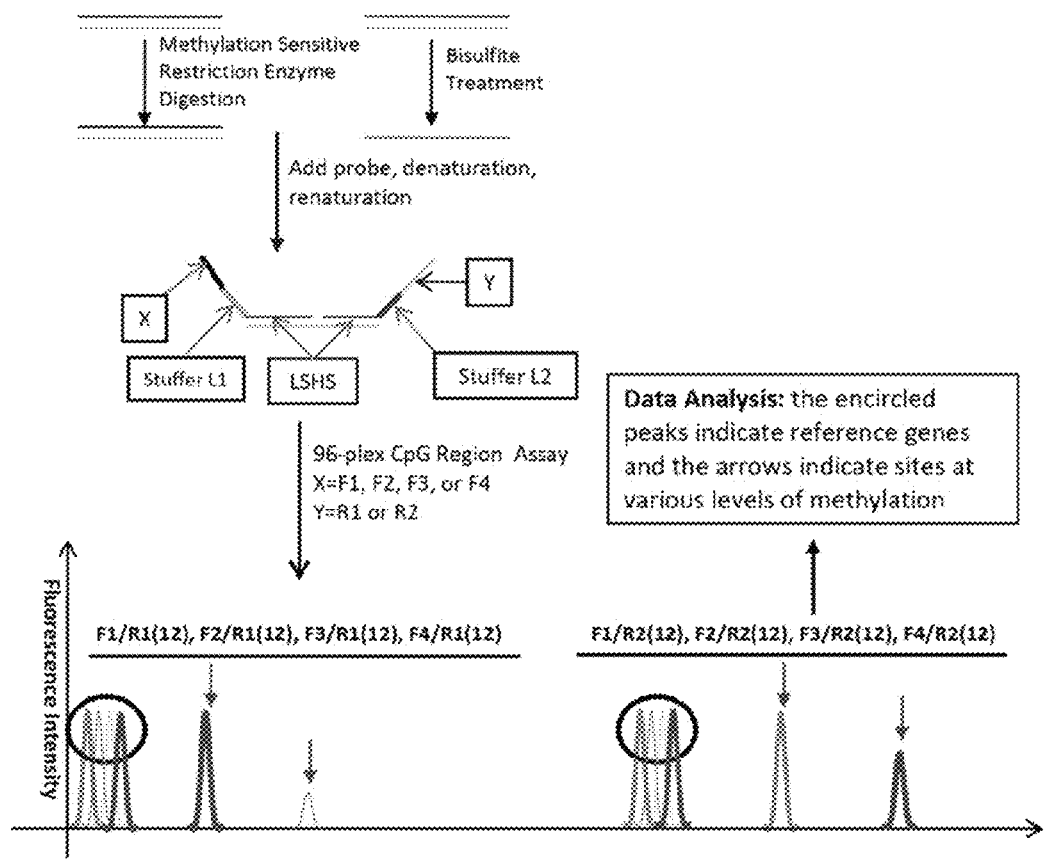
FIG. 9 is a schematic flowchart depicting an exemplary analysis of 96 methylation target sites in a multiplexed assay by employing both fluorescent dye labeled primers and primers with stuffer sequences for amplifying ligation products. The labels refer to the similar components as detailed in FIG. 5.

An exemplary multiplex DNA methylation detection method according to the present invention is illustrated in FIG. 9. In the example, 96 target methylation sites are analyzed in a single assay simultaneously. In some instances, DNA bearing the target methylation sites in a test sample may be treated with methylation sensitive restriction endonucleases, e.g., HpaII or HhaI, so that unmethylated DNA are cleaved at a position near or close to the methylation site. The treatment of methylation sensitive restriction endonucleases may be carried out before, at the same time, or after the probe hybridization step. In some embodiments, the treatment is carried out before the probe hybridization step. In this case, if the DNA in the test sample is cleaved, the probes designed to hybridize near or close to the methylation site on the target DNA may not be ligated and no amplification products may be produced. In contrast, if the DNA in the test sample is methylated at the methylation site and therefore cannot be cleaved by the methylation sensitive restriction endonuclease, the probes hybridized near or close to the methylation site on the target DNA may be ligated and the corresponding amplification products may be produced. In other embodiments, the treatment is carried out at the same time or after the probe hybridization step. In this case, probes may hybridize to the target DNA near or close to the methylation site, the methylation sensitive endonuclease may cleave the hybridized probe/target DNA duplex if the target DNA is not methylated and therefore no amplification product is produced. In contrast, if the target DNA is methylated, the methylation sensitive endonuclease may not cleave the hybridized probe/target DNA duplex and therefore amplification product is produced.

In both situations, as shown in FIG. 9, in an exemplary multiplex methylation detection method according to the present invention, for each target methylation site, a set of probes (here referred to as the right probe and the left probe as they appear in the figure) are designed. The left probe contains a locus-specific hybridization sequence (LSHS) and a primer binding site X, and a stuffer L1 sequence between the LSHS and the primer binding site X. The right probe contains a locus-specific hybridization sequence (LSHS), a primer binding site Y, and a stuffer L2 sequence between the LSHS and the primer binding site Y. By varying the length of stuffer L1 and stuffer L2 sequences, a 12-fold multiplexity may be achieved for the ligation products; ligation products for 12 target methylation sites can be distinguished on the basis of fragment size. In addition, by labeling the forward primers with FAM-blue, VIC-green, NED-yellow and PET-red and inserting a stuffer sequence in one of the reverse primers R2, the multiplexity for the methylation detection may be increased to 96 (=12×4×2). As such, the multiplex methylation detection may measure 96 target methylation sites simultaneously. A person skilled in the art may increase the multiplexity for methylation detection by varying the parameters, e.g., inserting stuffer sequences in more probes, labeling the primers with more fluorescent tags, or inserting stuffer sequences in more primers. As such, the multiplexity may be increased to 192, 384, 768, or more if desirable.

In other instances, the DNA in the test sample is treated with bisulfite so that unmethylated cytosines (here referred to as "C") are converted into uracils. The bisulfite treatment therefore makes nucleotide changes at unmethylation sites, converting an unmethylated "C" into "U" in the target DNA. In contrast, methylated "C" remains as "C" after bisulfite treatments. As such, specific probes are designed to bind either to the methylated allele or the unmethylated allele of the test DNA: the methylated allele with "Cs" at methylated C sites and "Us" at the unmethylated C sites, and the unmethylated allele with "Us" at all C sites. Depending on which allele needs to be detected, the design of these specific probes is briefly described below.

As shown in FIG. 9, 96 methylation sites may be detected in a single assay simultaneously when a bisulfite treated is first performed on the target DNA. For illustrative purposes, a set of probes (here referred to as the right probe and the left probe as they appear in the figure) are designed. The left probe contains a methylation-specific hybridization sequence (MSHS) with the methylation site recognition nucleotides "G", a primer binding site X, a stuffer L1 sequence between the MSHS and the primer binding site X. The right probe contains a methylation-specific hybridization sequence (MSHS) with the methylation site recognition nucleotides "G", a primer binding site Y, and a stuffer L2 sequence between the MSHS and the primer binding site. By varying the length of stuffer L1 and stuffer L2 sequences, a 12-fold multiplexity may be achieved for the ligation products; ligation products for 12 methylation sites can be distinguished on the basis of fragment size. In addition, by labeling the forward primers with FAM-blue, VIC-green, NED-yellow and PET-red and inserting a stuffer sequence in one of the reverse primers, the multiplexity for the methylation detection may be increased to 96 (=12×4×2). As such, the multiplex methylation detection may measure 96 target methylation sites simultaneously. A person skilled in the art may increase the multiplexity for methylation detection by varying the parameters, e.g., inserting stuffer sequences in more probes, labeling the primers with more fluorescent tags, or inserting stuffer sequences in more primers. As such, the multiplexity may be increased to 192, 384, 768, or more if desirable. In some embodiments, when only unmethylated alleles need to be detected, the unmethylation specific probes are used instead of the methylation specific hybridization probes. In other embodiments, when both methylated and unmethylated alleles need to be detected, both methylated and unmethylated specific probes are used. The rationale for designing the methylated and unmethylated specific probes is similar to those described supra, and therefore is not repeated here.

In both the method using methylation sensitive restriction enzymes and the method using bisulfite treatment, the analysis of the amplification products may determine the presence or absence of methylated nucleotides in a target DNA. In the method using methylation sensitive restriction enzymes, amplification peaks appear only if the DNA is methylated. In the method using bisulfite treatment and MSHS probes which have the methylation site recognition nucleotides "G", amplification peaks appear only if the DNA is methylated. Therefore, in both methods, the presence of peaks indicates the presence of methylated nucleotides in the target DNA, and the absence of peaks indicates the absence of methylated nucleotides in the target DNA. As shown in FIG. 9 bottom chart, the arrows point to the peaks in the amplification product, indicating that the corresponding methylation sites contain methylated nucleotides in the test sample. The absence of peaks corresponding to other methylation sites indicates that those other methylation sites in the test sample contain no methylated nucleotides. The encircled peaks are positive control, whose presence indicates the testing system is functional.

In some embodiments, the multiplex DNA methylation analysis may determine the relative amount of methylated DNA in a sample. To determine the relative amount of methylated DNA in a sample, the peak value for each target methylation site in a test sample is first normalized to the peak value of the reference target site, and then compared to the normalized peak value in a control sample. The selection of a reference target site is sometimes based on criteria including, but not limited to, the copy number of each reference target site being stable after methylation sensitive restriction enzyme digestion or bisulfite treatment in different samples and the sequences of the reference target sites being unique and not prone to interfering the reactions of the methylation sites of interest. In addition, when a plurality of reference target sites are used in a group, each reference target site is preferably from a different chromosome. In a multiplex DNA methylation analysis, multiple groups of target methylation sites and reference target sites may be analyzed simultaneously. The same set of primers is used to amply ligation products for both the target methylation sites and the reference target sites within each group. The relative amount of methylated DNA in the target methylation site is determined by comparing the normalized peak value for a target methylation site in the test sample to the normalized peak value for the target methylation site in the control sample. If the value increases 2 times, the relative amount of methylated DNA in the target methylation site increases 2 times. Other aspects of the normalization method are similar to those described for the normalization of peak values for CNV sites against reference target sites and therefore are not repeated here.

III. Detection of Small Copy Number Changes

In another aspect, the present invention is a method for detecting a small quantitative variation of a nucleic acid between two samples. A small quantitative variation of a nucleic acid may be a small copy number change of a nucleic acid, e.g., a gene, a part of a chromosome, or a whole chromosome. As used herein, a small quantitative variation of a nucleic acid refers to any copy number changes that are less than 50%. Indeed, in some embodiments of the present invention, the method may detect small copy number changes of about 0.1% to about 30%. In other embodiments, the method may detect small copy number changes of about 8%, 6%, 4%, 2%, 1%, or 0.1%.

For example, the copy number of human chromosome 21, human chromosome 18, human chromosome 13, human chromosome region 22q11.2, or the pseudoautosomal regions of human chromosomes X or Y in the maternal blood may change in a small scale if the fetus harbors a different copy number of those chromosome regions. In one instance, if a fetus has Down's syndrome, the copy number of chromosome 21 may increase in a small scale in maternal blood. The increase is usually less than 10%. As such, a method according to the present invention may be used to detect small copy number changes of human chromosome 21, human chromosome 18, human chromosome 13, human chromosome region 22q11.2, or the pseudoautosomal regions of human chromosomes X or Y in maternal blood. The pseudoautosomal regions (PAR1 and PAR2) of the human X and Y chromosomes are not inherited in a strictly sex-linked fashion and may be used to detect the copy number of the X and Y chromosome pairs. See, e.g., Mangs and Morris, The Human Pseudoautosomal Region (PAR): Origin, Function and Future, Curr Genomics. 2007 April; 8(2): 129-136, which is herein incorporated by reference.

In one embodiment, the method for detecting small copy number changes of a nucleic acid in a test sample comprises the steps of measuring the copy number of a plurality of target sites within the nucleic acid in the test sample, and determining the copy number of the nucleic acid by statistically analyzing the measured copy number for each of the plurality of target sites.

According to this present invention, to detect small copy number changes of a nucleic acid, a plurality of target sites in the nucleic acid are chosen for analysis so that a statistically significant result may be obtained to quantitatively determine a copy number change for the nucleic acid. As used herein, a plurality of targets sites refers to more than about 5 target sites, preferably more than about 10 target sites, more preferably more than 100 target sites. The number of target sites may increase to about 100-500 if a more sensitive detection is desirable. A person skilled in the art may decide the number of target sites based on the disclosure of the present invention or empirically according to prior testing results.

The measurement of copy numbers for each of the plurality of target sites may be accomplished by many techniques, including a multiplex nucleic acid analysis method similar to the CNV detection method as detailed supra, a multiplex nucleic acid analysis employing DNA sequencing techniques, and real-time PCR.

For one example, a multiplex nucleic acid analysis method similar to the CNV detection method as detailed supra is used. Similar to the scheme shown in FIG. 5, the copy number of 96 target sites may be measured in a single assay simultaneously. The descriptions of the designs of probes, primers and testing procedures are not repeated here except that the statistical analysis of peak intensities is described below.

In some embodiments, the fluorescent peak intensity of each target site in a test sample is measured and compared to a standard peak value of the same target site in the testing system to determine the copy number of the target site. A standard value may be a fluorescent intensity value corresponding to the target site in the specific testing system. A testing system means the whole experimental system including the reagents, primers, probes, procedures and devices used for the testing the copy number changes. One test sample is considered to share the same testing system with another test sample if the whole experimental system is the same except the initial DNA sample to be tested. As such a standard value may be obtained for a specific testing system based on prior testing results of DNA samples. If the DNA samples are from normal or wild-type subject, the standard value is a normal or wild-type standard value. If the DNA samples are from an abnormal subject, the standard value is an abnormal standard value.

In other embodiments, a control sample is used to generate control fluorescent peak intensity values for the target sites. The copy number for each target site is known for the control sample. When the fluorescent peak value for a target site in a test sample is obtained and compared to the peak value for the same target site in the control sample, the copy number of the target site may be determined.

In some preferred embodiments, similar to the normalization and copy number measurement methods described for CNV copy number change detection supra, the peak values for each gene target site (i.e., target DNA of interest, which is not necessarily within a gene but can be within non-coding genomic DNA) are normalized against peak values for one or more reference target sites. The copy number changes are measured by comparing the normalized peak value for each gene target site in the test sample to the normalized standard value for the same gene target site in the testing system or the normalized peak value for the same gene target site in the control sample. The normalization may correct the variations, e.g., the amount of DNA templates used for probe hybridization, the amount of ligation probes and PCR primers, the ligation efficiency of each set of probes, and the amount of DNA used for PCR amplification, in obtaining the peak values between different samples and between different gene target sites. To obtain peak values of reference target sites, probes for the reference target sites may be designed in a similar manner and used simultaneously with the probes for the gene target sites in the hybridization and ligation reactions. In addition, probes for the reference target sites and probes for the gene target sites may share the same primer binding sites so that the same set of primers may be used to amplify the ligation products for both the reference sites and the gene target sites.

As such in some instances, peak values for a plurality of reference target sites are obtained in parallel with the peak values for a plurality of gene target sites so that the peak value for each of the plurality of the gene target sites may be normalized against the peak value for each of the plurality of the reference target sites. The number of reference target sites may be about 1 to about 100, and the number of gene target sites may be about 1 to about 100. For one example, peak values for 6 reference target sites may be obtained together with the peak values for 6 gene target sites. In this example, 6 sets of probes for the 6 reference target sites and 6 sets of probes for the 6 gene target sites are added to a sample and ligation products are obtained after hybridization and ligation reactions. For another example, peak values for 100 reference target sites may be obtained together with the peak values for 100 gene target sites. In this example, 100 sets of probes for the 100 reference target sites and 100 sets of probes for the 100 gene target sites are added to a sample and ligation products are obtained after hybridization and ligation reactions. In both examples, a single set of primers may be used to amplify the ligation products and peak values are measured by analyzing the amplification products by capillary electrophoresis.

In some embodiments, the number of reference target sites used for a gene target site may affect the sensitivity of detecting copy number changes of the gene target site. The more reference target sites are used, the smaller of the copy number change of the gene target site may be detected. Accordingly, when it is desirable to detect more copy number changes, for example a 0.1% change of cancer cell-associated copy number variant, it is desirable to use relatively more reference target sites for each gene target site. A person skilled in the art may increase the number of reference target sites when it is apparent that more sensitive detection of copy number changes is desired.

In some embodiments, the normalization of the peak value for a gene target site in a sample is to obtain a ratio (here referred to as R) of the peak value for the gene target site against the peak value for a reference target site. As such, the copy number of a gene target site in a test sample may be measured by comparing the ratio for the gene target site in the test sample (here referred to as $R_{test}$) with the standard ratio for the same gene target site in the testing system (here referred to as $R_{standard}$) or with the ratio for the same gene target site in a control sample (here referred to as $R_{control}$).

In some instances, the copy number of a gene target site in a test sample is measured by comparing the ratio for the gene target site in the test sample ($R_{test}$) with the standard ratio for the same gene target site in the testing system ($R_{standard}$). The copy number of the gene target site in the testing system is known (here referred to as $C_{standard}$). In this case, the copy number of the gene target site in the test sample (here referred to as $C_{test}$) may be calculated as follow: $C_{test}=C_{standard} \times R_{test}/R_{standard}$.

In other instances, the copy number of a gene target site in a test sample may be measured by comparing the ratio for the gene target site in the test sample ($R_{test}$) with the ratio for the same gene target site in a control sample ($R_{control}$). The copy number of the gene target site in the testing system is known (here referred to as $C_{control}$). In this case, the copy number of the gene target site in the test sample ($C_{test}$) may be calculated as follow: $C_{test}=C_{control} \times R_{test}/R_{control}$.

As such, when 6 reference target sites are introduced to normalize the peak value for a gene target site, six copy number measurements ($C_{test}$) for the gene target site may be derived on the basis of the six peak values for the six reference target sites. Based on the six $C_{test}$ measurements, the copy number of the gene target site is obtained according to certain statistical analysis. In one embodiment, the median value of the six $C_{test}$ measurements is deemed the copy number of the gene target site. In another embodiment, the average value of the six $C_{test}$ measurements is deemed the copy number of the gene target site.

Based on the copy number for each of the plurality of target sites, the copy number for the nucleic acid may be determined by methods including, but not limited to, taking the average of the copy numbers of all target sites or the median value of the copy numbers for all target sites, or taking the average of the copy numbers of all target sites or the median value of the copy numbers of all target sites after abandoning some egregious values if desirable.

In some embodiments, the testing for each gene target site in the nucleic acid may be repeated so that multiple copy number calculation results may be obtained. For example, the testing for each gene target site within a nucleic acid may be repeated three times and three copy number calculation results for the nucleic acid may be obtained. The average or median value of the three copy number calculation results may be deemed as the copy number of the nucleic acid. As such, the number of repeats of the testing may also affect the sensitivity of the method. If a more sensitive detection of copy number changes is desired, the testing may be repeated more times. A person skilled in the art may increase the number of repeated testing if he or she desires to detect smaller copy number changes, e.g., 0.1%.

As such, the sensitivity of detecting small copy number changes of a nucleic acid in a sample may be influenced by many factors including, but not limited to, the number of gene target sites within the nucleic acid, the number of reference target sites used for each gene target site, and the number of repeated testing for each gene target site. The increase of the number of gene target sites within the nucleic acid, the number of reference target sites used for each gene target site, and/or the number of repeated testing for each gene target site may enhance the sensitivity of the detection. A person skilled in the art may adjust the numbers according to the present invention if a more sensitive detection is needed in measuring very small copy number changes of a nucleic acid of interest in a sample.

Various statistical methods may be applied to calculate the copy number of each target site based on experimental results and determine the copy number of the nucleic acid based on the calculated copy number of each target site. A specific example of statistical analysis of small copy number changes is detailed below in Example 4: "Detection of chromosome 21 copy number changes."

For another example, real-time PCR may be used to detect the copy number of each of the plurality of the selected target sites as is known in the art. Real-time PCR may determine the copy number of a target site in a monoplex or multiplex manner. Based on the copy numbers for each of the plurality of target sites, the copy number for the nucleic acid may be determined by methods including, but not limited to, taking the average of the copy numbers of all target sites or the median value of the copy numbers for all target sites, or taking the average of the copy numbers of all target sites or the median value of the copy numbers of all target sites after abandoning some egregious values if desirable.

IV. Kits for Multiplex Nucleic Acid Analysis and Small Copy Number Change Detection In yet another aspect of the present invention, a kit is provided for multiplex nucleic acid analysis and small copy number change detection. In one embodiment, the kit for assaying nucleic acids in a sample include one or more sets of probes corresponding to a target nucleic acid so that the probes in each set, when hybridized to the target nucleic acid may be ligated to form a third probe. In another embodiment, the kit further includes one or more sets of primers for amplifying the third probe.

Each set of probes may include a first probe having a first portion at least partially complementary to a first region of the target nucleic acid and a second portion as a first primer binding site, and a second probe having a first portion at least partially complementary to a second region of the target nucleic acid and a second portion as a second primer binding site. In some instances, the 5' end of the first probe is essentially adjacent to the 3' end of the second probe and the first and the second probes may be ligated to form a third probe. In other instances, the 5' end of the first probe is not adjacent to the 3' end of the second probe and the first and the second probes may not be ligated to form a third probe without filling the gaps. Gap filling may be achieved by another probe that can hybridize to the gap on the target nucleic acid or by extending one of the two probes in a polymerase reaction. For example, the 3' end of the second probe may be extended to fill the gap until the extended 3' end is substantially adjacent to the 5' end of the first probe.

In some embodiments, the kit may also contain reagents including, but not limited to, a ligase, e.g., a Taq DNA ligase or a T4 DNA ligase, a buffer for a ligation reaction, a DNA polymerase, e.g., a Taq DNA polymerase, a buffer for polymerase chain reaction, or a combination thereof.

In some embodiments, the set of primers in a kit may include a first primer at least partially complementary to the first primer binding site and a second primer at least partially complementary to the second primer binding site. In some instances, at least one primer of the set of primers is labeled with a detectable moiety. The moiety may be an oligonucleotide tag or a fluorescent dye such as a fluorescein fluorophore. A fluorophore may be FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, and Yakima Yellow.

In some embodiments, an oligonucleotide GTTTCTT was included in the 5' portion of at least one of the primers. In some preferred embodiments, the reverse primer used for amplifying the ligation products includes oligonucleotide GTTTCTT or its functional equivalents, e.g., GTTTCTTG.

In some embodiments, at least one primer of the set of primers includes a stuffer sequence with a length of about 10-500 nucleotides. The stuffer sequence in some primers may have about 10 to about 500 nucleotides. The stuffer sequence in other primers may be about 10 to about 60 nucleotides. In some preferred embodiments, no primer has more than about 125 nucleotides. In other preferred embodiments, no primer has more than about 75 nucleotides.

In other embodiments, at least one probe of the set of probes includes a stuffer sequence with a length of about 1-200 nucleotides. In other instances, the stuffer sequence has about 1 to about 55 nucleotides. In some preferred embodiments, the third probe has no more than about 250 nucleotides. In other preferred embodiments, the third probe has no more than about 140 nucleotides. In still some preferred embodiments, no probe has more than about 125 nucleotides. In still some other preferred embodiments, no probe has more than about 70 nucleotides. In some further preferred embodiments, no probe has more than about 60 nucleotides.

In some embodiments, the target nucleic acid is a dystrophin gene and the kit is for detecting Duchenne muscular dystrophy. The sets of probes in the kit comprise one or more probe pairs selected from SEQ ID NOs: 158-541.

In other embodiments, the target nucleic acid is on human chromosome 21 and the kit is for detecting fetal Down's syndrome in maternal blood. The sets of probes in the kit comprise one or more probe pairs selected from SEQ ID NOs: 559-942.

V. Examples

It should be understood that this invention is not limited to the particular methodologies, protocols and reagents, described herein. The terminology used herein is for the purpose of describing particular embodiments only, and is not intended to limit the scope of the present invention.

In addition, the reactions outlined below may be accomplished in a variety of ways, as will be appreciated by those in the art. Components of the reaction may be added simultaneously, or sequentially, in different orders, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, antimicrobial agents, etc., may be used, depending on the sample preparation methods and purity of the target.

While the present invention has been disclosed with reference to certain embodiments, numerous modifications, alterations, and changes to the described embodiments are possible without departing from the full scope of the invention, as described in the appended specification and claims. Other features, objects, and advantages of the disclosed subject matter will be apparent from the detailed description, figures, examples and claims. Methods and materials substantially similar or equivalent to those described herein can be used in the practice or testing of the presently disclosed subject matter.

Example 1: Multiplex SNP Detection

This example demonstrates a multiplex SNP detection method according to the present invention. In this example, 48 SNPs were detected simultaneously in a blood sample by employing fluorescent dye labeled forward primers and varying the length of the reverse primer by adding a stuffer sequence according to the scheme in FIG. 4.

The 48 SNPs were rs1056893, rs1058588, rs10790286, rs10791649, rs11107, rs11155787, rs11161732, rs1249950, rs12719860, rs1359185, rs1572983, rs2161916, rs2231926, rs2241280, rs2241571, rs2241802, rs2279072, rs2294092, rs2297129, rs2304035, rs2304102, rs2305150, rs2306331, rs2401751, rs2779500, rs2986014, rs3182535, rs3731631, rs3736582, rs3749877, rs3809806, rs3816800, rs4141253, rs4362, rs4371677, rs469783, rs4829830, rs4920098, rs624821, rs625372, rs639225, rs6784322, rs6892205, rs894344, rs934472, rs938883, rs9389034, and rs9791113. All SNP names and other information may be found in the National Center for Biotechnology Information dbSNP database. For each SNP, three probes were designed: the 3' probe (the right probe), and two 5' probes (the left probe) corresponding to two alleles. The 3' and 5' probes were designed in a manner so that when both are hybridized to the target sequence under a suitable condition, there is no gap between the two probes. The probes were synthesized by Life Technologies Corporation. The names, sequence ID numbers, primer binding sequences, and stuffer sequences for each of the 144 (3×48) probes are shown in Table 1.

For the 3' probe, the 5' end nucleotide was phosphorylated to provide a phosphate which would be connected to the hydroxyl group in the 3' end nucleotide of the 5' probe. Each 3' probe included a locus specific hybridization sequence (LSHS) in the 5' portion followed by a stuffer L2 sequence, and a primer binding sequence Y in the 3' portion. In some 3' probes, SNP_Y1 sequence, SEQ ID NO: 155 was used. In other 3' probes, SNP-Y2 sequence, SEQ ID NO: 156 was used.

Two different 5' probes were designed for each SNP with each 5' probe corresponding to a different allele. The 3' portion of each 5' probe was an allele-specific hybridization sequence (ASHS) and the 3' end nucleotide corresponded to the specific nucleotide in each individual allele. The 5' portion of each 5' probe had a primer binding sequence X. In this example, four primer binding sequence X: SNP_X1, SEQ ID NO: 151; SNP_X2, SEQ ID NO: 152; SNP_X3, SEQ ID NO: 153; SNP_X4, SEQ ID NO: 154 were used in the 5' probes. In some 5' probes, a stuffer A sequence was inserted between the 3' portion and the 5' portion of the 5' probes. In addition, in some 5' probes, a stuffer L1 sequence was inserted between the 5' portion and the stuffer A sequence. The position of the stuffer A and stuffer L1 sequences are interchangeable.

In addition, four forward primers and two reverse primers were designed for amplifying the ligation products. The four forward primers (SNP_F1, SEQ ID NO: 145; SNP_F2, SEQ ID NO: 146; SNP_F3, SEQ ID NO: 147; and SNP_F4, SEQ ID NO: 148) had unique sequences that were consistent with the four primer binding sequence X (SNP_X1, SEQ ID NO: 151; SNP_X2, SEQ ID NO: 152; SNP_X3, SEQ ID NO: 153; SNP_X4, SEQ ID NO: 154), respectively. The four forward primers (SNP_F1, SNP_F2, SNP_F3, and SNP_F4) were labeled on the 5' ends with four different fluorescent dyes: FAM-blue, VIC-green, NED-yellow, and PET-red, respectively. The two reverse primers (SNP_R1, SEQ ID NO: 149; and SNP_R2, SEQ ID NO: 150) had unique sequences that were reversely complementary to the pimer binding sequence Y (SNP_Y1 sequence, SEQ ID NO: 155 and SNP-Y2 sequence, SEQ ID NO: 156), respectively. The SNP_R primer also had a stuffer sequence SNP_R_Stuffer, SEQ ID NO:157 in the 5' portion. All primers and probes were synthesized by Life Technologies Corporation.

To perform the 48 multiplex SNP detection assay, a ligation product was first generated. Briefly, genomic DNA was extracted from a 2 ml whole blood sample using the classic phenol:chloroform method. The blood sample was collected from a healthy volunteer at Shanghai Ruijin Hospital, Shanghai, China. From the extracted genomic DNA, 100-200 microgram (µg) DNA was dissolved in 10 microliter (µl) 1×TE buffer (10 mM Tris.Cl, pH8.0, 1 mM EDTA from Sigma-Aldrich). The dissolved genomic DNA was denatured at 98° C. for 5 minutes and then immediately cooled down on ice. At the same time, a 2× ligation premix solution was prepared according to the following formula: a 10 µl 2× ligation premix was made of 2 µl 10× Taq ligase buffer, 1 µl 40 U/µl Taq Ligase from NewEngland Biolabs, Inc., 1 µl ProbeMix (each probe with a final concentration of 0.005 micromolar in 1×TE), and 6 µl ddH$_2$O (Distilled Milli-Q water from Milli-Q Advantage A10, Millipore). 10 µl 2× ligation premix was mixed with the denatured 10 µl genomic DNA and the mixture was allowed to undergo 4 cycles of denaturation, hybridization and ligation under the following conditions: 95° C. for 30 seconds, and then 58° C. for 4 hours. The ligation product thus obtained could be stored on ice for same day use or freezed in −20° C. for future use.

With the ligation product, an amplification step was then performed to obtain an amplification product. Briefly, a PCR reaction was performed using the amplification product as the template. The PCR reaction mixture was prepared as follows: a 20 µl reaction system was made by mixing 2 µl 10×PCR buffer (Qiagen, Germany), 2 µl 2.5 mM dNTP mix (2.5 mM each of dATP, dTTP, dCTP and dGTP from Takara Bio Inc.), 2 µl primer mix (SNP_F1, SNP_F2, SNP_F3, SNP_F4, SNP_R1 and SNP_R2 at final concentrations of 1 µM, 1 µM, 1 µM, 1 µM, 2 µM and 2 µM, respectively), 1 µl Ligation product, 0.2 µl 5 U/µl HotStarTaq Plus Taq DNA polymerase (Qiagen, Germany), and 12.8 µl ddH$_2$O. The PCR mixture was allowed to undergo a polymerase chain reaction under the following conditions: 95° C. for 2 minutes, followed by 35 cycles of 94° C. for 20 second, 57° C. for 40 second, and 72° C. for 1.5 minutes, and after the 35th cycle, the reaction mixture was kept at 60° C. for 1 hour. To analyze the amplification product, 1 µl of the amplification product was first diluted with ddH$_2$O 10 times into 10 µl. Then 1 µl was taken out of the 10 µl diluted amplification product and mixed with 0.1 µl GeneScan™ 500 LIZ® size standard (Life Technologies, Inc.) and 8.9 µl Hi-Di formamide (Life Technologies, Inc.). The mixture was detaured at 95° C. for 5 minutes and analyzed with capillary electrophoresis by ABI3130XL according to manufacturer's manual. The capillary electrophoresis data was processed using Genemapper 4.0.

TABLE 1

Names, sequence ID numbers, primer binding sites and stuffer sequences in the probes used for multiplex SNP detection. The names for 3' probe are in the format: SNP name_3, e.g., rs1056893_3 refers to the 3' probe for the SNP rs1056893. The names for the 5' probe are in the format: SNP name polymorphic nucleotide, e.g., rs1056893_C refers to the 5' probe for the SNP rs1056893 allele C; and similarly, rs1056893_T refers to the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 1 | rs1056893_3 | | | | ATTA | Y2 |
| 2 | rs1056893_C | X3 | | | | |
| 3 | rs1056893_T | X3 | | | TT | |

TABLE 1-continued

Names, sequence ID numbers, primer binding sites and stuffer sequences in the probes used for multiplex SNP detection. The names for 3' probe are in the format: SNP name_3, e.g., rs1056893_3 refers to the 3' probe for the SNP rs1056893. The names for the 5' probe are in the format: SNP name_polymorphic nucleotide, e.g., rs1056893_C refers to the 5' probe for the SNP rs1056893 allele C; and similarly, rs1056893_T refers to the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 4 | rs1058588_3 | | | | | Y2 |
| 5 | rs1058588_S | X2 | | | | |
| 6 | rs1058588_T | X2 | | TT | | |
| 7 | rs10790286_3 | | | | ATT | Y2 |
| 8 | rs10790286_C | X4 | | | | |
| 9 | rs10790286_T | X4 | | TT | | |
| 10 | rs10791649_3 | | | | ATTACGCGATTAC | Y2 |
| 11 | rs10791649_A | X4 | | TT | | |
| 12 | rs10791649_G | X4 | | | | |
| 13 | rs11107_3 | | | | ATTACGCGATTACG | Y1 |
| 14 | rs11107_A | X2 | A | TT | | |
| 15 | rs11107_G | X2 | A | | | |
| 16 | rs11155787_3 | | | | ATTACGCGATTAC | Y1 |
| 17 | rs11155787_C | X3 | A | | | |
| 18 | rs11155787_T | X3 | A | TT | | |
| 19 | rs11161732_3 | | | | ATTACGCGA | Y1 |
| 20 | rs11161732_A | X1 | ATTA | TT | | |
| 21 | rs11161732_G | X1 | ATTA | | | |
| 22 | rs1249950_3 | | | | ATTAC | Y1 |
| 23 | rs1249950_C | X1 | | | | |
| 24 | rs1249950_T | X1 | | TT | | |
| 25 | rs12719860_3 | | | | ATTACGCGATTAC | Y2 |
| 26 | rs12719860_A | X1 | ATTAC | TT | | |
| 27 | rs12719860_C | X1 | ATTAC | | | |
| 28 | rs1359185_3 | | | | ATTACGCGATTA | Y2 |
| 29 | rs1359185_A | X4 | ATT | TT | | |
| 30 | rs1359185_G | X4 | ATT | | | |
| 31 | rs1572983_3 | | | | ATTACGCGA | Y2 |
| 32 | rs1572983_C | X2 | | | | |
| 33 | rs1572983_T | X2 | TT | | | |
| 34 | rs2161916_3 | | | | A | Y2 |
| 35 | rs2161916_A | X4 | TT | | | |
| 36 | rs2161916_G | X4 | | | | |
| 37 | rs2231926_3 | | | | ATTACGC | Y1 |
| 38 | rs2231926_A | X4 | TT | | | |

TABLE 1-continued

Names, sequence ID numbers, primer binding sites and stuffer sequences in the probes used for multiplex SNP detection. The names for 3' probe are in the format: SNP name_3, e.g., rs1056893_3 refers to the 3' probe for the SNP rs1056893. The names for the 5' probe are in the format: SNP name polymorphic nucleotide, e.g., rs1056893_C refers to the 5' probe for the SNP rs1056893 allele C; and similarly, rs1056893_T refers to the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 39 | rs2231926_G | X4 | | | | |
| 40 | rs2241280_3 | | | | ATTACGCGAT | Y2 |
| 41 | rs2241280_A | X1 | ATTA | TT | | |
| 42 | rs2241280_G | X1 | ATTA | | | |
| 43 | rs2241571_3 | | | | AT | Y1 |
| 44 | rs2241571_C | X2 | | | | |
| 45 | rs2241571_T | X2 | | TT | | |
| 46 | rs2241802_3 | | | | ATTACGCGAT | Y2 |
| 47 | rs2241802_A | X4 | | TT | | |
| 48 | rs2241802_G | X4 | | | | |
| 49 | rs2279072_3 | | | | ATTACGCGATT | Y2 |
| 50 | rs2279072_C | X2 | | | | |
| 51 | rs2279072_T | X2 | | TT | | |
| 52 | rs2294092_3 | | | | ATTACGCGATT | Y1 |
| 53 | rs2294092_C | X1 | ATTAC | TT | | |
| 54 | rs2294092_G | X1 | ATTAC | | | |
| 55 | rs2297129_3 | Y2 | | | | Y2 |
| 56 | rs2297129_A | X3 | | TT | | |
| 57 | rs2297129_G | X3 | | | | |
| 58 | rs2304035_3 | | | | A | Y2 |
| 59 | rs2304035_A | X1 | | TT | | |
| 60 | rs2304035_G | X1 | | | | |
| 61 | rs2304102_3 | | | | ATTACGCGATTA | Y2 |
| 62 | rs2304102_A | X1 | | TT | | |
| 63 | rs2304102_G | X1 | | | | |
| 64 | rs2305150_3 | | | | ATTACGCGATTA | Y1 |
| 65 | rs2305150_C | X2 | ATT | | | |
| 66 | rs2305150_T | X2 | ATT | TT | | |
| 67 | rs2306331_3 | | | | ATTACGCG | Y1 |
| 68 | rs2306331_C | X2 | | | | |
| 69 | rs2306331_T | X2 | | TT | | |
| 70 | rs2401751_3 | | | | ATTA | Y1 |
| 71 | rs2401751_A | X2 | | TT | | |
| 72 | rs2401751_G | X2 | | | | |

TABLE 1-continued

Names, sequence ID numbers, primer binding sites and stuffer sequences in the probes used for multiplex SNP detection. The names for 3' probe are in the format: SNP name_3, e.g., rs1056893_3 refers to the 3' probe for the SNP rs1056893. The names for the 5' probe are in the format: SNP name_polymorphic nucleotide, e.g., rs1056893_C refers to the 5' probe for the SNP rs1056893 allele C; and similarly, rs1056893_T refers to the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 73 | rs2779500_3 | | | | ATTACGCGA | Y1 |
| 74 | rs2779500_C | X1 | | TT | | |
| 75 | rs2779500_G | X1 | | | | |
| 76 | rs2986014_3 | | | | ATT | Y1 |
| 77 | rs2986014_C | X3 | | | | |
| 78 | rs2986014_T | X3 | | TT | | |
| 79 | rs3182535_3 | | | | | Y1 |
| 80 | rs3182535_A | X3 | | TT | | |
| 81 | rs3182535_G | X3 | | | | |
| 82 | rs3731631_3 | | | | ATTACGCGATTAC | Y2 |
| 83 | rs3731631_A | X2 | AT | TT | | |
| 84 | rs3731631_G | X2 | AT | | | |
| 85 | rs3736582_3 | | | | ATTA | Y2 |
| 86 | rs3736582_C | X2 | | TT | | |
| 87 | rs3736582_G | X2 | | | | |
| 88 | rs3749877_3 | | | | ATTACGC | Y2 |
| 89 | rs3749877_A | X3 | | TT | | |
| 90 | rs3749877_G | X3 | | | | |
| 91 | rs3809806_3 | | | | ATTACGCG | Y1 |
| 92 | rs3809806_C | X4 | | | | |
| 93 | rs3809806_T | X4 | | TT | | |
| 94 | rs3816800_3 | | | | AT | Y1 |
| 95 | rs3816800_C | X1 | | TT | | |
| 96 | rs3816800_G | X1 | | | | |
| 97 | rs4141253_3 | | | | ATTACGCGATT | Y1 |
| 98 | rs4141253_C | X3 | | | | |
| 99 | rs4141253_T | X3 | | TT | | |
| 100 | rs4362_3 | | | | ATTACGC | Y2 |
| 101 | rs4362_C | X4 | | | | |
| 102 | rs4362_T | X4 | | TT | | |
| 103 | rs4371677_3 | | | | ATTACGCGATT | Y2 |
| 104 | rs4371677_A | X3 | | TT | | |
| 105 | rs4371677_G | X3 | | | | |
| 106 | rs469783_3 | | | | ATTACGCGATT | Y2 |
| 107 | rs469783_C | X3 | ATTACGCGAT | | | |

TABLE 1-continued

Names, sequence ID numbers, primer binding sites and stuffer sequences in the probes used for multiplex SNP detection. The names for 3' probe are in the format: SNP name_3, e.g., rs1056893_3 refers to the 3' probe for the SNP rs1056893. The names for the 5' probe are in the format: SNP name polymorphic nucleotide, e.g., rs1056893_C refers to the 5' probe for the SNP rs1056893 allele C; and similarly, rs1056893_T refers to the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 108 | rs469783_T | X3 | ATTACGCGAT | TT | | |
| 109 | rs4829830_3 | | | | ATTACGCGAT | Y1 |
| 110 | rs4829830_A | X2 | | TT | | |
| 111 | rs4829830_C | X2 | | | | |
| 112 | rs4920098_3 | | | | ATTACG | Y2 |
| 113 | rs4920098_C | X1 | | | | |
| 114 | rs4920098_T | X1 | | TT | | |
| 115 | rs624821_3 | | | | ATTACGCGATTA | Y1 |
| 116 | rs624821_A | X4 | | | | |
| 117 | rs624821_T | X4 | | TT | | |
| 118 | rs625372_3 | | | | | Y1 |
| 119 | rs625372_C | X4 | | | | |
| 120 | rs625372_T | X4 | TT | | | |
| 121 | rs639225_3 | | | | ATTACGCGATTA | Y2 |
| 122 | rs639225_A | X2 | ATTA | TT | | |
| 123 | rs639225_G | X2 | ATTA | | | |
| 124 | rs6784322_3 | | | | ATTACGCGATTACG | Y1 |
| 125 | rs6784322_A | X4 | A | | | |
| 126 | rs6784322_T | X4 | A | TT | | |
| 127 | rs6892205_3 | | | | ATTACGCGA | Y1 |
| 128 | rs6892205_A | X3 | AT | TT | | |
| 129 | rs6892205_G | X3 | AT | | | |
| 130 | rs894344_3 | | | | ATTACGCGAT | Y1 |
| 131 | rs894344_A | X1 | | TT | | |
| 132 | rs894344_G | X1 | | | | |
| 133 | rs934472_3 | | | | AT | Y1 |
| 134 | rs934472_A | X4 | | TT | | |
| 135 | rs934472_C | X4 | | | | |
| 136 | rs938883_3 | | | | ATTACGCGATTACGC | Y2 |
| 137 | rs938883_C | X3 | A | | | |
| 138 | rs938883_T | X3 | A | TT | | |
| 139 | rs9389034_3 | | | | ATTACGCG | Y1 |
| 140 | rs9389034_C | X3 | | | | |
| 141 | rs9389034_T | X3 | | TT | | |

TABLE 1-continued

Names, sequence ID numbers, primer binding sites and stuffer sequences
in the probes used for multiplex SNP detection. The names for 3' probe
are in the format: SNP name_3, e.g., rs1056893_3 refers to the 3' probe
for the SNP rs1056893. The names for the 5' probe are in the format: SNP
name polymorphic nucleotide, e.g., rs1056893_C refers to the 5' probe
for the SNP rs1056893 allele C; and similarly, rs1056893_T refers to
the 5' probe for the SNP rs1056893 allele T.

| SEQ ID NO. | Probe Name | Sequence X | Stuffer L1 | Stuffer A | Stuffer L2 | Sequence Y |
|---|---|---|---|---|---|---|
| 142 | rs9791113_3 | | | | ATTACGCG | Y2 |
| 143 | rs9791113_C | X1 | | TT | | |
| 144 | rs9791113_G | X1 | | | | |

Figure 10A:
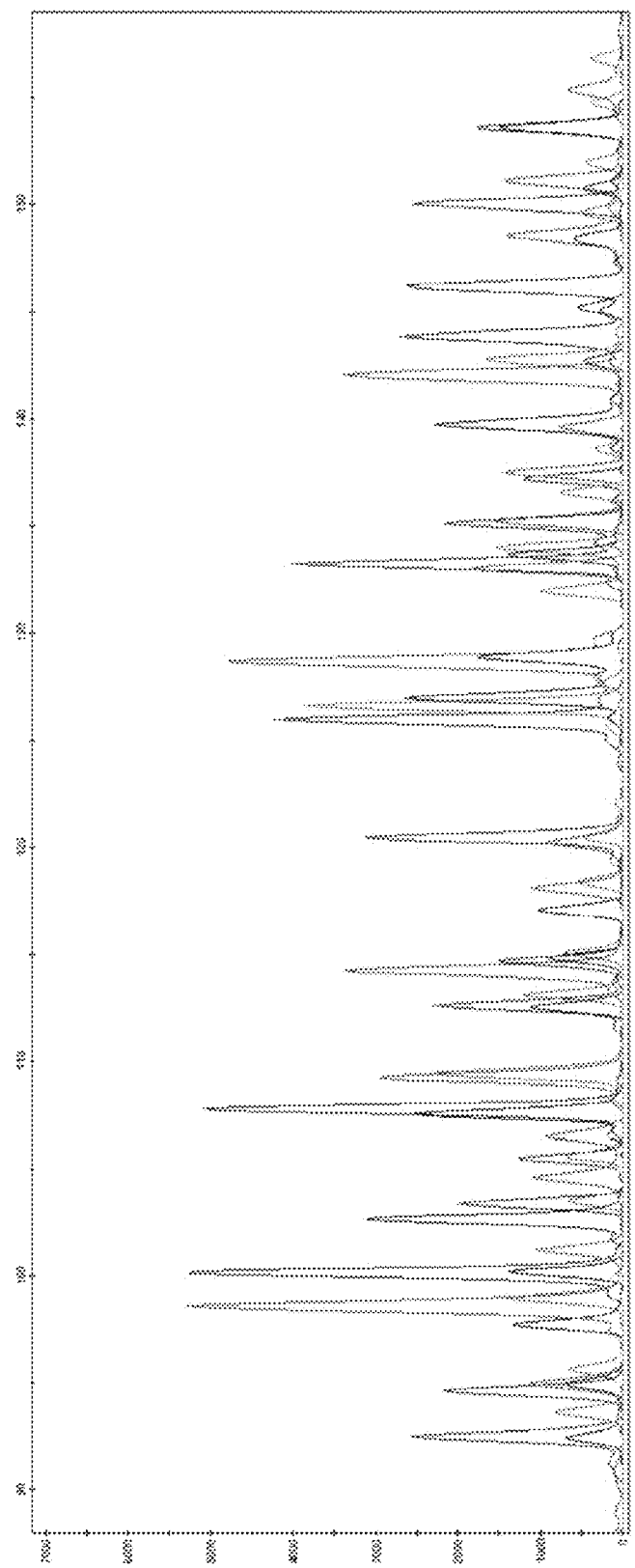

As shown in FIGS. 10A-E, the amplification products obtained in the assay could be separated and the peaks corresponding to each SNP allele could be individually identified by capillary electrophoresis. All the amplification products were from the same PCR reaction. FIG. 10A showed the chromatograms of all amplification products which were labeled with four different fluorescent dyes. Each peak represented one amplification product corresponding to an individual SNP allele. FIGS. 10B, 10C, 10D, and 10E, which were individually derived from FIG. 10A, showed the chromatograms for amplification products labeled with blue, green, yellow and red, respectively. As seen in FIGS. 10B, 10C, 10D, and 10E, the peaks from the amplification products labeled with the same fluorescent dye could be individually identified on the basis of different fragment sizes. The two alleles for each SNP were separated on the basis of a fragment size difference of about 2 nucleotides.

Figure 10B:
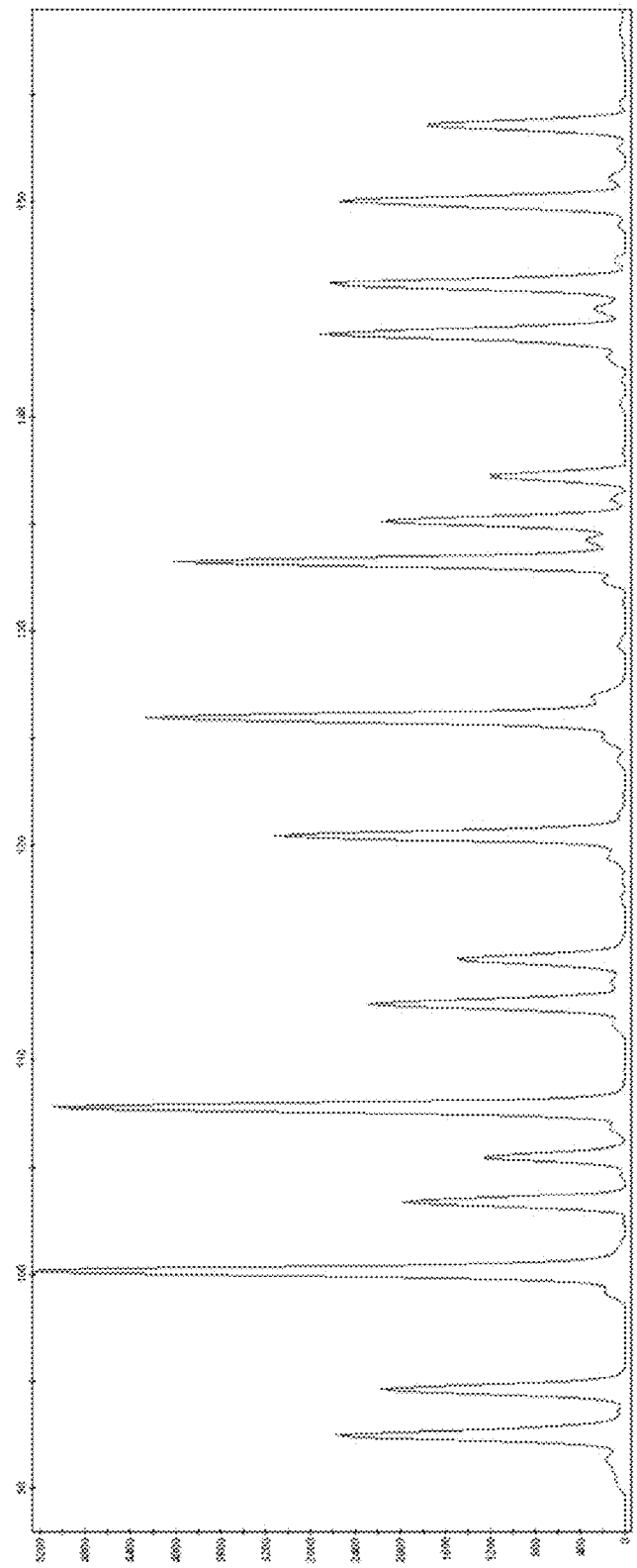
Figure 10D:
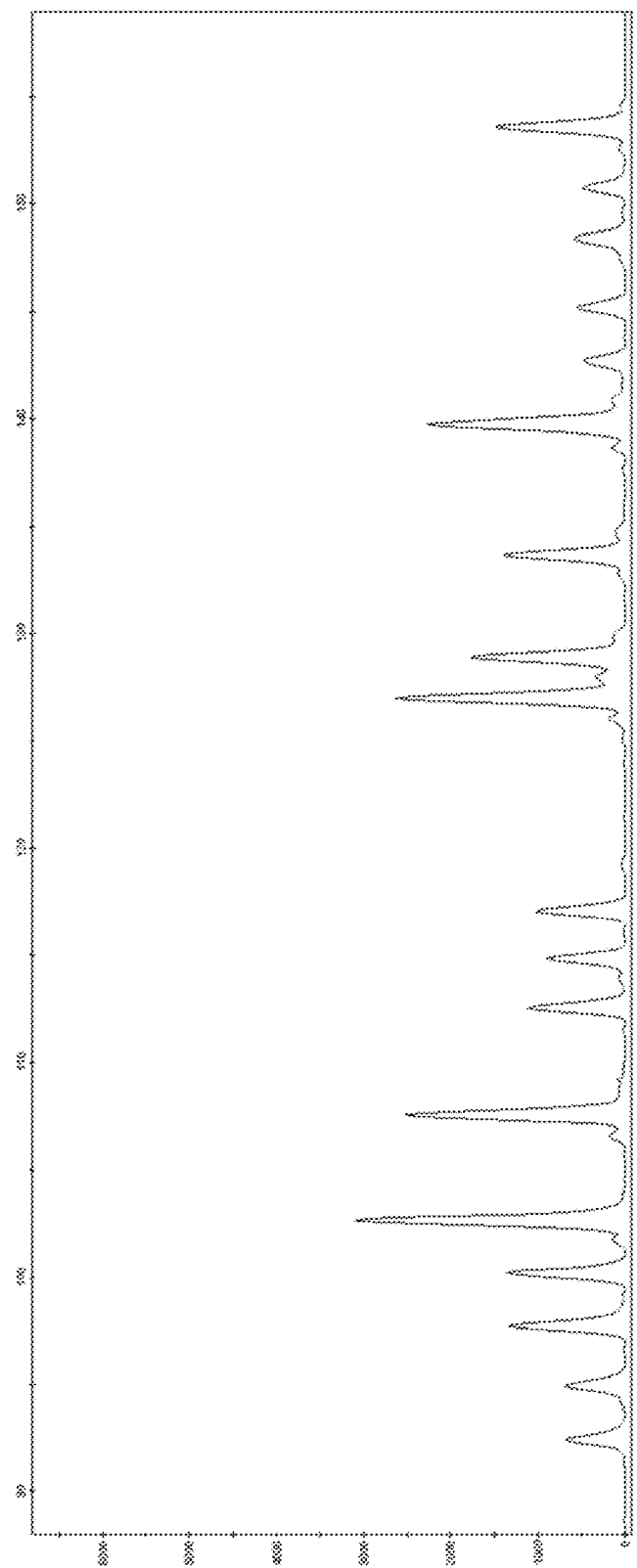
Figure 10E:
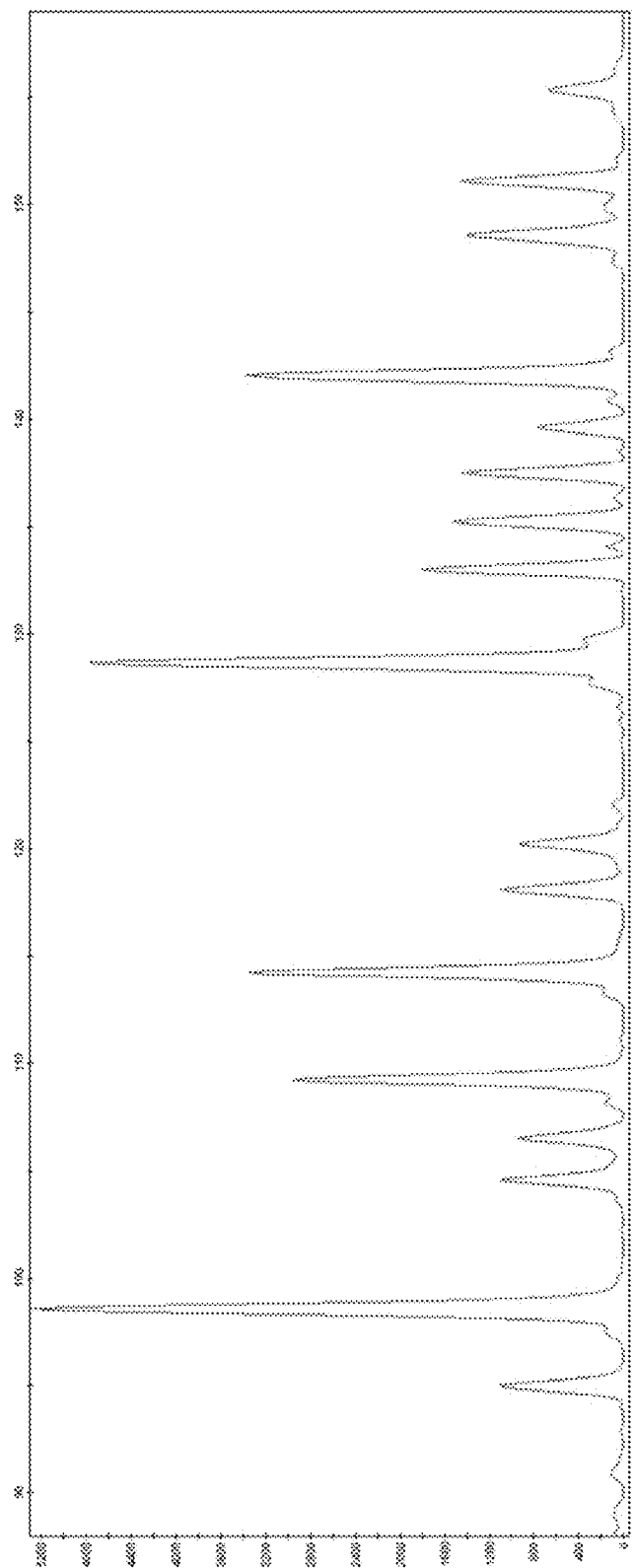

For example, SNP rs3816800 had two alleles with G and C, respectively. The ligated probe size for A1 allele was 95 base pair (bp) and the size for A2 97 bp; and the CE reference size for A1 allele was 92.46 and the size for A2 was 94.56. As shown in FIG. 10B, there were two peaks one with the fragment size of about 93 bp and the other with the fragment size of about 95 bp. Therefore, the genotype for SNP rs3816800 was determined to be heterozygous G/C.

A CE reference size for a SNP allele was obtained as follows: first, the corresponding set of probes were used to perform hybridization, ligations and amplification in a DNA sample harboring the SNP allele, and then the amplification products were analyzed by capillary electrophoresis to obtain the CE reference size for the SNP allele with the presence of a size standard. For example, the set of probes rs11161732_3, SEQ ID NO: 19 and rs11161732_A, SEQ ID NO: 20 were used to obtain the CE reference size for the rs11161732_A allele and the CE reference size was determined to be 114.64.

For another example, SNP rs1249950 had two alleles with C and T, respectively. The ligated probe size for A1 allele was 100 bp and the size for A2 102 bp; and the CE reference size for A1 allele was 97.82 and the size for A2 was 100.11. As shown in FIG. 10B, there was only one peak with the fragment size of about 100 bp. Therefore, the genotype for SNP rs1249950 was determined to be homozygous T/T.

As such, the genotypes of all the 48 SNP were determined according to the capillary electrophoresis results (see Table 2). These results were all consistent with the results obtained by direct DNA sequencing.

TABLE 2

The capillary electrophoresis results in terms of the ligation product size and genotypes of 48
SNPs. A1 refers to Allele #1; A2 refers to Allele #2; A1LP refers to Allele #1 Ligation
Product Size; A2LP refers to Allele #2 Ligation Product Size; REF refers to reference;
and CE refers to Capillary Electrophoresis.

| SNP rs# | A1 | A2 | PCR Primers | A1LP SIZE | A2LP SIZE | A1LP CE REF SIZE | A2LP CE REF SIZE | GENOTYPE |
|---|---|---|---|---|---|---|---|---|
| rs11161732 | G | A | SNP_F1/SNP_R1 | 115 | 117 | 112.56 | 114.64 | G/A |
| rs1249950 | C | T | SNP_F1/SNP_R1 | 100 | 102 | 97.82 | 100.11 | T/T |
| rs2294092 | G | C | SNP_F1/SNP_R1 | 120 | 122 | 118.23 | 120.55 | C/C |
| rs2779500 | G | C | SNP_F1/SNP_R1 | 105 | 107 | 103.2 | 105.41 | G/C |
| rs3816800 | G | C | SNP_F1/SNP_R1 | 95 | 97 | 92.46 | 94.56 | G/C |
| rs894344 | G | A | SNP_F1/SNP_R1 | 110 | 112 | 107.75 | 109.69 | G/G |
| rs12719860 | C | A | SNP_F1/SNP_R2 | 154 | 156 | 153.51 | 155.7 | C/C |
| rs2241280 | G | A | SNP_F1/SNP_R2 | 149 | 151 | 147.53 | 149.88 | A/A |
| rs2304035 | G | A | SNP_F1/SNP_R2 | 128 | 130 | 126.12 | 128.23 | G/G |
| rs2304102 | G | A | SNP_F1/SNP_R2 | 144 | 146 | 143.77 | 146.15 | G/A |
| rs4920098 | C | T | SNP_F1/SNP_R2 | 134 | 136 | 130.98 | 133.25 | T/T |
| rs9791113 | G | C | SNP_F1/SNP_R2 | 139 | 141 | 135.06 | 137.18 | G/C |
| rs11107 | G | A | SNP_F2/SNP_R1 | 115 | 117 | 113.01 | 114.86 | G/A |
| rs2241571 | C | T | SNP_F2/SNP_R1 | 95 | 97 | 93.51 | 95.49 | C/T |
| rs2305150 | C | T | SNP_F2/SNP_R1 | 120 | 122 | 118.24 | 120.33 | C/T |
| rs2306331 | C | T | SNP_F2/SNP_R1 | 105 | 107 | 103.44 | 105.59 | C/T |
| rs2401751 | G | A | SNP_F2/SNP_R1 | 100 | 102 | 98.97 | 101.18 | G/A |
| rs4829830 | C | A | SNP_F2/SNP_R1 | 110 | 112 | 109.48 | 111.44 | C/C |
| rs1058588 | C | T | SNP_F2/SNP_R2 | 128 | 130 | 126.65 | 128.78 | C/C |
| rs1572983 | C | T | SNP_F2/SNP_R2 | 139 | 141 | 136.39 | 138.43 | C/T |

TABLE 2-continued

The capillary electrophoresis results in terms of the ligation product size and genotypes of 48 SNPs. A1 refers to Allele #1; A2 refers to Allele #2; A1LP refers to Allele #1 Ligation Product Size; A2LP refers to Allele #2 Ligation Product Size; REF refers to reference; and CE refers to Capillary Electrophoresis.

| SNP rs# | A1 | A2 | PCR Primers | A1LP SIZE | A2LP SIZE | A1LP CE REF SIZE | A2LP CE REF SIZE | GENOTYPE |
|---|---|---|---|---|---|---|---|---|
| rs2279072 | C | T | SNP_F2/SNP_R2 | 144 | 146 | 142.77 | 145.27 | C/C |
| rs3731631 | G | A | SNP_F2/SNP_R2 | 149 | 151 | 149.5 | 151.89 | G/A |
| rs3736582 | G | C | SNP_F2/SNP_R2 | 134 | 136 | 132.01 | 134.03 | G/C |
| rs639225 | G | A | SNP_F2/SNP_R2 | 154 | 156 | 154.65 | 156.72 | G/A |
| rs11155787 | C | T | SNP_F3/SNP_R1 | 115 | 117 | 112.56 | 114.86 | C/T |
| rs2986014 | C | T | SNP_F3/SNP_R1 | 100 | 102 | 97.59 | 100.11 | C/T |
| rs3182535 | G | A | SNP_F3/SNP_R1 | 95 | 97 | 92.38 | 94.93 | G/A |
| rs4141253 | C | T | SNP_F3/SNP_R1 | 110 | 112 | 107.53 | 109.38 | C/C |
| rs6892205 | G | A | SNP_F3/SNP_R1 | 120 | 122 | 117.01 | 119.3 | G/G |
| rs9389034 | C | T | SNP_F3/SNP_R1 | 105 | 107 | 102.45 | 104.59 | C/C |
| rs1056893 | C | T | SNP_F3/SNP_R2 | 134 | 136 | 131.68 | 133.7 | T/T |
| rs2297129 | G | A | SNP_F3/SNP_R2 | 129 | 131 | 126.95 | 128.85 | G/A |
| rs3749877 | G | A | SNP_F3/SNP_R2 | 139 | 141 | 137.29 | 139.63 | A/A |
| rs4371677 | G | A | SNP_F3/SNP_R2 | 144 | 146 | 142.65 | 145.15 | G/A |
| rs469783 | C | T | SNP_F3/SNP_R2 | 154 | 156 | 153.63 | 155.58 | C/C |
| rs938883 | C | T | SNP_F3/SNP_R2 | 149 | 151 | 148.29 | 150.59 | C/T |
| rs2231926 | G | A | SNP_F4/SNP_R1 | 102 | 104 | 104.62 | 106.56 | G/A |
| rs3809806 | C | T | SNP_F4/SNP_R1 | 107 | 109 | 109.25 | 111.22 | C/C |
| rs624821 | A | T | SNP_F4/SNP_R1 | 112 | 114 | 114.09 | 116.13 | A/A |
| rs625372 | C | T | SNP_F4/SNP_R1 | 92 | 94 | 93.83 | 94.87 | T/T |
| rs6784322 | A | T | SNP_F4/SNP_R1 | 117 | 119 | 118.09 | 120.18 | A/T |
| rs934472 | C | A | SNP_F4/SNP_R1 | 97 | 99 | 98.51 | 100.64 | C/C |
| rs10790286 | C | T | SNP_F4/SNP_R2 | 131 | 133 | 133 | 135.14 | C/T |
| rs10791649 | G | A | SNP_F4/SNP_R2 | 146 | 148 | 148.51 | 151.06 | G/A |
| rs1359185 | G | A | SNP_F4/SNP_R2 | 151 | 153 | 153.16 | 155.24 | A/A |
| rs2161916 | G | A | SNP_F4/SNP_R2 | 125 | 127 | 126.73 | 128.78 | A/A |
| rs2241802 | G | A | SNP_F4/SNP_R2 | 141 | 143 | 141.98 | 144.4 | G/G |
| rs4362 | C | T | SNP_F4/SNP_R2 | 136 | 138 | 137.52 | 139.63 | C/T |

Example 2: Multiplex Detection of Copy Number Variants

This example demonstrates a multiplex CNV detection method according to the present invention. In this example, there were 192 target sequences including 129 target sites in the Duchenne muscular dystrophy (DMD) gene, and 63 target reference sites on chromosomes X, Y, 2-12, 14, 16-20. DMD is a recessive X-linked form of muscular dystrophy, which results in muscle degeneration. The disorder is caused by mutations in the dystrophin gene, located on the human X chromosome, which codes for the protein dystrophin, an important structural component within muscle tissue that provides structural stability to the dystroglycan complex (DGC) of the cell membrane. Approximately two-thirds of the mutations in DMD are copy number variants of one or more exons in the dystrophin gene. The exemplary multiplex CNV detection method employed fluorescent dye labeled forward primers and reverse primers with stuffer sequences according to the scheme in FIG. 5.

Specifically, probes were designed to cover 192 target sites with at least one target in each of the 79 exons of the DMD gene. Exons 22-42, 58-60, and 62-79 contained one target site. Exons 1, 3-15, 18-20, 47, 49, 54-57, and 61 contained two target sites. Exons 2, 16-17, 21, 43-46, 48, and 50-53 contain three target sites. For each target site, a probe pair was designed including a 3' probe (the left probe) and a 5' probe (the right probe). The 3' and 5' probes were designed in a manner so that when both are hybridized to the target sequence under a suitable condition, there is no gap between the two probes. The probes were synthesized by Life Technologies Corporation. The names, sequence ID numbers, primer binding sites and stuffer sequences of the 384 probes (192 probe pairs) for the 192 target sites are shown in Table 3.

For each 3' probe, the 5' end nucleotide was phosphorylated to provide a phosphate which would be connected to the hydroxyl group in the 3' end nucleotide of the 5' probe. Each 3' probe included a locus specific hybridization sequence (LSHS) in the 5' portion followed by a stuffer L2 sequence, and a primer binding sequence Y in the 3' portion. In this example, four primer binding sequence Y (MDM_Y1, SEQ ID NO: 554; MDM_Y2, SEQ ID NO: 555; MDM_Y3, SEQ ID NO: 556; MDM_Y4, SEQ ID NO: 557) were used in the 3' probes.

Each 5' probe included a locus specific hybridization sequence (LSHS) in the 3' portion followed by a stuffer L1 sequence and a primer binding sequence X in the 5' portion. In this example, four primer binding sequence X (MDM_X1, SEQ ID NO: 550; MDM_x2, SEQ ID NO: 551; MDM_X3, SEQ ID NO: 552; MDM_X4, SEQ ID NO: 553) were used in the 5' probes.

In addition, four forward primers and four reverse primers were designed for amplifying the ligation products. The four forward primers (DMD_F1, SEQ ID NO: 542; DMD_F2, SEQ ID NO: 543; DMD_F3, SEQ ID NO: 544; and DMD_F4 SEQ ID NO: 545) had unique sequences that were consistent with the four primer binding sequence X (MDM_X1, SEQ ID NO: 550; MDM_x2, SEQ ID NO: 551; MDM_X3, SEQ ID NO: 552; MDM_X4, SEQ ID NO: 553), respectively. The four forward primers: DMD_F1, DMD_F2, DMD_F3, and DMD_F4 were labeled on the 5' ends with four different fluorescent dyes: FAM-blue, VIC-green, NED-yellow, and PET-red, respectively. The four reverse primers (DMD_R1, SEQ ID No: 546; DMD_R2, SEQ ID No: 547; DMD_R3, SEQ ID No: 548; and DMD_R4, SEQ ID No: 549) had unique sequences there were reversely complementary to the four primer binding sequence Y (MDM_Y1, SEQ ID NO: 554; MDM_Y2, SEQ ID NO: 555; MDM_Y3, SEQ ID NO: 556; MDM_Y4, SEQ ID NO: 557), respectively. The DMD_R2 and DMD_R4 reverse primers also had a stuffer sequence DMD_R_Stuffer, SEQ ID No: 558 in the 5' portion. All primers and probes were synthesized by Life Technologies Corporation.

TABLE 3

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 158 | ChrX_A_3 | | | ATTACGCGA | Y4 |
| 159 | ChrX_A_5 | X2 | ATTACG | | |
| 160 | ChrX_B_3 | | | ATTACG | Y3 |
| 161 | ChrX_B_5 | X1 | | | |
| 162 | ChrX_C_3 | | | ATTAC | Y3 |
| 163 | ChrX_C_5 | X3 | ATTAC | | |
| 164 | ChrY_A_3 | | | | Y3 |
| 165 | ChrY_A_5 | X3 | | | |
| 166 | ChrY_B_3 | | | ATTACGCGA | Y3 |
| 167 | ChrY_B_5 | X3 | ATTACGCGATT | | |
| 168 | ChrY_C_3 | | | | Y4 |
| 169 | ChrY_C_5 | X3 | A | | |
| 170 | DMD_E01A_3 | | | ATTACGCGATT | Y4 |
| 171 | DMD_E01A_5 | X4 | AT | | |
| 172 | DMD_E01B_3 | | | ATTAC | Y4 |
| 173 | DMD_E01B_5 | X4 | ATTA | | |
| 174 | DMD_E02A_3 | | | ATTACGCGATT | Y4 |
| 175 | DMD_E02A_5 | X4 | ATTACGC | | |
| 176 | DMD_E02B_3 | | | ATTACGC | Y4 |
| 177 | DMD_E02B_5 | X4 | ATTACGC | | |
| 178 | DMD_E02C_3 | | | AT | Y4 |
| 179 | DMD_E02C_5 | X4 | | | |
| 180 | DMD_E03A_3 | | | ATTACGC | Y1 |
| 181 | DMD_E03A_5 | X4 | | | |
| 182 | DMD_E03B_5 | | | AT | Y2 |
| 183 | DMD_E03B_5 | X4 | | | |
| 184 | DMD_E04A_3 | | | ATT | Y1 |
| 185 | DMD_E04A_5 | X1 | | | |
| 186 | DMD_E04B_3 | | | ATTACGC | Y2 |
| 187 | DMD_E04B_5 | X4 | | | |
| 188 | DMD_E05A_3 | | | ATTACGCG | Y1 |
| 189 | DMD_E05A_5 | X3 | | | |
| 190 | DMD_E05B_3 | | | ATTACG | Y2 |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 191 | DMD_E05B_3 | X1 | ATTACG | | |
| 192 | DMD_E06A_3 | | | A | Y2 |
| 193 | DMD_E06A_5 | X3 | | | |
| 194 | DMD_E06B_3 | | | ATTACGCG | Y2 |
| 195 | DMD_E06B_5 | X1 | | | |
| 196 | DMD_E07A_3 | | | ATT | Y2 |
| 197 | DMD_E07A_5 | X1 | | | |
| 198 | DMD_E07B_3 | | | ATTACGCGA | Y1 |
| 199 | DMD_E07B_5 | X3 | ATT | | |
| 200 | DMD_E08A_3 | | | ATT | Y1 |
| 201 | DMD_E08A_5 | X2 | | | |
| 202 | DMD_E08B_3 | | | ATTAC | Y2 |
| 203 | DMD_E08B_5 | X2 | ATT | | |
| 204 | DMD_E09A_3 | | | ATTACGCGA | Y2 |
| 205 | DMD_E09A_5 | X1 | | | |
| 206 | DMD_E09B_3 | | | ATT | Y2 |
| 207 | DMD_E09B_5 | X3 | | | |
| 208 | DMD_E10A_3 | | | ATTACGCG | Y1 |
| 209 | DMD_E10A_5 | X3 | | | |
| 210 | DMD_E10B_3 | | | ATTACG | Y1 |
| 211 | DMD_E10B_5 | X2 | ATT | | |
| 212 | DMD_E11A_3 | | | ATTA | Y2 |
| 213 | DMD_E11A_5 | X1 | | | |
| 214 | DMD_E11B_3 | | | ATTAC | Y2 |
| 215 | DMD_E11B_5 | X2 | ATTA | | |
| 216 | DMD_E12A_3 | | | ATTACGC | Y1 |
| 217 | DMD_E12A_5 | X4 | A | | |
| 218 | DMD_E12B_3 | | | ATTACGCGAT | Y2 |
| 219 | DMD_E12B_5 | X4 | | | |
| 220 | DMD_E13A_3 | | | ATTACGCG | Y2 |
| 221 | DMD_E13A_5 | X3 | | | |
| 222 | DMD_E13B_3 | | | ATTACGCGA | Y1 |
| 223 | DMD_E13B_5 | X2 | | | |
| 224 | DMD_E14A_3 | | | AT | Y2 |
| 225 | DMD_E14A_5 | X4 | | | |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 226 | DMD_E14B_3 | | | ATTAC | Y1 |
| 227 | DMD_E14B_5 | X1 | ATTACGCG | | |
| 228 | DMD_E15A_3 | | | ATTACGC | Y1 |
| 229 | DMD_E15A_5 | X4 | ATTA | | |
| 230 | DMD_E15B_3 | | | ATTACGCG | Y1 |
| 231 | DMD_E15B_5 | X2 | A | | |
| 232 | DMD_E16A_3 | | | ATT | Y4 |
| 233 | DMD_E16A_5 | X2 | ATTAC | | |
| 234 | DMD_E16B_3 | | | ATTA | Y4 |
| 235 | DMD_E16B_5 | X2 | | | |
| 236 | DMD_E16C_3 | | | ATTAC | Y4 |
| 237 | DMD_E16C_5 | X1 | ATTACGCG | | |
| 238 | DMD_E17A_3 | | | A | Y3 |
| 239 | DMD_E17A_5 | X2 | A | | |
| 240 | DMD_E17B_3 | | | | Y4 |
| 241 | DMD_E17B_5 | X1 | | | |
| 242 | DMD_E17C_3 | | | ATTAC | Y3 |
| 243 | DMD_E17C_5 | X2 | | | |
| 244 | DMD_E18A_3 | | | ATTACGCGATTA | Y1 |
| 245 | DMD_E18A_5 | X2 | A | | |
| 246 | DMD_E18B_3 | | | ATTACGC | Y2 |
| 247 | DMD_E18B_5 | X4 | | | |
| 248 | DMD_E19A_3 | | | ATTA | Y2 |
| 249 | DMD_E19A_5 | X1 | | | |
| 250 | DMD_E19B_3 | | | ATTACGCGATT | Y2 |
| 251 | DMD_E19B_5 | X4 | | | |
| 252 | DMD_E20A_3 | | | ATT | Y2 |
| 253 | DMD_E20A_5 | X2 | | | |
| 254 | DMD_E20B_3 | | | ATTACG | Y1 |
| 255 | DMD_E20B_5 | X4 | | | |
| 256 | DMD_E21A_3 | | | A | Y4 |
| 257 | DMD_E21A_5 | X1 | | | |
| 258 | DMD_E21B_3 | | | | Y3 |
| 259 | DMD_E21B_5 | X4 | | | |
| 260 | DMD_E21C_3 | | | ATTA | Y3 |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 261 | DMD_E21C_5 | X2 | ATT | | |
| 262 | DMD_E22A_3 | | | | Y3 |
| 263 | DMD_E22A_5 | X1 | | | |
| 264 | DMD_E23A_3 | | | ATT | Y3 |
| 265 | DMD_E23A_5 | X4 | | | |
| 266 | DMD_E24A_3 | | | A | Y3 |
| 267 | DMD_E24A_5 | X4 | | | |
| 268 | DMD_E25A_3 | Y4 | | | |
| 269 | DMD_E25A_5 | X2 | | | |
| 270 | DMD_E26A_3 | | | ATT | Y3 |
| 271 | DMD_E26A_5 | X3 | | | |
| 272 | DMD_E27A_3 | Y3 | | | |
| 273 | DMD_E27A_5 | X3 | | | |
| 274 | DMD_E28A_3 | | | ATT | Y3 |
| 275 | DMD_E28A_5 | X4 | A | | |
| 276 | DMD_E29A_3 | | | AT | Y3 |
| 277 | DMD_E29A_5 | X1 | ATTACGC | | |
| 278 | DMD_E30A_3 | | | A | Y4 |
| 279 | DMD_E30A_5 | X2 | | | |
| 280 | DMD_E31A_3 | | | ATTAC | Y3 |
| 281 | DMD_E31A_5 | X4 | ATTACGCGATTACGC | | |
| 282 | DMD_E32A_3 | | | ATTACGCGAT | Y4 |
| 283 | DMD_E32A_5 | X3 | ATT | | |
| 284 | DMD_E33A_3 | | | ATTACG | Y4 |
| 285 | DMD_E33A_5 | X3 | | | |
| 286 | DMD_E34A_3 | | | AT | Y4 |
| 287 | DMD_E34A_5 | X1 | ATTACGCGATT | | |
| 288 | DMD_E35A_3 | | | ATTA | Y4 |
| 289 | DMD_E35A_5 | X3 | | | |
| 290 | DMD_E36A_3 | | | ATTA | Y3 |
| 291 | DMD_E36A_5 | X4 | ATTACG | | |
| 292 | DMD_E37A_3 | | | ATTACGC | Y4 |
| 293 | DMD_E37A_5 | X2 | ATTACGC | | |
| 294 | DMD_E38A_3 | | | ATTA | Y4 |
| 295 | DMD_E38A_5 | X3 | AT | | |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 296 | DMD_E39A_3 | | | ATTACG | Y4 |
| 297 | DMD_E39A_5 | X3 | ATTACGC | | |
| 298 | DMD_E40A_3 | | | ATT | Y3 |
| 299 | DMD_E40A_5 | X1 | ATTACGCG | | |
| 300 | DMD_E41A_3 | | | ATTA | Y3 |
| 301 | DMD_E41A_5 | X1 | | | |
| 302 | DMD_E42A_3 | | | ATTACG | Y3 |
| 303 | DMD_E42A_5 | X1 | A | | |
| 304 | DMD_E43A_3 | | | ATT | Y3 |
| 305 | DMD_E43A_5 | X4 | | | |
| 306 | DMD_E43B_3 | | | | Y3 |
| 307 | DMD_E43B_5 | X3 | | | |
| 308 | DMD_E43C_3 | | | ATTA | Y4 |
| 309 | DMD_E43C_5 | X2 | ATTACGCGA | | |
| 310 | DMD_E44A_3 | | | ATTA | Y1 |
| 311 | DMD_E44A_5 | X2 | | | |
| 312 | DMD_E44B_3 | | | ATTACGCG | Y2 |
| 313 | DMD_E44B_5 | X3 | ATT | | |
| 314 | DMD_E44C_3 | | | AT | Y2 |
| 315 | DMD_E44C_5 | X3 | ATTA | | |
| 316 | DMD_E45A_3 | | | ATT | Y1 |
| 317 | DMD_E45A_5 | X4 | A | | |
| 318 | DMD_E45B_3 | | | ATTACGCGA | Y1 |
| 319 | DMD_E45B_5 | X1 | A | | |
| 320 | DMD_E45C_3 | | | ATTACGCG | Y1 |
| 321 | DMD_E45C_5 | X1 | ATTACG | | |
| 322 | DMD_E46A_3 | | | ATTACGCGA | Y4 |
| 323 | DMD_E46A_5 | X3 | ATTACG | | |
| 324 | DMD_E46B_3 | | | ATTACG | Y4 |
| 325 | DMD_E46B_5 | X1 | | | |
| 326 | DMD_E46C_3 | | | ATT | Y4 |
| 327 | DMD_E46C_5 | X2 | ATT | | |
| 328 | DMD_E47A_3 | | | A | Y1 |
| 329 | DMD_E47A_5 | X4 | | | |
| 330 | DMD_E47B_3 | | | ATTACGCGATTA | Y2 |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 331 | DMD_E47B_5 | X1 | A | | |
| 332 | DMD_E48A_3 | | | ATTACG | Y3 |
| 333 | DMD_E48A_5 | X3 | AT | | |
| 334 | DMD_E48B_3 | | | | Y3 |
| 335 | DMD_E48B_5 | X2 | | | |
| 336 | DMD_E48C_3 | | | ATTACGCGAT | Y3 |
| 337 | DMD_E48C_5 | X3 | ATTACGC | | |
| 338 | DMD_E49A_3 | | | ATTACGCGAT | Y1 |
| 339 | DMD_E49A_5 | X1 | | | |
| 340 | DMD_E49B_3 | | | ATTACGCG | Y1 |
| 341 | DMD_E49B_5 | X2 | | | |
| 342 | DMD_E50A_3 | | | ATTA | Y4 |
| 343 | DMD_E50A_5 | X4 | | | |
| 344 | DMD_E50B_3 | | | | Y4 |
| 345 | DMD_E50B_5 | X4 | | | |
| 346 | DMD_E50C_3 | | | ATTACG | Y4 |
| 347 | DMD_E50C_5 | X4 | ATTAC | | |
| 348 | DMD_E51A_3 | | | ATTACGCG | Y1 |
| 349 | DMD_E51A_5 | X3 | ATTACGCGA | | |
| 350 | DMD_E51B_3 | | | ATT | Y1 |
| 351 | DMD_E51B_5 | X3 | | | |
| 352 | DMD_E51C_3 | | | ATTACGCGAT | Y2 |
| 353 | DMD_E51C_5 | X1 | | | |
| 354 | DMD_E52A_3 | | | ATTA | Y2 |
| 355 | DMD_E52A_5 | X2 | | | |
| 356 | DMD_E52B_3 | | | ATTAC | Y1 |
| 357 | DMD_E52B_5 | X1 | | | |
| 358 | DMD_E52C_3 | | | ATTACGCGATTAC | Y2 |
| 359 | DMD_E52C_5 | X2 | | | |
| 360 | DMD_E53A_3 | | | ATTAC | Y3 |
| 361 | DMD_E53A_5 | X1 | ATTACG | | |
| 362 | DMD_E53B_3 | | | A | Y3 |
| 363 | DMD_E53B_5 | X1 | | | |
| 364 | DMD_E53C_3 | | | | Y3 |
| 365 | DMD_E53C_5 | X2 | | | |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 366 | DMD_E54A_3 | | | ATTACGCG | Y2 |
| 367 | DMD_E54A_5 | X2 | | | |
| 368 | DMD_E54B_3 | | | A | Y2 |
| 369 | DMD_E54B_5 | X4 | | | |
| 370 | DMD_E55A_3 | | | ATTACGCG | Y1 |
| 371 | DMD_E55A_5 | X3 | | | |
| 372 | DMD_E55B_3 | | | ATTA | Y1 |
| 373 | DMD_E55B_5 | X3 | | | |
| 374 | DMD_E56A_3 | | | ATTACGCGA | Y2 |
| 375 | DMD_E56A_5 | X2 | | | |
| 376 | DMD_E56B_3 | Y2 | | | |
| 377 | DMD_E56B_5 | X4 | ATTA | | |
| 378 | DMD_E57A_3 | | | ATT | Y2 |
| 379 | DMD_E57A_5 | X3 | | | |
| 380 | DMD_E57B_3 | | | ATTACGCG | Y2 |
| 381 | DMD_E57B_5 | X3 | | | |
| 382 | DMD_E58A_3 | | | ATTACGC | Y3 |
| 383 | DMD_E58A_5 | X2 | ATT | | |
| 384 | DMD_E59A_3 | | | ATTA | Y3 |
| 385 | DMD_E59A_5 | X2 | | | |
| 386 | DMD_E60A_3 | | | ATT | Y1 |
| 387 | DMD_E60A_5 | X4 | | | |
| 388 | DMD_E61A_3 | | | ATT | Y1 |
| 389 | DMD_E61A_5 | X3 | | | |
| 390 | DMD_E61B_3 | | | AT | Y1 |
| 391 | DMD_E61B_5 | X4 | ATTACGCGA | | |
| 392 | DMD_E62A_3 | | | ATTA | Y1 |
| 393 | DMD_E62A_5 | X2 | | | |
| 394 | DMD_E63A_3 | | | ATTACGC | Y4 |
| 395 | DMD_E63A_5 | X2 | | | |
| 396 | DMD_E64A_3 | | | ATTACGCG | Y2 |
| 397 | DMD_E64A_5 | X3 | | | |
| 398 | DMD_E65A_3 | | | ATTA | Y2 |
| 399 | DMD_E65A_5 | X2 | | | |
| 400 | DMD_E66A_3 | | | ATTACGCGA | Y1 |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 401 | DMD_E66A_5 | X1 | | | |
| 402 | DMD_E67A_3 | | | ATTAC | Y1 |
| 403 | DMD_E67A_5 | X1 | | | |
| 404 | DMD_E68A_3 | | | ATTACGCG | Y4 |
| 405 | DMD_E68A_5 | X3 | ATT | | |
| 406 | DMD_E69A_3 | | | AT | Y3 |
| 407 | DMD_E69A_5 | X1 | | | |
| 408 | DMD_E70A_3 | | | ATTAC | Y3 |
| 409 | DMD_E70A_5 | X3 | AT | | |
| 410 | DMD_E71A_3 | | | ATTAC | Y4 |
| 411 | DMD_E71A_5 | X1 | | | |
| 412 | DMD_E72A_3 | | | ATTAC | Y3 |
| 413 | DMD_E72A_5 | X2 | AT | | |
| 414 | DMD_E73A_3 | | | ATTA | Y3 |
| 415 | DMD_E73A_5 | X2 | ATT | | |
| 416 | DMD_E74A_3 | | | ATTAC | Y3 |
| 417 | DMD_E74A_5 | X4 | ATT | | |
| 418 | DMD_E75A_3 | | | | Y3 |
| 419 | DMD_E75A_5 | X4 | | | |
| 420 | DMD_E76A_3 | | | AT | Y4 |
| 421 | DMD_E76A_5 | X1 | | | |
| 422 | DMD_E77A_3 | | | ATTACGC | Y4 |
| 423 | DMD_E77A_5 | X1 | ATTACGCGA | | |
| 424 | DMD_E78A_3 | | | | Y4 |
| 425 | DMD_E78A_5 | X3 | | | |
| 426 | DMD_E79A_3 | | | ATTACGCGA | Y4 |
| 427 | DMD_E79A_5 | X1 | ATTAC | | |
| 428 | REF10p_A_3 | | | ATTACGCG | Y2 |
| 429 | REF10p_A_5 | X1 | | | |
| 430 | REF10p_B_3 | | | ATTAC | Y4 |
| 431 | REF10p_B_5 | X4 | | | |
| 432 | REF10p_C_3 | | | ATTACGCGATT | Y3 |
| 433 | REF10p_C_5 | X4 | | | |
| 434 | REF10q_A_3 | | | | Y3 |
| 435 | REF10q_A_5 | X2 | | | |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 436 | REF10q_B_3 | | | ATTACGCGATTA | Y1 |
| 437 | REF10q_B_3 | X3 | ATTACGCGATTACGCG | | |
| 438 | REF11p_A_3 | | | ATTACGC | Y1 |
| 439 | REF11p_A_5 | X4 | | | |
| 440 | REF11p_B_3 | | | ATTACGCGATTAC | Y3 |
| 441 | REF11p_B_5 | | | X2 | AT |
| 442 | REF11q_A_3 | | | ATTACGCGATTAC | Y2 |
| 443 | REF11q_A_5 | X4 | ATTACGCGATTA | | |
| 444 | REF11q_B_3 | | | ATTACG | Y3 |
| 445 | REF11q_B_5 | X4 | | | |
| 446 | REF12p_A_3 | | | ATTACGCGATTACG | Y2 |
| 447 | REF12p_A_5 | X4 | ATT | | |
| 448 | REF12q_A_3 | | | ATTACGC | Y1 |
| 449 | REF12q_A_5 | X3 | | | |
| 450 | REF12q_B_3 | | | ATTACGCGA | Y4 |
| 451 | REF12q_B_5 | X1 | | | |
| 452 | REF14q_A_3 | | | | Y2 |
| 453 | REF14q_A_5 | X2 | | | |
| 454 | REF16p_A_3 | | | ATTACGCGATTAC | Y2 |
| 455 | REF16p_A_5 | X2 | ATTACG | | |
| 456 | REF16p_B_3 | | | ATTACGCGATTACG | Y4 |
| 457 | REF16p_B_5 | X2 | ATTACG | | |
| 458 | REF16q_A_3 | | | ATTACGCGAT | Y3 |
| 459 | REF16q_A_5 | X1 | ATTAC | | |
| 460 | REF16q_B_3 | | | | Y2 |
| 461 | REF16q_B_5 | X3 | | | |
| 462 | REF17q_A_3 | | | ATTACGCGATTA | Y2 |
| 463 | REF17q_A_5 | X1 | ATTACGCGATTACG | | |
| 464 | REF18p_A_3 | | | ATTACGCGATTA | Y1 |
| 465 | REF18p_A_5 | X1 | AT | | |
| 466 | REF18p_B_3 | | | ATTACGC | Y3 |
| 467 | REF18p_B_5 | X2 | | | |
| 468 | REF19q_A_3 | | | ATTACGCGATTAC | Y2 |
| 469 | REF19q_A_5 | X3 | ATTACGC | | |
| 470 | REF19q_B_3 | | | | Y4 |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 471 | REF19q_B_5 | X1 | | | |
| 472 | REF19q_C_3 | | | | Y3 |
| 473 | REF19q_C_5 | X4 | | | |
| 474 | REF20p_A_3 | | | ATTACGCGATT | Y1 |
| 475 | REF20p_A_5 | X2 | ATTA | | |
| 476 | REF20p_B_3 | | | ATTACGCGA | Y4 |
| 477 | REF20p_B_5 | X2 | | | |
| 478 | REF20q_A_3 | | | ATTACGCGATTA | Y2 |
| 479 | REF20q_A_5 | X1 | ATTACGC | | |
| 480 | REF20q_B_3 | | | ATTACGCGATTACGCGA | Y4 |
| 481 | REF20q_B_5 | X4 | | | |
| 482 | REF20q_C_3 | | | ATT | Y3 |
| 483 | REF20q_C_5 | X3 | | | |
| 484 | REF2p_A_3 | | | ATTACGCGAT | Y1 |
| 485 | REF2p_A_5 | X3 | ATTACGCGA | | |
| 486 | REF2p_B_3 | | | | Y4 |
| 487 | REF2p_B_5 | X2 | | | |
| 488 | REF2q_A_3 | | | ATTACGCGATTACG | Y4 |
| 489 | REF2q_A_5 | X3 | ATTACG | | |
| 490 | REF2q_B_3 | | | ATTACGCGATTA | Y2 |
| 491 | REF2q_B_5 | X2 | ATTACGCGAT | | |
| 492 | REF3p_A_3 | | | ATTACG | Y3 |
| 493 | REF3p_A_5 | X1 | | | |
| 494 | REF3p_B_3 | | | ATTACGCGATTAC | Y4 |
| 495 | REF3p_B_5 | X4 | ATTACGCGATTAC | | |
| 496 | REF3p_C_3 | | | | Y2 |
| 497 | REF3p_C_5 | X4 | | | |
| 498 | REF3p_D_3 | | | ATTACGCGA | Y1 |
| 499 | REF3p_D_5 | X1 | | | |
| 500 | REF3q_A_3 | | | ATTACGCGATTACG | Y1 |
| 501 | REF3q_A_5 | X4 | ATTACGCGATTAC | | |
| 502 | REF3q_B_3 | | | ATTACGCGA | Y4 |
| 503 | REF3q_B_5 | X3 | A | | |
| 504 | REF3q_C_3 | | | A | Y2 |
| 505 | REF3q_C_5 | X3 | | | |

TABLE 3-continued

Names, sequence ID numbers, primer binding sites and stuffer sequences in the probes used in the multiplex CNV analysis for DMD gene. X1, X2, X3 and X4 refer to MDM_X1, SEQ ID NO: 550; MDM_x2, SEQ ID NO: 551; MDM_X3, SEQ ID NO: 552; MDM_X4, SEQ ID NO: 553, respectively. Y1, Y2, Y3 and Y4 refer to MDM_Y1, SEQ ID NO: 554; MDM_Y2, SEQ ID NO: 555; MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 506 | REF4q_A_3 | | | | Y4 |
| 507 | REF4q_A_5 | X3 | | | |
| 508 | REF4q_B_3 | | | ATTACGC | Y1 |
| 509 | REF4q_B_5 | X2 | | | |
| 510 | REF5p_A_3 | | | A | Y1 |
| 511 | REF5p_A_5 | X2 | | | |
| 512 | REF5q_A_3 | | | ATTACGCGATTACGCG | Y1 |
| 513 | REF5q_A_5 | X1 | ATTACGCGATTACG | | |
| 514 | REF6p_A_3 | | | | Y1 |
| 515 | REF6p_A_5 | X3 | | | |
| 516 | REF6p_B_3 | | | | Y3 |
| 517 | REF6p_B_5 | X1 | | | |
| 518 | REF6q_A_3 | | | ATTACGCGATTACG | Y1 |
| 519 | REF6q_A_5 | X2 | ATTACGCGATT | | |
| 520 | REF6q_B_3 | | | ATTACGCGATTACGCG | Y4 |
| 521 | REF6q_B_5 | X1 | ATTAC | | |
| 522 | REF7p_A_3 | | | ATTACGC | Y2 |
| 523 | REF7p_A_5 | X4 | | | |
| 524 | REF7p_B_3 | | | ATTACGCGATT | Y3 |
| 525 | REF7p_B_5 | X3 | ATTAC | | |
| 526 | REF8p_A_3 | | | ATTACGCGA | Y1 |
| 527 | REF8p_A_5 | X4 | ATTACG | | |
| 528 | REF8p_B_3 | | | ATTAC | Y2 |
| 529 | REF8p_B_5 | X1 | | | |
| 530 | REF8q_A_3 | | | A | Y3 |
| 531 | REF8q_A_5 | X3 | | | |
| 532 | REF8q_B_3 | | | A | Y1 |
| 533 | REF8q_B_5 | X1 | ATTACGC | | |
| 534 | REF9p_A_3 | | | ATTACGCGATTAC | Y2 |
| 535 | REF9p_A_5 | X3 | ATTACGCGATT | | |
| 536 | REF9p_B_3 | | | | Y1 |
| 537 | REF9p_B_5 | X4 | | | |
| 538 | REF9q_A_3 | | | | Y4 |
| 539 | REF9q_A_5 | X4 | | | |

TABLE 3-continued

Names, sequence ID numbers, primer binding sites and stuffer sequences
in the probes used in the multiplex CNV analysis for DMD gene. X1, X2,
X3 and X4 refer to MDM_X1, SEQ ID NO: 550; MDM_x2, SEQ ID NO: 551;
MDM_X3, SEQ ID NO: 552; MDM_X4, SEQ ID NO: 553, respectively. Y1,
Y2, Y3 and Y4 refer to MDM_Y1, SEQ ID NO: 554; MDM_Y2, SEQ ID NO: 555;
MDM_Y3, SEQ ID NO: 556; MDM_Y4, SEQ ID NO: 557, respectively.

| SEQ ID NO. | Probe NAME | Sequenc X | Stuffer L1 | Stuffer L2 | Sequence Y |
|---|---|---|---|---|---|
| 540 | REF9q_B_3 | | | ATTACGCGA | Y2 |
| 541 | REF9q_B_5 | X2 | | | |

To perform the 192 multiplex CNV detection assay, a ligation product was first generated. Briefly, genomic DNA was extracted from 2 ml whole blood samples using the classic phenol:chloroform method. The blood samples were collected from a male DMD patient and a healthy male volunteer at Shanghai Ruijin Hospital, Shanghai, China. The genomic DNA from the male DMD patient was the test sample. The genomic DNA from the healthy volunteer was the control sample. From the extracted genomic DNA, 100-200 microgram (μg) DNA was dissolved in 10 microliter (μl) 1×TE buffer (10 mM Tris.Cl, pH8.0, 1 mM EDTA from Sigma-Aldrich). The dissolved genomic DNA was denatured at 98° C. for 5 minutes and then immediately cooled down on ice. At the same time, a 2× ligation premix solution was prepared according to the following formula: a 10 μl 2× ligation premix was made of 2 μl 10× Taq ligase buffer, 1 μl 40 U/μl Taq Ligase from NewEngland Biolabs, Inc., 1 μl ProbeMix (the 384 probes with a final concentration of 0.005 micromolar for each probe in 1×TE), and 6 μl ddH2O (Distilled Milli-Q water from Milli-Q Advantage A10, Millipore). 10 μl 2× ligation premix was mixed with the denatured 10 μl genomic DNA and the mixture was allowed to undergo 4 cycles of denaturation, hybridization, and ligation under the following conditions: 95° C. for 30 seconds, and then 58° C. for 4 hours. The ligation product thus obtained could be stored on ice for same day use or freezed in −20° C. for future use.

With the ligation product, an amplification step was then performed to obtain an amplification product. Briefly, two PCR reactions were performed using the same amplification product as template DNA. One PCR reaction had DMD_F1, DMD_F2, DMD_F3, DMD_F4, DMD_R1 and DMD_R2 as primers. The other PCR reaction had DMD_F1, DMD_F2, DMD_F3, DMD_F4, DMD_R3 and DMD_R4 as primers. The PCR reaction mixture was prepared as follows: a 20 μl reaction system was made by mixing 2 μl 10×PCR buffer (Qiagen, Germany), 2 μl 2.5 mM dNTP mix (2.5 mM each of dATP, dTTP, dCTP and dGTP from Takara Bio Inc.), 2 μl primer mix (DMD_F1, DMD_F2, DMD_F3, DMD_F4, DMD_R1 and DMD_R2 at final concentrations of 1 μM, 1 μM, 1 μM, 1 μM, 2 μM, and 2 μM, respectively; or DMD_F1, DMD_F2, DMD_F3, DMD_F4, DMD_R3 and DMD_R4 at final concentrations of 1 μM, 1 μM, 1 μM, 1 μM, 2 μM and 2 μM, respectively), 1 μl Ligation product, 0.2 μl 5 U/μl HotStarTaq Plus Taq DNA polymerase (Qiagen, Germany), and 12.8 μl ddH2O. The PCR mixture was allowed to undergo a polymerase chain reaction under the following conditions: 95° C. for 2 minutes; followed by 35 cycles of 94° C. for 20 second, 57° C. for 40 second, and 72° C. for 1.5 minutes; and after the 35th cycle, the reaction mixture was kept in 60° C. for 1 hour. To analyze the amplification product, 1 μl of the amplification product was first diluted with ddH2O 10 times into 10 μl. Then 1 μl was taken out of the 10 μl diluted amplification product and mixed with 0.1 μl GeneScan™ 500 LIZ® size standard (Life Technologies, Inc.) and 8.9 μl Hi-Di formamide (Life Technologies, Inc.). The mixture was detaured at 95° C. for 5 minutes and run through capillary electrophoresis by ABI3130XL according to manufacturer's manual. The chromatograms from the two PCR reactions were designated as Panel A and Panel B, respectively. The capillary electrophoresis data was processed using Genemapper 4.0 to obtain peak intensity values for each amplification product.

Figure 11A:
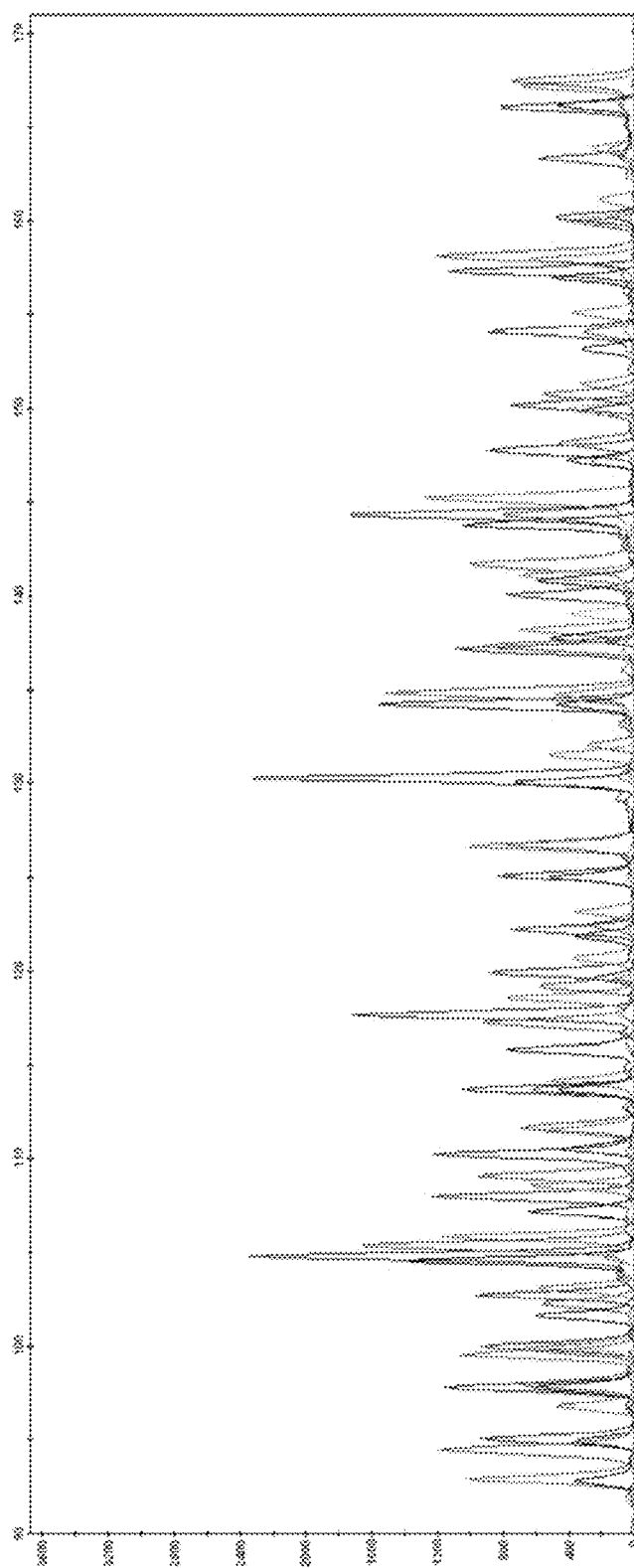
Figure 11B:
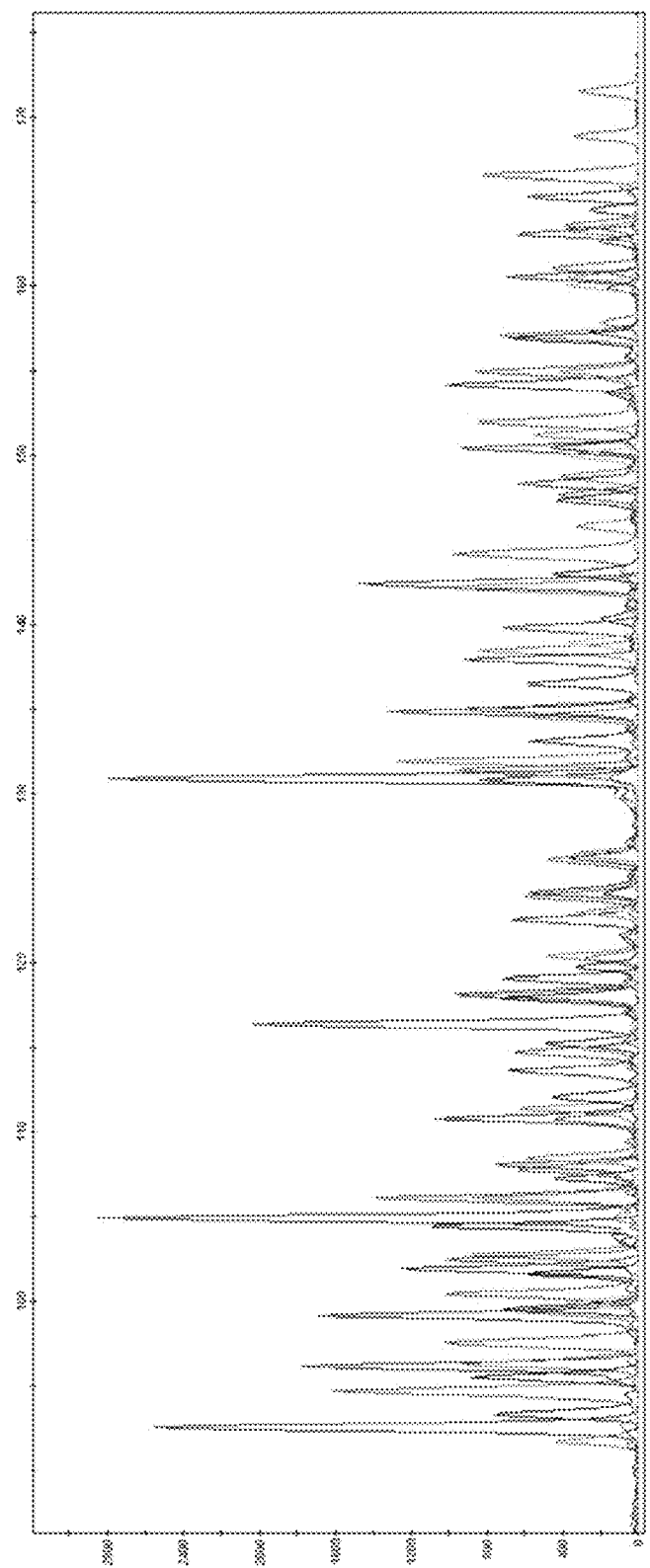
Figure 11C:
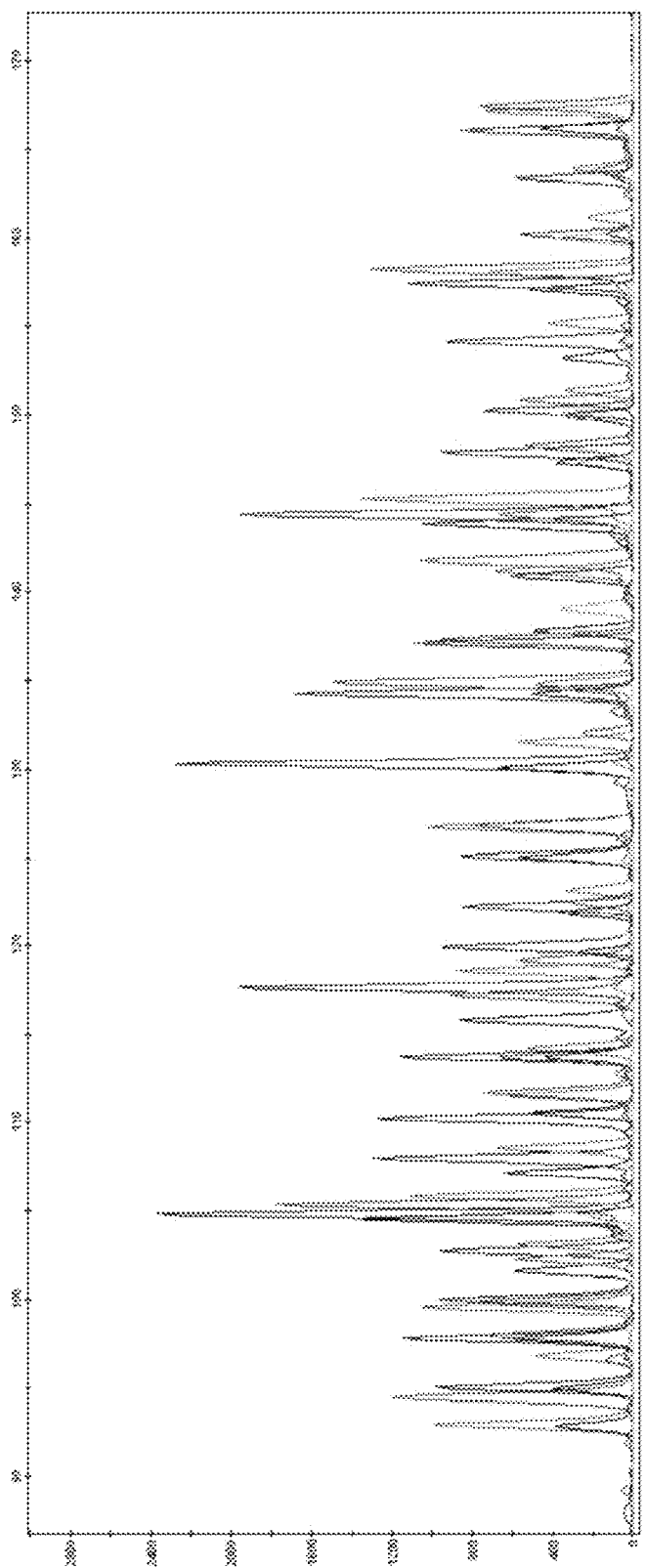
Figure 11D:
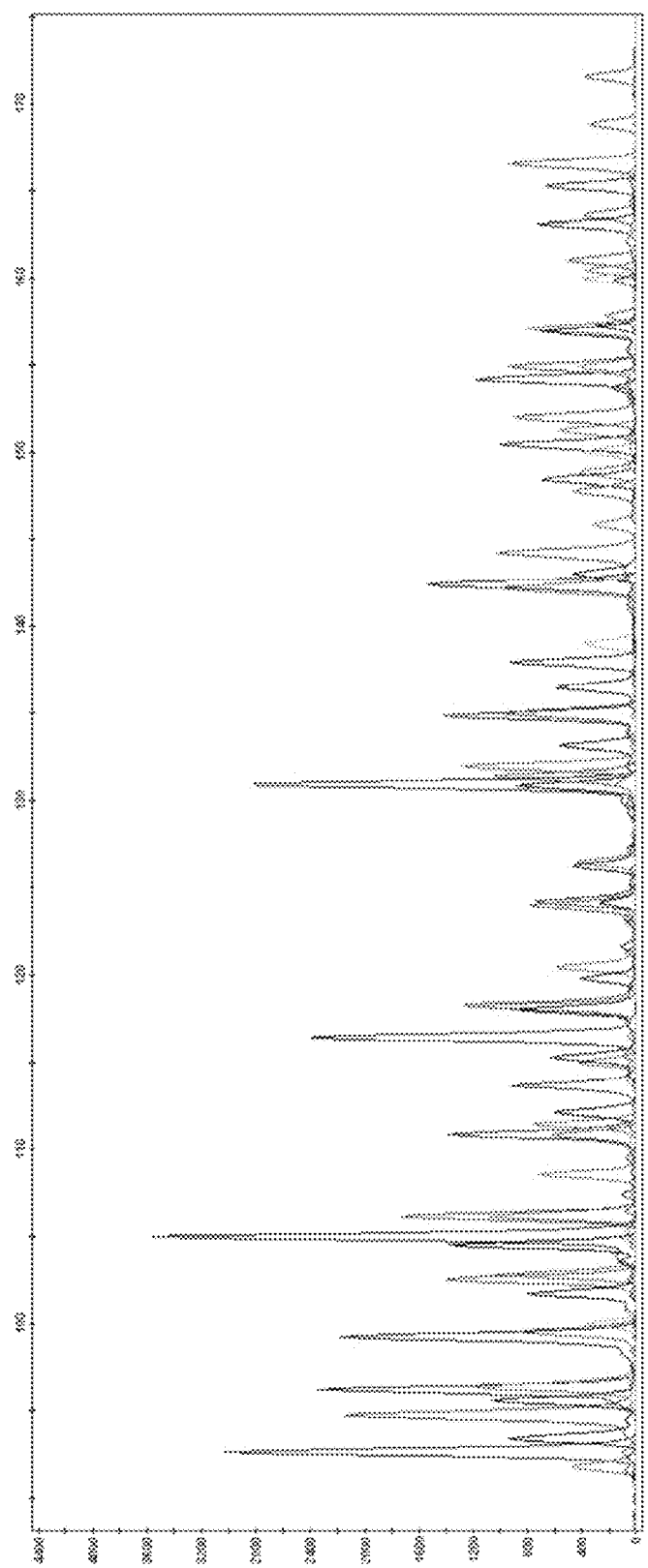

As shown in FIGS. 11A-H, the amplification products obtained in the assay could be separated by capillary electrophoresis and the peaks could be individually identified on the chromatograms. FIGS. 11A and 11B showed the chromatograms of all amplification products for the control sample panel A and panel B, respectively. Each panel represented the analysis of amplification products from one PCR reaction. FIGS. 11C and 11D showed the chromatograms of all amplification products for the patient sample panel A and panel B, respectively. Each peak represented one amplification product corresponding to an individual target site.

Figure 11E:
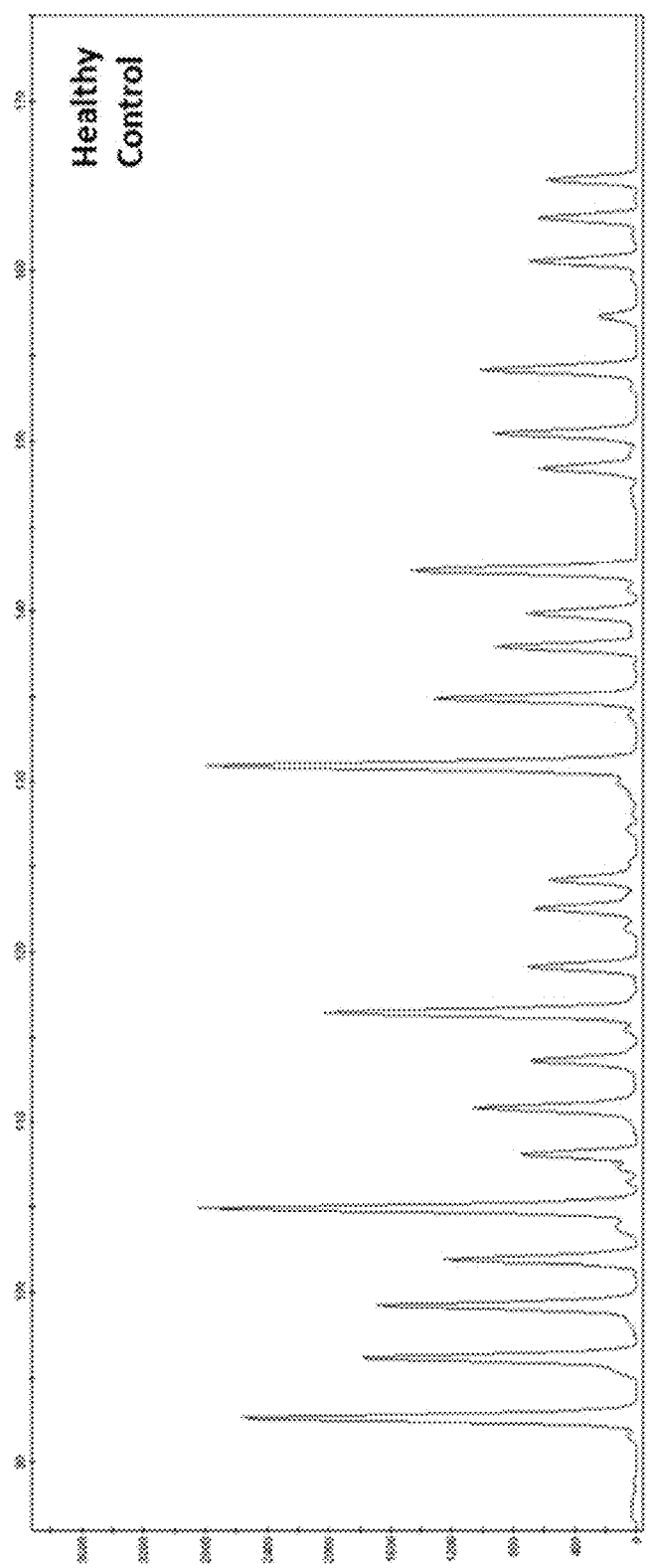
Figure 11F:
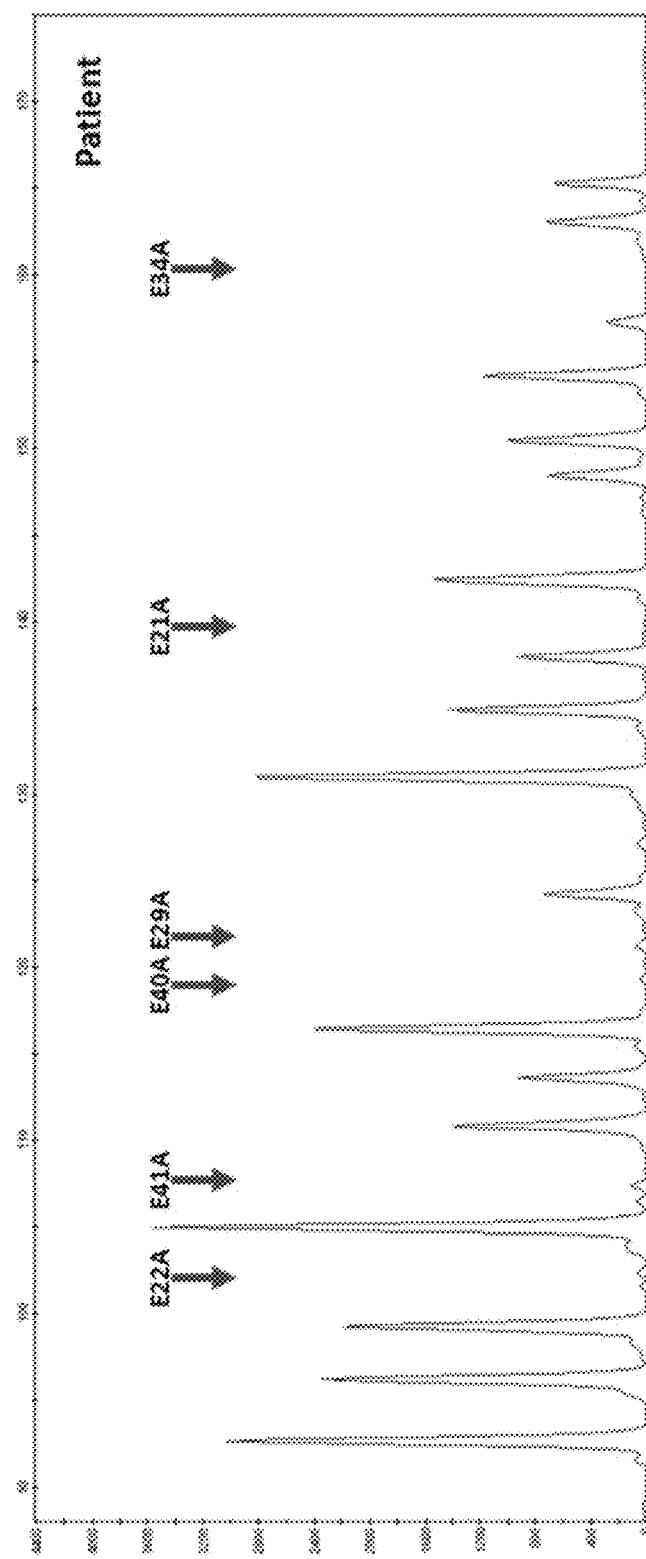
Figure 11G:
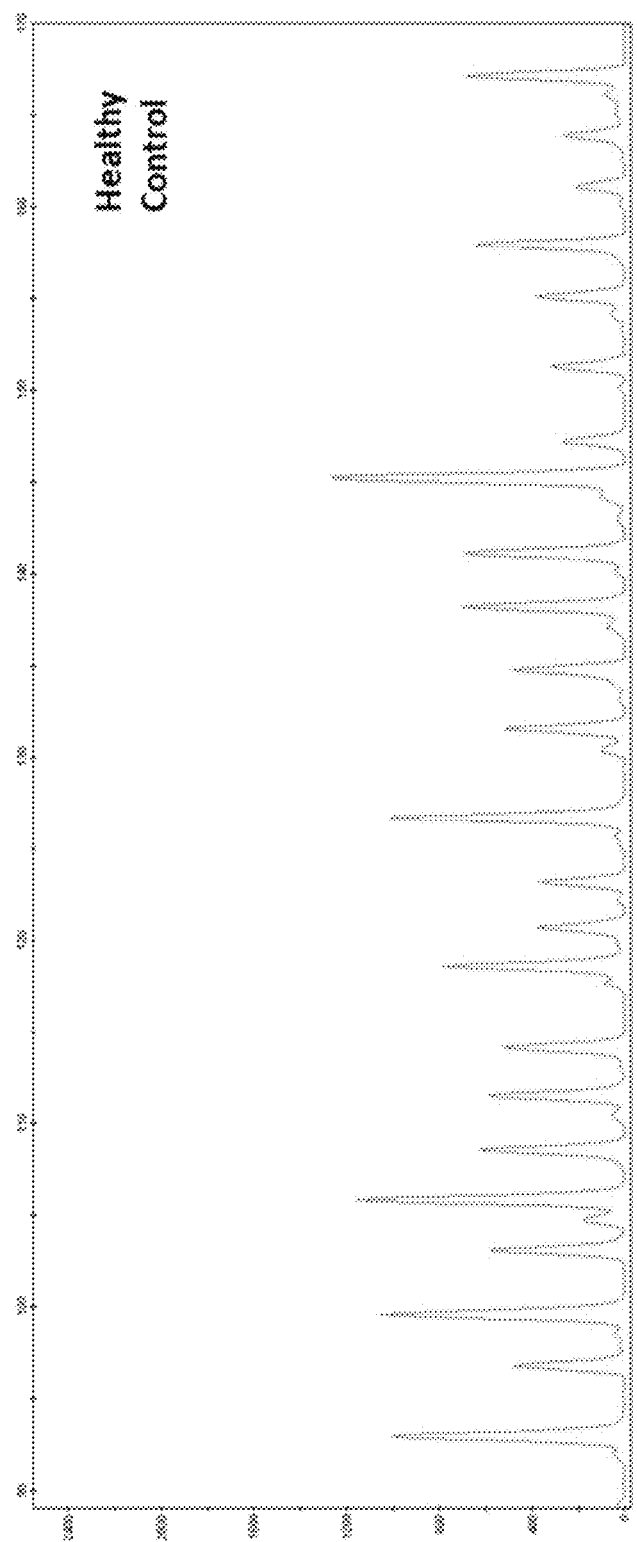

FIGS. 11E and 11F showed the chromatograms for amplification products labeled with blue fluorescent dyes for the control sample and the patient sample, respectively. FIGS. 11G and 11H showed the chromatograms for amplification products labeled with green fluorescent dyes for the control sample and the patient sample, respectively. As seen in FIGS. 11E-11H, the peaks from the amplification products labeled with the same fluorescent dye could be identified on the basis of different fragment sizes. By comparing the chromatograms from the control and the patient samples, the presence or absence of peaks of similar fragment sizes may be determined. For example, when comparing the chromatograms in FIGS. 11E and 11F, the peaks for the target sites E22A, E41A, E40A, E29A, E21A and E34A were missing in the chromatogram from the patient sample, indicating the deletion of the sequences in the DMD gene corresponding to these target sites. For another example, when comparing the chromatograms in FIGS. 11G and 11H, the peaks for the target sites E18A, and E20A are missing in the chromatogram from the patient sample, indicating the deletion of the sequences in the DMD gene corresponding to these target sites.

Alternatively, in another method to analyze the electrophoresis data, a ratio for the test sample ($R_{test}$) was obtained for each DMD, chromosome X, and chromosome Y target sites (herein also referred to as gene target sites) by dividing the peak intensity value of the gene target site with the peak intensity value of each of the reference target sites in the same group. The same PCR primer pair was used for each gene target site and the reference target site in the same group. For example, As shown in Table 4, in one group which shared the same primer pair DMD_F1/DMD_R1, there were amplification products for 12 probe loci (herein also referred to as probe target sites) including 8 gene target loci: DMD_E04A, DMD_E14B, DMD_E45B, DMD_E45C, DMD_E49A, DMD_E52B, DMD_E66A, and DMD_E67A; and 4 reference target loci: REF18p_A, REF3p_D, REF5q_A, and REF8q_B. To obtain the ratio for the locus DMD_E04A in the test sample ($R_{test}$), the peak intensity for the locus DMD_E04A was divided by the peak intensity for each of the reference target sites REF18p_A, REF3p_D, REF5q_A, and REF8q_B so that four ratios ($R_{test}$) were derived.

Similarly, a ratio ($R_{control}$) in the control sample was obtained for each gene target site. Assuming the copy number of the target nucleic acid in the control sample ($C_{control}$) is 1, the copy number of each gene target site ($C_{test}$) was then calculated according to the formula: $C_{test}=C_{control} \times R_{test}R_{control}$.

The copy number for a gene target site in the test sample equals to the ratio between the $R_{test}$ and the $R_{control}$, assuming the copy number of the target nucleic acid in the control sample is 1 (e.g., there is one X chromosome in a male patient). Because four reference target sites were introduced for each gene target site, four $R_{test}$ and therefore four $C_{test}$ were obtained for each gene target site. The median value the four $C_{test}$ was deemed as the copy number for that gene target site in the test sample. The copy numbers thus calculated for each gene target site are shown in Table 4. Copy numbers for gene target sites corresponding to exons 18-41 were zero, indicating that these exons were deleted in the DMD patient sample.

TABLE 4

Copy number calculation results based on peak intensity for each gene target site. LP SIZE refers to Ligation Product Size; REF refers to Reference; CE refers to Capillary Electrophoresis; Non-PAR refers to non-pseudoautosomal region.

| PANEL | PROBE LOCUS | TARGET REGION | PCR PRIMERS | LP SIZE | CE REF SIZE | COPY NUMBER MEASUREMENT |
|---|---|---|---|---|---|---|
| A | DMD_E04A | DMD EXON04 | DMD_F1/DMD_R1 | 101 | 97.95 | 1.02 |
| A | DMD_E14B | DMD EXON14 | DMD_F1/DMD_R1 | 125 | 122.35 | 1.02 |
| A | DMD_E45B | DMD EXON45 | DMD_F1/DMD_R1 | 116 | 113.84 | 1.08 |
| A | DMD_E45C | DMD EXON45 | DMD_F1/DMD_R1 | 122 | 120.03 | 1.07 |
| A | DMD_E49A | DMD EXON49 | DMD_F1/DMD_R1 | 113 | 110.3 | 1.04 |
| A | DMD_E52B | DMD EXON52 | DMD_F1/DMD_R1 | 104 | 102.87 | 1.03 |
| A | DMD_E66A | DMD EXON66 | DMD_F1/DMD_R1 | 110 | 108.1 | 1 |
| A | DMD_E67A | DMD EXON67 | DMD_F1/DMD_R1 | 98 | 94.86 | 1.07 |
| A | REF18p_A | REFERENCE | DMD_F1/DMD_R1 | 119 | 117.75 | / |
| A | REF3p_D | REFERENCE | DMD_F1/DMD_R1 | 107 | 104.93 | / |
| A | REF5q_A | REFERENCE | DMD_F1/DMD_R1 | 128 | 124.92 | / |
| A | REF8q_B | REFERENCE | DMD_F1/DMD_R1 | 102 | 100.21 | / |
| A | DMD_E05B | DMD EXON05 | DMD_F1/DMD_R2 | 164 | 163.68 | 0.98 |
| A | DMD_E06B | DMD EXON06 | DMD_F1/DMD_R2 | 148 | 147.96 | 0.99 |
| A | DMD_E07A | DMD EXON07 | DMD_F1/DMD_R2 | 139 | 137.04 | 1.04 |
| A | DMD_E09A | DMD EXON09 | DMD_F1/DMD_R2 | 151 | 150.45 | 0.97 |
| A | DMD_E11A | DMD EXON11 | DMD_F1/DMD_R2 | 136 | 134.22 | 1.06 |
| A | DMD_E19A | DMD EXON19 | DMD_F1/DMD_R2 | 142 | 140.22 | 0 |
| A | DMD_E47B | DMD EXON47 | DMD_F1/DMD_R2 | 159 | 160.53 | 1.08 |
| A | DMD_E51C | DMD EXON51 | DMD_F1/DMD_R2 | 154 | 154.36 | 0.96 |
| A | REF10p_A | REFERENCE | DMD_F1/DMD_R2 | 133 | 130.34 | / |
| A | REF17q_A | REFERENCE | DMD_F1/DMD_R2 | 166 | 166.35 | / |
| A | REF20q_A | REFERENCE | DMD_F1/DMD_R2 | 157 | 157.72 | / |
| A | REF8p_B | REFERENCE | DMD_F1/DMD_R2 | 145 | 144.59 | / |
| B | DMD_E22A | DMD EXON22 | DMD_F1/DMD_R3 | 104 | 102.07 | 0 |
| B | DMD_E29A | DMD EXON29 | DMD_F1/DMD_R3 | 125 | 122.73 | 0 |
| B | DMD_E40A | DMD EXON40 | DMD_F1/DMD_R3 | 122 | 119.3 | 0 |
| B | DMD_E41A | DMD EXON41 | DMD_F1/DMD_R3 | 110 | 108.32 | 0 |
| B | DMD_E42A | DMD EXON42 | DMD_F1/DMD_R3 | 116 | 113.83 | 1.12 |
| B | DMD_E53A | DMD EXON53 | DMD_F1/DMD_R3 | 128 | 124.34 | 1.1 |
| B | DMD_E53B | DMD EXON53 | DMD_F1/DMD_R3 | 101 | 99.46 | 1.01 |
| B | DMD_E69A | DMD EXON69 | DMD_F1/DMD_R3 | 98 | 96.33 | 1.05 |
| B | ChrX_B | ChrX Non-PAR | DMD_F1/DMD_R3 | 113 | 110.95 | 0.96 |
| B | REF16q_A | REFERENCE | DMD_F1/DMD_R3 | 119 | 116.64 | / |
| B | REF3p_A | REFERENCE | DMD_F1/DMD_R3 | 107 | 105.37 | / |
| B | REF6p_B | REFERENCE | DMD_F1/DMD_R3 | 95 | 92.77 | / |
| B | DMD_E16C | DMD EXON16 | DMD_F1/DMD_R4 | 162 | 163.37 | 1.01 |
| B | DMD_E17B | DMD EXON17 | DMD_F1/DMD_R4 | 139 | 138.03 | 0.99 |
| B | DMD_E21A | DMD EXON21 | DMD_F1/DMD_R4 | 141 | 140.14 | 0 |
| B | DMD_E34A | DMD EXON34 | DMD_F1/DMD_R4 | 160 | 160.74 | 0 |
| B | DMD_E46B | DMD EXON46 | DMD_F1/DMD_R4 | 150 | 150.99 | 0.98 |
| B | DMD_E71A | DMD EXON71 | DMD_F1/DMD_R4 | 148 | 148.7 | 0.99 |
| B | DMD_E76A | DMD EXON76 | DMD_F1/DMD_R4 | 136 | 134.94 | 0.98 |
| B | DMD_E77A | DMD EXON77 | DMD_F1/DMD_R4 | 166 | 165.44 | 0.94 |
| B | DMD_E79A | DMD EXON79 | DMD_F1/DMD_R4 | 159 | 157.44 | 0.99 |
| B | REF12q_B | REFERENCE | DMD_F1/DMD_R4 | 145 | 142.57 | / |
| B | REF19q_B | REFERENCE | DMD_F1/DMD_R4 | 133 | 131.12 | / |
| B | REF6q_B | REFERENCE | DMD_F1/DMD_R4 | 157 | 154.42 | / |
| A | DMD_E08A | DMD EXON08 | DMD_F2/DMD_R1 | 101 | 99.78 | 0.97 |

TABLE 4-continued

Copy number calculation results based on peak intensity for each gene target site. LP SIZE refers to Ligation Product Size; REF refers to Reference; CE refers to Capillary Electrophoresis; Non-PAR refers to non-pseudoautosomal region.

| PANEL | PROBE LOCUS | TARGET REGION | PCR PRIMERS | LP SIZE | CE REF SIZE | COPY NUMBER MEASUREMENT |
|---|---|---|---|---|---|---|
| A | DMD_E10B | DMD EXON10 | DMD_F2/DMD_R1 | 116 | 114.26 | 0.97 |
| A | DMD_E13B | DMD EXON13 | DMD_F2/DMD_R1 | 113 | 111.65 | 0.96 |
| A | DMD_E15B | DMD EXON15 | DMD_F2/DMD_R1 | 125 | 123.2 | 0.91 |
| A | DMD_E18A | DMD EXON18 | DMD_F2/DMD_R1 | 122 | 120.8 | 0 |
| A | DMD_E44A | DMD EXON44 | DMD_F2/DMD_R1 | 104 | 103.18 | 1.02 |
| A | DMD_E49B | DMD EXON49 | DMD_F2/DMD_R1 | 110 | 108.73 | 1.04 |
| A | DMD_E62A | DMD EXON62 | DMD_F2/DMD_R1 | 98 | 96.8 | 0.96 |
| A | REF20p_A | REFERENCE | DMD_F2/DMD_R1 | 119 | 118.73 | / |
| A | REF4q_B | REFERENCE | DMD_F2/DMD_R1 | 107 | 105.96 | / |
| A | REF5p_A | REFERENCE | DMD_F2/DMD_R1 | 95 | 92.81 | / |
| A | REF6q_A | REFERENCE | DMD_F2/DMD_R1 | 128 | 126.84 | / |
| A | DMD_E08B | DMD EXON08 | DMD_F2/DMD_R2 | 163 | 164.24 | 0.95 |
| A | DMD_E11B | DMD EXON11 | DMD_F2/DMD_R2 | 154 | 155.4 | 0.97 |
| A | DMD_E20A | DMD EXON20 | DMD_F2/DMD_R2 | 139 | 138.23 | 0 |
| A | DMD_E52A | DMD EXON52 | DMD_F2/DMD_R2 | 142 | 141.19 | 0.94 |
| A | DMD_E52C | DMD EXON52 | DMD_F2/DMD_R2 | 160 | 161.38 | 0.93 |
| A | DMD_E54A | DMD EXON54 | DMD_F2/DMD_R2 | 148 | 147.35 | 0.97 |
| A | DMD_E56A | DMD EXON56 | DMD_F2/DMD_R2 | 151 | 151.48 | 0.99 |
| A | DMD_E65A | DMD EXON65 | DMD_F2/DMD_R2 | 136 | 134.87 | 0.94 |
| A | REF14q_A | REFERENCE | DMD_F2/DMD_R2 | 133 | 131.43 | / |
| A | REF16p_A | REFERENCE | DMD_F2/DMD_R2 | 157 | 158.24 | / |
| A | REF2q_B | REFERENCE | DMD_F2/DMD_R2 | 166 | 167.39 | / |
| A | REF9q_B | REFERENCE | DMD_F2/DMD_R2 | 145 | 145.43 | / |
| B | DMD_E17A | DMD EXON17 | DMD_F2/DMD_R3 | 99 | 96.61 | 1.03 |
| B | DMD_E17C | DMD EXON17 | DMD_F2/DMD_R3 | 113 | 111.55 | 1.03 |
| B | DMD_E21C | DMD EXON21 | DMD_F2/DMD_R3 | 125 | 123.15 | 0 |
| B | DMD_E48B | DMD EXON48 | DMD_F2/DMD_R3 | 104 | 102.95 | 0.97 |
| B | DMD_E53C | DMD EXON53 | DMD_F2/DMD_R3 | 101 | 99.67 | 1.03 |
| B | DMD_E58A | DMD EXON58 | DMD_F2/DMD_R3 | 122 | 120.59 | 1 |
| B | DMD_E59A | DMD EXON59 | DMD_F2/DMD_R3 | 110 | 108.73 | 0.96 |
| B | DMD_E72A | DMD EXON72 | DMD_F2/DMD_R3 | 116 | 115.09 | 1.02 |
| B | DMD_E73A | DMD EXON73 | DMD_F2/DMD_R3 | 128 | 126.65 | 0.98 |
| B | REF10q_A | REFERENCE | DMD_F2/DMD_R3 | 93 | 92.06 | / |
| B | REF11p_B | REFERENCE | DMD_F2/DMD_R3 | 119 | 118.29 | / |
| B | REF18p_B | REFERENCE | DMD_F2/DMD_R3 | 107 | 106.2 | / |
| B | DMD_E16A | DMD EXON16 | DMD_F2/DMD_R4 | 154 | 155.18 | 0.96 |
| B | DMD_E16B | DMD EXON16 | DMD_F2/DMD_R4 | 148 | 149.05 | 1.18 |
| B | DMD_E25A | DMD EXON25 | DMD_F2/DMD_R4 | 139 | 138.79 | 0 |
| B | DMD_E30A | DMD EXON30 | DMD_F2/DMD_R4 | 136 | 134.72 | 0 |
| B | DMD_E37A | DMD EXON37 | DMD_F2/DMD_R4 | 163 | 163.48 | 0 |
| B | DMD_E43C | DMD EXON43 | DMD_F2/DMD_R4 | 160 | 160.74 | 0.87 |
| B | DMD_E46C | DMD EXON46 | DMD_F2/DMD_R4 | 166 | 166.08 | 1.18 |
| B | DMD_E63A | DMD EXON63 | DMD_F2/DMD_R4 | 151 | 151.38 | 1.06 |
| B | ChrX_A | ChrX Non-PAR | DMD_F2/DMD_R4 | 148 | 146.02 | 0.9 |
| B | REF16p_B | REFERENCE | DMD_F2/DMD_R4 | 157 | 157.23 | / |
| B | REF20p_B | REFERENCE | DMD_F2/DMD_R4 | 145 | 142.32 | / |
| B | REF2p_B | REFERENCE | DMD_F2/DMD_R4 | 133 | 131.1 | / |
| A | DMD_E05A | DMD EXON05 | DMD_F3/DMD_R1 | 116 | 113.74 | 0.99 |
| A | DMD_E07B | DMD EXON07 | DMD_F3/DMD_R1 | 122 | 119.71 | 0.99 |
| A | DMD_E10A | DMD EXON10 | DMD_F3/DMD_R1 | 113 | 110.62 | 1.03 |
| A | DMD_E51A | DMD EXON51 | DMD_F3/DMD_R1 | 125 | 122.06 | 0.96 |
| A | DMD_E51B | DMD EXON51 | DMD_F3/DMD_R1 | 101 | 97.89 | 0.95 |
| A | DMD_E55A | DMD EXON55 | DMD_F3/DMD_R1 | 110 | 107.27 | 0.99 |
| A | DMD_E55B | DMD EXON55 | DMD_F3/DMD_R1 | 104 | 101.74 | 0.93 |
| A | DMD_E61A | DMD EXON61 | DMD_F3/DMD_R1 | 98 | 94.88 | 1.1 |
| A | REF10q_B | REFERENCE | DMD_F3/DMD_R1 | 128 | 125.01 | / |
| A | REF12q_A | REFERENCE | DMD_F3/DMD_R1 | 107 | 104.7 | / |
| A | REF2p_A | REFERENCE | DMD_F3/DMD_R1 | 119 | 115.98 | / |
| A | REF6p_A | REFERENCE | DMD_F3/DMD_R1 | 95 | 92.7 | / |
| A | DMD_E06A | DMD EXON06 | DMD_F3/DMD_R2 | 136 | 134.22 | 1 |
| A | DMD_E09B | DMD EXON09 | DMD_F3/DMD_R2 | 142 | 140.95 | 0.94 |
| A | DMD_E13A | DMD EXON13 | DMD_F3/DMD_R2 | 154 | 153.36 | 1.02 |
| A | DMD_E44B | DMD EXON44 | DMD_F3/DMD_R2 | 160 | 160.42 | 0.88 |
| A | DMD_E44C | DMD EXON44 | DMD_F3/DMD_R2 | 163 | 163.71 | 0.95 |
| A | DMD_E57A | DMD EXON57 | DMD_F3/DMD_R2 | 139 | 137.9 | 0.96 |
| A | DMD_E57B | DMD EXON57 | DMD_F3/DMD_R2 | 148 | 147.35 | 0.93 |
| A | DMD_E64A | DMD EXON64 | DMD_F3/DMD_R2 | 151 | 150.11 | 0.97 |
| A | REF16q_B | REFERENCE | DMD_F3/DMD_R2 | 133 | 130.13 | / |
| A | REF19q_A | REFERENCE | DMD_F3/DMD_R2 | 157 | 157.24 | / |
| A | REF3q_C | REFERENCE | DMD_F3/DMD_R2 | 145 | 143.98 | / |
| A | REF9p_A | REFERENCE | DMD_F3/DMD_R2 | 166 | 166.34 | / |
| B | DMD_E26A | DMD EXON26 | DMD_F3/DMD_R3 | 110 | 107.5 | 0 |

TABLE 4-continued

Copy number calculation results based on peak intensity for each gene target site. LP SIZE refers to Ligation Product Size; REF refers to Reference; CE refers to Capillary Electrophoresis; Non-PAR refers to non-pseudoautosomal region.

| PANEL | PROBE LOCUS | TARGET REGION | PCR PRIMERS | LP SIZE | CE REF SIZE | COPY NUMBER MEASUREMENT |
|---|---|---|---|---|---|---|
| B | DMD_E27A | DMD EXON27 | DMD_F3/DMD_R3 | 101 | 99.78 | 0 |
| B | DMD_E43B | DMD EXON43 | DMD_F3/DMD_R3 | 98 | 95.66 | 0.96 |
| B | DMD_E48A | DMD EXON48 | DMD_F3/DMD_R3 | 118 | 115.51 | 1 |
| B | DMD_E48C | DMD EXON48 | DMD_F3/DMD_R3 | 128 | 125.33 | 1.2 |
| B | DMD_E70A | DMD EXON70 | DMD_F3/DMD_R3 | 115 | 112.29 | 1.01 |
| B | ChrX_C | ChrX Non-PAR | DMD_F3/DMD_R3 | 122 | 119.94 | 1.07 |
| B | ChrY_A | ChrY Non-PAR | DMD_F3/DMD_R3 | 104 | 101.87 | 1.01 |
| B | ChrY_B | ChrY Non-PAR | DMD_F3/DMD_R3 | 130 | 126.33 | 1.06 |
| B | REF20q_C | REFERENCE | DMD_F3/DMD_R3 | 107 | 104.85 | / |
| B | REF7p_B | REFERENCE | DMD_F3/DMD_R3 | 119 | 118.09 | / |
| B | REF8q_A | REFERENCE | DMD_F3/DMD_R3 | 95 | 93.55 | / |
| B | DMD_E32A | DMD EXON32 | DMD_F3/DMD_R4 | 163 | 162.74 | 0 |
| B | DMD_E33A | DMD EXON33 | DMD_F3/DMD_R4 | 142 | 140.58 | 0 |
| B | DMD_E35A | DMD EXON35 | DMD_F3/DMD_R4 | 148 | 147.63 | 0 |
| B | DMD_E38A | DMD EXON38 | DMD_F3/DMD_R4 | 151 | 150.99 | 0 |
| B | DMD_E39A | DMD EXON39 | DMD_F3/DMD_R4 | 166 | 164.62 | 0 |
| B | DMD_E46A | DMD EXON46 | DMD_F3/DMD_R4 | 163 | 160.1 | 0.96 |
| B | DMD_E68A | DMD EXON68 | DMD_F3/DMD_R4 | 157 | 154.02 | 0.95 |
| B | DMD_E78A | DMD EXON78 | DMD_F3/DMD_R4 | 136 | 133.08 | 0.98 |
| B | ChrY_C | ChrY Non-PAR | DMD_F3/DMD_R4 | 139 | 136.74 | 1.05 |
| B | REF2q_A | REFERENCE | DMD_F3/DMD_R4 | 157 | 157.2 | / |
| B | REF3q_B | REFERENCE | DMD_F3/DMD_R4 | 146 | 143.15 | / |
| B | REF4q_A | REFERENCE | DMD_F3/DMD_R4 | 133 | 131.02 | / |
| A | DMD_E03A | DMD EXON03 | DMD_F4/DMD_R1 | 110 | 111.76 | 1.03 |
| A | DMD_E12A | DMD EXON12 | DMD_F4/DMD_R1 | 114 | 113.87 | 0.95 |
| A | DMD_E15A | DMD EXON15 | DMD_F4/DMD_R1 | 119 | 119.22 | 0.98 |
| A | DMD_E20B | DMD EXON20 | DMD_F4/DMD_R1 | 107 | 109.13 | 0 |
| A | DMD_E45A | DMD EXON45 | DMD_F4/DMD_R1 | 96 | 98.31 | 0.95 |
| A | DMD_E47A | DMD EXON47 | DMD_F4/DMD_R1 | 98 | 100 | 0.98 |
| A | DMD_E60A | DMD EXON60 | DMD_F4/DMD_R1 | 101 | 102.36 | 0.98 |
| A | DMD_E61B | DMD EXON61 | DMD_F4/DMD_R1 | 122 | 122.48 | 0.96 |
| A | REF11p_A | REFERENCE | DMD_F4/DMD_R1 | 104 | 105.44 | / |
| A | REF3q_A | REFERENCE | DMD_F4/DMD_R1 | 125 | 126.72 | / |
| A | REF8p_A | REFERENCE | DMD_F4/DMD_R1 | 116 | 117.23 | / |
| A | REF9p_B | REFERENCE | DMD_F4/DMD_R1 | 92 | 94.43 | / |
| A | DMD_E03B | DMD EXON03 | DMD_F4/DMD_R2 | 130 | 132.06 | 0.97 |
| A | DMD_E04B | DMD EXON04 | DMD_F4/DMD_R2 | 148 | 151.02 | 1.07 |
| A | DMD_E12B | DMD EXON12 | DMD_F4/DMD_R2 | 160 | 164.03 | 1 |
| A | DMD_E14A | DMD EXON14 | DMD_F4/DMD_R2 | 139 | 141.8 | 1.02 |
| A | DMD_E18B | DMD EXON18 | DMD_F4/DMD_R2 | 151 | 154.36 | 0 |
| A | DMD_E19B | DMD EXON19 | DMD_F4/DMD_R2 | 157 | 160.11 | 0 |
| A | DMD_E54B | DMD EXON54 | DMD_F4/DMD_R2 | 136 | 137.26 | 1.01 |
| A | DMD_E56B | DMD EXON56 | DMD_F4/DMD_R2 | 145 | 148.68 | 1.14 |
| A | REF11q_A | REFERENCE | DMD_F4/DMD_R2 | 163 | 167.72 | / |
| A | REF12p_A | REFERENCE | DMD_F4/DMD_R2 | 154 | 158.37 | / |
| A | REF3p_C | REFERENCE | DMD_F4/DMD_R2 | 133 | 134.98 | / |
| A | REF7p_A | REFERENCE | DMD_F4/DMD_R2 | 142 | 144.34 | / |
| B | DMD_E21B | DMD EXON21 | DMD_F4/DMD_R3 | 98 | 100.62 | 0 |
| B | DMD_E23A | DMD EXON23 | DMD_F4/DMD_R3 | 95 | 97.78 | 0 |
| B | DMD_E24A | DMD EXON24 | DMD_F4/DMD_R3 | 107 | 107.99 | 0 |
| B | DMD_E28A | DMD EXON28 | DMD_F4/DMD_R3 | 113 | 114.88 | 0 |
| B | DMD_E31A | DMD EXON31 | DMD_F4/DMD_R3 | 128 | 126.18 | 0 |
| B | DMD_E36A | DMD EXON36 | DMD_F4/DMD_R3 | 121 | 120.6 | 0 |
| B | DMD_E43A | DMD EXON43 | DMD_F4/DMD_R3 | 110 | 110.95 | 1.05 |
| B | DMD_E74A | DMD EXON74 | DMD_F4/DMD_R3 | 122 | 124.12 | 1.01 |
| B | DMD_E75A | DMD EXON75 | DMD_F4/DMD_R3 | 101 | 102.59 | 1 |
| B | REF10p_C | REFERENCE | DMD_F4/DMD_R3 | 116 | 118.4 | / |
| B | REF11q_B | REFERENCE | DMD_F4/DMD_R3 | 104 | 106.31 | / |
| B | REF19q_C | REFERENCE | DMD_F4/DMD_R3 | 92 | 94.78 | / |
| B | DMD_E01A | DMD EXON01 | DMD_F4/DMD_R4 | 160 | 163.69 | 0.9 |
| B | DMD_E01B | DMD EXON01 | DMD_F4/DMD_R4 | 155 | 158.11 | 1.08 |
| B | DMD_E02A | DMD EXON02 | DMD_F4/DMD_R4 | 167 | 168.9 | 0.9 |
| B | DMD_E02B | DMD EXON02 | DMD_F4/DMD_R4 | 169 | 171.8 | 0.99 |
| B | DMD_E02C | DMD EXON02 | DMD_F4/DMD_R4 | 145 | 147.83 | 1.02 |
| B | DMD_E50A | DMD EXON50 | DMD_F4/DMD_R4 | 148 | 152.18 | 0.97 |
| B | DMD_E50B | DMD EXON50 | DMD_F4/DMD_R4 | 133 | 135.04 | 1.01 |
| B | DMD_E50C | DMD EXON50 | DMD_F4/DMD_R4 | 157 | 161.27 | 0.98 |
| B | REF10p_B | REFERENCE | DMD_F4/DMD_R4 | 142 | 144.28 | / |
| B | REF20q_B | REFERENCE | DMD_F4/DMD_R4 | 154 | 155.12 | / |
| B | REF3p_B | REFERENCE | DMD_F4/DMD_R4 | 163 | 166.76 | / |
| B | REF9q_A | REFERENCE | DMD_F4/DMD_R4 | 130 | 131.56 | / |

Example 3: Multiplex Point Mutation Screening

This example provides an exemplary method of multiplex point mutation screening according to the present invention. In this example, as in Example 2, there were 192 target sequences including 129 sites in the Duchenne muscular dystrophy (DMD) gene, and 63 reference sites on chromosomes X, Y, 2-12, 14, 16-20. Some mutations causing DMD are point mutations in the dystrophin gene. The multiplex point mutation screening in the DMD gene employed fluorescent dye labeled forward primers and reverse primers with stuffer sequences according to the scheme in FIG. 6.

In this exemplary mutation screening method, the same probes and primers as those designed and used in Example 2 were used for the hybridization, ligation, and amplification reactions except that the test genomic DNA was obtained from another male DMD patient. The amplification products were analyzed through capillary electrophoresis, the peak intensities were obtained, and the copy numbers for each target site were calculated as detailed in Example 2. For sake of brevity, the descriptions of the probes, primers, ligation reaction, amplification reaction, data procurement, and copy number calculation, are not repeated in this example.

Figure 12A:
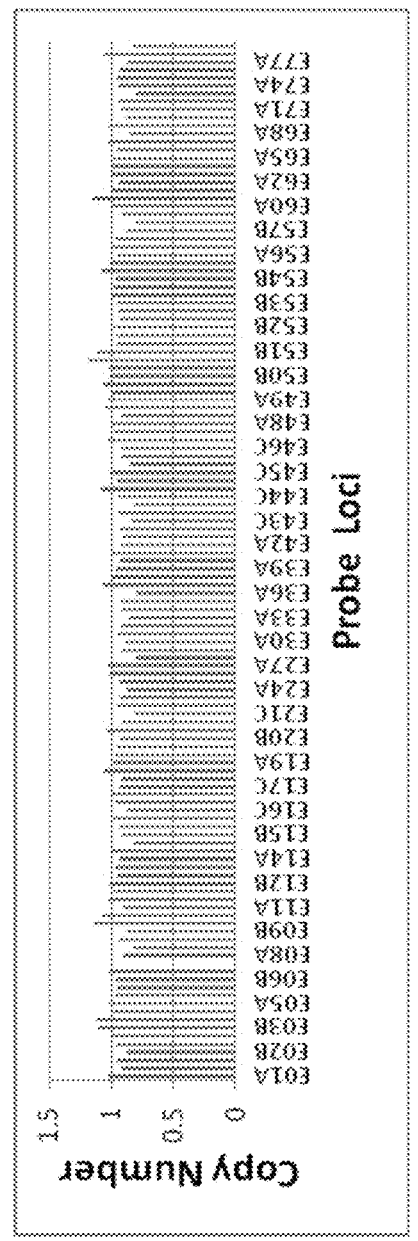
FIG. 12A shows a chart depicting the calculated copy numbers of all gene target sites in the dystrophin gene. The X axis refers to names of each gene target site. The Y axis refers to the calculated copy number for each gene target site.
Figure 12B:
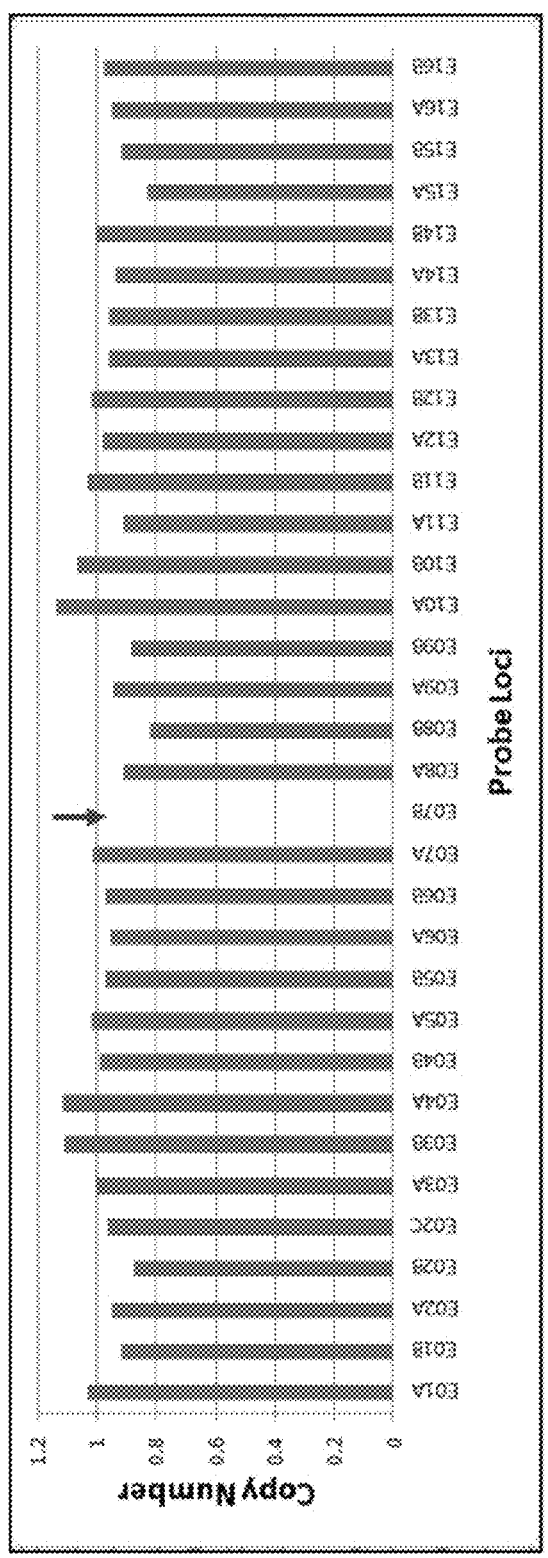
FIG. 12B is a close-up view of a part of the chart in FIG. 12A, showing the target sites E01A to E16B.
Figure 12C:
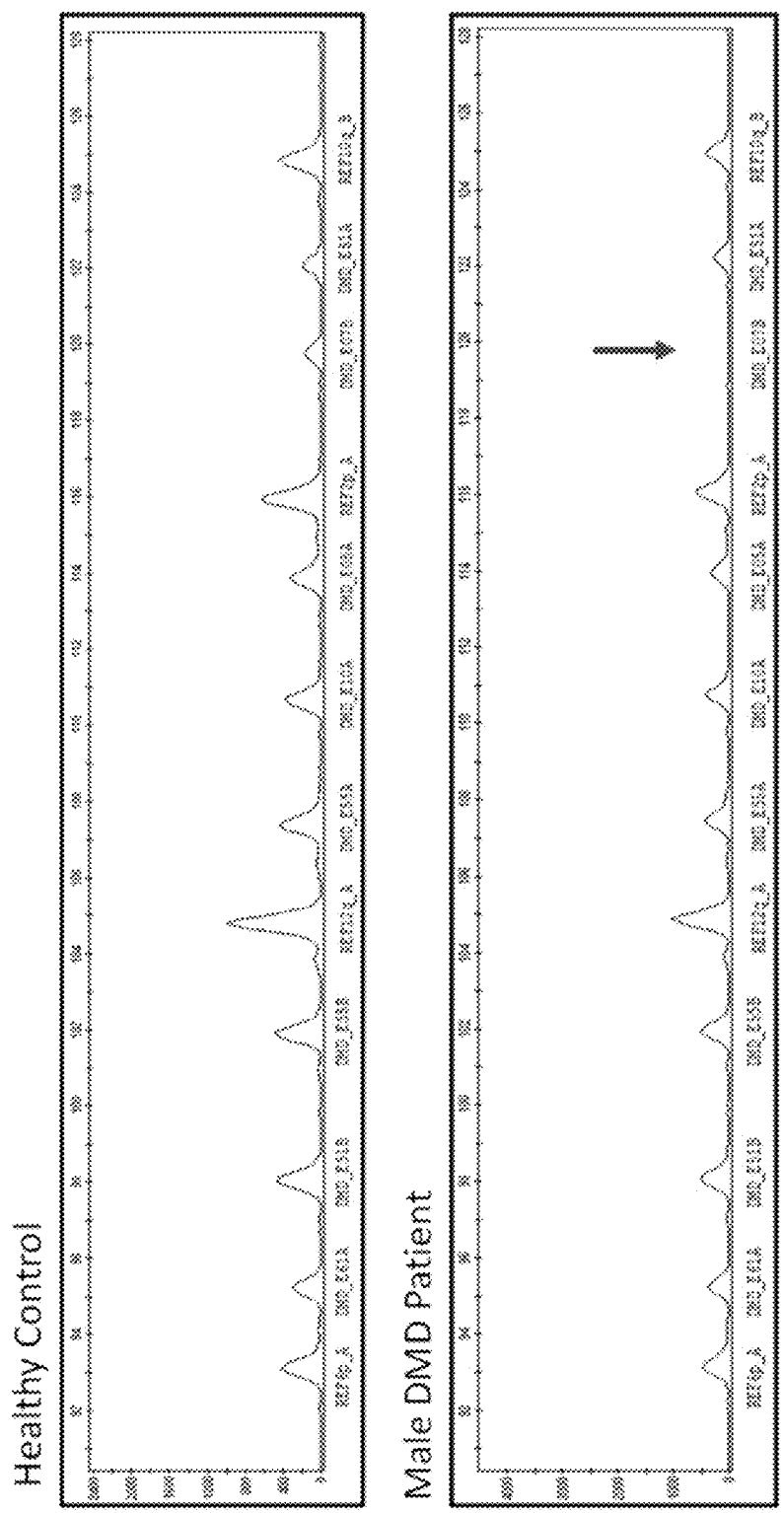
FIG. 12C shows the two chromatograms including the peak for DMD_E07B gene target site: one from a healthy control and the other from a male DMD patient.
Figure 12D:
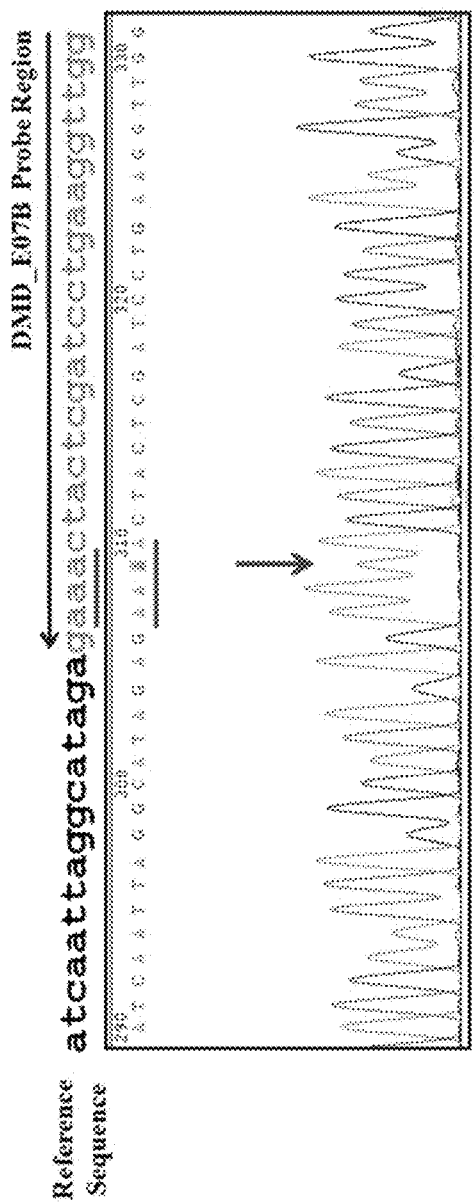
FIG. 12D shows a chromatogram of DNA sequencing result of the region surrounding the DMD_07EB gene target site.

The copy number thus calculated for all gene target sites are shown in FIG. 12A and partially shown in FIG. 12B. The copy number for E07B (exon 7B gene target site in the dystrophin gene) was zero, suggesting that the probes for this site could not match perfectly with the target site. On the other hand, the copy number for E07A was about 1, meaning that part of exon7 had a normal copy number and there was no whole exon 7 deletion in the test DNA sample. The lack of amplification product for the E07B gene target site could also be seen in the chromatograms (FIG. 12C), which showed that the peak corresponding to E07B gene target site was missing in the DMD test panel (lower panel) when compared to the peak in the control panel (upper panel). The E07B gene target site was then sequenced to find that there was an adenosine ("A") insertion in the E07B probe region. See the adenosine position as indicated by the arrow in FIG. 12D. Because of the adenosine insertion in exon 7 of the dystrophin gene, the DMD_07B_5 probe SEQ ID NO: 294 was unable to anneal to the target site, leading to the disappearance of the peak corresponding to the Exon07B target site.

Therefore, the multiplex mutation screening method can identify gene regions where mutations may exist. The screening may be carried out simultaneously with the detection for CNVs, as demonstrated in Examples 2 and 3 where the same set of probes and primers were used and the same procedure was followed to obtain electrophoresis data.

Example 4: Detection of Human Chromosome 21 Copy Number Changes

This example demonstrates a method of detecting human chromosome 21 copy number changes according to the present invention. In this example, a mere 2% increase of the copy number of human chromosome 21 in a sample could be detected. The method employed fluorescent dye labeled forward primers and reverse primers with stuffer sequences according to the scheme in FIG. 5.

In the exemplary method, probes were designed to cover 192 target sites including 96 sites on human chromosome 21, and 96 reference sites on human chromosomes 2-12, 14, and 16-20. For each target site, a probe pair was designed including a 3' probe (the right probe) and a 5' probe (the left probe). The 3' and 5' probes were designed in a manner so that when both are hybridized to the target sequence under a suitable condition, there is no gap between the two probes. The probes were synthesized by Life Technologies Corporation. The names, sequence ID numbers, primer binding sequences, and stuffer sequences of the 384 probes (192 probe pairs) are shown in Table 5. The probe pairs for the target sites on Chromosome 21 were SEQ ID NOs: 559-750. The probe pairs for the reference sites were SEQ ID NOs: 751-942.

Similar to the design in Example 2, for each 3' probe, the 5' end nucleotide was phosphorylated to provide a phosphate which would be connected to the hydroxyl group in the 3' end nucleotide of the 5' probe. Each 3' probe included a locus specific hybridization sequence (LSHS) in the 5' portion followed by a stuffer L2 sequence, and a primer binding sequence Y in the 3' portion. In this example, four primer binding sequence Y: Chr21_Y1, SEQ ID NO: 955; Chr21_Y2, SEQ ID NO: 956; Chr21_Y3, SEQ ID NO: 957; and Chr21_Y4, SEQ ID NO: 958 were used in the 3' probes.

Similar to the design in Example 2, each 5' probe included a locus specific hybridization sequence (LSHS) in the 3' portion followed by a stuffer L1 sequence and a primer binding sequence X in the 5' portion. In this example, four primer binding sequence X: Chr21_X1, SEQ ID NO: 951; Chr21_X2, SEQ ID NO: 952; Chr21_X3, SEQ ID NO: 953; and Chr21_X4, SEQ ID NO: 954 were used in the 5' probes.

In addition, similar to the design in Example 2, four forward primers and four reverse primers were designed for amplifying the ligation products. The four forward primers (Chr21_F1, SEQ ID NO: 943; Chr21_F2, SEQ ID NO: 944; Chr21_F3, SEQ ID NO: 945; and Chr21_F4, SEQ ID NO: 946) had unique sequences that were consistent with the four primer binding sequence X (Chr21_X1, SEQ ID NO: 951; Chr21_X2, SEQ ID NO: 952; Chr21_X3, SEQ ID NO: 953; and Chr21_X4, SEQ ID NO: 954), respectively. The four forward primers: Chr21_F1, Chr21_F2, Chr21_F3 and Chr21_F4 were labeled on the 5' ends with four different fluorescent dyes: FAM-blue, VIC-green, NED-yellow, and PET-red, respectively. The four reverse primers (Chr21_R1, SEQ ID NO: 947; Chr21_R2, SEQ ID NO: 948; Chr21_R3, SEQ ID NO: 949; and Chr21_R4, SEQ ID NO: 950) had unique sequences that were reversely complementary to the four primer binding sequence Y (Chr21_Y1, SEQ ID NO: 955; Chr21_Y2, SEQ ID NO: 956; Chr21_Y3, SEQ ID NO: 957; and Chr21_Y4, SEQ ID NO: 958), respectively. The Chr21_R2 and Chr21_R4 reverse primers also had a stuffer sequence Chr21_R_Stuffer, SEQ ID NO: 959 in the 5' portion. All primers were synthesized by Life Technologies Corporation.

TABLE 5

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 559 | Chr21_01_3 |  |  | ATT | Y1 |
| 560 | Chr21_01_5 | X2 |  |  |  |
| 561 | Chr21_02_3 |  |  | ATTACGCGAT | Y1 |
| 562 | Chr21_02_5 | X3 |  |  |  |
| 563 | Chr21_03_3 |  |  | ATTACGCG | Y1 |
| 564 | Chr21_03_5 | X3 | ATTACGCGA |  |  |
| 565 | Chr21_04_3 |  |  | ATTACGCGATTACG | Y2 |
| 566 | Chr21_04_5 | X1 | ATTAC |  |  |
| 567 | Chr21_05_3 |  |  | ATTACGCGATTA | Y1 |
| 568 | Chr21_05_5 | X2 | ATT |  |  |
| 569 | Chr21_06_3 |  |  | ATTACGCGATTA | Y2 |
| 570 | Chr21_06_5 | X1 | ATTACG |  |  |
| 571 | Chr21_07_3 |  |  | ATTACG | Y2 |
| 572 | Chr21_07_5 | X3 |  |  |  |
| 573 | Chr21_08_3 |  |  | ATTACGCGATT | Y2 |
| 574 | Chr21_08_5 | X1 | AT |  |  |
| 575 | Chr21_09_3 |  |  | ATTACGCGAT | Y2 |
| 576 | Chr21_09_5 | X3 |  |  |  |
| 577 | Chr21_10_3 |  |  | ATTACG | Y3 |
| 578 | Chr21_10_5 | X3 |  |  |  |
| 579 | Chr21_11_3 |  |  | ATTACGCGAT | Y3 |
| 580 | Chr21_11_5 | X3 |  |  |  |
| 581 | Chr21_12_3 |  |  | ATTACGCGATTA | Y3 |
| 582 | Chr21_12_5 | X1 | ATTACGCG |  |  |
| 583 | Chr21_13_3 |  |  | A | Y4 |
| 584 | Chr21_13_5 | X4 |  |  |  |
| 585 | Chr21_14_3 |  |  | ATTACGCGAT | Y4 |
| 586 | Chr21_14_5 | X2 |  |  |  |
| 587 | Chr21_15_3 |  |  | ATTACGCGAT | Y2 |
| 588 | Chr21_15_5 | X2 | ATTAC |  |  |
| 589 | Chr21_16_3 |  |  | ATTACGCGA | Y2 |
| 590 | Chr21_16_5 | X3 | ATTACGCG |  |  |
| 591 | Chr21_17_3 |  |  | ATTACGCGATTAC | Y2 |
| 592 | Chr21_17_5 | X2 | ATTAC |  |  |
| 593 | Chr21_18_3 |  |  | ATTACG | Y4 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 594 | Chr21_18_5 | X1 | | | |
| 595 | Chr21_19_3 | | | ATTACGCGATT | Y3 |
| 596 | Chr21_19_5 | X1 | | | |
| 597 | Chr21_20_3 | | | ATTACGCGAT | Y1 |
| 598 | Chr21_20_5 | X4 | | | |
| 599 | Chr21_21_3 | | | ATTACGCGATTA | Y3 |
| 600 | Chr21_21_5 | X3 | ATT | | |
| 601 | Chr21_22_3 | | | ATTACGCGA | Y4 |
| 602 | Chr21_22_5 | X2 | ATTACGC | | |
| 603 | Chr21_23_3 | | | ATTACGCGATTA | Y3 |
| 604 | Chr21_23_5 | X3 | ATTACGC | | |
| 605 | Chr21_24_3 | | | ATTACGCGA | Y1 |
| 606 | Chr21_24_5 | X4 | | | |
| 607 | Chr21_25_3 | | | ATTA | Y1 |
| 608 | Chr21_25_5 | X4 | | | |
| 609 | Chr21_26_3 | | | ATTA | Y2 |
| 610 | Chr21_26_5 | X4 | | | |
| 611 | Chr21_27_3 | | | ATTACGCGATTA | Y1 |
| 612 | Chr21_27_5 | X4 | ATTAC | | |
| 613 | Chr21_28_3 | | | AT | Y2 |
| 614 | Chr21_28_5 | X4 | | | |
| 615 | Chr21_29_3 | | | ATT | Y2 |
| 616 | Chr21_29_5 | X2 | | | |
| 617 | Chr21_30_3 | | | ATTACGCGA | Y2 |
| 618 | Chr21_30_5 | X4 | | | |
| 619 | Chr21_31_3 | | | ATTACGCGATT | Y3 |
| 620 | Chr21_31_5 | X2 | ATTACGCG | | |
| 621 | Chr21_32_3 | | | ATTA | Y3 |
| 622 | Chr21_32_5 | X4 | | | |
| 623 | Chr21_33_3 | | | ATTA | Y4 |
| 624 | Chr21_33_5 | X2 | | | |
| 625 | Chr21_34_3 | | | ATTACGCG | Y4 |
| 626 | Chr21_34_5 | X4 | AT | | |
| 627 | Chr21_35_3 | | | ATTACGCG | Y3 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 628 | Chr21_35_5 | X2 | ATTACGCGAT | | |
| 629 | Chr21_36_3 | | | ATTACGCGAT | Y4 |
| 630 | Chr21_36_5 | X3 | AT | | |
| 631 | Chr21_37_3 | | | ATTACGCGATT | Y1 |
| 632 | Chr21_37_5 | X2 | | | |
| 633 | Chr21_38_3 | | | ATTACGC | Y1 |
| 634 | Chr21_38_5 | X1 | | | |
| 635 | Chr21_39_3 | | | ATTACGCGATT | Y2 |
| 636 | Chr21_39_5 | X2 | | | |
| 637 | Chr21_40_3 | | | ATTACGCGATTAC | Y1 |
| 638 | Chr21_40_5 | X3 | AT | | |
| 639 | Chr21_41_3 | | | ATTACGC | Y2 |
| 640 | Chr21_41_5 | X1 | | | |
| 641 | Chr21_42_3 | | | ATTACGCGA | Y3 |
| 642 | Chr21_42_5 | X4 | | | |
| 643 | Chr21_43_3 | | | ATTACGC | Y3 |
| 644 | Chr21_43_5 | X1 | | | |
| 645 | Chr21_44_3 | | | ATTACGCGAT | Y2 |
| 646 | Chr21_44_5 | X4 | | | |
| 647 | Chr21_45_3 | | | ATTACGCGATTAC | Y3 |
| 648 | Chr21_45_5 | X1 | | | |
| 649 | Chr21_46_3 | | | AT | Y4 |
| 650 | Chr21_46_5 | X2 | | | |
| 651 | Chr21_47_3 | | | ATTACGCGATTACGC | Y4 |
| 652 | Chr21_47_5 | X3 | ATTACGCGATTACGCGATT | | |
| 653 | Chr21_48_3 | | | ATTACGCGATTA | Y1 |
| 654 | Chr21_48_5 | X3 | ATTACGCGATTAC | | |
| 655 | Chr21_49_3 | | | ATTACGCGATTACG | Y2 |
| 656 | Chr21_49_5 | X3 | ATTACGCGAT | | |
| 657 | Chr21_50_3 | | | ATTACGCGATTAC | Y4 |
| 658 | Chr21_50_5 | X1 | ATTAC | | |
| 659 | Chr21_51_3 | | | ATTACGCGATT | Y3 |
| 660 | Chr21_51_5 | X2 | | | |
| 661 | Chr21_52_3 | | | ATTACGCGATTA | Y4 |
| 662 | Chr21_52_5 | X4 | ATTA | | |

TABLE 5-continued

Names, sequence ID numbers, primer binding sequences and stuffer
sequences for the probes used in human chromosome 21 copy number
change detection. X1, X2, X3 and X4 refer to Chr21_X1, SEQ ID NO: 951;
Chr21_X2, SEQ ID NO: 952; Chr21_X3, SEQ ID NO: 953; and Chr21_X4,
SEQ ID NO: 954, respectively. Y1, Y2, Y3 and Y4 refer to Chr21_Y1,
SEQ ID NO: 955; Chr21_Y2, SEQ ID NO: 956; Chr21_Y3,
SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 663 | Chr21_53_3 | | | ATTACGCGATTA | Y1 |
| 664 | Chr21_53_5 | X2 | ATTAC | | |
| 665 | Chr21_54_3 | | | ATTA | Y1 |
| 666 | Chr21_54_5 | X1 | | | |
| 667 | Chr21_55_3 | | | ATTACGCGATT | Y2 |
| 668 | Chr21_55_5 | X4 | ATTAC | | |
| 669 | Chr21_56_3 | | | ATTACGCGATTAC | Y3 |
| 670 | Chr21_56_5 | X4 | ATTAC | | |
| 671 | Chr21_57_3 | | | ATTA | Y4 |
| 672 | Chr21_57_5 | X3 | | | |
| 673 | Chr21_58_3 | | | ATTACGCGAT | Y3 |
| 674 | Chr21_58_5 | X1 | ATTACGCGA | | |
| 675 | Chr21_59_3 | | | ATTACGCGATTAC | Y2 |
| 676 | Chr21_59_5 | X3 | | | |
| 677 | Chr21_60_3 | | | AT | Y1 |
| 678 | Chr21_60_5 | X3 | | | |
| 679 | Chr21_61_3 | | | ATTA | Y2 |
| 680 | Chr21_61_5 | X1 | | | |
| 681 | Chr21_62_3 | | | ATTACGCGA | Y2 |
| 682 | Chr21_62_5 | X2 | ATTACGCG | | |
| 683 | Chr21_63_3 | | | ATTACGCGATTAC | Y3 |
| 684 | Chr21_63_5 | X2 | | | |
| 685 | Chr21_64_3 | | | AT | Y2 |
| 686 | Chr21_64_5 | X3 | | | |
| 687 | Chr21_65_3 | | | ATTACGCGATTA | Y4 |
| 688 | Chr21_65_5 | X4 | | | |
| 689 | Chr21_66_3 | | | ATTACGCGATT | Y3 |
| 690 | Chr21_66_5 | X4 | ATTACG | | |
| 691 | Chr21_67_3 | | | ATTACGCGATTAC | Y4 |
| 692 | Chr21_67_5 | X1 | | | |
| 693 | Chr21_68_3 | | | ATTA | Y3 |
| 694 | Chr21_68_5 | X1 | | | |
| 695 | Chr21_69_3 | | | ATTACGCGATTACG | Y4 |
| 696 | Chr21_69_5 | X2 | ATTACGCGATTAC | | |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 697 | Chr21_70_3 | | | ATTACGCGATTAC | Y4 |
| 698 | Chr21_70_5 | X3 | ATT | | |
| 699 | Chr21_71_3 | | | ATTACGC | Y1 |
| 700 | Chr21_71_5 | X2 | | | |
| 701 | Chr21_72_3 | | | ATTACGC | Y2 |
| 702 | Chr21_72_5 | X2 | | | |
| 703 | Chr21_73_3 | | | ATTACGCGATTA | Y4 |
| 704 | Chr21_73_5 | X3 | ATTACGCGATT | | |
| 705 | Chr21_74_3 | | | ATTACGC | Y3 |
| 706 | Chr21_74_5 | X2 | | | |
| 707 | Chr21_75_3 | | | ATTACGCGATTAC | Y1 |
| 708 | Chr21_75_5 | X2 | ATTACGCG | | |
| 709 | Chr21_76_3 | | | ATTACGC | Y3 |
| 710 | Chr21_76_5 | X3 | ATTACGCGAT | | |
| 711 | Chr21_77_3 | | | ATTACGCGATTAC | Y1 |
| 712 | Chr21_77_5 | X1 | ATTACG | | |
| 713 | Chr21_78_3 | | | ATT | Y3 |
| 714 | Chr21_78_5 | X2 | | | |
| 715 | Chr21_79_3 | | | ATTACGCGATTA | Y1 |
| 716 | Chr21_79_5 | X1 | | | |
| 717 | Chr21_80_3 | | | ATTACGCGATTA | Y4 |
| 718 | Chr21_80_5 | X4 | ATT | | |
| 719 | Chr21_81_3 | | | ATTACGCGATTAC | Y1 |
| 720 | Chr21_81_5 | X1 | ATT | | |
| 721 | Chr21_82_3 | | | ATTACGCGATTACGC | Y2 |
| 722 | Chr21_82_5 | X1 | A | | |
| 723 | Chr21_83_3 | | | ATTA | Y4 |
| 724 | Chr21_83_5 | X1 | | | |
| 725 | Chr21_84_3 | | | ATTACGCGATTAC | Y3 |
| 726 | Chr21_84_5 | X4 | | | |
| 727 | Chr21_85_3 | | | AT | Y3 |
| 728 | Chr21_85_5 | X3 | | | |
| 729 | Chr21_86_3 | | | AT | Y4 |
| 730 | Chr21_86_5 | X3 | | | |
| 731 | Chr21_87_3 | | | ATTACG | Y4 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 732 | Chr21_87_5 | X1 | ATTACGCGATT | | |
| 733 | Chr21_88_3 | | | AT | Y3 |
| 734 | Chr21_88_5 | X4 | A | | |
| 735 | Chr21_89_3 | | | ATTA | Y4 |
| 736 | Chr21_89_5 | X4 | | | |
| 737 | Chr21_90_3 | | | ATTACGCGATT | Y1 |
| 738 | Chr21_90_5 | X4 | ATTACGC | | |
| 739 | Chr21_91_3 | | | ATTACGC | Y1 |
| 740 | Chr21_91_5 | X3 | | | |
| 741 | Chr21_92_3 | | | ATTACGCGATTAC | Y4 |
| 742 | Chr21_92_5 | X2 | | | |
| 743 | Chr21_93_3 | | | ATT | Y1 |
| 744 | Chr21_93_5 | X4 | | | |
| 745 | Chr21_94_3 | | | ATTACGCGATTAC | Y1 |
| 746 | Chr21_94_5 | X1 | ATTACGC | | |
| 747 | Chr21_95_3 | | | ATTACGCGATT | Y4 |
| 748 | Chr21_95_5 | X1 | | | |
| 749 | Chr21_96_3 | | | ATTACGCGATTACGC | Y2 |
| 750 | Chr21_96_5 | X4 | ATTA | | |
| 751 | REF10p_A_3 | | | | Y2 |
| 752 | REF10p_A_5 | X1 | | | |
| 753 | REF10p_B_3 | | | ATTAC | Y1 |
| 754 | REF10p_B_5 | X4 | | | |
| 755 | REF10p_C_3 | | | ATTAC | Y4 |
| 756 | REF10p_C_5 | X4 | | | |
| 757 | REF10p_D_3 | | | ATTACGCGATT | Y3 |
| 758 | REF10p_D_5 | X4 | | | |
| 759 | REF10Q_A_3 | | | ATTACGCG | Y1 |
| 760 | REF10Q_A_5 | X2 | ATTAC | | |
| 761 | REF10Q_B_3 | Y3 | | | |
| 762 | REF10Q_B_5 | X2 | | | |
| 763 | REF10Q_C_3 | | | ATTACGCGATTA | Y1 |
| 764 | REF10Q_C_5 | X3 | ATTACGCGATTACGCG | | |
| 765 | REF11p_A_3 | | | ATTACGC | Y1 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 766 | REF11p_A_5 | X4 | | | |
| 767 | REF11p_B_3 | | | ATTACGCGA | Y3 |
| 768 | REF11p_B_5 | X1 | ATTAC | | |
| 769 | REF11p_C_3 | | | ATTACGCGATTAC | Y3 |
| 770 | REF11p_C_5 | X2 | AT | | |
| 771 | REF11p_D_3 | | | ATTA | Y1 |
| 772 | REF11p_D_5 | X1 | | | |
| 773 | REF11q_A_3 | | | | Y4 |
| 774 | REF11q_A_5 | X3 | ATTACGCGATTA | | |
| 775 | REF11q_B_3 | | | ATTACGCGATTAC | Y2 |
| 776 | REF11q_B_5 | X4 | ATTACGCGATTA | | |
| 777 | REF11q_C_3 | | | ATTACG | Y3 |
| 778 | REF11q_C_5 | X4 | A | | |
| 779 | REF12p_A_3 | | | AT | Y4 |
| 780 | REF12p_A_5 | X4 | ATTACGCGAT | | |
| 781 | REF12p_B_3 | | | ATTACGCGATTAC | Y4 |
| 782 | REF12p_B_5 | X3 | ATTACGCGATTACGC | | |
| 783 | REF12p_C_3 | | | ATTACGCGATTACG | Y2 |
| 784 | REF12p_C_5 | X4 | ATT | | |
| 785 | REF12q_A_3 | | | ATTACGC | Y1 |
| 786 | REF12q_A_5 | X3 | | | |
| 787 | REF12q_B_3 | | | ATTACGCGAT | Y4 |
| 788 | REF12q_B_5 | X2 | ATTAC | | |
| 789 | REF12q_C_3 | | | ATTACGCGA | Y4 |
| 790 | REF12q_C_5 | X1 | | | |
| 791 | REF14q_A_3 | | | | Y2 |
| 792 | REF14q_A_5 | X2 | | | |
| 793 | REF14q_B_3 | | | | Y3 |
| 794 | REF14q_B_5 | X1 | | | |
| 795 | REF16p_A_3 | | | | Y2 |
| 796 | REF16p_A_5 | X4 | | | |
| 797 | REF16p_B_3 | | | | Y3 |
| 798 | REF16p_B_5 | X2 | ATTACGCGATTACGCGA | | |
| 799 | REF16p_C_3 | | | ATTACGCGATTAC | Y2 |
| 800 | REF16p_C_5 | X2 | ATTACG | | |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 801 | REF16p_D_3 | | | ATTACGCGATTACG | Y4 |
| 802 | REF16p_D_5 | X2 | ATTACG | | |
| 803 | REF16q_A_3 | | | ATTACGCGAT | Y3 |
| 804 | REF16q_A_5 | X1 | ATTACG | | |
| 805 | REF16q_B_3 | | | ATTACGCGATTA | Y3 |
| 806 | REF16q_B_5 | X4 | ATTACGCGA | | |
| 807 | REF16q_C_3 | | | ATTAC | Y1 |
| 808 | REF16q_C_5 | X3 | ATTACGCG | | |
| 809 | REF16q_D_3 | | | | Y2 |
| 810 | REF16q_D_5 | X3 | | | |
| 811 | REF17q_A_3 | | | | Y4 |
| 812 | REF17q_A_5 | X3 | AT | | |
| 813 | REF17q_B_3 | | | ATTACGCGATTA | Y2 |
| 814 | REF17q_B_5 | X1 | ATTACGCGATTACG | | |
| 815 | REF18p_A_3 | | | ATTACGCGATTA | Y1 |
| 816 | REF18p_A_5 | X1 | AT | | |
| 817 | REF18p_B_3 | | | ATTACGC | Y3 |
| 818 | REF18p_B_5 | X2 | | | |
| 819 | REF19p_A_3 | | | | Y4 |
| 820 | REF19p_A_5 | X4 | | | |
| 821 | REF19p_B_3 | | | AT | Y4 |
| 822 | REF19p_B_5 | X2 | | | |
| 823 | REF19q_A_3 | | | ATT | Y2 |
| 824 | REF19q_A_5 | X1 | | | |
| 825 | REF19q_B_3 | | | ATTACGCGATTAC | Y2 |
| 826 | REF19q_B_5 | X3 | ATTACGC | | |
| 827 | REF19q_C_3 | | | | Y4 |
| 828 | REF19q_C_5 | X1 | | | |
| 829 | REF19q_D_3 | Y3 | | | |
| 830 | REF19q_D_5 | | | | Y4 |
| 831 | REF20p_A_3 | | | ATTACGCGATT | Y1 |
| 832 | REF20p_A_5 | X2 | ATTA | | |
| 833 | REF20p_B_3 | | | A | Y2 |
| 834 | REF20p_B_5 | X4 | ATTACGCGAT | | |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 835 | REF20p_C_3 | | | ATTACGCGA | Y4 |
| 836 | REF20p_C_5 | X2 | A | | |
| 837 | REF20q_A_3 | | | ATTACGCGATTAC | Y2 |
| 838 | REF20q_A_5 | X3 | | | |
| 839 | REF20q_B_3 | | | ATTACGCGATTA | Y2 |
| 840 | REF20q_B_5 | X1 | ATTACGC | | |
| 841 | REF20q_C_3 | | | ATTACGCGAT-TACGCGA | Y4 |
| 842 | REF20q_C_5 | X4 | ATTAC | | |
| 843 | REF20q_D_3 | | | ATTAC | Y2 |
| 844 | REF20q_D_5 | X2 | | | |
| 845 | REF20q_E_3 | | | ATT | Y3 |
| 846 | REF20q_E_5 | X3 | | | |
| 847 | REF2p_A_3 | | | ATTACGCGAT | Y1 |
| 848 | REF2p_A_5 | X3 | ATTACGCGA | | |
| 849 | REF2p_B_3 | | | ATTACGCGATTAC | Y3 |
| 850 | REF2p_B_5 | X3 | ATTACGCGATT | | |
| 851 | REF2p_C_3 | | | | Y4 |
| 852 | REF2p_C_5 | X2 | | | |
| 853 | REF2p_D_3 | | | ATT | Y1 |
| 854 | REF2p_D_5 | X2 | | | |
| 855 | REF2q_A_3 | | | ATTACGCGATTACG | Y4 |
| 856 | REF2q_A_5 | X3 | ATTACG | | |
| 857 | REF2q_B_3 | | | ATTACGCGATTA | Y2 |
| 858 | REF2q_B_5 | X2 | ATTACGCGAT | | |
| 859 | REF3p_A_3 | | | ATTACG | Y3 |
| 860 | REF3p_A_5 | X1 | | | |
| 861 | REF3p_B_3 | | | ATTACGCGATTAC | Y4 |
| 862 | REF3p_B_5 | X4 | ATTACGCGATTAC | | |
| 863 | REF3p_C_3 | | | ATTA | Y2 |
| 864 | REF3p_C_5 | X4 | | | |
| 865 | REF3p_D_3 | | | ATTAC | Y1 |
| 866 | REF3p_D_5 | X3 | | | |
| 867 | REF3p_E_3 | | | ATTACGCGA | Y1 |
| 868 | REF3p_E_5 | X1 | | | |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 869 | REF3q_A_3 | | | ATTACGCGATTACG | Y1 |
| 870 | REF3q_A_5 | X4 | ATTACGCGATTAC | | |
| 871 | REF3q_B_3 | | | ATTACGCGA | Y4 |
| 872 | REF3q_B_5 | X3 | ATT | | |
| 873 | REF3q_C_3 | | | A | Y2 |
| 874 | REF3q_C_5 | X3 | | | |
| 875 | REF3q_D_3 | | | ATTAC | Y4 |
| 876 | REF3q_D_5 | X1 | | | |
| 877 | REF4q_A_3 | | | | Y4 |
| 878 | REF4q_A_5 | X3 | | | |
| 879 | REF4q_B_3 | | | | Y2 |
| 880 | REF4q_B_5 | X1 | ATTACGCGATTAC | | |
| 881 | REF4q_C_3 | | | ATTACGC | Y1 |
| 882 | REF4q_C_5 | X2 | | | |
| 883 | REF5p_A_3 | | | ATTACGCGATTAC | Y3 |
| 884 | REF5p_A_5 | X1 | ATTACGCGATTACGC | | |
| 885 | REF5p_B_3 | | | ATTACGCGA | Y1 |
| 886 | REF5p_B_5 | X4 | ATT | | |
| 887 | REF5p_C_3 | | | A | Y1 |
| 888 | REF5p_C_5 | X2 | | | |
| 889 | REF5q_A_3 | | | ATTAC | Y3 |
| 890 | REF5q_A_5 | X2 | | | |
| 891 | REF5q_B_3 | | | ATTACGCGATTA | Y4 |
| 892 | REF5q_B_5 | X1 | ATTACGCGATTACGCGA | | |
| 893 | REF5q_C_3 | | | ATTACGCGATTACGCG | Y1 |
| 894 | REF5q_C_5 | X1 | ATTACGCGATTACG | | |
| 895 | REF6p_A_3 | | | ATT | Y3 |
| 896 | REF6p_A_5 | X3 | | | |
| 897 | REF6p_B_3 | | | | Y1 |
| 898 | REF6p_B_5 | X3 | | | |
| 899 | REF6p_C_3 | | | | Y3 |
| 900 | REF6p_C_5 | X1 | | | |
| 901 | REF6q_A_3 | | | ATTACGCGATTACG | Y1 |
| 902 | REF6q_A_5 | X2 | ATTACGCGATT | | |
| 903 | REF6q_B_3 | | | ATTACGCGATTACGCG | Y4 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 904 | REF6q_B_5 | X1 | ATTACGC | | |
| 905 | REF6q_C_3 | | | ATTACGCG | Y3 |
| 906 | REF6q_C_5 | X4 | | | |
| 907 | REF7p_A_3 | | | ATTACGC | Y2 |
| 908 | REF7p_A_5 | X4 | | | |
| 909 | REF7p_B_3 | | | ATTACGCGATT | Y3 |
| 910 | REF7p_B_5 | X3 | ATTA | | |
| 911 | REF7p_C_3 | | | ATTAC | Y2 |
| 912 | REF7p_C_5 | X3 | | | |
| 913 | REF7p_D_3 | | | AT | Y4 |
| 914 | REF7p_D_5 | X1 | ATTACGCGATTACGCG | | |
| 915 | REF8p_A_3 | | | ATTACGCGA | Y1 |
| 916 | REF8p_A_5 | X4 | ATTACG | | |
| 917 | REF8p_B_3 | | | ATTACGCGATTACG | Y3 |
| 918 | REF8p_B_5 | X2 | ATTACGCGATTACG | | |
| 919 | REF8p_C_3 | | | ATTAC | Y2 |
| 920 | REF8p_C_5 | X1 | | | |
| 921 | REF8p_D_3 | | | AT | Y2 |
| 922 | REF8p_D_5 | X2 | ATTACGCGATT | | |
| 923 | REF8q_A_3 | | | A | Y3 |
| 924 | REF8q_A_5 | X3 | | | |
| 925 | REF8q_B_3 | | | A | Y1 |
| 926 | REF8q_B_5 | X1 | | | |
| 927 | REF8q_C_3 | | | ATTACGC | Y3 |
| 928 | REF8q_C_5 | X4 | ATTAC | | |
| 929 | REF9p_A_3 | | | ATTACGCGATTACGCG | Y4 |
| 930 | REF9p_A_5 | X2 | ATTACGCGATTACGC | | |
| 931 | REF9p_B_3 | | | ATTACGCGATTAC | Y2 |
| 932 | REF9p_B_5 | X3 | ATTACGCGATT | | |
| 933 | REF9p_C_3 | | | ATTACGC | Y1 |
| 934 | REF9p_C_5 | X1 | ATTACGC | | |
| 935 | REF9p_D_3 | | | | Y1 |
| 936 | REF9p_D_5 | X4 | | | |
| 937 | REF9q_A_3 | | | A | Y3 |

TABLE 5-continued

Names, sequence ID numbers, primer binding sequences and stuffer sequences for the probes used in human chromosome 21 copy number change detection. X1, X2, X3 and X4 refer to Chr21_X1, SEQ ID NO: 951; Chr21_X2, SEQ ID NO: 952; Chr21_X3, SEQ ID NO: 953; and Chr21_X4, SEQ ID NO: 954, respectively. Y1, Y2, Y3 and Y4 refer to Chr21_Y1, SEQ ID NO: 955; Chr21_Y2, SEQ ID NO: 956; Chr21_Y3, SEQ ID NO: 957; and Chr21_Y4, SEQ ID NO: 958, respectively.

| SEQ ID NO. | Probe Name | Sequence X | Stuffer L1 | Stuffer L2 | Sequence Y |
|---|---|---|---|---|---|
| 938 | REF9q_A_5 | X3 | ATTACGCGATTA | | |
| 939 | REF9q_B_3 | | | | Y4 |
| 940 | REF9q_B_5 | X4 | | | |
| 941 | REF9q_C_3 | | | ATTACGCGA | Y2 |
| 942 | REF9q_C_5 | X2 | | | |

In the example, five DNA samples with different human chromosome 21 copy numbers were prepared. Specifically, the five DNA samples (M0, M2, M4, M8, and M16) were prepared by mixing an aliquot of genomic DNA extract from a healthy volunteer with an aliquot of genomic DNA extract from a Down's Syndrome patient at a DNA quantity ratio of 100:0, 98:2, 96:4, 92:8, and 84:16 so that the copy numbers of human chromosome 21 in the five DNA samples increased 0%, 1%, 2%, 4%, and 8%, respectively. The copy numbers of chromosome 21 in M0, M2, M4, M8, and M16 DNA samples were designed to be 2.00, 2.02, 2.04, 2.08, and 2.16, respectively. This example is set out to detect the copy numbers of human chromosome 21 in M0, M2, M4, M8, and M16 DNA samples using an exemplary method according to this invention.

To detect copy numbers of chromosome 21 in the five DNA samples, the procedure of probe hybridization, probe ligation, ligation product amplification, and capillary electrophoresis as detailed below was performed for each sample and repeated three times.

For each DNA sample a ligation product was first generated with the 384 probes listed in Table 5. Briefly, about 100-200 microgram (μg) genomic DNA was dissolved in 10 microliter (μl) 1×TE buffer (10 mM Tris.Cl, pH8.0, 1 mM EDTA from Sigma-Aldrich). The dissolved genomic DNA was denatured at 98° C. for 5 minutes and then immediately cooled down on ice. A 2× ligation premix solution was prepared according to the following formula: a 10 μl 2× ligation premix was made by mixing 2 μl 10× Taq ligase buffer, 1 μl 40 U/μl Taq Ligase from NewEngland Biolabs, Inc., 1 μl ProbeMix (the 384 probes with a final concentration of 0.005 micromolar for each probe in 1×TE), and 6 μl ddH$_2$O (Distilled Milli-Q water from Milli-Q Advantage A10, Millipore). 10 μl 2× ligation premix was mixed with the denatured 10 μl genomic DNA and the mixture was allowed to undergo 4 cycles of denaturation, hybridization, and ligation under the following conditions: 95° C. for 30 seconds, and then 58° C. for 4 hours. The ligation product thus obtained can be stored on ice for same day use or freezed in − 20° C. for future use.

With the ligation product, an amplification step was then performed to obtain an amplification product. Briefly, two PCR reactions were performed using an aliquot from the same ligation product as the template. One PCR reaction had Chr21_F1, Chr21_F2, Chr21_F3 and Chr21_F4, Chr21_R1 and Chr21_R2 as primers. The other PCR reaction had Chr21_F1, Chr21_F2, Chr21_F3, Chr21_F4, Chr21_R3 and Chr21_R4 as primers. The PCR reaction mixture was prepared as follows: a 20 μl reaction system was made by mixing 2 μl 10×PCR buffer (Qiagen, Germany), 2 μl 2.5 mM dNTP mix (2.5 mM each of dATP, dTTP, dCTP and dGTP from Takara Bio Inc.), 2 μl primer mix (Chr21_F1, Chr21_F2, Chr21_F3 and Chr21_F4, Chr21_R1 and Chr21_R2 at final concentrations of 1 μM, 1 μM, 1 μM, 1 μM, 2 μM, and 2 μM, respectively; or Chr21_F1, Chr21_F2, Chr21_F3, Chr21_F4, Chr21_R3 and Chr21_R4 at final concentrations of 1 μM, 1 μM, 1 μM, 1 μM, 2 μM, and 2 μM, respectively), 1 μl ligation product, 0.2 μl 5 U/μl HotStarTaq Plus Taq DNA polymerase (Qiagen, Germany), and 12.8 μl ddH$_2$O. The PCR mixture was allowed to undergo a polymerase chain reaction under the following conditions: 95° C. for 2 minutes; followed by 35 cycles of 94° C. for 20 second, 57° C. for 40 second, and 72° C. for 1.5 minutes; and after the 35th cycle, the reaction mixture was kept in 60° C. for 1 hour.

To analyze the amplification product, 1 μl of the amplification product was first diluted with ddH$_2$O 10 times into 10 μl. Then 1 μl was taken out of the 10 μl diluted amplification product and mixed with 0.1 μl GeneScan™ 500 LIZ® size standard (Life Technologies, Inc.) and 8.9 μl Hi-Di formamide (Life Technologies, Inc.). The mixture was detaured at 95° C. for 5 minutes and run through capillary electrophoresis by ABI3130XL according to manufacturer's manual. The capillary electrophoresis data was processed using Genemapper 4.0 to obtain peak intensity values for each amplification product.

The chromatograms from the two PCR reactions were designated as Panel A and Panel B, respectively. In each panel, amplification products were categorized into eight groups. The amplification products in each group were amplified with the same primer pair. As such, in panel A, the eight groups corresponded to the eight primer pairs: F1/R1, F1/R2, F2/R1, F2/R2, F3/R1, F3/R2, F4/R1, and F4/R2; and in panel B, the eight groups corresponded to the eight primer pairs: F1/R3, F1/R4, F2/R3, F2/R4, F3/R3, F3/R4, F4/R3, and F4/R4. Each primer pair was designed to amplify 12 target sites including 6 target sites from human chromosome 21 and 6 reference target sites.

The amplification products obtained for each DNA sample could be separated and the peaks corresponding to each target site could be individually identified by capillary electrophoresis. For example, FIGS. 13A and 13F showed the chromatograms of all amplification products from the healthy control sample, i.e., the M0 sample with 0% increase of human chromosome 21 DNA in panel A and panel B, respectively. FIGS. 13B, 13C, 13D, and 13E, which were derived from the control sample panel A, showed the chromatograms of the amplification products labeled with blue, green, yellow, and red fluorescent dyes, respectively. Similarly, FIGS. 13G, 13H, 13I, and 13J, which were derived from the control sample panel B, show the chromatograms for the amplification products labeled with blue, green, yellow, and red fluorescent dyes, respectively. As seen in FIGS. 13B-13E and 13H-13J, the peaks from the amplification products labeled with the same fluorescent dye could be identified on the basis of fragment sizes. See Table 6 for the sizes of amplification products for the 192 target sites in the control sample. The fluorescent intensity for each peak could be obtained. These peak intensity values were used to determine copy number changes of chromosome 21 in the samples.

TABLE 6

Fragment sizes of the amplification products for the 192 target sites in the control sample. LP SIZE refers to Ligation Product Size; REF refers to Reference; CE refers to Capillary Electrophoresis.

| PANEL | GROUP | PROBE LOCUS | TARGET REGION | PCR Primers | LP SIZE | CE REF SIZE |
|---|---|---|---|---|---|---|
| A | 1 | Chr21_38 | Chromosome 21 | Chr21_F1/Chr21_R1 | 104 | 101.27 |
| A | 1 | Chr21_54 | Chromosome 21 | Chr21_F1/Chr21_R1 | 98 | 94.89 |
| A | 1 | Chr21_77 | Chromosome 21 | Chr21_F1/Chr21_R1 | 125 | 121.88 |
| A | 1 | Chr21_79 | Chromosome 21 | Chr21_F1/Chr21_R1 | 110 | 107.53 |
| A | 1 | Chr21_81 | Chromosome 21 | Chr21_F1/Chr21_R1 | 116 | 113.63 |
| A | 1 | Chr21_94 | Chromosome 21 | Chr21_F1/Chr21_R1 | 122 | 119.37 |
| A | 1 | REF11p_D | REFERENCE | Chr21_F1/Chr21_R1 | 101 | 99.32 |
| A | 1 | REF18p_A | REFERENCE | Chr21_F1/Chr21_R1 | 119 | 117.63 |
| A | 1 | REF3p_E | REFERENCE | Chr21_F1/Chr21_R1 | 107 | 104.76 |
| A | 1 | REF5q_C | REFERENCE | Chr21_F1/Chr21_R1 | 128 | 124.95 |
| A | 1 | REF8q_B | REFERENCE | Chr21_F1/Chr21_R1 | 95 | 92.79 |
| A | 1 | REF9p_C | REFERENCE | Chr21_F1/Chr21_R1 | 113 | 111.16 |
| A | 5 | Chr21_04 | Chromosome 21 | Chr21_F1/Chr21_R2 | 160 | 159.78 |
| A | 5 | Chr21_06 | Chromosome 21 | Chr21_F1/Chr21_R2 | 163 | 163.46 |
| A | 5 | Chr21_08 | Chromosome 21 | Chr21_F1/Chr21_R2 | 150 | 148.61 |
| A | 5 | Chr21_41 | Chromosome 21 | Chr21_F1/Chr21_R2 | 142 | 140.76 |
| A | 5 | Chr21_61 | Chromosome 21 | Chr21_F1/Chr21_R2 | 136 | 134.16 |
| A | 5 | Chr21_82 | Chromosome 21 | Chr21_F1/Chr21_R2 | 154 | 154.32 |
| A | 5 | REF10p_A | REFERENCE | Chr21_F1/Chr21_R2 | 133 | 130.3 |
| A | 5 | REF17q_B | REFERENCE | Chr21_F1/Chr21_R2 | 166 | 166.18 |
| A | 5 | REF19q_A | REFERENCE | Chr21_F1/Chr21_R2 | 139 | 137.98 |
| A | 5 | REF20q_B | REFERENCE | Chr21_F1/Chr21_R2 | 157 | 157.52 |
| A | 5 | REF4q_B | REFERENCE | Chr21_F1/Chr21_R2 | 151 | 151.76 |
| A | 5 | REF8p_C | REFERENCE | Chr21_F1/Chr21_R2 | 145 | 144.39 |
| B | 9 | Chr21_12 | Chromosome 21 | Chr21_F1/Chr21_R3 | 122 | 120.82 |
| B | 9 | Chr21_19 | Chromosome 21 | Chr21_F1/Chr21_R3 | 110 | 108.88 |
| B | 9 | Chr21_43 | Chromosome 21 | Chr21_F1/Chr21_R3 | 104 | 102.51 |
| B | 9 | Chr21_45 | Chromosome 21 | Chr21_F1/Chr21_R3 | 113 | 111.65 |
| B | 9 | Chr21_58 | Chromosome 21 | Chr21_F1/Chr21_R3 | 125 | 123.11 |
| B | 9 | Chr21_68 | Chromosome 21 | Chr21_F1/Chr21_R3 | 98 | 96.6 |
| B | 9 | REF11p_B | REFERENCE | Chr21_F1/Chr21_R3 | 116 | 115.19 |
| B | 9 | REF14q_B | REFERENCE | Chr21_F1/Chr21_R3 | 101 | 99.44 |
| B | 9 | REF16q_A | REFERENCE | Chr21_F1/Chr21_R3 | 120 | 117.57 |
| B | 9 | REF3p_A | REFERENCE | Chr21_F1/Chr21_R3 | 107 | 105.06 |
| B | 9 | REF5p_A | REFERENCE | Chr21_F1/Chr21_R3 | 128 | 125.52 |
| B | 9 | REF6p_C | REFERENCE | Chr21_F1/Chr21_R3 | 95 | 92.74 |
| B | 13 | Chr21_18 | Chromosome 21 | Chr21_F1/Chr21_R4 | 142 | 139.76 |
| B | 13 | Chr21_50 | Chromosome 21 | Chr21_F1/Chr21_R4 | 160 | 160.98 |
| B | 13 | Chr21_67 | Chromosome 21 | Chr21_F1/Chr21_R4 | 151 | 150.71 |
| B | 13 | Chr21_83 | Chromosome 21 | Chr21_F1/Chr21_R4 | 136 | 133.94 |
| B | 13 | Chr21_87 | Chromosome 21 | Chr21_F1/Chr21_R4 | 163 | 163 |
| B | 13 | Chr21_95 | Chromosome 21 | Chr21_F1/Chr21_R4 | 148 | 146.89 |
| B | 13 | REF12q_C | REFERENCE | Chr21_F1/Chr21_R4 | 145 | 142.39 |
| B | 13 | REF19q_C | REFERENCE | Chr21_F1/Chr21_R4 | 133 | 131.04 |
| B | 13 | REF3q_D | REFERENCE | Chr21_F1/Chr21_R4 | 139 | 137.19 |
| B | 13 | REF5q_B | REFERENCE | Chr21_F1/Chr21_R4 | 166 | 166.06 |
| B | 13 | REF6q_B | REFERENCE | Chr21_F1/Chr21_R4 | 159 | 156.41 |
| B | 13 | REF7p_D | REFERENCE | Chr21_F1/Chr21_R4 | 154 | 154.2 |
| A | 2 | Chr21_01 | Chromosome 21 | Chr21_F2/Chr21_R1 | 98 | 97.28 |
| A | 2 | Chr21_05 | Chromosome 21 | Chr21_F2/Chr21_R1 | 116 | 114.32 |
| A | 2 | Chr21_37 | Chromosome 21 | Chr21_F2/Chr21_R1 | 110 | 108.49 |
| A | 2 | Chr21_53 | Chromosome 21 | Chr21_F2/Chr21_R1 | 125 | 123.41 |
| A | 2 | Chr21_71 | Chromosome 21 | Chr21_F2/Chr21_R1 | 104 | 103.17 |
| A | 2 | Chr21_75 | Chromosome 21 | Chr21_F2/Chr21_R1 | 124 | 121.91 |
| A | 2 | REF10q_A | REFERENCE | Chr21_F2/Chr21_R1 | 113 | 111.9 |
| A | 2 | REF20p_A | REFERENCE | Chr21_F2/Chr21_R1 | 119 | 118.5 |
| A | 2 | REF2p_D | REFERENCE | Chr21_F2/Chr21_R1 | 101 | 100.11 |
| A | 2 | REF4q_C | REFERENCE | Chr21_F2/Chr21_R1 | 107 | 105.82 |
| A | 2 | REF5p_C | REFERENCE | Chr21_F2/Chr21_R1 | 95 | 92.94 |

TABLE 6-continued

Fragment sizes of the amplification products for the 192 target sites in the control sample. LP SIZE refers to Ligation Product Size; REF refers to Reference; CE refers to Capillary Electrophoresis.

| PANEL | GROUP | PROBE LOCUS | TARGET REGION | PCR Primers | LP SIZE | CE REF SIZE |
|---|---|---|---|---|---|---|
| A | 2 | REF6q_A | REFERENCE | Chr21_F2/Chr21_R1 | 128 | 126.71 |
| A | 6 | Chr21_15 | Chromosome 21 | Chr21_F2/Chr21_R2 | 154 | 155.7 |
| A | 6 | Chr21_17 | Chromosome 21 | Chr21_F2/Chr21_R2 | 160 | 160.33 |
| A | 6 | Chr21_29 | Chromosome 21 | Chr21_F2/Chr21_R2 | 136 | 135.05 |
| A | 6 | Chr21_39 | Chromosome 21 | Chr21_F2/Chr21_R2 | 148 | 148.76 |
| A | 6 | Chr21_62 | Chromosome 21 | Chr21_F2/Chr21_R2 | 163 | 163.8 |
| A | 6 | Chr21_72 | Chromosome 21 | Chr21_F2/Chr21_R2 | 142 | 141.14 |
| A | 6 | REF14q_A | REFERENCE | Chr21_F2/Chr21_R2 | 133 | 131.48 |
| A | 6 | REF16p_C | REFERENCE | Chr21_F2/Chr21_R2 | 157 | 158.2 |
| A | 6 | REF20q_D | REFERENCE | Chr21_F2/Chr21_R2 | 139 | 138.1 |
| A | 6 | REF2q_B | REFERENCE | Chr21_F2/Chr21_R2 | 166 | 167.35 |
| A | 6 | REF8p_D | REFERENCE | Chr21_F2/Chr21_R2 | 151 | 152 |
| A | 6 | REF9q_C | REFERENCE | Chr21_F2/Chr21_R2 | 145 | 145.32 |
| B | 10 | Chr21_31 | Chromosome 21 | Chr21_F2/Chr21_R3 | 122 | 120.6 |
| B | 10 | Chr21_35 | Chromosome 21 | Chr21_F2/Chr21_R3 | 125 | 123.44 |
| B | 10 | Chr21_51 | Chromosome 21 | Chr21_F2/Chr21_R3 | 110 | 108.56 |
| B | 10 | Chr21_63 | Chromosome 21 | Chr21_F2/Chr21_R3 | 113 | 112.4 |
| B | 10 | Chr21_74 | Chromosome 21 | Chr21_F2/Chr21_R3 | 104 | 102.84 |
| B | 10 | Chr21_78 | Chromosome 21 | Chr21_F2/Chr21_R3 | 98 | 97.74 |
| B | 10 | REF10q_B | REFERENCE | Chr21_F2/Chr21_R3 | 95 | 94.16 |
| B | 10 | REF11p_C | REFERENCE | Chr21_F2/Chr21_R3 | 119 | 118.21 |
| B | 10 | REF16p_B | REFERENCE | Chr21_F2/Chr21_R3 | 117 | 115.11 |
| B | 10 | REF18p_B | REFERENCE | Chr21_F2/Chr21_R3 | 107 | 106.22 |
| B | 10 | REF5q_A | REFERENCE | Chr21_F2/Chr21_R3 | 101 | 99.55 |
| B | 10 | REF8p_B | REFERENCE | Chr21_F2/Chr21_R3 | 128 | 127.17 |
| B | 14 | Chr21_14 | Chromosome 21 | Chr21_F2/Chr21_R4 | 148 | 146.39 |
| B | 14 | Chr21_22 | Chromosome 21 | Chr21_F2/Chr21_R4 | 160 | 159.1 |
| B | 14 | Chr21_33 | Chromosome 21 | Chr21_F2/Chr21_R4 | 139 | 137.76 |
| B | 14 | Chr21_46 | Chromosome 21 | Chr21_F2/Chr21_R4 | 136 | 136.18 |
| B | 14 | Chr21_69 | Chromosome 21 | Chr21_F2/Chr21_R4 | 163 | 164.44 |
| B | 14 | Chr21_92 | Chromosome 21 | Chr21_F2/Chr21_R4 | 151 | 151.88 |
| B | 14 | REF12q_B | REFERENCE | Chr21_F2/Chr21_R4 | 155 | 154.32 |
| B | 14 | REF16p_D | REFERENCE | Chr21_F2/Chr21_R4 | 157 | 157.18 |
| B | 14 | REF19p_B | REFERENCE | Chr21_F2/Chr21_R4 | 142 | 140.51 |
| B | 14 | REF20p_C | REFERENCE | Chr21_F2/Chr21_R4 | 146 | 143.27 |
| B | 14 | REF2p_C | REFERENCE | Chr21_F2/Chr21_R4 | 133 | 132.04 |
| B | 14 | REF9p_A | REFERENCE | Chr21_F2/Chr21_R4 | 168 | 167.19 |
| A | 3 | Chr21_02 | Chromosome 21 | Chr21_F3/Chr21_R1 | 110 | 107.31 |
| A | 3 | Chr21_03 | Chromosome 21 | Chr21_F3/Chr21_R1 | 122 | 119.34 |
| A | 3 | Chr21_40 | Chromosome 21 | Chr21_F3/Chr21_R1 | 116 | 113.52 |
| A | 3 | Chr21_48 | Chromosome 21 | Chr21_F3/Chr21_R1 | 125 | 122.97 |
| A | 3 | Chr21_60 | Chromosome 21 | Chr21_F3/Chr21_R1 | 98 | 95.46 |
| A | 3 | Chr21_91 | Chromosome 21 | Chr21_F3/Chr21_R1 | 104 | 101.27 |
| A | 3 | REF10q_C | REFERENCE | Chr21_F3/Chr21_R1 | 128 | 124.84 |
| A | 3 | REF12q_A | REFERENCE | Chr21_F3/Chr21_R1 | 107 | 104.55 |
| A | 3 | REF16q_C | REFERENCE | Chr21_F3/Chr21_R1 | 113 | 109.55 |
| A | 3 | REF2p_A | REFERENCE | Chr21_F3/Chr21_R1 | 119 | 115.79 |
| A | 3 | REF3p_D | REFERENCE | Chr21_F3/Chr21_R1 | 101 | 98.87 |
| A | 3 | REF6p_B | REFERENCE | Chr21_F3/Chr21_R1 | 95 | 92.83 |
| A | 7 | Chr21_07 | Chromosome 21 | Chr21_F3/Chr21_R2 | 142 | 141.01 |
| A | 7 | Chr21_09 | Chromosome 21 | Chr21_F3/Chr21_R2 | 148 | 147.51 |
| A | 7 | Chr21_16 | Chromosome 21 | Chr21_F3/Chr21_R2 | 160 | 159.66 |
| A | 7 | Chr21_49 | Chromosome 21 | Chr21_F3/Chr21_R2 | 163 | 164.13 |
| A | 7 | Chr21_59 | Chromosome 21 | Chr21_F3/Chr21_R2 | 151 | 150.82 |
| A | 7 | Chr21_64 | Chromosome 21 | Chr21_F3/Chr21_R2 | 136 | 133.71 |
| A | 7 | REF16q_D | REFERENCE | Chr21_F3/Chr21_R2 | 133 | 130.03 |
| A | 7 | REF19q_B | REFERENCE | Chr21_F3/Chr21_R2 | 157 | 157.18 |
| A | 7 | REF20q_A | REFERENCE | Chr21_F3/Chr21_R2 | 154 | 153.74 |
| A | 7 | REF3q_C | REFERENCE | Chr21_F3/Chr21_R2 | 145 | 143.89 |
| A | 7 | REF7p_C | REFERENCE | Chr21_F3/Chr21_R2 | 139 | 136.52 |
| A | 7 | REF9p_B | REFERENCE | Chr21_F3/Chr21_R2 | 166 | 166.29 |
| B | 11 | Chr21_10 | Chromosome 21 | Chr21_F3/Chr21_R3 | 104 | 102.63 |
| B | 11 | Chr21_11 | Chromosome 21 | Chr21_F3/Chr21_R3 | 110 | 107.92 |
| B | 11 | Chr21_21 | Chromosome 21 | Chr21_F3/Chr21_R3 | 116 | 113.79 |
| B | 11 | Chr21_23 | Chromosome 21 | Chr21_F3/Chr21_R3 | 123 | 119.9 |
| B | 11 | Chr21_76 | Chromosome 21 | Chr21_F3/Chr21_R3 | 125 | 122.24 |
| B | 11 | Chr21_85 | Chromosome 21 | Chr21_F3/Chr21_R3 | 98 | 95.93 |
| B | 11 | REF20q_E | REFERENCE | Chr21_F3/Chr21_R3 | 107 | 104.63 |
| B | 11 | REF2p_B | REFERENCE | Chr21_F3/Chr21_R3 | 128 | 125.85 |
| B | 11 | REF6p_A | REFERENCE | Chr21_F3/Chr21_R3 | 101 | 97.85 |
| B | 11 | REF7p_B | REFERENCE | Chr21_F3/Chr21_R3 | 118 | 117.13 |
| B | 11 | REF8q_A | REFERENCE | Chr21_F3/Chr21_R3 | 95 | 93.51 |

TABLE 6-continued

Fragment sizes of the amplification products for the 192 target sites in the control sample. LP SIZE refers to Ligation Product Size; REF refers to Reference; CE refers to Capillary Electrophoresis.

| PANEL | PROBE GROUP | LOCUS | TARGET REGION | PCR Primers | LP SIZE | CE REF SIZE |
|---|---|---|---|---|---|---|
| B | 11 | REF9q_A | REFERENCE | Chr21_F3/Chr21_R3 | 113 | 110.48 |
| B | 15 | Chr21_36 | Chromosome 21 | Chr21_F3/Chr21_R4 | 151 | 149.38 |
| B | 15 | Chr21_47 | Chromosome 21 | Chr21_F3/Chr21_R4 | 171 | 169.07 |
| B | 15 | Chr21_57 | Chromosome 21 | Chr21_F3/Chr21_R4 | 139 | 137.19 |
| B | 15 | Chr21_70 | Chromosome 21 | Chr21_F3/Chr21_R4 | 160 | 160.11 |
| B | 15 | Chr21_73 | Chromosome 21 | Chr21_F3/Chr21_R4 | 163 | 162.49 |
| B | 15 | Chr21_86 | Chromosome 21 | Chr21_F3/Chr21_R4 | 136 | 133.49 |
| B | 15 | REF11q_A | REFERENCE | Chr21_F3/Chr21_R4 | 154 | 153.63 |
| B | 15 | REF12p_B | REFERENCE | Chr21_F3/Chr21_R4 | 166 | 165.95 |
| B | 15 | REF17q_A | REFERENCE | Chr21_F3/Chr21_R4 | 142 | 140.51 |
| B | 15 | REF2q_A | REFERENCE | Chr21_F3/Chr21_R4 | 157 | 157.07 |
| B | 15 | REF3q_B | REFERENCE | Chr21_F3/Chr21_R4 | 148 | 145.34 |
| B | 15 | REF4q_A | REFERENCE | Chr21_F3/Chr21_R4 | 133 | 130.93 |
| A | 4 | Chr21_20 | Chromosome 21 | Chr21_F4/Chr21_R1 | 110 | 111.27 |
| A | 4 | Chr21_24 | Chromosome 21 | Chr21_F4/Chr21_R1 | 107 | 108.17 |
| A | 4 | Chr21_25 | Chromosome 21 | Chr21_F4/Chr21_R1 | 101 | 102.32 |
| A | 4 | Chr21_27 | Chromosome 21 | Chr21_F4/Chr21_R1 | 123 | 123.56 |
| A | 4 | Chr21_90 | Chromosome 21 | Chr21_F4/Chr21_R1 | 119 | 121.11 |
| A | 4 | Chr21_93 | Chromosome 21 | Chr21_F4/Chr21_R1 | 95 | 97.84 |
| A | 4 | REF10p_B | REFERENCE | Chr21_F4/Chr21_R1 | 98 | 99.66 |
| A | 4 | REF11p_A | REFERENCE | Chr21_F4/Chr21_R1 | 104 | 105.4 |
| A | 4 | REF3q_A | REFERENCE | Chr21_F4/Chr21_R1 | 125 | 126.71 |
| A | 4 | REF5p_B | REFERENCE | Chr21_F4/Chr21_R1 | 113 | 113.89 |
| A | 4 | REF8p_A | REFERENCE | Chr21_F4/Chr21_R1 | 116 | 117.2 |
| A | 4 | REF9p_D | REFERENCE | Chr21_F4/Chr21_R1 | 92 | 94.54 |
| A | 8 | Chr21_26 | Chromosome 21 | Chr21_F4/Chr21_R2 | 139 | 139.76 |
| A | 8 | Chr21_28 | Chromosome 21 | Chr21_F4/Chr21_R2 | 133 | 132.57 |
| A | 8 | Chr21_30 | Chromosome 21 | Chr21_F4/Chr21_R2 | 145 | 147.39 |
| A | 8 | Chr21_44 | Chromosome 21 | Chr21_F4/Chr21_R2 | 148 | 150.35 |
| A | 8 | Chr21_55 | Chromosome 21 | Chr21_F4/Chr21_R2 | 160 | 162.72 |
| A | 8 | Chr21_96 | Chromosome 21 | Chr21_F4/Chr21_R2 | 158 | 160.55 |
| A | 8 | REF11q_B | REFERENCE | Chr21_F4/Chr21_R2 | 163 | 167.59 |
| A | 8 | REF12p_C | REFERENCE | Chr21_F4/Chr21_R2 | 154 | 158.31 |
| A | 8 | REF16p_A | REFERENCE | Chr21_F4/Chr21_R2 | 136 | 137.87 |
| A | 8 | REF20p_B | REFERENCE | Chr21_F4/Chr21_R2 | 151 | 154.55 |
| A | 8 | REF3p_C | REFERENCE | Chr21_F4/Chr21_R2 | 133 | 134.83 |
| A | 8 | REF7p_A | REFERENCE | Chr21_F4/Chr21_R2 | 142 | 144.39 |
| B | 12 | Chr21_32 | Chromosome 21 | Chr21_F4/Chr21_R3 | 101 | 105.27 |
| B | 12 | Chr21_42 | Chromosome 21 | Chr21_F4/Chr21_R3 | 107 | 109.94 |
| B | 12 | Chr21_56 | Chromosome 21 | Chr21_F4/Chr21_R3 | 119 | 121.47 |
| B | 12 | Chr21_66 | Chromosome 21 | Chr21_F4/Chr21_R3 | 122 | 124.86 |
| B | 12 | Chr21_84 | Chromosome 21 | Chr21_F4/Chr21_R3 | 113 | 114.87 |
| B | 12 | Chr21_88 | Chromosome 21 | Chr21_F4/Chr21_R3 | 96 | 97.26 |
| B | 12 | REF10p_D | REFERENCE | Chr21_F4/Chr21_R3 | 116 | 118.32 |
| B | 12 | REF11q_C | REFERENCE | Chr21_F4/Chr21_R3 | 105 | 107.24 |
| B | 12 | REF16q_B | REFERENCE | Chr21_F4/Chr21_R3 | 125 | 126.62 |
| B | 12 | REF19q_D | REFERENCE | Chr21_F4/Chr21_R3 | 92 | 94.79 |
| B | 12 | REF6q_C | REFERENCE | Chr21_F4/Chr21_R3 | 98 | 99.55 |
| B | 12 | REF8q_C | REFERENCE | Chr21_F4/Chr21_R3 | 110 | 110.86 |
| B | 16 | Chr21_13 | Chromosome 21 | Chr21_F4/Chr21_R4 | 133 | 134.61 |
| B | 16 | Chr21_34 | Chromosome 21 | Chr21_F4/Chr21_R4 | 147 | 147.73 |
| B | 16 | Chr21_52 | Chromosome 21 | Chr21_F4/Chr21_R4 | 157 | 160.54 |
| B | 16 | Chr21_65 | Chromosome 21 | Chr21_F4/Chr21_R4 | 151 | 154.67 |
| B | 16 | Chr21_80 | Chromosome 21 | Chr21_F4/Chr21_R4 | 160 | 163.37 |
| B | 16 | Chr21_89 | Chromosome 21 | Chr21_F4/Chr21_R4 | 139 | 141.64 |
| B | 16 | REF10p_C | REFERENCE | Chr21_F4/Chr21_R4 | 142 | 144.27 |
| B | 16 | REF12p_A | REFERENCE | Chr21_F4/Chr21_R4 | 148 | 151.53 |
| B | 16 | REF19p_A | REFERENCE | Chr21_F4/Chr21_R4 | 136 | 137.42 |
| B | 16 | REF20q_C | REFERENCE | Chr21_F4/Chr21_R4 | 157 | 158.24 |
| B | 16 | REF3p_B | REFERENCE | Chr21_F4/Chr21_R4 | 163 | 166.72 |
| B | 16 | REF9q_B | REFERENCE | Chr21_F4/Chr21_R4 | 130 | 131.49 |

To determine the copy number changes of chromosome 21, the following exemplary statistical method was applied. The copy number for each of the 96 target sites on chromosome 21 was calculated. A ratio for a chromosome 21 target site in the test sample ($R_{test}$) was obtained by dividing the peak intensity value of the chromosome 21 target site with the peak intensity value of each of the six reference target sites in the same group. As such, six ratios ($R_{test}$) were obtained for the chromosome 21 target site. Similarly, a ratio for the chromosome 21 target site was obtained in the control sample ($R_{control}$). It was known that the copy number of chromosome 21 in the control sample M0 ($C_{control}$) was 2. The copy number of chromosome 21 in the test sample ($C_{test}$) was calculated according to the formula:

$C_{test}=C_{control} \times R_{test}/R_{control}$. Because there were six reference target sites for each chromosome 21 target site, six $C_{test}$ values were derived for each chromosome 21 target site. The median of the six $C_{test}$ was then deemed copy number for the chromosome 21 target site in the test sample.

For example, referring to Table 6, $R_{test}$ and $R_{control}$ for the target site Chr21_01 were obtained as follows. Chr21_01 was in the group consisting of twelve chromosome 21 target sites: Chr21_01, Chr21_05, Chr21_37, Chr21_53, Chr21_71, and Chr21_75 and six reference target sites: REF10q_A, REF20p_A, REF2p_D, REF4q_C, REF5p_C, and REF6q_A. Six $R_{test}$ values for Chr21_01 target site in the test sample were obtained by dividing the peak intensity of the Chr21_01 target site with the peak intensity of each of the six reference target sites: REF10q_A, REF20p_A, REF2p_D, REF4q_C, REF5p_C, and REF6q_A. Similarly, six $R_{test}$ values for Chr21_01 target site in the control sample (i.e., the M0 DNA sample) were obtained. For each of the six reference target sites: REF10q_A, REF20p_A, REF2p_D, REF4q_C, REF5p_C, and REF6q_A, a $C_{test}$ was derived for Chr21_01 target site. Therefore, a total of six $C_{test}$ were derived for Chr21_01 target site in the test sample. The median of the six $C_{test}$ values was deemed as the copy number for Chr21_01 target site in the test sample.

As such the copy number for each of the 96 chromosome 21 target sites was calculated. Because the testing was repeated three times for each DNA sample, three R values for each of the 96 chromosome 21 target sites could be derived from the testing results for each sample. See Table 7 for the R values. The median copy number value in each testing for the 96 chromosome 21 target sites was considered the copy number of chromosome 21 in the testing and listed in the last row in Table 7. In addition, the copy number of chromosome 21 in each DNA sample was derived by averaging the three median values in the three repeated tests. For example, the copy number for M4 DNA sample was 2.037, which is the average of 2.04, 2.03 and 2.04.

TABLE 7

Copy number measurement of human chromosome 21. R1, R2, and R3 refer to calculated copy numbers in the three repeated testing for each DNA sample.

| PROBE | M0 | | | M2 | | | M4 | | | M8 | | | M16 | | |
|---|---|---|---|---|---|---|---|---|---|---|---|---|---|---|---|
| LOCUS | R1 | R2 | R3 | R1 | R2 | R3 | R1 | R2 | R3 | R1 | R2 | R3 | R1 | R2 | R3 |
| Chr21_01 | 2.00 | 2.12 | 1.99 | 1.86 | 1.95 | 1.95 | 1.95 | 1.98 | 1.97 | 2.05 | 1.95 | 2.00 | 2.23 | 2.09 | 2.04 |
| Chr21_02 | 2.08 | 2.07 | 1.96 | 1.98 | 1.99 | 1.91 | 1.88 | 1.96 | 1.83 | 1.95 | 2.02 | 1.82 | 2.18 | 2.02 | 2.22 |
| Chr21_03 | 2.04 | 2.00 | 1.96 | 1.90 | 1.95 | 2.09 | 1.93 | 2.04 | 1.99 | 2.12 | 2.07 | 1.91 | 2.11 | 2.18 | 2.14 |
| Chr21_04 | 2.06 | 1.97 | 2.01 | 1.93 | 2.06 | 2.02 | 2.07 | 2.18 | 2.09 | 2.05 | 2.02 | 2.13 | 2.19 | 2.24 | 1.94 |
| Chr21_05 | 2.08 | 1.94 | 2.00 | 2.06 | 1.95 | 1.88 | 1.99 | 2.08 | 2.14 | 2.08 | 1.97 | 2.13 | 2.19 | 2.08 | 2.10 |
| Chr21_06 | 2.03 | 2.11 | 2.00 | 1.93 | 2.08 | 2.00 | 1.91 | 2.12 | 1.98 | 2.16 | 2.05 | 2.06 | 2.18 | 2.16 | 2.14 |
| Chr21_07 | 2.04 | 2.02 | 1.99 | 2.03 | 1.95 | 2.03 | 2.07 | 1.90 | 2.07 | 2.18 | 1.98 | 2.02 | 2.10 | 2.11 | 2.07 |
| Chr21_08 | 1.93 | 2.00 | 2.17 | 2.00 | 2.00 | 1.97 | 2.06 | 2.06 | 2.07 | 1.97 | 1.92 | 2.25 | 2.18 | 2.30 | 2.20 |
| Chr21_09 | 1.92 | 2.17 | 1.95 | 2.12 | 2.26 | 2.17 | 2.18 | 2.10 | 2.06 | 2.21 | 2.21 | 2.06 | 2.29 | 2.34 | 2.12 |
| Chr21_10 | 2.05 | 2.00 | 1.94 | 2.06 | 2.10 | 1.93 | 2.06 | 1.96 | 2.11 | 2.17 | 2.02 | 2.22 | 2.10 | 2.17 | 2.12 |
| Chr21_11 | 2.12 | 1.97 | 1.96 | 2.15 | 2.05 | 1.93 | 2.00 | 1.98 | 2.13 | 2.21 | 2.16 | 2.10 | 2.22 | 2.11 | 2.24 |
| Chr21_12 | 1.92 | 2.09 | 2.09 | 2.16 | 2.31 | 2.11 | 1.96 | 1.97 | 2.12 | 2.18 | 2.04 | 2.20 | 2.29 | 2.19 | 2.31 |
| Chr21_13 | 1.90 | 2.17 | 1.96 | 2.24 | 2.07 | 2.10 | 2.00 | 1.95 | 1.99 | 2.05 | 1.98 | 1.94 | 2.23 | 1.96 | 2.17 |
| Chr21_14 | 1.94 | 2.09 | 2.06 | 1.99 | 2.00 | 2.01 | 2.07 | 2.05 | 2.02 | 2.00 | 1.97 | 2.09 | 2.22 | 2.19 | 2.18 |
| Chr21_15 | 2.00 | 2.11 | 1.94 | 2.01 | 2.13 | 2.17 | 2.09 | 1.96 | 2.08 | 2.18 | 2.27 | 2.20 | 2.23 | 2.16 | 2.17 |
| Chr21_16 | 1.98 | 1.98 | 1.97 | 2.00 | 1.93 | 2.03 | 1.98 | 1.94 | 2.24 | 2.08 | 2.11 | 2.18 | 2.05 | 2.15 | 2.19 |
| Chr21_17 | 2.00 | 2.08 | 1.94 | 1.69 | 2.08 | 2.02 | 1.99 | 2.05 | 2.01 | 2.24 | 1.94 | 2.04 | 1.91 | 2.06 | 2.04 |
| Chr21_18 | 1.97 | 2.06 | 2.03 | 1.99 | 1.92 | 2.04 | 2.04 | 2.03 | 2.02 | 2.08 | 2.11 | 2.08 | 2.09 | 2.10 | 2.03 |
| Chr21_19 | 2.00 | 2.06 | 1.97 | 2.22 | 2.16 | 2.00 | 2.14 | 2.08 | 2.03 | 2.15 | 2.16 | 2.17 | 2.16 | 2.17 | 2.21 |
| Chr21_20 | 2.13 | 2.01 | 2.03 | 1.92 | 1.86 | 2.13 | 2.06 | 2.17 | 2.01 | 2.11 | 2.12 | 2.17 | 2.19 | 2.01 | 2.14 |
| Chr21_21 | 2.07 | 2.00 | 2.00 | 1.95 | 1.91 | 2.18 | 1.98 | 2.07 | 2.00 | 2.25 | 1.99 | 2.09 | 1.95 | 2.08 | 1.97 |
| Chr21_22 | 2.04 | 1.97 | 2.04 | 2.09 | 2.05 | 2.14 | 2.08 | 2.07 | 2.13 | 2.06 | 1.95 | 2.14 | 2.09 | 2.21 | 2.20 |
| Chr21_23 | 2.02 | 2.06 | 1.93 | 2.09 | 2.09 | 1.99 | 2.16 | 2.17 | 2.10 | 2.28 | 2.16 | 2.28 | 2.23 | 2.15 | 2.20 |
| Chr21_24 | 1.95 | 2.00 | 2.08 | 1.92 | 2.00 | 1.96 | 2.05 | 2.04 | 2.04 | 2.04 | 1.97 | 2.09 | 2.13 | 2.18 | 2.19 |
| Chr21_25 | 2.08 | 2.01 | 2.04 | 1.89 | 2.08 | 1.99 | 1.98 | 2.03 | 1.97 | 2.05 | 2.15 | 1.99 | 2.35 | 2.06 | 1.97 |
| Chr21_26 | 2.01 | 1.95 | 2.09 | 2.23 | 1.95 | 2.09 | 2.01 | 1.99 | 1.94 | 2.02 | 2.08 | 1.99 | 2.07 | 2.10 | 2.04 |
| Chr21_27 | 2.08 | 1.90 | 2.10 | 1.89 | 1.82 | 1.99 | 2.06 | 2.31 | 2.33 | 2.06 | 1.80 | 2.07 | 2.11 | 2.04 | 2.40 |
| Chr21_28 | 2.09 | 1.92 | 2.00 | 1.87 | 2.02 | 1.99 | 2.04 | 2.00 | 1.97 | 2.11 | 1.98 | 2.06 | 2.06 | 2.09 | 2.09 |
| Chr21_29 | 1.99 | 1.99 | 1.98 | 2.00 | 2.01 | 1.97 | 1.94 | 1.98 | 1.95 | 2.03 | 2.00 | 2.06 | 2.18 | 2.00 | 2.19 |
| Chr21_30 | 2.05 | 1.98 | 1.98 | 1.90 | 1.97 | 1.95 | 2.05 | 1.94 | 1.98 | 2.16 | 2.02 | 2.01 | 2.11 | 2.02 | 2.05 |
| Chr21_31 | 1.99 | 2.02 | 1.86 | 1.83 | 1.87 | 1.93 | 1.95 | 1.96 | 1.88 | 1.98 | 2.08 | 1.94 | 2.11 | 1.94 | 1.98 |
| Chr21_32 | 1.98 | 2.01 | 1.93 | 2.08 | 1.97 | 2.01 | 2.13 | 2.01 | 2.00 | 2.02 | 2.03 | 2.05 | 2.19 | 2.02 | 2.11 |
| Chr21_33 | 2.03 | 1.99 | 2.01 | 2.01 | 1.99 | 2.02 | 1.93 | 1.95 | 2.10 | 2.17 | 2.12 | 2.07 | 2.12 | 2.10 | 2.17 |
| Chr21_34 | 1.89 | 1.97 | 2.06 | 2.04 | 2.03 | 2.02 | 2.10 | 2.14 | 2.11 | 2.09 | 2.00 | 2.00 | 1.99 | 2.01 | 2.12 |
| Chr21_35 | 2.01 | 2.01 | 1.83 | 1.96 | 2.02 | 1.94 | 1.91 | 1.97 | 1.99 | 1.93 | 1.99 | 1.98 | 2.11 | 2.06 | 2.07 |
| Chr21_36 | 2.07 | 1.86 | 2.03 | 1.99 | 2.10 | 2.01 | 2.05 | 2.03 | 2.07 | 2.11 | 1.96 | 2.22 | 2.12 | 2.31 | 2.32 |
| Chr21_37 | 2.01 | 1.98 | 1.95 | 1.92 | 1.91 | 1.87 | 1.91 | 1.97 | 2.05 | 2.06 | 2.07 | 2.00 | 2.17 | 1.99 | 1.97 |
| Chr21_38 | 1.95 | 1.95 | 2.21 | 2.18 | 2.07 | 2.06 | 2.01 | 1.89 | 2.01 | 2.10 | 2.04 | 1.95 | 2.21 | 2.19 | 2.17 |
| Chr21_39 | 2.02 | 2.10 | 1.90 | 2.06 | 2.10 | 2.22 | 2.25 | 2.05 | 2.04 | 2.19 | 2.13 | 2.15 | 2.28 | 2.09 | 2.27 |
| Chr21_40 | 1.90 | 1.93 | 2.09 | 1.96 | 1.91 | 1.96 | 1.97 | 2.02 | 1.89 | 1.95 | 2.10 | 1.99 | 1.93 | 2.15 | 2.17 |
| Chr21_41 | 2.10 | 2.06 | 1.97 | 2.16 | 2.19 | 2.11 | 1.99 | 2.06 | 2.05 | 2.25 | 1.99 | 2.27 | 2.31 | 2.16 | 2.33 |
| Chr21_42 | 2.06 | 1.93 | 2.04 | 2.22 | 1.96 | 2.13 | 2.12 | 2.02 | 2.01 | 2.20 | 2.28 | 2.05 | 2.23 | 2.23 | 2.37 |
| Chr21_43 | 2.04 | 2.07 | 1.98 | 2.19 | 2.04 | 2.10 | 2.08 | 2.14 | 2.12 | 2.22 | 2.10 | 2.12 | 2.28 | 2.23 | 2.26 |
| Chr21_44 | 2.08 | 1.91 | 2.00 | 2.02 | 1.92 | 1.92 | 2.14 | 2.03 | 2.04 | 2.15 | 2.05 | 1.90 | 2.05 | 2.18 | 2.14 |
| Chr21_45 | 1.97 | 1.94 | 2.01 | 1.88 | 1.83 | 1.83 | 1.86 | 2.00 | 1.92 | 1.84 | 1.81 | 1.96 | 1.97 | 1.93 | 1.99 |
| Chr21_46 | 2.00 | 2.13 | 2.01 | 2.21 | 2.19 | 2.32 | 2.14 | 2.09 | 2.20 | 2.20 | 2.27 | 2.11 | 2.45 | 2.47 | 2.84 |
| Chr21_47 | 2.20 | 1.98 | 2.02 | 2.18 | 2.11 | 2.02 | 2.06 | 2.04 | 2.02 | 2.22 | 2.06 | 2.10 | 2.15 | 2.06 | 2.31 |
| Chr21_48 | 2.03 | 1.97 | 1.85 | 1.78 | 1.76 | 1.86 | 2.02 | 2.07 | 1.99 | 2.08 | 1.91 | 2.13 | 2.20 | 2.22 | 2.18 |
| Chr21_49 | 1.96 | 2.09 | 1.98 | 1.95 | 2.08 | 1.99 | 2.07 | 1.97 | 2.10 | 2.10 | 2.06 | 2.24 | 1.98 | 2.18 | 2.03 |

TABLE 7-continued

Copy number measurement of human chromosome 21. R1, R2, and R3 refer to calculated copy numbers in the three repeated testing for each DNA sample.

| PROBE | M0 | | | M2 | | | M4 | | | M8 | | | M16 | | |
|---|---|---|---|---|---|---|---|---|---|---|---|---|---|---|---|
| LOCUS | R1 | R2 | R3 | R1 | R2 | R3 | R1 | R2 | R3 | R1 | R2 | R3 | R1 | R2 | R3 |
| Chr21_50 | 1.96 | 1.96 | 2.03 | 2.02 | 2.13 | 2.08 | 2.11 | 2.09 | 1.99 | 2.21 | 2.15 | 2.09 | 2.09 | 2.27 | 2.11 |
| Chr21_51 | 2.01 | 2.02 | 2.03 | 2.14 | 2.00 | 2.04 | 1.97 | 1.97 | 1.96 | 2.26 | 2.13 | 2.05 | 2.31 | 2.13 | 2.14 |
| Chr21_52 | 2.04 | 2.04 | 1.99 | 2.20 | 2.06 | 2.01 | 2.11 | 2.11 | 2.21 | 2.10 | 2.00 | 2.25 | 2.25 | 2.39 | 2.06 |
| Chr21_53 | 1.95 | 2.07 | 1.83 | 1.81 | 1.93 | 1.82 | 2.03 | 2.11 | 1.92 | 1.85 | 2.01 | 2.12 | 2.13 | 2.05 | 2.01 |
| Chr21_54 | 2.05 | 1.91 | 2.04 | 2.07 | 2.07 | 2.03 | 2.01 | 1.91 | 2.02 | 2.03 | 2.20 | 2.09 | 2.32 | 2.22 | 2.09 |
| Chr21_55 | 2.06 | 1.97 | 2.00 | 1.96 | 1.97 | 1.95 | 1.97 | 2.08 | 1.99 | 1.92 | 2.02 | 2.11 | 2.05 | 2.08 | 1.96 |
| Chr21_56 | 2.10 | 2.01 | 1.91 | 2.10 | 1.98 | 1.96 | 1.91 | 1.88 | 1.93 | 2.03 | 1.93 | 2.03 | 2.18 | 1.99 | 1.94 |
| Chr21_57 | 2.03 | 1.97 | 2.14 | 2.13 | 2.14 | 2.17 | 1.99 | 1.98 | 1.96 | 2.17 | 2.16 | 1.88 | 2.39 | 1.93 | 2.35 |
| Chr21_58 | 1.91 | 1.99 | 2.01 | 2.00 | 2.02 | 1.97 | 2.06 | 2.00 | 2.13 | 1.97 | 1.93 | 2.12 | 2.06 | 2.17 | 2.21 |
| Chr21_59 | 1.97 | 2.03 | 2.01 | 2.13 | 2.00 | 2.03 | 2.06 | 2.07 | 2.06 | 1.99 | 2.15 | 2.09 | 2.09 | 2.28 | 2.12 |
| Chr21_60 | 1.98 | 2.00 | 2.16 | 1.96 | 1.98 | 2.07 | 2.03 | 2.07 | 2.16 | 2.05 | 2.08 | 2.07 | 1.98 | 2.16 | 2.16 |
| Chr21_61 | 2.02 | 1.99 | 2.11 | 2.23 | 1.99 | 2.09 | 1.93 | 2.01 | 2.07 | 2.11 | 2.09 | 2.06 | 2.20 | 2.17 | 2.05 |
| Chr21_62 | 2.10 | 2.01 | 1.92 | 1.84 | 2.21 | 2.18 | 2.13 | 2.05 | 2.08 | 2.21 | 2.08 | 2.18 | 2.23 | 2.24 | 2.14 |
| Chr21_63 | 1.95 | 2.00 | 2.01 | 2.12 | 1.97 | 2.02 | 2.07 | 1.96 | 1.98 | 2.04 | 2.11 | 2.09 | 2.22 | 2.06 | 2.15 |
| Chr21_64 | 1.91 | 2.15 | 2.05 | 2.19 | 2.07 | 2.12 | 2.14 | 1.96 | 2.15 | 2.22 | 2.20 | 2.14 | 2.15 | 2.14 | 2.26 |
| Chr21_65 | 1.99 | 2.02 | 2.05 | 2.01 | 1.97 | 2.16 | 1.94 | 1.94 | 1.97 | 1.98 | 2.02 | 2.03 | 2.16 | 2.12 | 2.30 |
| Chr21_66 | 1.96 | 1.98 | 2.08 | 1.97 | 1.92 | 2.10 | 2.01 | 2.01 | 1.93 | 2.03 | 2.06 | 2.07 | 2.23 | 2.04 | 1.99 |
| Chr21_67 | 2.02 | 1.96 | 2.01 | 2.06 | 2.03 | 2.05 | 2.05 | 2.14 | 2.16 | 1.99 | 2.18 | 2.19 | 2.15 | 2.14 | 2.37 |
| Chr21_68 | 1.98 | 1.93 | 2.03 | 2.04 | 2.07 | 1.90 | 2.07 | 2.02 | 2.05 | 2.10 | 2.06 | 2.11 | 2.18 | 2.12 | 2.15 |
| Chr21_69 | 2.07 | 2.02 | 1.96 | 2.11 | 2.15 | 2.23 | 2.21 | 2.09 | 2.23 | 2.16 | 2.24 | 2.07 | 2.31 | 2.18 | 2.20 |
| Chr21_70 | 2.20 | 1.91 | 2.09 | 1.93 | 1.90 | 2.11 | 2.11 | 2.11 | 2.02 | 2.04 | 1.87 | 2.08 | 2.21 | 2.21 | 2.10 |
| Chr21_71 | 2.12 | 2.07 | 1.97 | 2.06 | 2.08 | 2.07 | 2.10 | 2.09 | 2.08 | 2.09 | 2.10 | 1.99 | 2.19 | 2.13 | 2.15 |
| Chr21_72 | 2.01 | 2.01 | 1.97 | 1.83 | 1.96 | 1.92 | 2.02 | 1.97 | 1.98 | 2.03 | 1.92 | 2.09 | 2.11 | 2.11 | 2.05 |
| Chr21_73 | 2.23 | 1.98 | 2.00 | 2.04 | 2.04 | 1.95 | 2.03 | 1.96 | 2.22 | 2.00 | 1.96 | 2.16 | 1.99 | 2.21 | 2.17 |
| Chr21_74 | 2.05 | 1.89 | 2.04 | 2.09 | 2.08 | 1.99 | 2.05 | 2.00 | 2.07 | 2.13 | 2.17 | 2.04 | 2.20 | 2.17 | 2.34 |
| Chr21_75 | 2.10 | 2.09 | 1.98 | 2.04 | 2.23 | 1.79 | 2.01 | 2.04 | 2.08 | 2.17 | 2.00 | 1.96 | 2.03 | 2.16 | 2.18 |
| Chr21_76 | 2.05 | 2.00 | 1.98 | 1.87 | 1.92 | 1.93 | 1.89 | 2.01 | 1.79 | 1.86 | 1.86 | 2.05 | 1.93 | 2.05 | 1.97 |
| Chr21_77 | 2.00 | 1.98 | 2.11 | 1.88 | 1.97 | 1.96 | 1.97 | 1.81 | 2.09 | 2.11 | 2.02 | 2.06 | 2.09 | 2.24 | 2.02 |
| Chr21_78 | 1.95 | 2.05 | 2.00 | 2.11 | 2.12 | 2.00 | 2.16 | 2.07 | 1.99 | 2.31 | 2.24 | 2.04 | 2.25 | 2.27 | 2.27 |
| Chr21_79 | 1.94 | 2.06 | 2.01 | 2.11 | 1.98 | 2.10 | 2.06 | 2.00 | 2.10 | 2.13 | 2.08 | 2.02 | 2.09 | 2.12 | 2.21 |
| Chr21_80 | 2.09 | 2.10 | 1.93 | 2.27 | 2.14 | 1.95 | 2.05 | 2.09 | 2.05 | 2.08 | 1.87 | 2.09 | 2.22 | 2.19 | 2.10 |
| Chr21_81 | 2.09 | 2.08 | 1.83 | 2.11 | 2.18 | 2.08 | 2.27 | 2.02 | 2.08 | 2.32 | 1.98 | 1.78 | 2.25 | 2.05 | 2.18 |
| Chr21_82 | 1.98 | 2.04 | 2.11 | 2.00 | 2.17 | 2.06 | 2.15 | 2.14 | 2.07 | 2.15 | 2.22 | 2.27 | 2.25 | 2.13 | 2.34 |
| Chr21_83 | 2.05 | 1.97 | 1.96 | 2.02 | 2.04 | 2.12 | 1.98 | 1.98 | 1.97 | 2.04 | 2.12 | 2.07 | 2.17 | 2.23 | 2.26 |
| Chr21_84 | 1.99 | 2.04 | 2.00 | 2.01 | 1.90 | 2.20 | 2.12 | 2.17 | 1.89 | 2.02 | 1.90 | 2.10 | 2.14 | 1.94 | 1.99 |
| Chr21_85 | 1.93 | 2.07 | 1.99 | 2.12 | 2.10 | 2.17 | 2.08 | 2.09 | 2.13 | 2.23 | 2.25 | 2.07 | 2.26 | 2.07 | 2.24 |
| Chr21_86 | 2.07 | 1.97 | 2.05 | 2.07 | 2.10 | 1.97 | 1.80 | 1.89 | 2.07 | 2.15 | 2.16 | 2.11 | 2.21 | 2.09 | 2.14 |
| Chr21_87 | 1.95 | 2.03 | 2.02 | 1.91 | 1.93 | 1.94 | 1.99 | 2.05 | 1.86 | 2.00 | 1.92 | 2.07 | 1.98 | 2.32 | 2.09 |
| Chr21_88 | 1.98 | 1.97 | 2.27 | 2.26 | 2.11 | 2.28 | 1.94 | 2.20 | 2.44 | 2.25 | 2.25 | 2.21 | 1.98 | 1.99 | 2.34 |
| Chr21_89 | 2.00 | 1.97 | 2.00 | 2.02 | 2.00 | 1.98 | 1.92 | 1.88 | 1.85 | 1.92 | 1.97 | 2.12 | 2.11 | 2.00 | 2.17 |
| Chr21_90 | 2.03 | 1.98 | 1.94 | 2.08 | 2.31 | 2.00 | 2.00 | 2.16 | 2.11 | 2.11 | 2.08 | 1.98 | 2.16 | 2.25 | 2.22 |
| Chr21_91 | 1.91 | 2.04 | 2.20 | 2.06 | 1.97 | 2.20 | 2.03 | 2.09 | 2.12 | 2.21 | 2.16 | 1.97 | 2.11 | 2.08 | 2.15 |
| Chr21_92 | 2.14 | 2.10 | 1.91 | 2.32 | 2.33 | 2.36 | 2.27 | 2.18 | 2.22 | 2.09 | 2.13 | 2.15 | 2.34 | 2.28 | 2.45 |
| Chr21_93 | 1.94 | 2.01 | 2.06 | 2.02 | 2.00 | 2.03 | 2.19 | 2.14 | 2.04 | 2.05 | 2.07 | 2.01 | 2.28 | 2.19 | 2.21 |
| Chr21_94 | 2.01 | 1.92 | 2.03 | 1.93 | 1.97 | 2.17 | 2.09 | 1.77 | 2.03 | 2.00 | 2.12 | 2.12 | 2.24 | 2.13 | 2.15 |
| Chr21_95 | 2.05 | 2.06 | 1.94 | 2.08 | 1.97 | 2.13 | 2.02 | 1.99 | 2.12 | 2.13 | 2.20 | 2.07 | 2.13 | 2.32 | 2.24 |
| Chr21_96 | 2.00 | 1.94 | 2.15 | 1.86 | 1.93 | 2.15 | 1.94 | 2.03 | 2.06 | 1.99 | 2.04 | 2.24 | 2.07 | 2.23 | 2.27 |
| Median-> | 2.01 | 2.00 | 2.00 | 2.02 | 2.01 | 2.02 | 2.04 | 2.03 | 2.04 | 2.09 | 2.06 | 2.08 | 2.17 | 2.14 | 2.16 |

Figure 14:
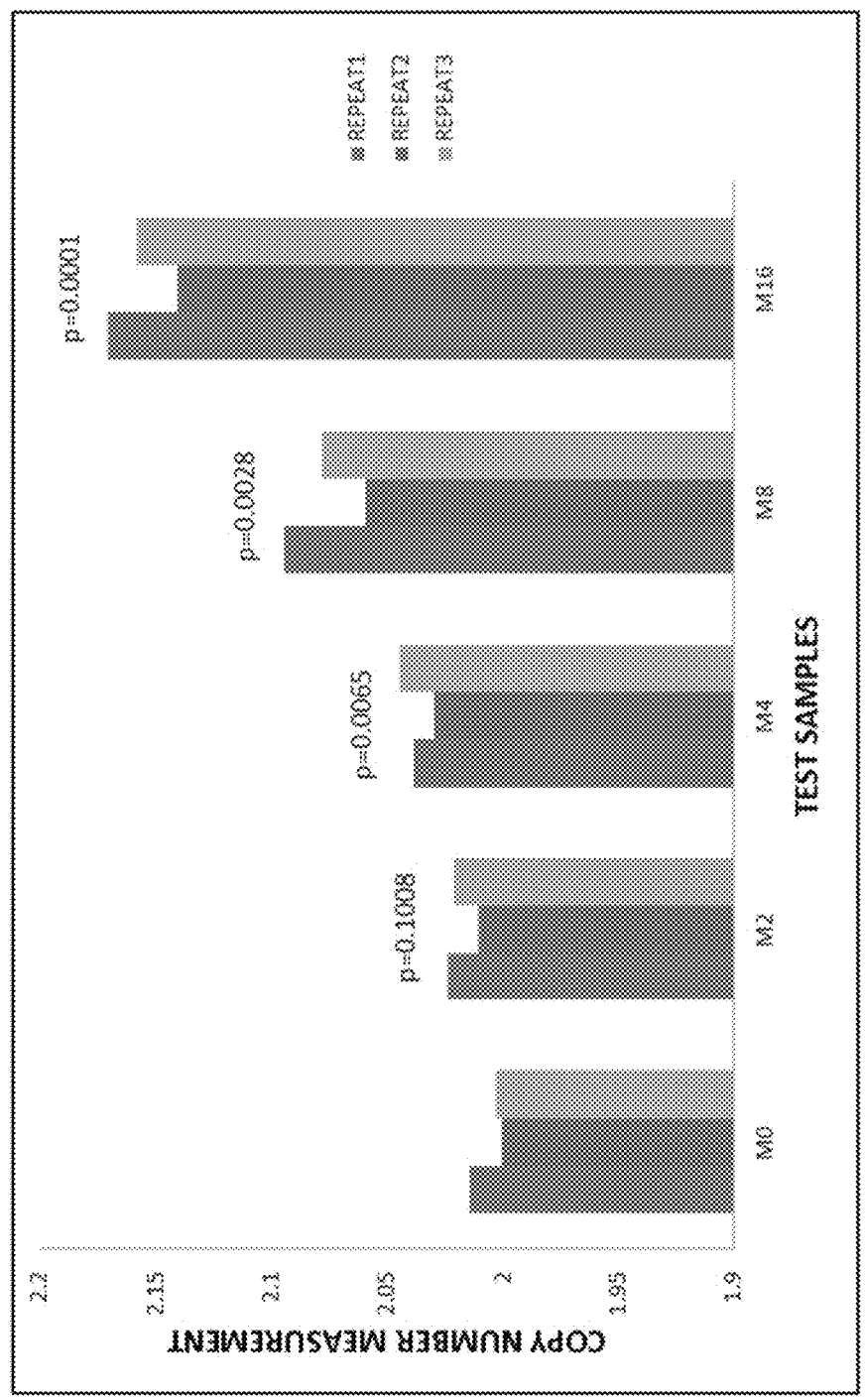
FIG. 14 shows a chart depicting the calculated human chromosome 21 copy number in the five DNA samples. The X axis refers to the five samples: M0, M2, M4, M8, and M16. The Y axis refers to the calculated copy numbers. For each DNA sample, the testing was repeated three times. The p values were derived from Student's t test with the average copy number for M0 DNA sample as the reference.

This exemplary method was sensitive enough to detect a chromosome 21 copy number increase as small as about 2%. The copy number obtained for the five DNA samples were statistically analyzed by performing Student's t test using M0 as the control sample. As shown in FIG. 14, there was no statistically significant difference (P=0.1008<0.01) between the copy number in M2 versus M0, suggesting that the exemplary method was not sensitive enough to detect the copy number difference between sample M2 and sample M0. However, there was statistically significant difference (P=0.0065<0.01) between the copy number in M4 versus M0, suggesting that the exemplary method was sensitive enough to detect the copy number difference between sample M4 and sample M0. The same is true between M8 and M0, and between M16 and M0 because the P values were 0.0028 and 0.0001, respectively. Because the designed copy number of Chromosome 21 in M4 sample was 2.04, which was a 2% increase from the normal copy number of 2.00, the exemplary method was able to detect an increase as small as 2% in a statistically significant manner.

Figure 15:
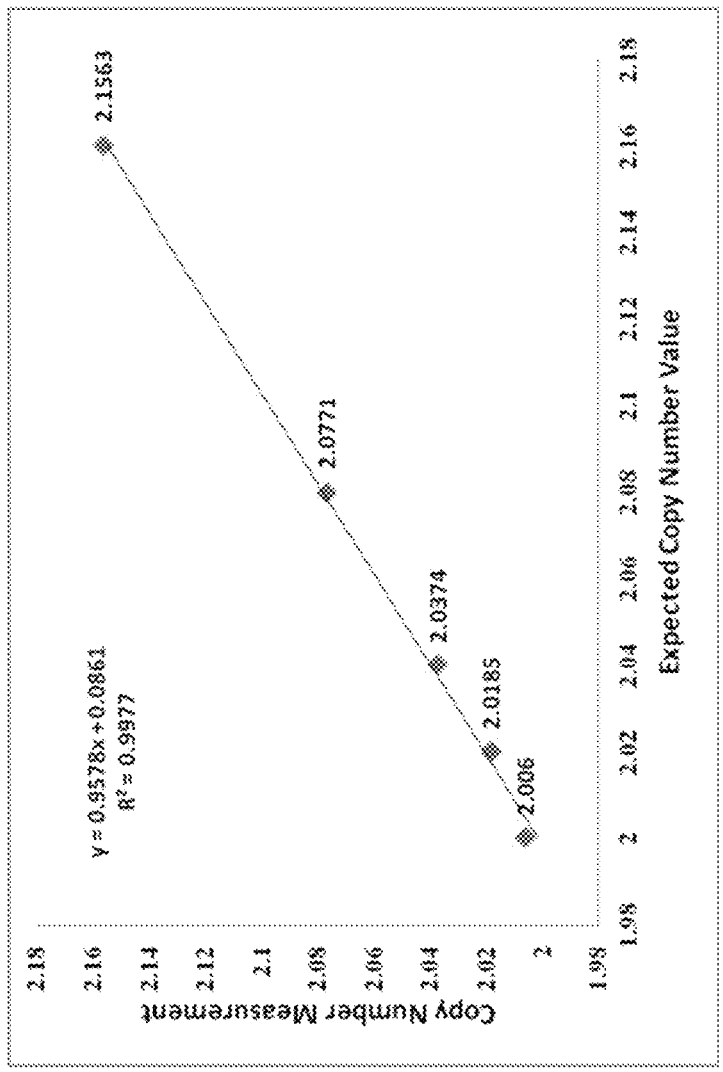
FIG. 15 shows a graph depicting the lineal correlation between the calculated copy number and the expected copy number for the five DNA samples.

Indeed, there was a strong correlation between the calculated or measured copy number and the designed copy number in the five DNA samples. By plotting the measured copy number over the designed copy number in the five DNA samples, a strong correlation could be seen. As shown in FIG. 15, the linear correlation between the two corresponding values gave rise to a $R^2$ of 0.9977.

Therefore, the exemplary method according to the present invention could be used to detect small copy number changes. The exemplary method was sensitive enough to detect a 2% copy number change. The sensitivity may be increased if more regions on chromosome 21 are used as target sites, if more reference target sites are used for some of the target sites on chromosome 21, or if the testing in a sample was repeated for additional times. As such, a person skilled in the art may design and use probes for more target sites on chromosome 21, e.g., 100-500 target sites on chromosome 21, design and use probes for more reference target sites, e.g., 50 reference target sites, and/or repeat the testing in the sample for additional time, e.g., 6-10 times, and by doing so the sensitivity for detecting small copy number changes of chromosome 21 may be increased so that a change less than 2% can be achieved.

What we claim are:

1. A method of assaying nucleic acids in a sample, comprising the steps of:
   a. adding multiple sets of probes into the sample to form a mixture, each set of probes comprising:
      i. a first probe having a first portion at least partially complementary to a first region of a target nucleic acid in the sample and a second portion forming a first primer binding site;
      ii. a second probe having a first portion at least partially complementary to a second region of the target nucleic acid in the sample and a second portion forming a second primer binding site, wherein the 3' end of the first probe is substantially adjacent to the 5' end of the second probe when both probes are hybridized to the target nucleic acid;
   b. denaturing nucleic acids in the mixture;
   c. hybridizing the set of probes to the complementary regions of the target nucleic acid;
   d. performing a ligation reaction in the presence of a ligase enzyme on the set of hybridized probes to connect the substantially adjacent 3' end of the first probe and the 5' end of the second probe to form a third probe, wherein steps b-d are repeated 1-100 times;
   e. amplifying the third probe with multiple sets of primers to obtain an amplification product, each set of primers comprising:
      i. a first primer at least partially complementary to the first primer binding site in one or more first probes of the multiple sets of probes;
      ii. a second primer at least partially complementary to the second primer binding site in one or more second probes of the multiple sets of probes;
   f. assaying the presence, absence or quantity of the target nucleic acid in the sample by determining the presence, absence or quantity of the third probe in the amplification product; and
   wherein at least one primer of each set of primers is labeled with a detectable moiety; and
   wherein at least one primer of the multiple sets of primers includes a stuffer sequence; and
   wherein at least one probe of the multiple sets of probes includes a stuffer sequence.

2. The method of claim 1, wherein more than about 48, 96, 192, or 384 sets of probes are used to assay the presence, absence or quantity of more than about 48, 96, 192, or 384 target nucleic acids in the sample, respectively.

3. The method of claim 1, wherein the sample is a sample of blood, plasma, serum, urine, sputum, spinal fluid, cerebrospinal fluid, pleural fluid, nipple aspirates, lymph fluid, fluid of the respiratory, intestinal, or genitourinary tracts, tear fluid, saliva, breast milk, fluid from the lymphatic system, semen, cerebrospinal fluid, intra-organ system fluid, ascitic fluid, tumor cyst fluid, amniotic fluid, biopsy tissue, paraffin-embedded tissue or a combination thereof from an animal.

4. The method of claim 1, wherein the target nucleic acid is extracted from the sample before forming a mixture with the set of probes.

5. The method of claim 1, wherein the target nucleic acid is DNA, RNA, or cDNA.

6. The method of claim 1, wherein the moiety is a fluorescent dye selected from the group consisting of FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, TAZ, SID, Oregon Green, Rhodamine Green, Rhodamine Red, Texas Red, and Yakima Yellow.

7. The method of claim 1, wherein the stuffer sequence in the at least one primer of the multiple sets of primers has about 10 to about 500 nucleotides, preferably about 10 to about 60 nucleotides.

8. The method of claim 1, wherein no primer has more than about 125 nucleotides, preferably about 75 nucleotides.

9. The method of claim 1, wherein at least one primer of each set of primers includes an oligonucleotide comprising a sequence GTTTCTT or a functional equivalent variant of the oligonucleotide comprising a sequence GTTTCTT.

10. The method of claim 1, wherein the stuffer sequence in the at least one probe of the multiple sets of probes has about 1 to about 200 nucleotides, preferably about 1 to about 55 nucleotides.

11. The method of claim 1, wherein the third probe has no more than about 250 nucleotides.

12. The method of claim 1, wherein no probe has more than about 125 nucleotides.

13. The method of 1, wherein the determination of the presence, absence or quantity of the third probe in the amplification product is carried out by measuring the presence, absence or quantity of the third probe in the amplification product on the basis of detectable moieties, fragment sizes, or both.

14. The method of claim 13, wherein the measurement is carried out using capillary electrophoresis.

15. The method of claim 1, wherein the target nucleic acid has a single nucleotide polymorphism.

16. The method of claim 15, wherein either the first or the second probe is an allele-specific probe corresponding to the single nucleotide polymorphism.

17. The method of claim 16, wherein the second, third, or fourth nucleotide away from the polymorphic nucleotide in the allele-specific probe does not match the corresponding nucleotide in the target region.

18. The method of claim 1, wherein the target nucleic acid has an insertion, a duplication, or a deletion of polynucleotide.

19. The method of claim 18, wherein the target nucleic acid is the dystrophin gene having a deletion of one or more exons and the sets of probes for assaying the dystrophin gene comprise one or more probe pairs selected from SEQ ID NOs: 158-541.

20. The method of claim 1, wherein the target nucleic acid contains an unknown point mutation, insertion, or deletion of one or more nucleotides.

21. The method of claim 20, wherein the unknown point mutation, insertion, or deletion of one or more nucleotides is in the dystrophin gene and the sets of probes for assaying the dystrophin gene comprise one or more probe pairs selected from SEQ ID NOs: 158-541.

22. The method of claim 1, wherein the target nucleic acid is a messenger RNA.

23. The method of claim 1, wherein the target nucleic acid includes one or more methylated nucleotides.

24. The method of claim 1, wherein the target nucleic acid is from a pathogen including a virus and a bacterium.

25. The method of claim 1, wherein the target nucleic acid is from a transgenic organism including a transgenic plant selected from the group consisting of transgenic corn, transgenic rice, transgenic soybean and transgenic cotton, and a transgenic animal selected from the group consisting of a transgenic cow, a transgenic pig, a transgenic sheep and a transgenic dog.

26. The method of claim 1, wherein the denaturing step is carried at about 90° C. to about 99° C. for about 5 seconds to about 30 minutes, and the hybridization and the ligation steps are carried out simultaneously at about 4° C. to about 70° C. for about 1 minute to about 48 hours, preferably the denaturing step is carried at about 95° C. for about 30 seconds, and the hybridization and the ligation steps are carried out simultaneously at about 58° C. for about 4 hours.

27. The method of claim 26, wherein the steps of denaturing, hybridization and ligation are repeated 2-10 times.

28. The method of claim 1, wherein two or more sets of probes are used to hybridize to two or more target sites in the target nucleic acid, with each set of probes hybridizing to a different target site.

29. The method of claim 28, wherein the target nucleic acid has a copy number change of about 0.1% to about 30% between two samples.

30. The method of claim 29, wherein the copy number change of the target nucleic acid is about 2%, about 4%, or about 8%.

31. The method of claim 28, wherein for each set of probes hybridizing to a target site in the target nucleic acid, one or more sets of reference probes are used to hybridize to one or more reference target sites, with each set of reference probes hybridizing to a different reference target site.

32. The method of claim 31, wherein about 1 to about 100 sets of reference probes are used, preferably about 6 to about 12 sets of reference probes are used.

33. The method of claim 31, wherein one set of primers is used to amply a group of the third probes, said group of the third probes comprises multiple third probes which are formed from multiple sets of probes hybridizing to multiple target sites and from multiple sets of reference probes hybridizing to multiple reference target sites.

34. The method of claim 33, wherein the multiple third probes in the group are formed from about 1 to about 100 sets of probes hybridizing to target sites and about 1 to about 100 sets of reference probes.

35. The method of claim 29, wherein about 50 to about 500 sets of probes are used to hybridize to about 50 to about 500 target sites on the target nucleic acid.

36. The method of claim 29, wherein the target nucleic acid corresponds to at least a part of human chromosome 21, human chromosome 18, human chromosome 13, human chromosome region 22q11.2, or the pseudoautosomal regions of human chromosomes X or Y in a maternal blood or urine sample.

37. The method of claim 36, wherein the target nucleic acid corresponds to a part of human chromosome 21 and the sets of probes for assaying the part of human chromosome 21 comprise probe pairs selected from SEQ ID NOs: 559-942.

38. A kit for assaying nucleic acids in a sample, comprising:
  a. multiple sets of probes corresponding to a target nucleic acid, each set of probes comprising:
    i. a first probe having a first portion at least partially complementary to a first region of a target nucleic acid in the sample and a second portion forming a first primer binding site; ii. a second probe having a first portion at least partially complementary to a second region of the target nucleic acid in the sample and a second portion forming a second primer binding site, wherein the 5' end of the first probe is essentially adjacent to the 3' end of the second probe when both probes are hybridized to the target nucleic acid and the first and the second probes may be ligated to form a third probe;
  b. multiple sets of primers for amplifying the third probe, with at least one primer of each set of the one or more sets of primers being labeled with a detectable moiety and with at least one primer of the multiple sets of primers including a stuffer sequence, wherein each set of the multiple sets of primers comprising: i. a first primer at least partially complementary to the first primer binding site in one or more first probes of the multiple sets of probes; and ii. a second primer at least partially complementary to the second primer binding site in one or more second probes of the multiple sets of probes;
  c. reagents including a ligase, a buffer for a ligation reaction, a DNA polymerase, a buffer for a polymerase chain reaction, or a combination thereof; and
  d. optionally a brochure containing instructions of using the kit.

39. The kit of claim 38, wherein the moiety is a fluorescent dye selected from the group consisting of FAM (5- or 6-carboxyfluorescein), VIC, NED, PET, Fluorescein, FITC, IRD-700/800, CY3, CY5, CY3.5, CY5.5, HEX, TET, TAMRA, JOE, ROX, BODIPY TMR, TAZ, SID, Oregon Green, Rhodamine Green, Rhodamine Red, Texas Red, and Yakima Yellow.

40. The kit of claim 38, wherein the stuffer sequence in the at least one primer of the multiple sets of primers has about 10 to about 500 nucleotides.

41. The kit of claim 38, wherein at least one probe of each set of probes includes a stuffer sequence having about 1 to about 200 nucleotides.

42. The kit of claim 38, wherein the target nucleic acid is a dystrophin gene and the kit includes one or more sets of probes comprises probe pairs selected from SEQ ID NOs: 158-541 for detecting Duchenne muscular dystrophy.

43. The kit of claim 38, wherein the target nucleic acid is on human chromosome 21 and the kit includes one or more sets of probes comprises probe pairs selected from SEQ ID NOs: 559-942 for detecting fetal Down's syndrome in a maternal blood or urine sample.

44. The method of claim 29, further comprising a step of determining the copy number of the target nucleic acid in a sample by taking the average of the copy numbers of all target sites on the target nucleic acid or by taking the average of the copy numbers of all target sites on the target nucleic acid after abandoning egregious values.

45. The method of claim 29, further comprising a step of determining the copy number of the target nucleic acid in a sample by taking the median value of the copy numbers of all target sites on the target nucleic acid or by taking the median value of the copy numbers of all target sites on the target nucleic acid after abandoning egregious values.

* * * * *

```
                        SEQUENCE LISTING

<160> NUMBER OF SEQ ID NOS: 959

<210> SEQ ID NO 1
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 1
gagaagagtt cagcagcttt ctggattata gcgccggtca atagagaaa              49

<210> SEQ ID NO 2
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 2
ttattgcacg cgtcagccta tttccactgg attccatcca cagg                   44

<210> SEQ ID NO 3
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 3
ttattgcacg cgtcagccta tttttccact ggattccatc cacaga                 46

<210> SEQ ID NO 4
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 4
ttcagggaca accctccata aatgtagcgc cggtcaatag agaaa                  45

<210> SEQ ID NO 5
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 5
tattcgctca taacgggttc gcctctccca cctgccttg tc                      42

<210> SEQ ID NO 6
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 6
tattcgctca taacgggttc gttcctctcc cacctgccct tgtt                   44
```

<210> SEQ ID NO 7
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 7
tcagaggctc tttgagagga gggatttagc gccggtcaat agagaaa           47

<210> SEQ ID NO 8
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 8
tgctaactag atcgcgggtt gtgtgagccc cttggtgaca gag               43

<210> SEQ ID NO 9
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 9
tgctaactag atcgcgggtt gtttgtgagc cccttggtga cagaa             45

<210> SEQ ID NO 10
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 10
gattgtatct gcagctcaag accacattac gcgattacta gcgccggtca atagagaaa    59

<210> SEQ ID NO 11
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 11
tgctaactag atcgcgggtt gttccagttg gatcaccatg aacgaggt          48

<210> SEQ ID NO 12
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 12
tgctaactag atcgcgggtt gccagttgga tcaccatgaa cgaagc            46

<210> SEQ ID NO 13
<211> LENGTH: 59
<212> TYPE: DNA
<213> ORGANISM: Artificial
<220> FEATURE:

-continued

<223> OTHER INFORMATION: synthetic oligonucleotide primers or probes

<400> SEQUENCE: 13
caggatgaac aaccaagtga ttcaattacg cgattacgag tccgttagcc cgatggtaa    59

<210> SEQ ID NO 14
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 14
tattcgctca taacgggttc gattccacca gctccaatca gactagccta              50

<210> SEQ ID NO 15
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 15
tattcgctca taacgggttc gaccaccagc tccaatcaga ctagcttg                48

<210> SEQ ID NO 16
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 16
tcaaatgtgc agagttccag agtctattac gcgattacag tccgttagcc cgatggtaa    59

<210> SEQ ID NO 17
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 17
ttattgcacg cgtcagccta tagcatgttg tccatctgac tccctacc                48

<210> SEQ ID NO 18
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 18
ttattgcacg cgtcagccta tattgcatgt tgtccatctg actccctgct              50

<210> SEQ ID NO 19
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 19
ctgttcctgg agaaaaggta attatttgaa ttacgcgaag tccgttagcc cgatggtaa    59

```
<210> SEQ ID NO 20
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 20
acacgaccgg taacgcttag aattatttcc aggattttcc ccaggtccat            50

<210> SEQ ID NO 21
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 21
acacgaccgg taacgcttag aattatccag gattttcccc aggtctac              48

<210> SEQ ID NO 22
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 22
aagcagaaat ggaaggaacg ggattacagt ccgttagccc gatggtaa              48

<210> SEQ ID NO 23
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 23
acacgaccgg taacgcttag agggtcaagc gcattcagga gtac                  44

<210> SEQ ID NO 24
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 24
acacgaccgg taacgcttag attgggtcaa gcgcattcag gagcat                46

<210> SEQ ID NO 25
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 25
tcaaagtcag ggatttcaac ctagcattac gcgattacta gcgccggtca atagagaaa  59

<210> SEQ ID NO 26
<211> LENGTH: 56
<212> TYPE: DNA
<213> ORGANISM: Artificial
<220> FEATURE:
<223> OTHER INFORMATION: synthetic oligonucleotide primers or probes
```

<400> SEQUENCE: 26
acacgaccgg taacgcttag aattacttgc actatgagct catctcttca cagaga      56

<210> SEQ ID NO 27
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 27
acacgaccgg taacgcttag aattacgcac tatgagctca tctcttcaca gagc        54

<210> SEQ ID NO 28
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 28
ctattcatat tccaacagcc tccagaatta cgcgattata gcgccggtca atagagaaa   59

<210> SEQ ID NO 29
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 29
tgctaactag atcgcgggtt gattttaaga aaaaactcac ccagctgtta gca         53

<210> SEQ ID NO 30
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 30
tgctaactag atcgcgggtt gattaagaaa aaactcaccc agctgttaac g           51

<210> SEQ ID NO 31
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 31
agctacaggc ctgattccct ttcattacgc gatagcgccg gtcaatagag aaa         53

<210> SEQ ID NO 32
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 32
tattcgctca taacgggttc gtgttgatga gccagtgcat atacg                  45

<210> SEQ ID NO 33
<211> LENGTH: 47

```
<212> TYPE: DNA
<213> ORGANISM: Artificial
<220> FEATURE:
<223> OTHER INFORMATION: synthetic oligonucleotide primers or probes

<400> SEQUENCE: 33
tattcgctca taacgggttc gtttgttgat gagccagtgc atatgca                    47

<210> SEQ ID NO 34
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 34
ggggtgccaa cagatgtgtt atagcgccgg tcaatagaga aa                         42

<210> SEQ ID NO 35
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 35
tgctaactag atcgcgggtt gttacctcag gggccatcca gcat                       44

<210> SEQ ID NO 36
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 36
tgctaactag atcgcgggtt gacctcaggg gccatccagt ac                         42

<210> SEQ ID NO 37
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 37
ttgcggctgg atcaagtgat attacgcagt ccgttagccc gatggtaa                   48

<210> SEQ ID NO 38
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 38
tgctaactag atcgcgggtt gttcactgct gtgacctttt gatagtca                   48

<210> SEQ ID NO 39
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 39
```
tgctaactag atcgcgggtt gcactgctgt gaccttttga tagtcg         46

<210> SEQ ID NO 40
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 40
gccatgaaca gtaaaggaag attgtacgat tacgcgatta gcgccggtca atagagaaa         59

<210> SEQ ID NO 41
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 41
acacgaccgg taacgcttag aattattgga gtgagaagtg ccctcttcct t         51

<210> SEQ ID NO 42
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 42
acacgaccgg taacgcttag aattaggagt gagaagtgcc ctcttcttc         49

<210> SEQ ID NO 43
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 43
catccttgga gagccacatg aatagtccgt tagcccgatg gtaa         44

<210> SEQ ID NO 44
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 44
tattcgctca taacgggttc gaacaagggc ttcatcagca tcg         43

<210> SEQ ID NO 45
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 45
tattcgctca taacgggttc gttaacaagg gcttcatcag cacca         45

<210> SEQ ID NO 46
<211> LENGTH: 55
<212> TYPE: DNA
<213> ORGANISM: Artificial

```
<220> FEATURE:
<223> OTHER INFORMATION: synthetic oligonucleotide primers or probes

<400> SEQUENCE: 46
aaattcagat ccacaagtcg aggaattacg cgattagcgc cggtcaatag agaaa          55

<210> SEQ ID NO 47
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 47
tgctaactag atcgcgggtt gttgctcctt cagttggttc tccacct                   47

<210> SEQ ID NO 48
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 48
tgctaactag atcgcgggtt ggctccttca gttggttctc catcc                     45

<210> SEQ ID NO 49
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 49
acaggagaaa aatgcttcag tcaaagatta cgcgatttag cgccggtcaa tagagaaa       58

<210> SEQ ID NO 50
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 50
tattcgctca taacgggttc gcttcccctt catccgaatg ttgac                     45

<210> SEQ ID NO 51
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 51
tattcgctca taacgggttc gttcttcccc ttcatccgaa tgttgat                   47

<210> SEQ ID NO 52
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 52
ttgggaacta ggccacctat taatatgatt acgcgattag tccgttagcc cgatggtaa      59
```

<210> SEQ ID NO 53
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 53
acacgaccgg taacgcttag aattactttt tgatgatgaa gcatactatg catcg    55

<210> SEQ ID NO 54
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 54
acacgaccgg taacgcttag aattactttg atgatgaagc atactatgca tcc    53

<210> SEQ ID NO 55
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 55
gtaaggaggt gcttcatctt caggctagcg ccggtcaata gagaaa    46

<210> SEQ ID NO 56
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 56
ttattgcacg cgtcagccta tttcagacgg tcctctcttg caca    44

<210> SEQ ID NO 57
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 57
ttattgcacg cgtcagccta tcagacggtc ctctcttgca cg    42

<210> SEQ ID NO 58
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 58
atctccttga ggaaaaatgg cttcatagcg ccggtcaata gagaaa    46

<210> SEQ ID NO 59
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 59
acacgaccgg taacgcttag atttggccac atcctggatg tga        43

<210> SEQ ID NO 60
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 60
acacgaccgg taacgcttag atggccacat cctggatgtg g        41

<210> SEQ ID NO 61
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 61
tctttggttt gctcttgaac ctgaattacg cgattatagc gccggtcaat agagaaa        57

<210> SEQ ID NO 62
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 62
acacgaccgg taacgcttag attcccgaga agagggttct tactgtgt        48

<210> SEQ ID NO 63
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 63
acacgaccgg taacgcttag acccgagaag agggttctta ctgtgc        46

<210> SEQ ID NO 64
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 64
ttctcttcac aaaaggctct gaagacatta cgcgattaag tccgttagcc cgatggtaa        59

<210> SEQ ID NO 65
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 65
tattcgctca taacgggttc gattgcctcc tcaccaccat ctgatctatc atg        53

<210> SEQ ID NO 66

<210> SEQ ID NO 66
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 66
tattcgctca taacgggttc gattttgcct cctcaccacc atctgatcta tcgta        55

<210> SEQ ID NO 67
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 67
ggggaaaatc tggctaacaa cagattacgc gagtccgtta gcccgatggt aa           52

<210> SEQ ID NO 68
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 68
tattcgctca taacgggttc gaagaacagc tggaatcatt tctcg                   45

<210> SEQ ID NO 69
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 69
tattcgctca taacgggttc gttaagaaca gctggaatca tttctca                 47

<210> SEQ ID NO 70
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 70
gtcaatctgg gctctatcca agcattaagt ccgttagccc gatggtaa                48

<210> SEQ ID NO 71
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 71
tattcgctca taacgggttc gttccattac ggatccgacc gttcaa                  46

<210> SEQ ID NO 72
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 72
tattcgctca taacgggttc gccattacgg atccgaccgt tcag    44

<210> SEQ ID NO 73
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 73
ttgtcgacaa tgacgacatt ggattacgcg aagtccgtta gcccgatggt aa    52

<210> SEQ ID NO 74
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 74
acacgaccgg taacgcttag attccatcac ttgggaacag tttctgg    47

<210> SEQ ID NO 75
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 75
acacgaccgg taacgcttag accatcactt gggaacagtt tctgc    45

<210> SEQ ID NO 76
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 76
tcttatgtct gtccctcaca ggtgtattag tccgttagcc cgatggtaa    49

<210> SEQ ID NO 77
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 77
ttattgcacg cgtcagccta tggcccagat tcctccaaga acc    43

<210> SEQ ID NO 78
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 78
ttattgcacg cgtcagccta tttggcccag attcctccaa gagct    45

<210> SEQ ID NO 79
<211> LENGTH: 45
<212> TYPE: DNA

```
<213> ORGANISM: Artificial
<220> FEATURE:
<223> OTHER INFORMATION: synthetic oligonucleotide primers or probes

<400> SEQUENCE: 79
ggagaaagac attgagaccg tcagagtccg ttagcccgat ggtaa            45

<210> SEQ ID NO 80
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 80
ttattgcacg cgtcagccta ttttgtcggc ctccaaggga tggt             44

<210> SEQ ID NO 81
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 81
ttattgcacg cgtcagccta ttgtcggcct ccaagggata gc               42

<210> SEQ ID NO 82
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 82
agcttcagga cagagatgtc actgaattac gcgattacta gcgccggtca atagagaaa    59

<210> SEQ ID NO 83
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 83
tattcgctca taacgggttc gatttcctgt cgagagcact tgtccactgt t         51

<210> SEQ ID NO 84
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 84
tattcgctca taacgggttc gatcctgtcg agagcacttg tccactgtc            49

<210> SEQ ID NO 85
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 85
gaagaaagct agaaaagccc aacccattat agcgccggtc aatagagaaa           50
```

<210> SEQ ID NO 86
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 86
tattcgctca taacgggttc gttcctgaga ccatccacct gaagc                45

<210> SEQ ID NO 87
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 87
tattcgctca taacgggttc gcctgagacc atccacctga agg                  43

<210> SEQ ID NO 88
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 88
tcaacagcct ccttcttttt ctgtagatta cgctagcgcc ggtcaataga gaaa      54

<210> SEQ ID NO 89
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 89
ttattgcacg cgtcagccta ttttctcaat tgtcgtttg ccggtt                46

<210> SEQ ID NO 90
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 90
ttattgcacg cgtcagccta ttctcaattt gtcgtttgcc gatc                 44

<210> SEQ ID NO 91
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 91
cattctgtaa aggagtcagg tcctggatta cgcgagtccg ttagcccgat ggtaa     55

<210> SEQ ID NO 92
<211> LENGTH: 44
<212> TYPE: DNA
<213> ORGANISM: Artificial
<220> FEATURE:

<223> OTHER INFORMATION: synthetic oligonucleotide primers or probes

<400> SEQUENCE: 92
tgctaactag atcgcgggtt gcctggtttt ggtccaaaag ctgg         44

<210> SEQ ID NO 93
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 93
tgctaactag atcgcgggtt gttcctggtt ttggtccaaa agctga       46

<210> SEQ ID NO 94
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 94
gttttcccca cacaacttca gcatagtccg ttagcccgat ggtaa        45

<210> SEQ ID NO 95
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 95
acacgaccgg taacgcttag attttcagat ccctccaggg gtgg         44

<210> SEQ ID NO 96
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 96
acacgaccgg taacgcttag attcagatcc ctccaggggt gc           42

<210> SEQ ID NO 97
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 97
aatttgtcct catcacagac ggaattacgc gattagtccg ttagcccgat ggtaa    55

<210> SEQ ID NO 98
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 98
ttattgcacg cgtcagccta ttctcaccaa taaattcatt gtggacg      47

```
<210> SEQ ID NO 99
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 99
ttattgcacg cgtcagccta ttttctcacc aataaattca ttgtggaca                49

<210> SEQ ID NO 100
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 100
aagtacctgg agcagagcga ggattacgct agcgccggtc aatagagaaa               50

<210> SEQ ID NO 101
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 101
tgctaactag atcgcgggtt gtggaactgg atgatgaagc tgtcg                    45

<210> SEQ ID NO 102
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 102
tgctaactag atcgcgggtt gtttggaact ggatgatgaa gctgtca                  47

<210> SEQ ID NO 103
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 103
gtgcttggct ttcgattact tttctattac gcgatttagc gccggtcaat agagaaa       57

<210> SEQ ID NO 104
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 104
ttattgcacg cgtcagccta tttaaggcta cccccatgat agtctcct                 48

<210> SEQ ID NO 105
<211> LENGTH: 46
<212> TYPE: DNA
<213> ORGANISM: Artificial
<220> FEATURE:
<223> OTHER INFORMATION: synthetic oligonucleotide primers or probes
```

<400> SEQUENCE: 105
ttattgcacg cgtcagccta taaggctacc cccatgatag tcttcc    46

<210> SEQ ID NO 106
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 106
agtctcatta acaatgcatt tcagctyatt acgcgattta gcgccggtca atagagaaa    59

<210> SEQ ID NO 107
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 107
ttattgcacg cgtcagccta tattacgcga tcagtcagca gtaatgatcg gtcg    54

<210> SEQ ID NO 108
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 108
ttattgcacg cgtcagccta tattacgcga tttcagtcag cagtaatgat cggtca    56

<210> SEQ ID NO 109
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 109
tctcatcaac aacagaggtc tctgtgatta cgcgatagtc cgttagcccg atggtaa    57

<210> SEQ ID NO 110
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 110
tattcgctca taacgggttc gtttggcaga gatgtgtgag ggtgagt    47

<210> SEQ ID NO 111
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 111
tattcgctca taacgggttc gtggcagaga tgtgtgaggg tgagg    45

<210> SEQ ID NO 112
<211> LENGTH: 49

-continued

```
<212> TYPE: DNA
<213> ORGANISM: Artificial
<220> FEATURE:
<223> OTHER INFORMATION: synthetic oligonucleotide primers or probes

<400> SEQUENCE: 112
cacgtttcct acaagcacag caattacgta gcgccggtca atagagaaa                49

<210> SEQ ID NO 113
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 113
acacgaccgg taacgcttag agccgcaaag agagcctaaa gaag                    44

<210> SEQ ID NO 114
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 114
acacgaccgg taacgcttag attgccgcaa agagagccta aaggaa                  46

<210> SEQ ID NO 115
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 115
gggaagtccc ctaaatgatt attggattac gcgattaagt ccgttagccc gatggtaa     58

<210> SEQ ID NO 116
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 116
tgctaactag atcgcgggtt gggttggaat actgcagact gcctgt                  46

<210> SEQ ID NO 117
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 117
tgctaactag atcgcgggtt gttggttgga atactgcaga ctgcctga                48

<210> SEQ ID NO 118
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 118
```
gggtgtgaag atcctcctca gcagtccgtt agcccgatgg taa         43

<210> SEQ ID NO 119
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 119
tgctaactag atcgcgggtt gtgacttgca gatgccccaa g         41

<210> SEQ ID NO 120
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 120
tgctaactag atcgcgggtt gtttgacttg cagatgcccc gaa         43

<210> SEQ ID NO 121
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 121
gctgtgattt cttggacaat attggaatta cgcgattata gcgccggtca atagagaaa         59

<210> SEQ ID NO 122
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 122
tattcgctca taacgggttc gattatttca agatttccaa cattacacac tccaca         56

<210> SEQ ID NO 123
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 123
tattcgctca taacgggttc gattatcaag atttccaaca ttacacactc cacg         54

<210> SEQ ID NO 124
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 124
tcctctgtct acctttctcc cacaattacg cgattacgag tccgttagcc cgatggtaa         59

<210> SEQ ID NO 125
<211> LENGTH: 50
<212> TYPE: DNA
<213> ORGANISM: Artificial

```
<220> FEATURE:
<223> OTHER INFORMATION: synthetic oligonucleotide primers or probes

<400> SEQUENCE: 125
tgctaactag atcgcgggtt gaccttactg agaccatcag aaggcagaga              50

<210> SEQ ID NO 126
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 126
tgctaactag atcgcgggtt gattccttac tgagaccatc agaaggcaga gt           52

<210> SEQ ID NO 127
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 127
gcttgctgga aaaagtaaaa taaatgagta ttacgcgaag tccgttagcc cgatggtaa    59

<210> SEQ ID NO 128
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 128
ttattgcacg cgtcagccta tatttctgtt ttactgtttt cctctgaaaa actct        55

<210> SEQ ID NO 129
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 129
ttattgcacg cgtcagccta tatctgtttt actgttttcc tctgaaaaac tcc          53

<210> SEQ ID NO 130
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 130
ggctgtgact actcaactcc agataaaatt acgcgatagt ccgttagccc gatggtaa     58

<210> SEQ ID NO 131
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 131
acacgaccgg taacgcttag atttcttgct gaagtgtccc acccat                  46
```

<210> SEQ ID NO 132
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 132
acacgaccgg taacgcttag atcttgctga agtgtcccac ctac                44

<210> SEQ ID NO 133
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 133
tctcaacggt tgtcaattcc accatagtcc gttagcccga tggtaa              46

<210> SEQ ID NO 134
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 134
tgctaactag atcgcgggtt gttcgaaaga tgctgaaaac cgtca               45

<210> SEQ ID NO 135
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 135
tgctaactag atcgcgggtt gcgaaagatg ctgaaaaccg tcc                 43

<210> SEQ ID NO 136
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 136
agcttcttgc ctctatgtgg gaaattacgc gattacgcta gcgccggtca atagagaaa    59

<210> SEQ ID NO 137
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 137
ttattgcacg cgtcagccta taccctttac agtgtatggc agctcatcc            49

<210> SEQ ID NO 138
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 138
ttattgcacg cgtcagccta tattcccttt acagtgtatg gcagctcacc t        51

<210> SEQ ID NO 139
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 139
tacagccacc ttttgggttt caattacgcg agtccgttag cccgatggta a        51

<210> SEQ ID NO 140
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 140
ttattgcacg cgtcagccta tgaaactgcc atgtcaccct tctcac             46

<210> SEQ ID NO 141
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 141
ttattgcacg cgtcagccta tttgaaactg ccatgtcacc cttctcat           48

<210> SEQ ID NO 142
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 142
ctggagtcaa tgtaagttca gtgccattac gcgtagcgcc ggtcaataga gaaa    54

<210> SEQ ID NO 143
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 143
acacgaccgg taacgcttag attgcgacga gcagtacatg cagatc             46

<210> SEQ ID NO 144
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 144
acacgaccgg taacgcttag agcgacgagc agtacatgca gatg               44

<210> SEQ ID NO 145

```
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 145
acacgaccgg taacgcttag a                                             21

<210> SEQ ID NO 146
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 146
tattcgctca taacgggttc g                                             21

<210> SEQ ID NO 147
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 147
ttattgcacg cgtcagccta t                                             21

<210> SEQ ID NO 148
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 148
tgctaactag atcgcgggtt g                                             21

<210> SEQ ID NO 149
<211> LENGTH: 29
<212> TYPE: DNA
<213> ORGANISM: Artificial
<220> FEATURE:
<223> OTHER INFORMATION: synthetic oligonucleotide primers or probes

<400> SEQUENCE: 149
gtttcttgtt accatcgggc taacggact                                     29

<210> SEQ ID NO 150
<211> LENGTH: 62
<212> TYPE: DNA
<213> ORGANISM: Artificial
<220> FEATURE:
<223> OTHER INFORMATION: synthetic oligonucleotide primers or probes

<400> SEQUENCE: 150
gtttcttcga cgatacgacg atacgacgat acgacgatac gtttctctat tgaccggcgc   60
ta                                                                  62

<210> SEQ ID NO 151
<211> LENGTH: 21
<212> TYPE: DNA
<213> ORGANISM: Artificial
<220> FEATURE:
<223> OTHER INFORMATION: synthetic oligonucleotide primers or probes
```

```
<400> SEQUENCE: 151
acacgaccgg taacgcttag a                                              21

<210> SEQ ID NO 152
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 152
tattcgctca taacgggttc g                                              21

<210> SEQ ID NO 153
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 153
ttattgcacg cgtcagccta t                                              21

<210> SEQ ID NO 154
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 154
tgctaactag atcgcgggtt g                                              21

<210> SEQ ID NO 155
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 155
agtccgttag cccgatggta a                                              21

<210> SEQ ID NO 156
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 156
tagcgccggt caatagagaa a                                              21

<210> SEQ ID NO 157
<211> LENGTH: 34
<212> TYPE: DNA
<213> ORGANISM: Artificial
<220> FEATURE:
<223> OTHER INFORMATION: synthetic oligonucleotide primers or probes

<400> SEQUENCE: 157
cgacgatacg acgatacgac gatacgacga tacg                                34

<210> SEQ ID NO 158
```

```
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 158
agagccatga acggagaggt ggattacgcg atagcgccgg tcaatagaga aa            52

<210> SEQ ID NO 159
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 159
tattcgctca taacgggttc gattacgcag agcatgcttc agttgccatg               50

<210> SEQ ID NO 160
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 160
cctggcctgc tctagcttct tatatctacc attacgagtc cgttagcccg atggtaa       57

<210> SEQ ID NO 161
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 161
acacgaccgg taacgcttag aaactaggaa ttggacaagc cagtaggg                 48

<210> SEQ ID NO 162
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 162
taatttagtg ctttgcatct ctcattcttc attattacag tccgttagcc cgatggtaa     59

<210> SEQ ID NO 163
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 163
ttattgcacg cgtcagccta tattactcta tcttgctgtg tggtgagaaa agaaa         55

<210> SEQ ID NO 164
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 164
```

```
ctgattcctt taccacatag aggctgagag tccgttagcc cgatggtaa              49

<210> SEQ ID NO 165
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 165
ttattgcacg cgtcagccta tcctacttgc aggactcaat ccgaact              47

<210> SEQ ID NO 166
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 166
tatgggtgag ctatctactt acagcgagtg attacgcgaa gtccgttagc ccgatggtaa    60

<210> SEQ ID NO 167
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 167
ttattgcacg cgtcagccta tattacgcga ttcatggtta aagtgatggg ttagcaggac    60

<210> SEQ ID NO 168
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 168
agtggcacat agctattttc agccgatagc gccggtcaat agagaaa              47

<210> SEQ ID NO 169
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 169
ttattgcacg cgtcagccta taggacaccc cgacatgact cctaaa               46

<210> SEQ ID NO 170
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 170
taccaggttt tttttatcgc tgccttgatt acgcgattta gcgccggtca atagagaaa     59

<210> SEQ ID NO 171
<211> LENGTH: 55
<212> TYPE: DNA
```

```
<213> ORGANISM: Artificial
<220> FEATURE:
<223> OTHER INFORMATION: synthetic oligonucleotide primers or probes

<400> SEQUENCE: 171
tgctaactag atcgcgggtt gatgcctact ggagcaataa agtttgaaga acttt         55

<210> SEQ ID NO 172
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 172
tccgaaggta attgcctccc agattactag cgccggtcaa tagagaaa                 48

<210> SEQ ID NO 173
<211> LENGTH: 61
<212> TYPE: DNA
<213> ORGANISM: Artificial
<220> FEATURE:
<223> OTHER INFORMATION: synthetic oligonucleotide primers or probes

<400> SEQUENCE: 173
tgctaactag atcgcgggtt gattaaaaaa gtaacacttc agttttcct attcgttttt     60 c                                                                    61

<210> SEQ ID NO 174
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 174
aaacattcac aaaatgggta aatgcacaat tacgcgattt agcgccggtc aatagagaaa    60

<210> SEQ ID NO 175
<211> LENGTH: 61
<212> TYPE: DNA
<213> ORGANISM: Artificial
<220> FEATURE:
<223> OTHER INFORMATION: synthetic oligonucleotide primers or probes

<400> SEQUENCE: 175
tgctaactag atcgcgggtt gattacgcgc attttagatg aaagagaaga tgttcaaaag    60
a                                                                    61

<210> SEQ ID NO 176
<211> LENGTH: 63
<212> TYPE: DNA
<213> ORGANISM: Artificial
<220> FEATURE:
<223> OTHER INFORMATION: synthetic oligonucleotide primers or probes

<400> SEQUENCE: 176
taatatttcc agatttgcac agctaaaata aaatgattac gctagcgccg gtcaatagag    60
aaa                                                                  63

<210> SEQ ID NO 177
<211> LENGTH: 60
<212> TYPE: DNA
<213> ORGANISM: Artificial
```

```
<220> FEATURE:
<223> OTHER INFORMATION: synthetic oligonucleotide primers or probes

<400> SEQUENCE: 177
tgctaactag atcgcgggtt gattacgctc tgctgcttac tccttaaata agagtgaaca    60

<210> SEQ ID NO 178
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 178
gcatcactca tgtttaattc catttatcaa tgattagcgc cggtcaatag agaaa    55

<210> SEQ ID NO 179
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 179
tgctaactag atcgcgggtt gtttaatttg gatgccccaa acca    44

<210> SEQ ID NO 180
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 180
aacctcttca gtgacctaca ggatgggatt acgcaaatca cccgctctag ggaag    55

<210> SEQ ID NO 181
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 181
tgctaactag atcgcgggtt gttcagtttg ggaagcagca tattgag    47

<210> SEQ ID NO 182
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 182
ttcgaggagg tctaggaggc gatccagtcg caacgctaaa tg    42

<210> SEQ ID NO 183
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 183
tgctaactag atcgcgggtt gcagtttttg ccctgtcagg cc    42
```

<210> SEQ ID NO 184
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 184
tgaacaatgt caacaaggca ctgcattaaa tcacccgctc tagggaag            48

<210> SEQ ID NO 185
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 185
acacgaccgg taacgcttag aaaggatcca caagagttca tgccc               45

<210> SEQ ID NO 186
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 186
attgttctgc aaaacccgca gtgattacgc atccagtcgc aacgctaaat g         51

<210> SEQ ID NO 187
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 187
tgctaactag atcgcgggtt gccagacctt gtccaggta ctacttacat t          51

<210> SEQ ID NO 188
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 188
gtaagaatcc tgatgaatgg tttccttttg attacgcgaa atcacccgct ctagggaag    59

<210> SEQ ID NO 189
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 189
ttattgcacg cgtcagccta tgatttggaa tataatcctc cactggcag            49

<210> SEQ ID NO 190
<211> LENGTH: 59
<212> TYPE: DNA
<213> ORGANISM: Artificial
<220> FEATURE:
<223> OTHER INFORMATION: synthetic oligonucleotide primers or probes

```
<400> SEQUENCE: 190
taaatcaacc tgttaaagaa aggggtaaaa caattacgat ccagtcgcaa cgctaaatg      59

<210> SEQ ID NO 191
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 191
acacgaccgg taacgcttag aattacgcca tctacgatgt cagtacttcc aatattcac      59

<210> SEQ ID NO 192
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 192
tctgatggcc tggctttgaa tgaatccagt cgcaacgcta aatg                      44

<210> SEQ ID NO 193
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 193
ttattgcacg cgtcagccta ttgtaatcaa cttcaccacc agctgg                    46

<210> SEQ ID NO 194
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 194
gctcaggaga atcttttcac tgttggtatt acgcgatcca gtcgcaacgc taaatg         56

<210> SEQ ID NO 195
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 195
acacgaccgg taacgcttag aaattacgag ttgattgtcg gaccca                    46

<210> SEQ ID NO 196
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 196
agtcagccac acaacgactg gaaattatcc agtcgcaacg ctaaatg                   47

<210> SEQ ID NO 197
```

```
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 197
acacgaccgg taacgcttag agactggaat agtgtggttt gccagc                    46

<210> SEQ ID NO 198
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 198
tctatgccta attgatatct ggcgatgtta ttacgcgaaa atcacccgct ctagggaag       59

<210> SEQ ID NO 199
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 199
ttattgcacg cgtcagccta tattaattta ccaaccttca ggatcgagta gtttc           55

<210> SEQ ID NO 200
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 200
catccaggaa gtggaaatgt tgccattaaa tcacccgctc tagggaag                   48

<210> SEQ ID NO 201
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 201
tattcgctca taacgggttc ggcctcaaca agtgagcatt gaagc                      45

<210> SEQ ID NO 202
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 202
tcaacatctg taagcacatt aacactacac atcattacat ccagtcgcaa cgctaaatg       59

<210> SEQ ID NO 203
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 203
```
tattcgctca taacgggttc gattcattaa gatggacttc ttatctggat aggtggta    58

<210> SEQ ID NO 204
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 204
ctaagcctcg attcaagagc tatgccatta cgcgaatcca gtcgcaacgc taaatg    56

<210> SEQ ID NO 205
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 205
acacgaccgg taacgcttag agcacaggga tatgagagaa cttcttccc    49

<210> SEQ ID NO 206
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 206
gcagcctgtg tgtaggcata gctcattatc cagtcgcaac gctaaatg    48

<210> SEQ ID NO 207
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 207
ttattgcacg cgtcagccta tcgtgtaggg tcagaggtgg tgacataa    48

<210> SEQ ID NO 208
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 208
ggcagttcat tgatggagag tgaagtaaat tacgcgaaat cacccgctct agggaag    57

<210> SEQ ID NO 209
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 209
ttattgcacg cgtcagccta tttggaagct cctgaagaca agtcattt    48

<210> SEQ ID NO 210
<211> LENGTH: 59
<212> TYPE: DNA

```
<213> ORGANISM: Artificial
<220> FEATURE:
<223> OTHER INFORMATION: synthetic oligonucleotide primers or probes

<400> SEQUENCE: 210
gccacgataa tacttcttct aaagctgttt gaattacgaa atcacccgct ctagggaag      59

<210> SEQ ID NO 211
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 211
tattcgctca taacgggttc gatttgcaat gtgtcctcag cagaaagaa                  49

<210> SEQ ID NO 212
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 212
ccatcagggc cgggttggta ttaatccagt cgcaacgcta aatg                       44

<210> SEQ ID NO 213
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 213
acacgaccgg taacgcttag aagggtaca tgatggattt gacagc                      46

<210> SEQ ID NO 214
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 214
taggagattc atctgctctt gtacttcagt ttcattacat ccagtcgcaa cgctaaatg       59

<210> SEQ ID NO 215
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 215
tattcgctca taacgggttc gattacctga ggcattccca tcttgaatt                  49

<210> SEQ ID NO 216
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 216
acaaggaaaa tggaggaaga gcctcattac gcaaatcacc cgctctaggg aag             53
```

<210> SEQ ID NO 217
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 217
tgctaactag atcgcgggtt gagaatgact ggctaacaaa aacagaagaa aga    53

<210> SEQ ID NO 218
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 218
gggcatctat tggacattga aaggaatta cgcgatatcc agtcgcaacg ctaaatg    57

<210> SEQ ID NO 219
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 219
tgctaactag atcgcgggtt gaatagaatt tataatatat ggaatgttcg catttgg    57

<210> SEQ ID NO 220
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 220
aattctctca ctcacatggt ggtggtatta cgcgatccag tcgcaacgct aaatg    55

<210> SEQ ID NO 221
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 221
ttattgcacg cgtcagccta taagaagatc tagaacaaga acaagtcagg gtc    53

<210> SEQ ID NO 222
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 222
gcagttgcgt gatctccact agattcatta cgcgaaaatc acccgctcta gggaag    56

<210> SEQ ID NO 223
<211> LENGTH: 49
<212> TYPE: DNA
<213> ORGANISM: Artificial
<220> FEATURE:

<223> OTHER INFORMATION: synthetic oligonucleotide primers or probes

<400> SEQUENCE: 223
tattcgctca taacgggttc gtctgacctt aagttgttct tccaaagca         49

<210> SEQ ID NO 224
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 224
gtattgggag atcgatgggc aaaatatcca gtcgcaacgc taaatg            46

<210> SEQ ID NO 225
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 225
tgctaactag atcgcgggtt ggctgtgctt gattgtctct tctccag           47

<210> SEQ ID NO 226
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 226
tatctcagtc tcctatgtac gctagaagtt ggaattacaa atcacccgct ctagggaag    59

<210> SEQ ID NO 227
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 227
acacgaccgg taacgcttag aattacgcgt taaaaatggc atgaataatt tgccaaag     58

<210> SEQ ID NO 228
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 228
aacaagattc acacaactgg ctttaaagat cattacgcaa atcacccgct ctagggaag    59

<210> SEQ ID NO 229
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 229
tgctaactag atcgcgggtt gattatggct ttcagaaaaa gaagatgcag tg          52

```
<210> SEQ ID NO 230
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 230
ggccagtttt tgaagacttg ataacatttc attacgcgaa atcacccgct ctagggaag      59

<210> SEQ ID NO 231
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 231
tattcgctca taacgggttc gatttttata agaccattga aagctagaaa gtacatac       58

<210> SEQ ID NO 232
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 232
gggataattt agtccaaaaa cttgaaaaga gtacaattta gcgccggtca atagagaaa      59

<210> SEQ ID NO 233
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 233
tattcgctca taacgggttc gattacgctg gataactttg cccggtgtt                 49

<210> SEQ ID NO 234
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 234
tcttttctag atccgctttt aaaacctgtt aaaattatag cgccggtcaa tagagaaa       58

<210> SEQ ID NO 235
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 235
tattcgctca taacgggttc gcagtttgcc catggattgc tttt                      44

<210> SEQ ID NO 236
<211> LENGTH: 59
<212> TYPE: DNA
<213> ORGANISM: Artificial
<220> FEATURE:
<223> OTHER INFORMATION: synthetic oligonucleotide primers or probes
```

```
<400> SEQUENCE: 236
ggcttattct gtgatctttc ttgttttaac aggattacta gcgccggtca atagagaaa        59

<210> SEQ ID NO 237
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 237
acacgaccgg taacgcttag aattacgcga ctatagtggt gtatggaatg caaccca          57

<210> SEQ ID NO 238
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 238
acctccccaa aagaagaggc agaaagtccg ttagcccgat ggtaa                       45

<210> SEQ ID NO 239
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 239
tattcgctca taacgggttc gatgctcaag aggaacttcc accacc                      46

<210> SEQ ID NO 240
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 240
ttcccttgtg gtcaccgtag ttacttagcg ccggtcaata gagaaa                      46

<210> SEQ ID NO 241
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 241
acacgaccgg taacgcttag atcttgagca tgctttacca ggatctg                     47

<210> SEQ ID NO 242
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 242
tttgccactc caagcagtct ttactgatta cagtccgtta gcccgatggt aa               52

<210> SEQ ID NO 243
<211> LENGTH: 53
```

```
<212> TYPE: DNA
<213> ORGANISM: Artificial
<220> FEATURE:
<223> OTHER INFORMATION: synthetic oligonucleotide primers or probes

<400> SEQUENCE: 243
tattcgctca taacgggttc gcaacaagca agaacagttt ctcattattt tcc           53

<210> SEQ ID NO 244
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 244
ctcagaagct gtgttgcaga gtcctgatta cgcgattaaa atcacccgct ctagggaag     59

<210> SEQ ID NO 245
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 245
tattcgctca taacgggttc gatgatataa ctgaacttca cagctggatt actcg         55

<210> SEQ ID NO 246
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 246
cgaaagattg caaattcagg actctgatta cgcatccagt cgcaacgcta aatg          54

<210> SEQ ID NO 247
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 247
tgctaactag atcgcgggtt gtcttttaag tctgagaagt tgccttcctt c             51

<210> SEQ ID NO 248
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 248
gccatagagc gagaaaaagc tgagaattaa tccagtcgca acgctaaatg               50

<210> SEQ ID NO 249
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 249
```
acacgaccgg taacgcttag aactcatctt tgctctcatg ctgcag    46

<210> SEQ ID NO 250
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 250
ttcaccatct gttccaccag ggattacgcg attatccagt cgcaacgcta aatg    54

<210> SEQ ID NO 251
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 251
tgctaactag atcgcgggtt gtaagaagat tatctaaatc aactcgtgta attacca    57

<210> SEQ ID NO 252
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 252
ggtggatcga attctgccag ttgattatcc agtcgcaacg ctaaatg    47

<210> SEQ ID NO 253
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 253
tattcgctca taacgggttc gcaagcctca gaacaactga acagcc    46

<210> SEQ ID NO 254
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 254
tcagcagtag ttgtcatctg ctccaaatta cgaaatcacc cgctctaggg aag    53

<210> SEQ ID NO 255
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 255
tgctaactag atcgcgggtt gggtgggttg gattttcaac cagttt    46

<210> SEQ ID NO 256
<211> LENGTH: 48
<212> TYPE: DNA
<213> ORGANISM: Artificial

<220> FEATURE:
<223> OTHER INFORMATION: synthetic oligonucleotide primers or probes

<400> SEQUENCE: 256
tttaagcaag tcttttctga tgtgcattag cgccggtcaa tagagaaa         48

<210> SEQ ID NO 257
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 257
acacgaccgg taacgcttag acagactttg tggcctttac aaatcat          47

<210> SEQ ID NO 258
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 258
gtccttgtcc tttctctttc agggagtccg ttagcccgat ggtaa            45

<210> SEQ ID NO 259
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 259
tgctaactag atcgcgggtt gcaaagtctg catccaggaa catgg            45

<210> SEQ ID NO 260
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 260
cctacaacct gtattaacaa ggaacgaaat actgattaag tccgttagcc cgatggtaa    59

<210> SEQ ID NO 261
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 261
tattcgctca taacgggttc gatttgaaac aataatttct gtaaatggaa ccattctc     58

<210> SEQ ID NO 262
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 262
ggtctgtgaa tatttgaatg tcaaaacaat aaaagtccgt tagcccgatg gtaa        54

<210> SEQ ID NO 263
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 263
acacgaccgg taacgcttag agcagagact cggggaattg ca                42

<210> SEQ ID NO 264
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 264
tctcctccca gctggttgag cattagtccg ttagcccgat ggtaa            45

<210> SEQ ID NO 265
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 265
tgctaactag atcgcgggtt gttgagggac gctggaagaa gc                42

<210> SEQ ID NO 266
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 266
agcagctgaa acagtgcaga gtaagattta agtccgttag cccgatggta a     51

<210> SEQ ID NO 267
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 267
tgctaactag atcgcgggtt gcccttgggg attcagaaat tctaaaaa         48

<210> SEQ ID NO 268
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 268
gtatagacaa tctctttcac tgtggcttgt agcgccggtc aatagagaaa        50

<210> SEQ ID NO 269
<211> LENGTH: 43
<212> TYPE: DNA
<213> ORGANISM: Artificial
<220> FEATURE:
<223> OTHER INFORMATION: synthetic oligonucleotide primers or probes

```
<400> SEQUENCE: 269
tattcgctca taacgggttc ggtgggatca catgtgccaa cag                   43

<210> SEQ ID NO 270
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 270
gctgaagaag agtatcttga gagagatttt gaaattagtc cgttagcccg atggtaa    57

<210> SEQ ID NO 271
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 271
ttattgcacg cgtcagccta tgagatgcac gaatggatga cacaa                 45

<210> SEQ ID NO 272
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 272
gtcagttgct tttcttggtc tttgtcaagt ccgttagccc gatggtaa              48

<210> SEQ ID NO 273
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 273
ttattgcacg cgtcagccta taatgggaaa tgcaagactt tggaa                 45

<210> SEQ ID NO 274
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 274
gctagatgta agttgtaaat taagccaaat gatgaattag tccgttagcc cgatggtaa  59

<210> SEQ ID NO 275
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 275
tgctaactag atcgcgggtt gacggagctg aggaaatctc tgaggt                46

<210> SEQ ID NO 276
```

```
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 276
catgaagagg tatgaagata agtgaaaaat ctctttatag tccgttagcc cgatggtaa      59

<210> SEQ ID NO 277
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 277
acacgaccgg taacgcttag aattacgcga gacatttaat tctcgttgga gggaacta       58

<210> SEQ ID NO 278
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 278
gcaagtacat ctgggaatca gcttccatag cgccggtcaa tagagaaa                  48

<210> SEQ ID NO 279
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 279
tattcgctca taacgggttc gcaaatgcct caggaagccc ag                        42

<210> SEQ ID NO 280
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 280
cagattgatg ttgcacaggt atatgttatt tcaattacag tccgttagcc cgatggtaa      59

<210> SEQ ID NO 281
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 281
tgctaactag atcgcgggtt gattacgcga ttacgcggct gcccaaagag tcctgtct       58

<210> SEQ ID NO 282
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 282
```

```
gtatgtattt ctggtggcaa atacgcagat tacgcgatta gcgccggtca atagagaaa        59

<210> SEQ ID NO 283
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 283
ttattgcacg cgtcagccta tattggaagt agtacagtca cagctaaatc attgtgtg         58

<210> SEQ ID NO 284
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 284
gtgtgtgcat gctgagacca caattacgta gcgccggtca atagagaaa                   49

<210> SEQ ID NO 285
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 285
ttattgcacg cgtcagccta ttgcattata atgagctggg agcaaag                     47

<210> SEQ ID NO 286
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 286
aggtaaaacc tatatcactg aaggttattt tgaacaatta gcgccggtca atagagaaa        59

<210> SEQ ID NO 287
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 287
acacgaccgg taacgcttag aattacgcga ttggattctg aagttgcctg gggaa            55

<210> SEQ ID NO 288
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 288
ttggtggaag ataaactcag tcttctgaat agtattatag cgccggtcaa tagagaaa         58

<210> SEQ ID NO 289
<211> LENGTH: 44
<212> TYPE: DNA
```

```
<213> ORGANISM: Artificial
<220> FEATURE:
<223> OTHER INFORMATION: synthetic oligonucleotide primers or probes

<400> SEQUENCE: 289
ttattgcacg cgtcagccta tcagttttgg gcaagaagga gacg                    44

<210> SEQ ID NO 290
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 290
gacgtgctta aggtagcaaa taaaatatga aagattaag tccgttagcc cgatggtaa     59

<210> SEQ ID NO 291
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 291
tgctaactag atcgcgggtt gattacggag aaaagaaac cccagcaaaa agaa          54

<210> SEQ ID NO 292
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 292
gtaggaagat ctactccaag gtggaaactt gattacgcta gcgccggtca atagagaaa    59

<210> SEQ ID NO 293
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 293
tattcgctca taacgggttc gattacgcgc catttcacac agaattaaga ctggaaag     58

<210> SEQ ID NO 294
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 294
ggaagacttc aataaagata tggtaaattg gttgattata gcgccggtca atagagaaa    59

<210> SEQ ID NO 295
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 295
ttattgcacg cgtcagccta tatcagcagg gggtgaatct gaaaga                  46
```

<210> SEQ ID NO 296
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 296
caacttacaa caaagaatca cagatgagag aaaattacgt agcgccggtc aatagagaaa    60

<210> SEQ ID NO 297
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 297
ttattgcacg cgtcagccta tattacgcgg tactgtaaaa gaattgttgc aaagaggaga    60

<210> SEQ ID NO 298
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 298
cagagatgaa aggaaaataa aggtaatgtt gttttattag tccgttagcc cgatggtaa    59

<210> SEQ ID NO 299
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 299
acacgaccgg taacgcttag aattacgcga aaaaattagc cagcctacct gagcc    55

<210> SEQ ID NO 300
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 300
actttgcaca aattgtgagt tgttactgga ttaagtccgt tagcccgatg gtaa    54

<210> SEQ ID NO 301
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 301
acacgaccgg taacgcttag agcaaatttg ctcagtttcg aagactca    48

<210> SEQ ID NO 302
<211> LENGTH: 59
<212> TYPE: DNA
<213> ORGANISM: Artificial
<220> FEATURE:

<223> OTHER INFORMATION: synthetic oligonucleotide primers or probes

<400> SEQUENCE: 302
gctaaggact ttgaagatct ctttaagcaa gaattacgag tccgttagcc cgatggtaa    59

<210> SEQ ID NO 303
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 303
acacgaccgg taacgcttag aacaacttct caatgctcct gacctctgt    49

<210> SEQ ID NO 304
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 304
tacaaggacc gacaagggta ggtaacaatt agtccgttag cccgatggta a    51

<210> SEQ ID NO 305
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 305
tgctaactag atcgcgggtt ggatttccaa tgggaaaaag ttaacaaaat g    51

<210> SEQ ID NO 306
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 306
ttcctgtagc ttcacccttt ccacaagtcc gttagcccga tggtaa    46

<210> SEQ ID NO 307
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 307
ttattgcacg cgtcagccta ttggaaatca agctgggaga gagc    44

<210> SEQ ID NO 308
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 308
gtctgtgatt tacctattga atttgaacat gtcaattata gcgccggtca atagagaaa    59

```
<210> SEQ ID NO 309
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 309
tattcgctca taacgggttc gattacgcga gagcgatcca ctctctcagg atgag          55

<210> SEQ ID NO 310
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 310
ttgacagatc tgttgagaaa tggcgattaa aatcacccgc tctagggaag               50

<210> SEQ ID NO 311
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 311
tattcgctca taacgggttc gccatatgct tttacctgca ggcgat                   46

<210> SEQ ID NO 312
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 312
ctgttcagct tctgttagcc actgattaaa attacgcgat ccagtcgcaa cgctaaatg    59

<210> SEQ ID NO 313
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 313
ttattgcacg cgtcagccta tattaattct caggaatttg tgtctttctg agaaa         55

<210> SEQ ID NO 314
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 314
atctggactc tttaacttct taaagatcag gttctgatat ccagtcgcaa cgctaaatg    59

<210> SEQ ID NO 315
<211> LENGTH: 58
<212> TYPE: DNA
<213> ORGANISM: Artificial
<220> FEATURE:
<223> OTHER INFORMATION: synthetic oligonucleotide primers or probes
```

```
<400> SEQUENCE: 315
ttattgcacg cgtcagccta tattattgtt ttttcgaaat tgtatttatc ttcagcac        58

<210> SEQ ID NO 316
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 316
tggcaggagg tctgcaaaca gcattaaatc acccgctcta gggaag                    46

<210> SEQ ID NO 317
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 317
tgctaactag atcgcgggtt gatgggaagc ctgaatctgc gg                        42

<210> SEQ ID NO 318
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 318
gttgcattca atgttctgac aacagtttga ttacgcgaaa atcacccgct ctagggaag      59

<210> SEQ ID NO 319
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 319
acacgaccgg taacgcttag aagaggattg ctgaattatt tcttcccca                 49

<210> SEQ ID NO 320
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 320
tgtatttctt tctttgccag tacaactgca attacgcgaa atcacccgct ctagggaag      59

<210> SEQ ID NO 321
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 321
acacgaccgg taacgcttag aattacgtca tagggaaatt ttcacatgga gcttt          55

<210> SEQ ID NO 322
<211> LENGTH: 59
```

-continued

```
<212> TYPE: DNA
<213> ORGANISM: Artificial
<220> FEATURE:
<223> OTHER INFORMATION: synthetic oligonucleotide primers or probes

<400> SEQUENCE: 322
gtaattttat tttctcaaat cccccaggga ttacgcgata gcgccggtca atagagaaa          59

<210> SEQ ID NO 323
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 323
ttattgcacg cgtcagccta tattacggca actaaaagaa aagcttgagc aagtcaag           58

<210> SEQ ID NO 324
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 324
agtgggatac tagcaatgtt atctgcttcc attacgtagc gccggtcaat agagaaa            57

<210> SEQ ID NO 325
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 325
acacgaccgg taacgcttag attagttgct gctcttttcc aggttca                      47

<210> SEQ ID NO 326
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 326
gaagaacaaa agaatatctt gtcagaattt caaagaattt agcgccggtc aatagagaaa        60

<210> SEQ ID NO 327
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 327
tattcgctca taacgggttc gattaaaaaa taacaatttt attcttcttt ctccaggcta        60

<210> SEQ ID NO 328
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 328
```

```
cctgcgccag ggaattctca aaaatcaccc gctctaggga ag                           42
```

<210> SEQ ID NO 329
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 329

```
tgctaactag atcgcgggtt ggtttcagtt actggtggaa gagttgcc                    48
```

<210> SEQ ID NO 330
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 330

```
tatcttgctc ttctgggctt atgggaatta cgcgattaat ccagtcgcaa cgctaaatg        59
```

<210> SEQ ID NO 331
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 331

```
acacgaccgg taacgcttag aagagatttg tctgcttgag cttattttca agtt             54
```

<210> SEQ ID NO 332
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 332

```
gttggaaatt tataaccaac caaaccaaga attacgagtc cgttagcccg atggtaa          57
```

<210> SEQ ID NO 333
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 333

```
ttattgcacg cgtcagccta tatgctgctg tggttatctc ctattaggaa tca              53
```

<210> SEQ ID NO 334
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 334

```
tcttcaaggt cttcaagctt tttttcaaga gtccgttagc ccgatggtaa                  50
```

<210> SEQ ID NO 335
<211> LENGTH: 46
<212> TYPE: DNA
<213> ORGANISM: Artificial

```
<220> FEATURE:
<223> OTHER INFORMATION: synthetic oligonucleotide primers or probes

<400> SEQUENCE: 335
tattcgctca taacgggttc gccacagcag cagatgattt aactgc                    46

<210> SEQ ID NO 336
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 336
ctgagaaaca aggagaaatt gaagctcaat tacgcgatag tccgttagcc cgatggtaa      59

<210> SEQ ID NO 337
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 337
ttattgcacg cgtcagccta tattacgctg tattttcctt tcaggtttcc agagctttac     60

<210> SEQ ID NO 338
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 338
atagcagttc aagctaaaca accggatgat tacgcgataa atcacccgct ctagggaag      59

<210> SEQ ID NO 339
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 339
acacgaccgg taacgcttag agggttcttt tccccaggaa actgaa                    46

<210> SEQ ID NO 340
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 340
acaaaatctc ttccacatcc ggttgattac gcgaaatcac ccgctctagg gaag           54

<210> SEQ ID NO 341
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 341
tattcgctca taacgggttc gtttccttgt acaaatgctg cccttag                   48
```

<210> SEQ ID NO 342
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 342
gtaagtatac tggatcccat tctctttggc tattatagcg ccggtcaata gagaaa      56

<210> SEQ ID NO 343
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 343
tgctaactag atcgcgggtt gcctggactg accactattg gagcct      46

<210> SEQ ID NO 344
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 344
tgctttgccc tcagctcttg aatagcgccg gtcaatagag aaa      43

<210> SEQ ID NO 345
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 345
tgctaactag atcgcgggtt gtcagtccag gagctaggtc aggc      44

<210> SEQ ID NO 346
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 346
ttgataaata tttgtagggt ggttggctaa aaattacgta gcgccggtca atagagaaa      59

<210> SEQ ID NO 347
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 347
tgctaactag atcgcgggtt gattacggag aaagggtttt tgtatggagc aa      52

<210> SEQ ID NO 348
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 348
actaaggaaa ctgccatctc caaactagaa attacgcgaa atcacccgct ctagggaag      59

<210> SEQ ID NO 349
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 349
ttattgcacg cgtcagccta tattacgcga tgttactctg gtgacacaac ctgtggtt       58

<210> SEQ ID NO 350
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 350
cctccaacat caaggaagat ggcattaaat cacccgctct agggaag                   47

<210> SEQ ID NO 351
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 351
ttattgcacg cgtcagccta tcggttgaaa tctgccagag caggta                    46

<210> SEQ ID NO 352
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 352
atggtgggtg accttgagga tatcaattac gcgatatcca gtcgcaacgc taaatg         56

<210> SEQ ID NO 353
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 353
acacgaccgg taacgcttag agcttgatca agttataaaa tcacagaggg tg             52

<210> SEQ ID NO 354
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 354
gtccccagtt ggaagaactc attaccatta atccagtcgc aacgctaaat g              51

<210> SEQ ID NO 355

```
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 355
tattcgctca taacgggttc gcaatgcagg atttggaaca gaggc              45

<210> SEQ ID NO 356
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 356
tcaaattttg ggcagcggta atgattacaa atcacccgct ctagggaag          49

<210> SEQ ID NO 357
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 357
acacgaccgg taacgcttag aagcctcttg attgctggtc ttgtttt            47

<210> SEQ ID NO 358
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 358
caaagcatgc attgatgggt gtgattacgc gattacatcc agtcgcaacg ctaaatg    57

<210> SEQ ID NO 359
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 359
tattcgctca taacgggttc gatacattt taaatcaatt cagggcttat atagttg     57

<210> SEQ ID NO 360
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 360
cacagaaacc aaggttagta tcaaagatac ctttattaca gtccgttagc ccgatggtaa  60

<210> SEQ ID NO 361
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 361
```

```
acacgaccgg taacgcttag aattacgtcc ctatacagta gatgcaatcc aaaagaaaat    60
```

<210> SEQ ID NO 362
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 362

```
ctgtcctaag acctgctcag cttcttcaag tccgttagcc cgatggtaa              49
```

<210> SEQ ID NO 363
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 363

```
acacgaccgg taacgcttag acatgactca agcttggctc tggc                   44
```

<210> SEQ ID NO 364
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 364

```
ttcagaaccg gaggcaacag ttagtccgtt agcccgatgg taa                    43
```

<210> SEQ ID NO 365
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 365

```
tattcgctca taacgggttc ggaatcagtg ggatgaagta caagaacacc             50
```

<210> SEQ ID NO 366
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 366

```
cgccagtggc agacaaatgt agaattacgc gatccagtcg caacgctaaa tg          52
```

<210> SEQ ID NO 367
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 367

```
tattcgctca taacgggttc gaaaatctat agcagttggc caaagacctc             50
```

<210> SEQ ID NO 368
<211> LENGTH: 44
<212> TYPE: DNA

<213> ORGANISM: Artificial
<220> FEATURE:
<223> OTHER INFORMATION: synthetic oligonucleotide primers or probes

<400> SEQUENCE: 368
tttcagggcc aagtcatttg ccaatccagt cgcaacgcta aatg        44

<210> SEQ ID NO 369
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 369
tgctaactag atcgcgggtt gcatctgcag aataatcccg gagaag        46

<210> SEQ ID NO 370
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 370
tggacctgga aaagtttctt gcctattacg cgaaatcacc cgctctaggg aag        53

<210> SEQ ID NO 371
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 371
ttattgcacg cgtcagccta tactcataga ttactgcaac agttcccccc        49

<210> SEQ ID NO 372
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 372
ttcagcttct gtaagccagg caagattaaa atcacccgct ctagggaag        49

<210> SEQ ID NO 373
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 373
ttattgcacg cgtcagccta tgcatcctgt aggacattgg cagttgt        47

<210> SEQ ID NO 374
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 374
cctccaaggt gaaattgaag ctcacattac gcgaatccag tcgcaacgct aaatg        55

<210> SEQ ID NO 375
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 375
tattcgctca taacgggttc gcatattctt cttcctgctg tcctgtagga           50

<210> SEQ ID NO 376
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 376
aattcatttg tggcctttt gctccaatcc agtcgcaacg ctaaatg              47

<210> SEQ ID NO 377
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 377
tgctaactag atcgcgggtt gattaagaca atgaggaaaa tttggccatt tt         52

<210> SEQ ID NO 378
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 378
tcccatttgg aagccagttc tgaattatcc agtcgcaacg ctaaatg              47

<210> SEQ ID NO 379
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 379
ttattgcacg cgtcagccta ttggtacgct gctgttcttt ttcagg               46

<210> SEQ ID NO 380
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 380
ttctgaactg ctggaaagtc gccattacgc gatccagtcg caacgctaaa tg         52

<210> SEQ ID NO 381
<211> LENGTH: 50
<212> TYPE: DNA
<213> ORGANISM: Artificial
<220> FEATURE:

<223> OTHER INFORMATION: synthetic oligonucleotide primers or probes

<400> SEQUENCE: 381
ttattgcacg cgtcagccta taatgtccta ccctatgtac atcgttctgc    50

<210> SEQ ID NO 382
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 382
cctttggaag gactagagaa actctaccag gattacgcag tccgttagcc cgatggtaa    59

<210> SEQ ID NO 383
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 383
tattcgctca taacgggttc gatttgagac tgtacgaata tttctgacag agcag    55

<210> SEQ ID NO 384
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 384
gtcaaggtac cgtctacttc tttgcttcaa ttaagtccgt tagcccgatg gtaa    54

<210> SEQ ID NO 385
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 385
tattcgctca taacgggttc ggactctctc caagatcacc tcgagaaa    48

<210> SEQ ID NO 386
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 386
aggagaaatt gcgcctctga aagaattaaa tcacccgctc tagggaag    48

<210> SEQ ID NO 387
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 387
tgctaactag atcgcgggtt gtgactattg cacacaggca cttcg    45

```
<210> SEQ ID NO 388
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 388
tggtccagca tctcagcact ttcattaaat cacccgctct agggaag          47

<210> SEQ ID NO 389
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 389
ttattgcacg cgtcagccta ttgcatgaag cccacaggga ctt              43

<210> SEQ ID NO 390
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 390
tgttctctca ttctatataa tgaggaacaa ttaaaaataa atcacccgct ctagggaag    59

<210> SEQ ID NO 391
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 391
tgctaactag atcgcgggtt gattacgcga cctgggagga aaaggagaga aatga        55

<210> SEQ ID NO 392
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 392
cctgggagag agccatctcg cattaaaatc acccgctcta gggaag           46

<210> SEQ ID NO 393
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 393
tattcgctca taacgggttc gcttttcagc gtctgtccag ggtc             44

<210> SEQ ID NO 394
<211> LENGTH: 53
<212> TYPE: DNA
<213> ORGANISM: Artificial
<220> FEATURE:
<223> OTHER INFORMATION: synthetic oligonucleotide primers or probes
```

-continued

<400> SEQUENCE: 394
gtaaggacat ggccatgttt cctccattac gctagcgccg gtcaatagag aaa    53

<210> SEQ ID NO 395
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 395
tattcgctca taacgggttc gcccaaaatg acagagctct accagtcttt ag    52

<210> SEQ ID NO 396
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 396
atgaaactcc gaagactgca gaaggattac gcgatccagt cgcaacgcta aatg    54

<210> SEQ ID NO 397
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 397
ttattgcacg cgtcagccta taatgtcaga ttctcagctt ataggactgc c    51

<210> SEQ ID NO 398
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 398
ccagcacaac ctcaagcaaa atgattaatc cagtcgcaac gctaaatg    48

<210> SEQ ID NO 399
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 399
tattcgctca taacgggttc gagctgcatg tgatgccttg ga    42

<210> SEQ ID NO 400
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 400
aaaactggca tcatttccct gtgtaaaatt acgcgaaaat cacccgctct agggaag    57

<210> SEQ ID NO 401
<211> LENGTH: 45

```
<212> TYPE: DNA
<213> ORGANISM: Artificial
<220> FEATURE:
<223> OTHER INFORMATION: synthetic oligonucleotide primers or probes

<400> SEQUENCE: 401
acacgaccgg taacgcttag agggaggatc cgtgtcctgt ctttt            45

<210> SEQ ID NO 402
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 402
ctgggcctcc ttctgcatga ttattacaaa tcacccgctc tagggaag         48

<210> SEQ ID NO 403
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 403
acacgaccgg taacgcttag aggattttgt gaccagcgca gg               42

<210> SEQ ID NO 404
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 404
ttggattcag gtattaggaa ccaaaaaaaa attacgcgta gcgccggtca atagagaaa    59

<210> SEQ ID NO 405
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 405
ttattgcacg cgtcagccta tatttgtaac atctgcaaag agtgtccaat ca          52

<210> SEQ ID NO 406
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 406
gtaagtttga cgccagcctg acgatagtcc gttagcccga tggtaa           46

<210> SEQ ID NO 407
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 407
```

```
acacgaccgg taacgcttag accatggtgg aatattgcac tccg            44
```

<210> SEQ ID NO 408
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 408

```
gtgagtagta gcaaaagcag aacacactct tgattacagt ccgttagccc gatggtaa    58
```

<210> SEQ ID NO 409
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 409

```
ttattgcacg cgtcagccta tatgtcttag aggggacaa catggaaac             49
```

<210> SEQ ID NO 410
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 410

```
ctgatcaact tctggccagt agattctgat tactagcgcc ggtcaataga gaaa      54
```

<210> SEQ ID NO 411
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 411

```
acacgaccgg taacgcttag acattttttg ttttgcagtc ccgttact            48
```

<210> SEQ ID NO 412
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 412

```
gtatgagact agttgtatgc caggcaaata ttgattacag tccgttagcc cgatggtaa    59
```

<210> SEQ ID NO 413
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 413

```
tattcgctca taacgggttc gattcacgca ttgaacatta tgctagcag            49
```

<210> SEQ ID NO 414
<211> LENGTH: 60
<212> TYPE: DNA
<213> ORGANISM: Artificial

```
<220> FEATURE:
<223> OTHER INFORMATION: synthetic oligonucleotide primers or probes

<400> SEQUENCE: 414
atgtaagtat cccatctctt tttacaaaat gttccattaa gtccgttagc ccgatggtaa      60

<210> SEQ ID NO 415
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 415
tattcgctca taacgggttc gatttcttat ctaaatgata gcatctctcc taatgagagc      60

<210> SEQ ID NO 416
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 416
gtgagttttc tttctagctt tgtcattggt atgattacag tccgttagcc cgatggtaa       59

<210> SEQ ID NO 417
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 417
tgctaactag atcgcgggtt gattgaatcc tagcagatct tgaggaagaa aacag            55

<210> SEQ ID NO 418
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 418
cacagttaca caggctaagg cagctagtcc gttagcccga tggtaa                      46

<210> SEQ ID NO 419
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 419
tgctaactag atcgcgggtt gggaagacca caataaacag ctggagt                     47

<210> SEQ ID NO 420
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 420
gcagtcaaac ttcggactcc atggattagc gccggtcaat agagaaa                     47
```

<210> SEQ ID NO 421
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 421
acacgaccgg taacgcttag acctatgctg ctccgagtgg ttg        43

<210> SEQ ID NO 422
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 422
gtaagctcca atacctagaa gggactcaga ttattacgct agcgccggtc aatagagaaa        60

<210> SEQ ID NO 423
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 423
acacgaccgg taacgcttag aattacgcga aactcaacaa ctccttccct agttcaagag        60

<210> SEQ ID NO 424
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 424
gttagtgaga ttcaggctca cggcctagcg ccggtcaata gagaaa        46

<210> SEQ ID NO 425
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 425
ttattgcacg cgtcagccta tccctggaa agccaatgag agag        44

<210> SEQ ID NO 426
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 426
gaagtctttt ccacatggca gatgattatt acgcgatagc gccggtcaat agagaaa        57

<210> SEQ ID NO 427
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 427
acacgaccgg taacgcttag aattactttc tctttgtttt ccaggacaca atgtag      56

<210> SEQ ID NO 428
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 428
acgcatgcag ccctctccaa tccagtcgca acgctaaatg      40

<210> SEQ ID NO 429
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 429
acacgaccgg taacgcttag acaggcataa caaacagctc aattccc      47

<210> SEQ ID NO 430
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 430
ctttcagagg tcgagccaca gctattacta gcgccggtca atagagaaa      49

<210> SEQ ID NO 431
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 431
tgctaactag atcgcgggtt gtgagttatc aggcaaacat caggagg      47

<210> SEQ ID NO 432
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 432
tttcaggtag catgtccatc caaaggatta cgcgattagt ccgttagccc gatggtaa      58

<210> SEQ ID NO 433
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 433
tgctaactag atcgcgggtt gggtgattct agtatattct gggcactggg      50

<210> SEQ ID NO 434

```
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 434
actgggctca atgccacttg cagtccgtta gcccgatggt aa                            42

<210> SEQ ID NO 435
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 435
tattcgctca taacgggttc gcagtgctca taaacctgtg gcc                           43

<210> SEQ ID NO 436
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 436
catccttgag caactctggg ttctacaatt acgcgattaa aatcacccgc tctagggaag         60

<210> SEQ ID NO 437
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 437
ttattgcacg cgtcagccta tattacgcga ttacgcgggc tgggaacctc aagagtgagg         60

<210> SEQ ID NO 438
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 438
tggagttcat catgcccagg gattacgcaa atcacccgct ctagggaag                     49

<210> SEQ ID NO 439
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 439
tgctaactag atcgcgggtt ggcagcaaag gcacatttac tccgtat                       47

<210> SEQ ID NO 440
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 440
```
gcatgtgtgc tgtactccag aatggattac gcgattacag tccgttagcc cgatggtaa    59

<210> SEQ ID NO 441
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 441
tattcgctca taacgggttc gatgggagag tttacctgga cacataggag ag    52

<210> SEQ ID NO 442
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 442
gttgtcctct ctgttacggc ctcatcatta cgcgattaca tccagtcgca acgctaaatg    60

<210> SEQ ID NO 443
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 443
tgctaactag atcgcgggtt gattacgcga ttacctttga ctggtttgtg gccatct    57

<210> SEQ ID NO 444
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 444
tccatcatgg ccgccatcta ttacgagtcc gttagcccga tggtaa    46

<210> SEQ ID NO 445
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 445
tgctaactag atcgcgggtt gccttcctgc tcatcactct ttcctatgtc    50

<210> SEQ ID NO 446
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 446
cagaagtgga atggtttctg gtggattacg cgattacgat ccagtcgcaa cgctaaatg    59

<210> SEQ ID NO 447
<211> LENGTH: 49
<212> TYPE: DNA

```
<213> ORGANISM: Artificial
<220> FEATURE:
<223> OTHER INFORMATION: synthetic oligonucleotide primers or probes

<400> SEQUENCE: 447
tgctaactag atcgcgggtt gattctggag tgagggaag aagctgtta                    49

<210> SEQ ID NO 448
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 448
acagaatgac agggtttgtg aagtcgatta cgcaaatcac ccgctctagg gaag            54

<210> SEQ ID NO 449
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 449
ttattgcacg cgtcagccta tcagcgctca ttctttagtc tccga                      45

<210> SEQ ID NO 450
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 450
tactctttgg agggcctttc ctagccatta cgcgatagcg ccggtcaata gagaaa          56

<210> SEQ ID NO 451
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 451
acacgaccgg taacgcttag aggtgggaaa gctctcctct ggc                        43

<210> SEQ ID NO 452
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 452
ctcatggagc ccaagaagga ttcaatccag tcgcaacgct aaatg                      45

<210> SEQ ID NO 453
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 453
tattcgctca taacgggttc gtggacagct tgtcccacct cc                         42
```

```
<210> SEQ ID NO 454
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 454
ccccaaagat gctgcctgta gatgattacg cgattacatc cagtcgcaac gctaaatg      58

<210> SEQ ID NO 455
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 455
tattcgctca taacgggttc gattacgcca ctgtcccctt catctgatga ttt            53

<210> SEQ ID NO 456
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 456
gcttgccagg caaacaaaga gattattacg cgattacgta gcgccggtca atagagaaa      59

<210> SEQ ID NO 457
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 457
tattcgctca taacgggttc gattacgcca aattagatgg aatcgcagtg ca             52

<210> SEQ ID NO 458
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 458
cactgtattc taccctgtc accaagtcat tacgcgatag tccgttagcc cgatggtaa       59

<210> SEQ ID NO 459
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 459
acacgaccgg taacgcttag aattacggta tggccactga aagcataacc ag             52

<210> SEQ ID NO 460
<211> LENGTH: 41
<212> TYPE: DNA
<213> ORGANISM: Artificial
<220> FEATURE:
```

<223> OTHER INFORMATION: synthetic oligonucleotide primers or probes

<400> SEQUENCE: 460
aatcatgatc cggccctcca atccagtcgc aacgctaaat g          41

<210> SEQ ID NO 461
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 461
ttattgcacg cgtcagccta tccaccccag gaatatccaa ttagca      46

<210> SEQ ID NO 462
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 462
agtgctttgc ttatagcagc ctgaaccatt acgcgattaa tccagtcgca acgctaaatg   60

<210> SEQ ID NO 463
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 463
acacgaccgg taacgcttag aattacgcga ttacgtcaca cagagtcacc ctccttctga   60

<210> SEQ ID NO 464
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 464
tgtggcctat aaggatttgg gtatggatta cgcgattaaa atcacccgct ctagggaag    59

<210> SEQ ID NO 465
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 465
acacgaccgg taacgcttag aatcgtacag actttaggga gcctgtgttc ag           52

<210> SEQ ID NO 466
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 466
ggcactgtct gatgtggttc tgaaaattac gcagtccgtt agcccgatgg taa          53

```
<210> SEQ ID NO 467
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 467
tattcgctca taacgggttc gtgtaagtct ctcctcccac ctgggt         46

<210> SEQ ID NO 468
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 468
ttttcttccc atagtgtgcc actgcattac gcgattacat ccagtcgcaa cgctaaatg   59

<210> SEQ ID NO 469
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 469
ttattgcacg cgtcagccta tattacgcgc ttcctgggag cagaattgtt ct         52

<210> SEQ ID NO 470
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 470
aggacactcg gaacagccag gtagcgccgg tcaatagaga aa             42

<210> SEQ ID NO 471
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 471
acacgaccgg taacgcttag aggtgagttg agaatcatgc caagg            45

<210> SEQ ID NO 472
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 472
tcacttggga agcacagctc tggagtccgt tagcccgatg gtaa           44

<210> SEQ ID NO 473
<211> LENGTH: 40
<212> TYPE: DNA
<213> ORGANISM: Artificial
<220> FEATURE:
<223> OTHER INFORMATION: synthetic oligonucleotide primers or probes
```

<400> SEQUENCE: 473
tgctaactag atcgcgggtt ggacaggaag ggtgtggcgc                40

<210> SEQ ID NO 474
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 474
taatgatctc gttaggggtg tgaatggatt acgcgattaa atcacccgct ctagggaag        59

<210> SEQ ID NO 475
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 475
tattcgctca taacgggttc gattaaaggc caggcctgta tttagttagt gg              52

<210> SEQ ID NO 476
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 476
gagaacggac cgttgacaca tggattacgc gatagcgccg gtcaatagag aaa             53

<210> SEQ ID NO 477
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 477
tattcgctca taacgggttc gggcacagac accgtcaaag cttaag                     46

<210> SEQ ID NO 478
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 478
ggtggttctg cattgtacct gagaaaatta cgcgattaat ccagtcgcaa cgctaaatg       59

<210> SEQ ID NO 479
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 479
acacgaccgg taacgcttag aattacgcgc caccctccag tagccttttc ct              52

<210> SEQ ID NO 480
<211> LENGTH: 59

```
<212> TYPE: DNA
<213> ORGANISM: Artificial
<220> FEATURE:
<223> OTHER INFORMATION: synthetic oligonucleotide primers or probes

<400> SEQUENCE: 480
tcaaccccta aacccettgc cattacgcga ttacgcgata gcgccggtca atagagaaa        59

<210> SEQ ID NO 481
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 481
tgctaactag atcgcgggtt gcagctgttt cctacctact ctgattccc                   49

<210> SEQ ID NO 482
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 482
aaagatcaca aatcagcttg gcaggattag tccgttagcc cgatggtaa                   49

<210> SEQ ID NO 483
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 483
ttattgcacg cgtcagccta tgctctgtgc tcatgtatca ctcttcactc                  50

<210> SEQ ID NO 484
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 484
gcctgaaaaa ttgtctctat cagggaaaat tacgcgataa atcacccgct ctagggaag        59

<210> SEQ ID NO 485
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 485
ttattgcacg cgtcagccta tattacgcga ggctttcttc ccatcccagt ca               52

<210> SEQ ID NO 486
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 486
```
caagcgaagg aaacagcctg ctagcgccgg tcaatagaga aa    42

<210> SEQ ID NO 487
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 487
tattcgctca taacgggttc ggtgaggttt gccctgggag tagag    45

<210> SEQ ID NO 488
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 488
tctgaagcca aaatttgccc attcattacg cgattacgta gcgccggtca atagagaaa    59

<210> SEQ ID NO 489
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 489
ttattgcacg cgtcagccta tattacgtgg ctacagttta gggagagggc tt    52

<210> SEQ ID NO 490
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 490
accagatcca ggagactgtt aggtcacatt acgcgattaa tccagtcgca acgctaaatg    60

<210> SEQ ID NO 491
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 491
tattcgctca taacgggttc gattacgcga tgggtgatag tggagagtct taccttccac    60

<210> SEQ ID NO 492
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 492
tacatcaggt cacctgactc tgtgccatta cgagtccgtt agcccgatgg taa    53

<210> SEQ ID NO 493
<211> LENGTH: 46
<212> TYPE: DNA
<213> ORGANISM: Artificial

```
-continued

<220> FEATURE:
<223> OTHER INFORMATION: synthetic oligonucleotide primers or probes

<400> SEQUENCE: 493
acacgaccgg taacgcttag aagatgcaag acatttgaga agggga            46

<210> SEQ ID NO 494
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 494 cttttgtga ttaacctccc cagggattac gcgattacta gcgccggtca atagagaaa    59

<210> SEQ ID NO 495
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 495
tgctaactag atcgcgggtt gattacgcga ttactgtgag gttggcaaca caacactt    58

<210> SEQ ID NO 496
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 496
acttcgcagc tcagtgcagc caatccagtc gcaacgctaa atg                43

<210> SEQ ID NO 497
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 497
tgctaactag atcgcgggtt ggccactggg gctttaggaa tggt              44

<210> SEQ ID NO 498
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 498
tgaatggcca agtccttttg gagattacgc gaaaatcacc cgctctaggg aag        53

<210> SEQ ID NO 499
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 499
acacgaccgg taacgcttag agcaagtagg attgcaaagg aggagg            46
```

<210> SEQ ID NO 500
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 500
tcagggtatt gaatcttgtg ggggattacg cgattacgaa atcacccgct ctagggaag    59

<210> SEQ ID NO 501
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 501
tgctaactag atcgcgggtt gattacgcga ttactgagtt cacatcacag cgagggat     58

<210> SEQ ID NO 502
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 502
gaatggacag ttttccagat ggtggattac gcgatagcgc cggtcaatag agaaa        55

<210> SEQ ID NO 503
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 503
ttattgcacg cgtcagccta tattctgctg gcagacacca tttgt                   45

<210> SEQ ID NO 504
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 504
caagaagggt agtgagattc tagcagccaa tccagtcgca acgctaaatg               50

<210> SEQ ID NO 505
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 505
ttattgcacg cgtcagccta tgatgaaggg tctttggctt cctttagac                49

<210> SEQ ID NO 506
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 506
ttccaccctg gctacacatc ctgtagcgcc ggtcaataga gaaa         44

<210> SEQ ID NO 507
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 507
ttattgcacg cgtcagccta tgccttatct ggggacccac gtt          43

<210> SEQ ID NO 508
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 508
acaagtagcc tgtcttcagt tcccctcatt acgcaaatca cccgctctag ggaag    55

<210> SEQ ID NO 509
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 509
tattcgctca taacgggttc gttcatctgg atccatgacg atgg         44

<210> SEQ ID NO 510
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 510
agacaaatag cagcggtggt gccaaaatca cccgctctag ggaag        45

<210> SEQ ID NO 511
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 511
tattcgctca taacgggttc gccaagaggg aaggcaggca ga           42

<210> SEQ ID NO 512
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 512
cagggaagga gagagcaggg tttattacgc gattacgcga aatcacccgc tctagggaag    60

<210> SEQ ID NO 513

```
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 513
acacgaccgg taacgcttag aattacgcga ttacgagaga gatgggggaa ggaagagaga      60

<210> SEQ ID NO 514
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 514
catccccagt gtgggaccat gaaatcaccc gctctaggga ag                         42

<210> SEQ ID NO 515
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 515
ttattgcacg cgtcagccta ttgcctagct gtgtgacatg attgg                      45

<210> SEQ ID NO 516
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 516
ctctggtggc cttgaaaaac aaccagtccg ttagcccgat ggtaa                      45

<210> SEQ ID NO 517
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 517
acacgaccgg taacgcttag agccagcctt agccaaatgc ag                         42

<210> SEQ ID NO 518
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 518
ctttctacct cccacagtgt ttgggattac gcgattacga aatcacccgc tctagggaag      60

<210> SEQ ID NO 519
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 519
```

```
tattcgctca taacgggttc gattacgcga ttggcttctc agttctaagc ctcacaaatc    60
```

<210> SEQ ID NO 520
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 520

```
cagccaagga ttttttcccc cgattacgcg attacgcgta gcgccggtca atagagaaa    59
```

<210> SEQ ID NO 521
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 521

```
acacgaccgg taacgcttag aattacgcat tcaaacagct ttccgacatc ac            52
```

<210> SEQ ID NO 522
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 522

```
cctggagccc tgaacaagta caaatgatta cgcatccagt cgcaacgcta aatg          54
```

<210> SEQ ID NO 523
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 523

```
tgctaactag atcgcgggtt ggctggggcc ttttttcagc at                       42
```

<210> SEQ ID NO 524
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 524

```
ttaagtgctg tgatgttagc tgctggtatt acgcgattag tccgttagcc cgatggtaa    59
```

<210> SEQ ID NO 525
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 525

```
ttattgcacg cgtcagccta tattaccgct ttgcttctgt ggtctcgagt aa            52
```

<210> SEQ ID NO 526
<211> LENGTH: 59
<212> TYPE: DNA

```
<213> ORGANISM: Artificial
<220> FEATURE:
<223> OTHER INFORMATION: synthetic oligonucleotide primers or probes

<400> SEQUENCE: 526
ctaggactag ggtcttgcat agagccttca ttacgcgaaa atcacccgct ctagggaag      59

<210> SEQ ID NO 527
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 527
tgctaactag atcgcgggtt gattacgccc aatggttgca agaggttcc                 49

<210> SEQ ID NO 528
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 528
ctctctcgag ctaacattgt ggagggatta catccagtcg caacgctaaa tg             52

<210> SEQ ID NO 529
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 529
acacgaccgg taacgcttag acactgtgat tcagcagtga agtcctg                   47

<210> SEQ ID NO 530
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 530
agtggtcagg tggcttccag caagtccgtt agcccgatgg taa                       43

<210> SEQ ID NO 531
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 531
ttattgcacg cgtcagccta ttgttttgca ttcctcttcc tggc                      44

<210> SEQ ID NO 532
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 532
agcctctggg ggcctcacaa aaatcacccg ctctagggaa g                         41
```

<210> SEQ ID NO 533
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 533
acacgaccgg taacgcttag aattacgctt ttccctgtta catagtgctg ggc        53

<210> SEQ ID NO 534
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 534
tatagaggct gctaaatcga cctgcgatta cgcgattaca tccagtcgca acgctaaatg    60

<210> SEQ ID NO 535
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 535
ttattgcacg cgtcagccta tattacgcga ttgggatgtg gtgtacacct accatcagtt    60

<210> SEQ ID NO 536
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 536
tcagggtggg ggaagtggca aatcacccgc tctagggaag                         40

<210> SEQ ID NO 537
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 537
tgctaactag atcgcgggtt gagattattg aaggtggccc aggc                    44

<210> SEQ ID NO 538
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 538
tggaaaggga aggggaagtg gtagcgccgg tcaatagaga aa                      42

<210> SEQ ID NO 539
<211> LENGTH: 42
<212> TYPE: DNA
<213> ORGANISM: Artificial
<220> FEATURE:

<223> OTHER INFORMATION: synthetic oligonucleotide primers or probes

<400> SEQUENCE: 539
tgctaactag atcgcgggtt gacagcccac accatgagct ca                          42

<210> SEQ ID NO 540
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 540
tctagccctg cttttctct cccgattacg cgaatccagt cgcaacgcta aatg              54

<210> SEQ ID NO 541
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 541
tattcgctca taacgggttc ggtgccggag aagatgattc atgac                       45

<210> SEQ ID NO 542
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 542
acacgaccgg taacgcttag a                                                 21

<210> SEQ ID NO 543
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 543
tattcgctca taacgggttc g                                                 21

<210> SEQ ID NO 544
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 544
ttattgcacg cgtcagccta t                                                 21

<210> SEQ ID NO 545
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 545
tgctaactag atcgcgggtt g                                                 21

```
<210> SEQ ID NO 546
<211> LENGTH: 29
<212> TYPE: DNA
<213> ORGANISM: Artificial
<220> FEATURE:
<223> OTHER INFORMATION: synthetic oligonucleotide primers or probes

<400> SEQUENCE: 546
gtttcttgct tccctagagc gggtgattt                                       29

<210> SEQ ID NO 547
<211> LENGTH: 67
<212> TYPE: DNA
<213> ORGANISM: Artificial
<220> FEATURE:
<223> OTHER INFORMATION: synthetic oligonucleotide primers or probes

<400> SEQUENCE: 547
gtttcttcga cgatacgacg atacgacgat acgacgatac gacgatcatt tagcgttgcg    60
actggat                                                              67

<210> SEQ ID NO 548
<211> LENGTH: 29
<212> TYPE: DNA
<213> ORGANISM: Artificial
<220> FEATURE:
<223> OTHER INFORMATION: synthetic oligonucleotide primers or probes

<400> SEQUENCE: 548
gtttcttgtt accatcgggc taacggact                                       29

<210> SEQ ID NO 549
<211> LENGTH: 67
<212> TYPE: DNA
<213> ORGANISM: Artificial
<220> FEATURE:
<223> OTHER INFORMATION: synthetic oligonucleotide primers or probes

<400> SEQUENCE: 549
gtttcttcga cgatacgacg atacgacgat acgacgatac gacgattttc tctattgacc    60
ggcgcta                                                              67

<210> SEQ ID NO 550
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 550
acacgaccgg taacgcttag a                                               21

<210> SEQ ID NO 551
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 551
tattcgctca taacgggttc g                                               21

<210> SEQ ID NO 552
<211> LENGTH: 21
<212> TYPE: DNA
```

```
<213> ORGANISM: Artificial
<220> FEATURE:
<223> OTHER INFORMATION: synthetic oligonucleotide primers or probes

<400> SEQUENCE: 552
ttattgcacg cgtcagccta t                                              21

<210> SEQ ID NO 553
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 553
tgctaactag atcgcgggtt g                                              21

<210> SEQ ID NO 554
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 554
aaatcacccg ctctagggaa g                                              21

<210> SEQ ID NO 555
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 555
atccagtcgc aacgctaaat g                                              21

<210> SEQ ID NO 556
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 556
agtccgttag cccgatggta a                                              21

<210> SEQ ID NO 557
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 557
tagcgccggt caatagagaa a                                              21

<210> SEQ ID NO 558
<211> LENGTH: 39
<212> TYPE: DNA
<213> ORGANISM: Artificial
<220> FEATURE:
<223> OTHER INFORMATION: synthetic oligonucleotide primers or probes

<400> SEQUENCE: 558
cgacgatacg acgatacgac gatacgacga tacgacgat                           39
```

<210> SEQ ID NO 559
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 559
tcctcgctct gaaccttggc aattaaatca cccgctctag ggaag         45

<210> SEQ ID NO 560
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 560
tattcgctca taacgggttc gtgtttggaa tcatgccagg atctc         45

<210> SEQ ID NO 561
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 561
tgagcaatgg gaagtagaag gagacaatta cgcgataaat cacccgctct agggaag         57

<210> SEQ ID NO 562
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 562
ttattgcacg cgtcagccta ttcctgtcct gtcatccatc agtga         45

<210> SEQ ID NO 563
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 563
ccagcgaggg tctctagttt gctaatatag attacgcgaa atcacccgct ctagggaag         59

<210> SEQ ID NO 564
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 564
ttattgcacg cgtcagccta tattacgcga cctaaccaag aggtgggga taaga         55

<210> SEQ ID NO 565
<211> LENGTH: 59
<212> TYPE: DNA
<213> ORGANISM: Artificial
<220> FEATURE:

<223> OTHER INFORMATION: synthetic oligonucleotide primers or probes

<400> SEQUENCE: 565
aaaccttccc tctccaaacc caggattacg cgattacgat ccagtcgcaa cgctaaatg    59

<210> SEQ ID NO 566
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 566
acacgaccgg taacgcttag aattacaagt tggagagaac tctctgacca ctctg    55

<210> SEQ ID NO 567
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 567
ccatcctcta acccagagag catttcatta cgcgattaaa atcacccgct ctagggaag    59

<210> SEQ ID NO 568
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 568
tattcgctca taacgggttc gattgcatct gctggtcaat gtgtcacct    49

<210> SEQ ID NO 569
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 569
cttctccctt ctcttccttc tccacaatta cgcgattaat ccagtcgcaa cgctaaatg    59

<210> SEQ ID NO 570
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 570
acacgaccgg taacgcttag aattacgttt aaacttctgc ttctccctac tttccatc    58

<210> SEQ ID NO 571
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 571
agtgattatt ggatgacagg ctgccattac gatccagtcg caacgctaaa tg    52

```
<210> SEQ ID NO 572
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 572
ttattgcacg cgtcagccta ttggaatttg ggcctgagag agga            44

<210> SEQ ID NO 573
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 573
cggctgtcac tgaaatgtca gcaattacgc gattatccag tcgcaacgct aaatg     55

<210> SEQ ID NO 574
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 574
acacgaccgg taacgcttag aatggggaca aagtcccctc tactttctg        49

<210> SEQ ID NO 575
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 575
tccctctcct tattcttttg gggagaatta cgcgatatcc agtcgcaacg ctaaatg    57

<210> SEQ ID NO 576
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 576
ttattgcacg cgtcagccta taacaagtac cctgggcatg ctctt           45

<210> SEQ ID NO 577
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 577
caggggtggg agttgtgttg aaattacgag tccgttagcc cgatggtaa        49

<210> SEQ ID NO 578
<211> LENGTH: 47
<212> TYPE: DNA
<213> ORGANISM: Artificial
<220> FEATURE:
<223> OTHER INFORMATION: synthetic oligonucleotide primers or probes
```

<400> SEQUENCE: 578
ttattgcacg cgtcagccta ttgtgaatca gggaaagagg atgaagg			47

<210> SEQ ID NO 579
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 579
tggaaagcat aaaggggaag gatccattac gcgatagtcc gttagcccga tggtaa			56

<210> SEQ ID NO 580
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 580
ttattgcacg cgtcagccta ttcaatctct gagcagttgg gggata			46

<210> SEQ ID NO 581
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 581
atctgtaggt cattgccatc agtgcaatta cgcgattaag tccgttagcc cgatggtaa			59

<210> SEQ ID NO 582
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 582
acacgaccgg taacgcttag aattacgcga atggttctga gaccggtctt tctgt			55

<210> SEQ ID NO 583
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 583
gcatccccag tggatgtgtt caatagcgcc ggtcaataga gaaa			44

<210> SEQ ID NO 584
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 584
tgctaactag atcgcgggtt gtgcctcaag gttcctcaga ggg			43

<210> SEQ ID NO 585
<211> LENGTH: 55

```
<212> TYPE: DNA
<213> ORGANISM: Artificial
<220> FEATURE:
<223> OTHER INFORMATION: synthetic oligonucleotide primers or probes

<400> SEQUENCE: 585
gaagggatcg acaaccacaa tcagattacg cgattagcgc cggtcaatag agaaa          55

<210> SEQ ID NO 586
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 586
tattcgctca taacgggttc gaagacctat gcaaacaacc ttccagg                    47

<210> SEQ ID NO 587
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 587
cccagttact tacttcctgc tgtggttgat tacgcgatat ccagtcgcaa cgctaaatg      59

<210> SEQ ID NO 588
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 588
tattcgctca taacgggttc gattacggga accaagtttg ggtggaaat                  49

<210> SEQ ID NO 589
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 589
tcacacatct ctgttcttcc atccttaaaa ttacgcgaat ccagtcgcaa cgctaaatg      59

<210> SEQ ID NO 590
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 590
ttattgcacg cgtcagccta tattacgcgc agggaggacg tctacagagc ctagt          55

<210> SEQ ID NO 591
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 591
```
caaagtgcaa tgtgatcctc tggagattac gcgattacat ccagtcgcaa cgctaaatg    59

<210> SEQ ID NO 592
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 592
tattcgctca taacgggttc gattaccatc tctaccttgt acaggcaagc acttg    55

<210> SEQ ID NO 593
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 593
aatgtggaag aacatgccac ccaattacgt agcgccggtc aatagagaaa    50

<210> SEQ ID NO 594
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 594
acacgaccgg taacgcttag aggcatagaa ggcaagtagg caaagg    46

<210> SEQ ID NO 595
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 595
gcttattctt tgcctggagc cagttattac gcgattagtc cgttagcccg atggtaa    57

<210> SEQ ID NO 596
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 596
acacgaccgg taacgcttag attgctttga aacaagggtg agcag    45

<210> SEQ ID NO 597
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 597
tcacagccca cattcttagc atggattacg cgataaatca cccgctctag ggaag    55

<210> SEQ ID NO 598
<211> LENGTH: 47
<212> TYPE: DNA
<213> ORGANISM: Artificial

```
<220> FEATURE:
<223> OTHER INFORMATION: synthetic oligonucleotide primers or probes

<400> SEQUENCE: 598
tgctaactag atcgcgggtt gtgtcaacat ctcttgttcc cttcagg         47

<210> SEQ ID NO 599
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 599
acctgggtat tatggctaag ggaaggatta cgcgattaag tccgttagcc cgatggtaa    59

<210> SEQ ID NO 600
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 600
ttattgcacg cgtcagccta tattaggcct gaagttatct gcatccaaa              49

<210> SEQ ID NO 601
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 601
ctgggagaaa taaaggtaag aggcagagaa ttacgcgata gcgccggtca atagagaaa    59

<210> SEQ ID NO 602
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 602
tattcgctca taacgggttc gattacgctg tgtctttgag gtggtagagg aagga        55

<210> SEQ ID NO 603
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 603
tttaaacccc aaccaggact cagagaatta cgcgattaag tccgttagcc cgatggtaa    59

<210> SEQ ID NO 604
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 604
ttattgcacg cgtcagccta tattacgcgc ttagacgtac agttcactcc cagtgg       56
```

<210> SEQ ID NO 605
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 605
agcccctcca tgagtttgtt ctgaattacg cgaaaatcac ccgctctagg gaag          54

<210> SEQ ID NO 606
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 606
tgctaactag atcgcgggtt gcagcaataa caattttgga ggccc                    45

<210> SEQ ID NO 607
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 607
aatccttagc aaggatggca aggcattaaa atcacccgct ctagggaag                49

<210> SEQ ID NO 608
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 608
tgctaactag atcgcgggtt gccagtgcct ttgggataaa gcag                     44

<210> SEQ ID NO 609
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 609
caacacatcc tcccaagcag gcattaatcc agtcgcaacg ctaaatg                  47

<210> SEQ ID NO 610
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 610
tgctaactag atcgcgggtt ggcaaagaag actgcatatc aagggc                   46

<210> SEQ ID NO 611
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 611
gtgatagcag gacagagtga cccaaaatta cgcgattaaa atcacccgct ctagggaag    59

<210> SEQ ID NO 612
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 612
tgctaactag atcgcgggtt gattacttta aatccagaga ccctctgtac ttccag    56

<210> SEQ ID NO 613
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 613
gccaccagcc caaactaagc aatatccagt cgcaacgcta aatg    44

<210> SEQ ID NO 614
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 614
tgctaactag atcgcgggtt gaagaagcag gacgccagca tt    42

<210> SEQ ID NO 615
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 615
gccaaaatgc caagtgtggt gcattatcca gtcgcaacgc taaatg    46

<210> SEQ ID NO 616
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 616
tattcgctca taacgggttc gcagccactt ttctgagagg gcct    44

<210> SEQ ID NO 617
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 617
catccaaagg aagacagcct gtgaattacg cgaatccagt cgcaacgcta aatg    54

<210> SEQ ID NO 618

```
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 618
tgctaactag atcgcgggtt gcttgggtca tcaggacgtc catta             45

<210> SEQ ID NO 619
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 619
ctctgggaaa cagccagttg ttgtattatt acgcgattag tccgttagcc cgatggtaa    59

<210> SEQ ID NO 620
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 620
tattcgctca taacgggttc gattacgcgt gcaagaaaag aggcctaagg aagac         55

<210> SEQ ID NO 621
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 621
ttgtgggtaa tatgggctgt tgggattaag tccgttagcc cgatggtaa                49

<210> SEQ ID NO 622
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 622
tgctaactag atcgcgggtt gtgtccatgt gctgggtctt tgtt                     44

<210> SEQ ID NO 623
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 623
ctttgtccag atccggagtc agcattatag cgccggtcaa tagagaaa                 48

<210> SEQ ID NO 624
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 624
```
tattcgctca taacgggttc gaaagaacat cacctcaagc ctggg    45

<210> SEQ ID NO 625
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 625
gacagacggg agtcgagtgt attcacatta cgcgtagcgc cggtcaatag agaaa    55

<210> SEQ ID NO 626
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 626
tgctaactag atcgcgggtt ggcaggcaga gagtgtgtgc tgag    44

<210> SEQ ID NO 627
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 627
cctgaagaac ttcactcaca gtctctttcc attacgcgag tccgttagcc cgatggtaa    59

<210> SEQ ID NO 628
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 628
tattcgctca taacgggttc gattacgcga tggtgcagga actaggatcc ccagatat    58

<210> SEQ ID NO 629
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 629
ctgtacaaat gaagacacag cctggattat tacgcgatta gcgccggtca atagagaaa    59

<210> SEQ ID NO 630
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 630
ttattgcacg cgtcagccta tattttcatt tcagccacag accgtg    46

<210> SEQ ID NO 631
<211> LENGTH: 56
<212> TYPE: DNA

<213> ORGANISM: Artificial
<220> FEATURE:
<223> OTHER INFORMATION: synthetic oligonucleotide primers or probes

<400> SEQUENCE: 631
ggcataaata agagcatcac ccgcattacg cgattaaatc acccgctcta gggaag        56

<210> SEQ ID NO 632
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 632
tattcgctca taacgggttc ggaggaagaa gccttcttgc ttttgg        46

<210> SEQ ID NO 633
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 633
caccatctcc gctaccaacc tgattacgca aatcacccgc tctagggaag        50

<210> SEQ ID NO 634
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 634
acacgaccgg taacgcttag acctcccagg gattaggcta gaatca        46

<210> SEQ ID NO 635
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 635
catttccagg gtgagcatca aatgattacg cgattatcca gtcgcaacgc taaatg        56

<210> SEQ ID NO 636
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 636
tattcgctca taacgggttc gtccacggtg gattaagtgt ttctgc        46

<210> SEQ ID NO 637
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 637
gagtgatcag aactggcctg aacctattac gcgattacaa atcacccgct ctagggaag        59

<210> SEQ ID NO 638
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 638
ttattgcacg cgtcagccta tatgggccgg agtaactaac tgagaatcg           49

<210> SEQ ID NO 639
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 639
tttaaaatgc atgcctgcgg aaattacgca tccagtcgca acgctaaatg          50

<210> SEQ ID NO 640
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 640
acacgaccgg taacgcttag accaagtgcc ctggtgtggt ttattt              46

<210> SEQ ID NO 641
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 641
ggacctgatc aatggtattt ctgcctatta cgcgaagtcc gttagcccga tggtaa    56

<210> SEQ ID NO 642
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 642
tgctaactag atcgcgggtt gggtgtgcat gttggatgca ggt                 43

<210> SEQ ID NO 643
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 643
cccttccaca ggattctgag ttggattacg cagtccgtta gcccgatggt aa       52

<210> SEQ ID NO 644
<211> LENGTH: 44
<212> TYPE: DNA
<213> ORGANISM: Artificial
<220> FEATURE:

<223> OTHER INFORMATION: synthetic oligonucleotide primers or probes

<400> SEQUENCE: 644
acacgaccgg taacgcttag agggacccct ccattgtgtg tttt          44

<210> SEQ ID NO 645
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 645
cctccctgaa aaaccacaga tttccattac gcgatatcca gtcgcaacgc taaatg    56

<210> SEQ ID NO 646
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 646
tgctaactag atcgcgggtt ggctgaacca ttctgaggca agaaca         46

<210> SEQ ID NO 647
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 647
caagaggagc ctggtaaagt cctcaattac gcgattacag tccgttagcc cgatggtaa    59

<210> SEQ ID NO 648
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 648
acacgaccgg taacgcttag aggattctgg atgaggtgat gttggg         46

<210> SEQ ID NO 649
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 649
gagcgtcagt tggtaggaga gagtttagcg ccggtcaata gagaaa         46

<210> SEQ ID NO 650
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 650
tattcgctca taacgggttc gagtgctcac tgtgcctact gtgg          44

-continued

<210> SEQ ID NO 651
<211> LENGTH: 62
<212> TYPE: DNA
<213> ORGANISM: Artificial
<220> FEATURE:
<223> OTHER INFORMATION: synthetic oligonucleotide primers or probes

<400> SEQUENCE: 651
tgattcactg tggctgtcac ctcttattac gcgattacgc gtagcgccgg tcaatagaga    60
aa    62

<210> SEQ ID NO 652
<211> LENGTH: 63
<212> TYPE: DNA
<213> ORGANISM: Artificial
<220> FEATURE:
<223> OTHER INFORMATION: synthetic oligonucleotide primers or probes

<400> SEQUENCE: 652
ttattgcacg cgtcagccta tattacgcga ttacgcgatg cccttgcagg atttgacacc    60
tct    63

<210> SEQ ID NO 653
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 653
agttgttgcc cttggtaagg ctatgaatta cgcgattaaa atcacccgct ctagggaag    59

<210> SEQ ID NO 654
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 654
ttattgcacg cgtcagccta tattacgcga ttacggaagt gcattggtgg gactctga    58

<210> SEQ ID NO 655
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 655
ttctgcctgt gttgtattcc tggcattacg cgattacgat ccagtcgcaa cgctaaatg    59

<210> SEQ ID NO 656
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 656
ttattgcacg cgtcagccta tattacgcga tgaaggtctg aggctgtggt aggtaacc    58

<210> SEQ ID NO 657
<211> LENGTH: 59
<212> TYPE: DNA

```
<213> ORGANISM: Artificial
<220> FEATURE:
<223> OTHER INFORMATION: synthetic oligonucleotide primers or probes

<400> SEQUENCE: 657
tggtgggaat gccctagaat ctaggattac gcgattacta gcgccggtca atagagaaa      59

<210> SEQ ID NO 658
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 658
acacgaccgg taacgcttag aattacgata cctaatggag gaatgggtgt tatcc          55

<210> SEQ ID NO 659
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 659
tgccaaaaga taaccacagg tggaattacg cgattagtcc gttagcccga tggtaa         56

<210> SEQ ID NO 660
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 660
tattcgctca taacgggttc ggggtgcctt taaaaggcta acatgc                    46

<210> SEQ ID NO 661
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 661
attctggctc tgaatgagtc tgagcaatta cgcgattata gcgccggtca atagagaaa      59

<210> SEQ ID NO 662
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 662
tgctaactag atcgcgggtt gattagacct gctcacagag catgaagtct aa             52

<210> SEQ ID NO 663
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 663
gaactgaacc cggtagagtc atctccatta cgcgattaaa atcacccgct ctagggaag      59
```

<210> SEQ ID NO 664
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 664
tattcgctca taacgggttc gattacgaat agtattgtgg tctcctttac ccactcag        58

<210> SEQ ID NO 665
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 665
caccattctg aacacctggg caattaaaat cacccgctct agggaag        47

<210> SEQ ID NO 666
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 666
acacgaccgg taacgcttag actccttccc cagcaaatgg aaa        43

<210> SEQ ID NO 667
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 667
ggccacctat ttaactctcc tccaagaatt acgcgattat ccagtcgcaa cgctaaatg        59

<210> SEQ ID NO 668
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 668
tgctaactag atcgcgggtt gattacacta gcaagaaaac agagggagac atctg        55

<210> SEQ ID NO 669
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 669
ttcagtctcc agttctgcat gttggattac gcgattacag tccgttagcc cgatggtaa        59

<210> SEQ ID NO 670
<211> LENGTH: 52
<212> TYPE: DNA
<213> ORGANISM: Artificial
<220> FEATURE:

<223> OTHER INFORMATION: synthetic oligonucleotide primers or probes

<400> SEQUENCE: 670
tgctaactag atcgcgggtt gattactgct cttcgaggtt cttttcttcc tc    52

<210> SEQ ID NO 671
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 671
ctgattgcat ttcctggacc tcaaattata gcgccggtca atagagaaa    49

<210> SEQ ID NO 672
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 672
ttattgcacg cgtcagccta tcgtggaaaa tggcactgct aaca    44

<210> SEQ ID NO 673
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 673
gactggattg agaaggagtg tgtgagttat tacgcgatag tccgttagcc cgatggtaa    59

<210> SEQ ID NO 674
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 674
acacgaccgg taacgcttag aattacgcga gtacaccaac atatggactc ctggagag    58

<210> SEQ ID NO 675
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 675
gggggaattt atggtgaaaa gggaattacg cgattacatc cagtcgcaac gctaaatg    58

<210> SEQ ID NO 676
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 676
ttattgcacg cgtcagccta tgacactgcc ctctctcatg tcctctt    47

```
<210> SEQ ID NO 677
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 677
gtgaaggatc caggcatcct tccataaatc acccgctcta gggaag           46

<210> SEQ ID NO 678
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 678
ttattgcacg cgtcagccta tgagaaggat atagcatggc gggg             44

<210> SEQ ID NO 679
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 679
gcaaattcct ccaagcaggt gtttattaat ccagtcgcaa cgctaaatg        49

<210> SEQ ID NO 680
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 680
acacgaccgg taacgcttag acgggctgca tgaggtgaaa a                41

<210> SEQ ID NO 681
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 681
cactggtcac cacctcttaa attcatttca ttacgcgaat ccagtcgcaa cgctaaatg    59

<210> SEQ ID NO 682
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 682
tattcgctca taacgggttc gattacgcga aagtcctttc ttgtcctcca ctacatcc     58

<210> SEQ ID NO 683
<211> LENGTH: 58
<212> TYPE: DNA
<213> ORGANISM: Artificial
<220> FEATURE:
<223> OTHER INFORMATION: synthetic oligonucleotide primers or probes
```

```
<400> SEQUENCE: 683
gtgtgacatc atttgttgcc aggaattacg cgattacagt ccgttagccc gatggtaa        58

<210> SEQ ID NO 684
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 684
tattcgctca taacgggttc ggagacaggg cagacatctt gactgat                    47

<210> SEQ ID NO 685
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 685
cacccattgc ctgttgggca tatccagtcg caacgctaaa tg                         42

<210> SEQ ID NO 686
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 686
ttattgcacg cgtcagccta taaaacgcag tagagaatgg tgatggag                   48

<210> SEQ ID NO 687
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 687
catggatgac acctgagtgt attggaatta cgcgattata gcgccggtca atagagaaa       59

<210> SEQ ID NO 688
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 688
tgctaactag atcgcgggtt gccccaccaa ttcctgttgt ccttaa                     46

<210> SEQ ID NO 689
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 689
tcctggtctc tcctctgctt agtgaggatt acgcgattag tccgttagcc cgatggtaa       59

<210> SEQ ID NO 690
<211> LENGTH: 55
```

```
<212> TYPE: DNA
<213> ORGANISM: Artificial
<220> FEATURE:
<223> OTHER INFORMATION: synthetic oligonucleotide primers or probes

<400> SEQUENCE: 690
tgctaactag atcgcgggtt gattacggat tttgtccaat ggcctttcta gtgtc      55

<210> SEQ ID NO 691
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 691
gaggaggaac agaccatcag caacaattac gcgattacta gcgccggtca atagagaaa   59

<210> SEQ ID NO 692
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 692
acacgaccgg taacgcttag actcatttac ctcactgcac tgtggg      46

<210> SEQ ID NO 693
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 693
atctgggcca ccctgaatga gaattaagtc cgttagcccg atggtaa      47

<210> SEQ ID NO 694
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 694
acacgaccgg taacgcttag agaggcaggg gatgtctgtg aga      43

<210> SEQ ID NO 695
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 695
ctttcccgag tgtcttcaaa agggattacg cgattacgta gcgccggtca atagagaaa   59

<210> SEQ ID NO 696
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 696
```
tattcgctca taacgggttc gattacgcga ttactctgca cctgagtgtt gaaggtga        58

<210> SEQ ID NO 697
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 697
aatataggag atggaccccca aggcaattac gcgattacta gcgccggtca atagagaaa       59

<210> SEQ ID NO 698
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 698
ttattgcacg cgtcagccta tattaataat atttggggag agaatatttg gggag            55

<210> SEQ ID NO 699
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 699
ggattgcctt ggggccacta ttacgcaaat cacccgctct agggaag                     47

<210> SEQ ID NO 700
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 700
tattcgctca taacgggttc gctttcttct cactgcctta gtgtcctca                   49

<210> SEQ ID NO 701
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 701
aatccagagc ccccatctcg cattacgcat ccagtcgcaa cgctaaatg                   49

<210> SEQ ID NO 702
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 702
tattcgctca taacgggttc ggctcagagg cagaaaatac ttgggtg                     47

<210> SEQ ID NO 703
<211> LENGTH: 59
<212> TYPE: DNA
<213> ORGANISM: Artificial

<220> FEATURE:
<223> OTHER INFORMATION: synthetic oligonucleotide primers or probes

<400> SEQUENCE: 703
aactcccaca gaacaagcac agaaaaatta cgcgattata gcgccggtca atagagaaa    59

<210> SEQ ID NO 704
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 704
ttattgcacg cgtcagccta tattacgcga tttcttggtg acactggtag gctatgga    58

<210> SEQ ID NO 705
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 705
tctgctgcag gaggtgggag attacgcagt ccgttagccc gatggtaa    48

<210> SEQ ID NO 706
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 706
tattcgctca taacgggttc gcatctctag aagccacacc cttaagcc    48

<210> SEQ ID NO 707
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 707
gacagagagc aagttttgca cgaggattac gcgattacaa atcacccgct ctagggaag    59

<210> SEQ ID NO 708
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 708
tattcgctca taacgggttc gattacgcgc aatactctct gaaaccagag aggaggg    57

<210> SEQ ID NO 709
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 709
ctgtgaggtt gctaataaca atcacatctg gattacgcag tccgttagcc cgatggtaa    59

<210> SEQ ID NO 710
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 710
ttattgcacg cgtcagccta tattacgcga taacttcccc tgacgcgaca ttaatact         58

<210> SEQ ID NO 711
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 711
aagtgttgca catctgcaaa gtgccattac gcgattacaa atcacccgct ctagggaag        59

<210> SEQ ID NO 712
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 712
acacgaccgg taacgcttag aattacgaat aattcattca ctctctcagc cagtcaat         58

<210> SEQ ID NO 713
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 713
ccagggaggg gcacattgtt attagtccgt tagcccgatg gtaa                         44

<210> SEQ ID NO 714
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 714
tattcgctca taacgggttc ggcacttgcc ttgagtgtgt gtaacc                       46

<210> SEQ ID NO 715
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 715
ttcatatggg gcaaagttca ggcattacgc gattaaaatc acccgctcta gggaag           56

<210> SEQ ID NO 716
<211> LENGTH: 46
<212> TYPE: DNA
<213> ORGANISM: Artificial
<220> FEATURE:
<223> OTHER INFORMATION: synthetic oligonucleotide primers or probes

```
<400> SEQUENCE: 716
acacgaccgg taacgcttag acaagaccta gatggaatgc agcgaa            46

<210> SEQ ID NO 717
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 717
cggaatagaa aggtcctagc acagggatta cgcgattata gcgccggtca atagagaaa   59

<210> SEQ ID NO 718
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 718
tgctaactag atcgcgggtt gattgagtaa tgggaactcc atgaacactt tctaa       55

<210> SEQ ID NO 719
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 719 cttttttgcac acatggggta ctccgattac gcgattacaa atcacccgct ctagggaag  59

<210> SEQ ID NO 720
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 720
acacgaccgg taacgcttag aattcactca ggaccaggtc tggagaatt             49

<210> SEQ ID NO 721
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 721
tccattgtgt gaacacttgg ggcattacgc gattacgcat ccagtcgcaa cgctaaatg   59

<210> SEQ ID NO 722
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 722
acacgaccgg taacgcttag aatttagttt ggccacacac tgacagttc             49

<210> SEQ ID NO 723
```

```
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 723
ctctggaaac atctcagccc atcaattata gcgccggtca atagagaaa           49

<210> SEQ ID NO 724
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 724
acacgaccgg taacgcttag agttggcacc ccattcccat t                   41

<210> SEQ ID NO 725
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 725
ctgtgatcac ttgagggtga ggacaattac gcgattacag tccgttagcc cgatggtaa  59

<210> SEQ ID NO 726
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 726
tgctaactag atcgcgggtt gccacctctt atgtccctg agcaat               46

<210> SEQ ID NO 727
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 727
tgcaaggtgt gtctctcact cccatagtcc gttagcccga tggtaa              46

<210> SEQ ID NO 728
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 728
ttattgcacg cgtcagccta tggggccata tgggacagaa aagt                44

<210> SEQ ID NO 729
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 729
```
tggaaaccca tccaacctct ccattagcgc cggtcaatag agaaa         45

<210> SEQ ID NO 730
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 730
ttattgcacg cgtcagccta ttcaggaaga atgtactctg gcccc         45

<210> SEQ ID NO 731
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 731
ttgttacaga agaaattcaa ggtgcaaagt agattacgta gcgccggtca atagagaaa   59

<210> SEQ ID NO 732
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 732
acacgaccgg taacgcttag aattacgcga ttcctgggag agaaggggag attaggat    58

<210> SEQ ID NO 733
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 733
gcagtgctgc agtgaagagg agttatagtc cgttagcccg atggtaa       47

<210> SEQ ID NO 734
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 734
tgctaactag atcgcgggtt gacaccctcc cacctggagc a             41

<210> SEQ ID NO 735
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 735
tgtttttatt gcaaagccgc ccattatagc gccggtcaat agagaaa       47

<210> SEQ ID NO 736
<211> LENGTH: 46
<212> TYPE: DNA

```
<213> ORGANISM: Artificial
<220> FEATURE:
<223> OTHER INFORMATION: synthetic oligonucleotide primers or probes

<400> SEQUENCE: 736
tgctaactag atcgcgggtt gcctctttgg gtcataaggc ctgatt            46

<210> SEQ ID NO 737
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 737
cctcaacgcc ctgttttctg tatagtcatt acgcgattaa atcacccgct ctagggaag     59

<210> SEQ ID NO 738
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 738
tgctaactag atcgcgggtt gattacgcct gcattctgct gtgtgtctgc tt            52

<210> SEQ ID NO 739
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 739
gttccctgtt cccaaatgca gcattacgca aatcacccgc tctagggaag             50

<210> SEQ ID NO 740
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 740
ttattgcacg cgtcagccta tccagatcat ccttgaggga cagtct               46

<210> SEQ ID NO 741
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 741
tttagtgtag caaacaagag gcggcattac gcgattacta gcgccggtca atagagaaa    59

<210> SEQ ID NO 742
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 742
tattcgctca taacgggttc gttaccgcag tcaccagtaa tgttgg               46
```

<210> SEQ ID NO 743
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 743
catgagatga gccccgggga ttaaatcacc cgctctaggg aag          43

<210> SEQ ID NO 744
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 744
tgctaactag atcgcgggtt ggctgtgctg gtgatggctg agat          44

<210> SEQ ID NO 745
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 745
actcatgtga tcgtcaccct ccttgattac gcgattacaa atcacccgct ctagggaag          59

<210> SEQ ID NO 746
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 746
acacgaccgg taacgcttag aattacgcca aatcaagtct cctccttcaa ctggg          55

<210> SEQ ID NO 747
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 747
cctgcactgt gggtgtcatc cattacgcga tttagcgccg gtcaatagag aaa          53

<210> SEQ ID NO 748
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 748
acacgaccgg taacgcttag acactagaaa tcagacagaa atctgccca          49

<210> SEQ ID NO 749
<211> LENGTH: 59
<212> TYPE: DNA
<213> ORGANISM: Artificial
<220> FEATURE:

```
<223> OTHER INFORMATION: synthetic oligonucleotide primers or probes

<400> SEQUENCE: 749
agagtgcacc cagatggaat ggaattacgc gattacgcat ccagtcgcaa cgctaaatg      59

<210> SEQ ID NO 750
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 750
tgctaactag atcgcgggtt gattagaaga acttagataa cccaccacct ccc            53

<210> SEQ ID NO 751
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 751
acgcatgcag ccctctccaa tccagtcgca acgctaaatg                           40

<210> SEQ ID NO 752
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 752
acacgaccgg taacgcttag acaggcataa caaacagctc aattccc                   47

<210> SEQ ID NO 753
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 753
aggctgcagc ggggaaaata ttacaaatca cccgctctag ggaag                     45

<210> SEQ ID NO 754
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 754
tgctaactag atcgcgggtt ggcctgaaaa atgtggctca tcctc                     45

<210> SEQ ID NO 755
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 755
ctttcagagg tcgagccaca gctattacta gcgccggtca atagagaaa                 49
```

```
<210> SEQ ID NO 756
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 756
tgctaactag atcgcgggtt gtgagttatc aggcaaacat caggagg            47

<210> SEQ ID NO 757
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 757
tttcaggtag catgtccatc caaaggatta cgcgattagt ccgttagccc gatggtaa    58

<210> SEQ ID NO 758
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 758
tgctaactag atcgcgggtt gggtgattct agtatattct gggcactggg         50

<210> SEQ ID NO 759
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 759
attatggtgg cagagacctg cagcattacg cgaaatcacc cgctctaggg aag       53

<210> SEQ ID NO 760
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 760
tattcgctca taacgggttc gattacgctg gccccatttc tcattactat tg        52

<210> SEQ ID NO 761
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 761
actgggctca atgccacttg cagtccgtta gcccgatggt aa                 42

<210> SEQ ID NO 762
<211> LENGTH: 45
<212> TYPE: DNA
<213> ORGANISM: Artificial
<220> FEATURE:
<223> OTHER INFORMATION: synthetic oligonucleotide primers or probes
```

```
<400> SEQUENCE: 762
tattcgctca taacgggttc gctcagtgct cataaacctg tggcc              45

<210> SEQ ID NO 763
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 763
catccttgag caactctggg ttctacaatt acgcgattaa aatcaccgc tctagggaag   60

<210> SEQ ID NO 764
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 764
ttattgcacg cgtcagccta tattacgcga ttacgcgggc tgggaacctc aagagtgagg   60

<210> SEQ ID NO 765
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 765
tggagttcat catgcccagg gattacgcaa atcacccgct ctagggaag              49

<210> SEQ ID NO 766
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 766
tgctaactag atcgcgggtt ggcagcaaag gcacatttac tccgtat              47

<210> SEQ ID NO 767
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 767
ttttaggtga tgagggttgt gatgggatta cgcgaagtcc gttagcccga tggtaa       56

<210> SEQ ID NO 768
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 768
acacgaccgg taacgcttag aattactctg cctggctctc attagaactg tg           52

<210> SEQ ID NO 769
<211> LENGTH: 59
```

```
<212> TYPE: DNA
<213> ORGANISM: Artificial
<220> FEATURE:
<223> OTHER INFORMATION: synthetic oligonucleotide primers or probes

<400> SEQUENCE: 769
gcatgtgtgc tgtactccag aatggattac gcgattacag tccgttagcc cgatggtaa      59

<210> SEQ ID NO 770
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 770
tattcgctca taacgggttc gatgggagag tttacctgga cacataggag ag             52

<210> SEQ ID NO 771
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 771
gttccctcca tcgatgtgct taaccattaa aatcacccgc tctagggaag                50

<210> SEQ ID NO 772
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 772
acacgaccgg taacgcttag acatcaaccg ggcctgtctg ttt                       43

<210> SEQ ID NO 773
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 773
cctaatactg gcagtgaata agccccatag cgccggtcaa tagagaaa                  48

<210> SEQ ID NO 774
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 774
ttattgcacg cgtcagccta tattacgcga ttagcccctg cagaggtttt agctagactt     60

<210> SEQ ID NO 775
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 775
```
gttgtcctct ctgttacggc ctcatcatta cgcgattaca tccagtcgca acgctaaatg    60

<210> SEQ ID NO 776
<211> LENGTH: 57
<212> TYPE: DNA
<213> ORGANISM: Artificial
<220> FEATURE:
<223> OTHER INFORMATION: synthetic oligonucleotide primers or probes

<400> SEQUENCE: 776
tgctaactag atcgcgggtt gattacgcga ttacctttga ctggtttgtg gccatct    57

<210> SEQ ID NO 777
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 777
tccatcatgg ccgccatcta ttacgagtcc gttagcccga tggtaa    46

<210> SEQ ID NO 778
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 778
tgctaactag atcgcgggtt gaccttcctg ctcatcactc tttcctatgt c    51

<210> SEQ ID NO 779
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 779
ttcgtggatt gtccatgggt gattagcgcc ggtcaataga gaaa    44

<210> SEQ ID NO 780
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 780
tgctaactag atcgcgggtt gattacgcga tcaactcctg attacccatt ctcagagg    58

<210> SEQ ID NO 781
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 781
tggttttatc cagtctgagt ctcccaatta cgcgattact agcgccggtc aatagagaaa    60

<210> SEQ ID NO 782
<211> LENGTH: 60
<212> TYPE: DNA
<213> ORGANISM: Artificial

```
<220> FEATURE:
<223> OTHER INFORMATION: synthetic oligonucleotide primers or probes

<400> SEQUENCE: 782
ttattgcacg cgtcagccta tattacgcga ttacgcgaaa gtcagagctg cgcttttttcc    60

<210> SEQ ID NO 783
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 783
cagaagtgga atggtttctg gtggattacg cgattacgat ccagtcgcaa cgctaaatg     59

<210> SEQ ID NO 784
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 784
tgctaactag atcgcgggtt gattctggag tgaggggaag aagctgtta                49

<210> SEQ ID NO 785
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 785
acagaatgac agggtttgtg aagtcgatta cgcaaatcac ccgctctagg gaag          54

<210> SEQ ID NO 786
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 786
ttattgcacg cgtcagccta tcagcgctca ttctttagtc tccga                    45

<210> SEQ ID NO 787
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 787
tcaatccttc tcccagaagc agaggattac gcgattagcg ccggtcaata gagaaa        56

<210> SEQ ID NO 788
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 788
tattcgctca taacgggttc gattacaaag atgtgggtag acaccagaaa tgc           53
```

<210> SEQ ID NO 789
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 789
tactctttgg agggcctttc ctagccatta cgcgatagcg ccggtcaata gagaaa      56

<210> SEQ ID NO 790
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 790
acacgaccgg taacgcttag aggtgggaaa gctctcctct ggc      43

<210> SEQ ID NO 791
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 791
ctcatggagc ccaagaagga ttcaatccag tcgcaacgct aaatg      45

<210> SEQ ID NO 792
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 792
tattcgctca taacgggttc gtggacagct tgtcccacct cc      42

<210> SEQ ID NO 793
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 793
agcagaacta gtggctctcc cctttgagtc cgttagcccg atggtaa      47

<210> SEQ ID NO 794
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 794
acacgaccgg taacgcttag atcaccagtt tctggatcac tctccc      46

<210> SEQ ID NO 795
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 795
tctccatgtt tttcctgcac tccttatcca gtcgcaacgc taaatg            46

<210> SEQ ID NO 796
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 796
tgctaactag atcgcgggtt gtctaaaccc cactgctgct gctc              44

<210> SEQ ID NO 797
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 797
ctgttcatat ccactggcag agatgagagt ccgttagccc gatggtaa          48

<210> SEQ ID NO 798
<211> LENGTH: 61
<212> TYPE: DNA
<213> ORGANISM: Artificial
<220> FEATURE:
<223> OTHER INFORMATION: synthetic oligonucleotide primers or probes

<400> SEQUENCE: 798
tattcgctca taacgggttc gattacgcga ttacgcgagc ccaaaggggg taaggacaca    60
t                                                                   61

<210> SEQ ID NO 799
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 799
ccccaaagat gctgcctgta gatgattacg cgattacatc cagtcgcaac gctaaatg    58

<210> SEQ ID NO 800
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 800
tattcgctca taacgggttc gattacgcca ctgtcccctt catctgatga ttt          53

<210> SEQ ID NO 801
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 801
gcttgccagg caaacaaaga gattattacg cgattacgta gcgccggtca atagagaaa    59

<210> SEQ ID NO 802
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 802
tattcgctca taacgggttc gattacgcca aattagatgg aatcgcagtg ca        52

<210> SEQ ID NO 803
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 803
cactgtattc taccsctgtc accaagtcat tacgcgatag tccgttagcc cgatggtaa        59

<210> SEQ ID NO 804
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 804
acacgaccgg taacgcttag aattacgggt atggccactg aaagcataac cag        53

<210> SEQ ID NO 805
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 805
gttctttgct ccctgtgact cttcccatta cgcgattaag tccgttagcc cgatggtaa        59

<210> SEQ ID NO 806
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 806
tgctaactag atcgcgggtt gattacgcga cagagggatg ctctgcatat acacagtg        58

<210> SEQ ID NO 807
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 807
cacacctcag tctaaagagg ctgcttgatt acaaatcacc cgctctaggg aag        53

<210> SEQ ID NO 808
<211> LENGTH: 52
<212> TYPE: DNA
<213> ORGANISM: Artificial
<220> FEATURE:
<223> OTHER INFORMATION: synthetic oligonucleotide primers or probes

```
<400> SEQUENCE: 808
ttattgcacg cgtcagccta tattacgcgc caccctgaag aagcttcatg cc            52

<210> SEQ ID NO 809
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 809
aatcatgatc cggccctcca atccagtcgc aacgctaaat g                       41

<210> SEQ ID NO 810
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 810
ttattgcacg cgtcagccta tccaccccag gaatatccaa ttagca                  46

<210> SEQ ID NO 811
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 811
ttggccatca tgcagttagt gggtagcgcc ggtcaataga gaaa                    44

<210> SEQ ID NO 812
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 812
ttattgcacg cgtcagccta tatccccag actttataga tgtgtaactg cc            52

<210> SEQ ID NO 813
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 813
agtgctttgc ttatagcagc ctgaaccatt acgcgattaa tccagtcgca acgctaaatg   60

<210> SEQ ID NO 814
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 814
acacgaccgg taacgcttag aattacgcga ttacgtcaca cagagtcacc ctccttctga   60

<210> SEQ ID NO 815
```

```
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 815
tgtggcctat aaggatttgg gtatggatta cgcgattaaa atcacccgct ctagggaag    59

<210> SEQ ID NO 816
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 816
acacgaccgg taacgcttag aatcgtacag actttaggga gcctgtgttc ag          52

<210> SEQ ID NO 817
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 817
ggcactgtct gatgtggttc tgaaaattac gcagtccgtt agcccgatgg taa         53

<210> SEQ ID NO 818
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 818
tattcgctca taacgggttc gtgtaagtct ctcctcccac ctgggt                 46

<210> SEQ ID NO 819
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 819
tggtgcagct ctggggagct agcgccggtc aatagagaaa                        40

<210> SEQ ID NO 820
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 820
tgctaactag atcgcgggtt gtcttaacac acagagatgg ccataagtcc             50

<210> SEQ ID NO 821
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 821
```
ctccaacctt accctacacc tcaactccat tagcgccggt caatagagaa a    51

<210> SEQ ID NO 822
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 822
tattcgctca taacgggttc gccctgatct caacccacac ctcaa    45

<210> SEQ ID NO 823
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 823
atcaagggcg catgttatga tagggattat ccagtcgcaa cgctaaatg    49

<210> SEQ ID NO 824
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 824
acacgaccgg taacgcttag accctttgta ggggcactgg ctta    44

<210> SEQ ID NO 825
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 825
ttttcttccc atagtgtgcc actgcattac gcgattacat ccagtcgcaa cgctaaatg    59

<210> SEQ ID NO 826
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 826
ttattgcacg cgtcagccta tattacgcgc ttcctgggag cagaattgtt ct    52

<210> SEQ ID NO 827
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 827
aggacactcg gaacagccag gtagcgccgg tcaatagaga aa    42

<210> SEQ ID NO 828
<211> LENGTH: 45
<212> TYPE: DNA

```
<213> ORGANISM: Artificial
<220> FEATURE:
<223> OTHER INFORMATION: synthetic oligonucleotide primers or probes

<400> SEQUENCE: 828
acacgaccgg taacgcttag aggtgagttg agaatcatgc caagg            45

<210> SEQ ID NO 829
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 829
tcacttggga agcacagctc tggagtccgt tagcccgatg gtaa             44

<210> SEQ ID NO 830
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 830
tgctaactag atcgcgggtt ggacaggaag ggtgtggcgc                  40

<210> SEQ ID NO 831
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 831
taatgatctc gttaggggtg tgaatggatt acgcgattaa atcacccgct ctagggaag      59

<210> SEQ ID NO 832
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 832
tattcgctca taacgggttc gattaaaggc caggcctgta tttagttagt gg            52

<210> SEQ ID NO 833
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 833
caccatggct cattcattat cagggaatcc agtcgcaacg ctaaatg                  47

<210> SEQ ID NO 834
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 834
tgctaactag atcgcgggtt gattacgcga tgtgtactcc atgggctctt actggaag      58
```

<210> SEQ ID NO 835
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 835
gagaacggac cgttgacaca tggattacgc gatagcgccg gtcaatagag aaa        53

<210> SEQ ID NO 836
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 836
tattcgctca taacgggttc gggcacagac accgtcaaag cttaag                46

<210> SEQ ID NO 837
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 837
aaatactcag ctctgccggc ctagattacg cgattacatc cagtcgcaac gctaaatg   58

<210> SEQ ID NO 838
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 838
ttattgcacg cgtcagccta tcatgagcca gggatctaga gtagggttag             50

<210> SEQ ID NO 839
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 839
ggtggttctg cattgtacct gagaaaatta cgcgattaat ccagtcgcaa cgctaaatg  59

<210> SEQ ID NO 840
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 840
acacgaccgg taacgcttag aattacgcgc caccctccag tagccttttc ct          52

<210> SEQ ID NO 841
<211> LENGTH: 59
<212> TYPE: DNA
<213> ORGANISM: Artificial
<220> FEATURE:

<223> OTHER INFORMATION: synthetic oligonucleotide primers or probes

<400> SEQUENCE: 841 tcaacccta aacccttgc cattacgcga ttacgcgata gcgccggtca atagagaaa    59

<210> SEQ ID NO 842
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 842
tgctaactag atcgcgggtt gattcagctg tttcctacct actctgattc cc    52

<210> SEQ ID NO 843
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 843
ttgtggattc tccccaccat agcattacat ccagtcgcaa cgctaaatg    49

<210> SEQ ID NO 844
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 844
tattcgctca taacgggttc gcacgtgact gagagtcaac ggct    44

<210> SEQ ID NO 845
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 845
aaagatcaca aatcagcttg gcaggattag tccgttagcc cgatggtaa    49

<210> SEQ ID NO 846
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 846
ttattgcacg cgtcagccta tgctctgtgc tcatgtatca ctcttcactc    50

<210> SEQ ID NO 847
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 847
gcctgaaaaa ttgtctctat cagggaaaat tacgcgataa atcacccgct ctagggaag    59

```
<210> SEQ ID NO 848
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 848
ttattgcacg cgtcagccta tattacgcga ggctttcttc ccatcccagt ca         52

<210> SEQ ID NO 849
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 849
caggtcatgg caatatcact tctcccatta cgcgattaca gtccgttagc ccgatggtaa    60

<210> SEQ ID NO 850
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 850
ttattgcacg cgtcagccta tattacgcga ttcctagaac tctctgtccc gtaatgggtt    60

<210> SEQ ID NO 851
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 851
caagcgaagg aaacagcctg ctagcgccgg tcaatagaga aa                      42

<210> SEQ ID NO 852
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 852
tattcgctca taacgggttc ggtgaggttt gccctgggag tagag                   45

<210> SEQ ID NO 853
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 853
agatttcagg agggctggag agataaaatt aaatcacccg ctctagggaa g            51

<210> SEQ ID NO 854
<211> LENGTH: 42
<212> TYPE: DNA
<213> ORGANISM: Artificial
<220> FEATURE:
<223> OTHER INFORMATION: synthetic oligonucleotide primers or probes
```

<400> SEQUENCE: 854
tattcgctca taacgggttc gttggataca ctggcctggc ct            42

<210> SEQ ID NO 855
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 855
tctgaagcca aaatttgccc attcattacg cgattacgta gcgccggtca atagagaaa    59

<210> SEQ ID NO 856
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 856
ttattgcacg cgtcagccta tattacgtgg ctacagttta gggagagggc tt           52

<210> SEQ ID NO 857
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 857
accagatcca ggagactgtt aggtcacatt acgcgattaa tccagtcgca acgctaaatg    60

<210> SEQ ID NO 858
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 858
tattcgctca taacgggttc gattacgcga tgggtgatag tggagagtct taccttccac    60

<210> SEQ ID NO 859
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 859
tacatcaggt cacctgactc tgtgccatta cgagtccgtt agcccgatgg taa           53

<210> SEQ ID NO 860
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 860
acacgaccgg taacgcttag aagatgcaag acatttgaga agggga           46

<210> SEQ ID NO 861
<211> LENGTH: 59

```
<212> TYPE: DNA
<213> ORGANISM: Artificial
<220> FEATURE:
<223> OTHER INFORMATION: synthetic oligonucleotide primers or probes

<400> SEQUENCE: 861 cttttttgtga ttaacctccc cagggattac gcgattacta gcgccggtca atagagaaa      59

<210> SEQ ID NO 862
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 862
tgctaactag atcgcgggtt gattacgcga ttactgtgag gttggcaaca caacactt         58

<210> SEQ ID NO 863
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 863
acttcgcagc tcagtgcagc caatccagtc gcaacgctaa atg                         43

<210> SEQ ID NO 864
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 864
tgctaactag atcgcgggtt ggccactggg gctttaggaa tggt                        44

<210> SEQ ID NO 865
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 865
tgtctgggct ggcactgatg aattacaaat cacccgctct agggaag                     47

<210> SEQ ID NO 866
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 866
ttattgcacg cgtcagccta ttccaaaatt ctggtgtccc tcactc                      46

<210> SEQ ID NO 867
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 867
```
tgaatggcca agtcctttg gagattacgc gaaaatcacc cgctctaggg aag    53

<210> SEQ ID NO 868
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 868
acacgaccgg taacgcttag agcaagtagg attgcaaagg aggagg    46

<210> SEQ ID NO 869
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 869
tcagggtatt gaatcttgtg ggggattacg cgattacgaa atcacccgct ctagggaag    59

<210> SEQ ID NO 870
<211> LENGTH: 58
<212> TYPE: DNA
<213> ORGANISM: Artificial
<220> FEATURE:
<223> OTHER INFORMATION: synthetic oligonucleotide primers or probes

<400> SEQUENCE: 870
tgctaactag atcgcgggtt gattacgcga ttactgagtt cacatcacag cgagggat    58

<210> SEQ ID NO 871
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 871
gaatggacag ttttccagat ggtggattac gcgatagcgc cggtcaatag agaaa    55

<210> SEQ ID NO 872
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 872
ttattgcacg cgtcagccta tattttctgc tggcagacac catttgt    47

<210> SEQ ID NO 873
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 873
caagaagggt agtgagattc tagcagccaa tccagtcgca acgctaaatg    50

<210> SEQ ID NO 874
<211> LENGTH: 49
<212> TYPE: DNA
<213> ORGANISM: Artificial

```
<220> FEATURE:
<223> OTHER INFORMATION: synthetic oligonucleotide primers or probes

<400> SEQUENCE: 874
ttattgcacg cgtcagccta tgatgaaggg tctttggctt cctttagac                49

<210> SEQ ID NO 875
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 875
taactcctcc atgcagtcct cccaattact agcgccggtc aatagagaaa               50

<210> SEQ ID NO 876
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 876
acacgaccgg taacgcttag attctttctg tgctcccacc cct                     43

<210> SEQ ID NO 877
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 877
ttccaccctg gctacacatc ctgtagcgcc ggtcaataga gaaa                    44

<210> SEQ ID NO 878
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 878
ttattgcacg cgtcagccta tgccttatct ggggacccac gtt                     43

<210> SEQ ID NO 879
<211> LENGTH: 50
<212> TYPE: DNA
<213> ORGANISM: Artificial
<220> FEATURE:
<223> OTHER INFORMATION: synthetic oligonucleotide primers or probes

<400> SEQUENCE: 879
agtaagtcct gtctcctgtt tgtgttcgga tccagtcgca acgctaaatg              50

<210> SEQ ID NO 880
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 880
acacgaccgg taacgcttag aattacgcga ttaccattaa agggagctgg gggca         55
```

<210> SEQ ID NO 881
<211> LENGTH: 55
<212> TYPE: DNA
<213> ORGANISM: Artificial
<220> FEATURE:
<223> OTHER INFORMATION: synthetic oligonucleotide primers or probes

<400> SEQUENCE: 881
acaagtagcc tgtcttcagt tcccctcatt acgcaaatca cccgctctag ggaag      55

<210> SEQ ID NO 882
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 882
tattcgctca taacgggttc gttcatctgg atccatgacg atgg      44

<210> SEQ ID NO 883
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 883
tcagccacat cttccctatt cctctgatta cgcgattaca gtccgttagc ccgatggtaa      60

<210> SEQ ID NO 884
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 884
acacgaccgg taacgcttag aattacgcga ttacgcaaag gaaatgtggt tgccacacag      60

<210> SEQ ID NO 885
<211> LENGTH: 56
<212> TYPE: DNA
<213> ORGANISM: Artificial
<220> FEATURE:
<223> OTHER INFORMATION: synthetic oligonucleotide primers or probes

<400> SEQUENCE: 885
gggggagggc agattagata aaacaatta cgcgaaaatc acccgctcta gggaag      56

<210> SEQ ID NO 886
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 886
tgctaactag atcgcgggtt gattgacaga acacatagcc tgggcaaat      49

<210> SEQ ID NO 887
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 887
agacaaatag cagcggtggt gccaaaatca cccgctctag ggaag          45

<210> SEQ ID NO 888
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 888
tattcgctca taacgggttc gccaagaggg aaggcaggca ga             42

<210> SEQ ID NO 889
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 889
atgtcctact ccaccagttc ccagcattac agtccgttag cccgatggta a   51

<210> SEQ ID NO 890
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 890
tattcgctca taacgggttc gaggaacaca ctgactccgc cc             42

<210> SEQ ID NO 891
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 891
gttattcctg aaagatggag aagggggcatt acgcgattat agcgccggtc aatagagaaa    60

<210> SEQ ID NO 892
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 892
acacgaccgg taacgcttag aattacgcga ttacgcgatc gtaggaatgc cccagcttct    60

<210> SEQ ID NO 893
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 893
cagggaagga gagagcaggg tttattacgc gattacgcga aatcacccgc tctagggaag    60

<210> SEQ ID NO 894

```
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 894
acacgaccgg taacgcttag aattacgcga ttacgagaga gatgggggaa ggaagagaga      60

<210> SEQ ID NO 895
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 895
cgaggaaaaa aattaggggt gggaattagt ccgttagccc gatggtaa                   48

<210> SEQ ID NO 896
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 896
ttattgcacg cgtcagccta tccttcaccc taacaccaaa cacca                      45

<210> SEQ ID NO 897
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 897
catccccagt gtgggaccat gaaatcaccc gctctaggga ag                         42

<210> SEQ ID NO 898
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 898
ttattgcacg cgtcagccta ttgcctagct gtgtgacatg attgg                      45

<210> SEQ ID NO 899
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 899
ctctggtggc cttgaaaaac aaccagtccg ttagcccgat ggtaa                      45

<210> SEQ ID NO 900
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 900
```

```
acacgaccgg taacgcttag agccagcctt agccaaatgc ag                    42
```

<210> SEQ ID NO 901
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 901

```
ctttctacct cccacagtgt ttgggattac gcgattacga aatcacccgc tctagggaag    60
```

<210> SEQ ID NO 902
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 902

```
tattcgctca taacgggttc gattacgcga ttggcttctc agttctaagc ctcacaaatc    60
```

<210> SEQ ID NO 903
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 903

```
cagccaagga tttttttccc cgattacgcg attacgcgta gcgccggtca atagagaaa     59
```

<210> SEQ ID NO 904
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 904

```
acacgaccgg taacgcttag aattacgcgc attcaaacag ctttccgaca tcac          54
```

<210> SEQ ID NO 905
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 905

```
tttggttccc acccccaca ttacgcgagt ccgttagccc gatggtaa                  48
```

<210> SEQ ID NO 906
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 906

```
tgctaactag atcgcgggtt gcctctctct catcgacccc cc                       42
```

<210> SEQ ID NO 907
<211> LENGTH: 54
<212> TYPE: DNA

```
<213> ORGANISM: Artificial
<220> FEATURE:
<223> OTHER INFORMATION: synthetic oligonucleotide primers or probes

<400> SEQUENCE: 907
cctggagccc tgaacaagta caaatgatta cgcatccagt cgcaacgcta aatg      54

<210> SEQ ID NO 908
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 908
tgctaactag atcgcgggtt ggctggggcc tttttttcagc at                  42

<210> SEQ ID NO 909
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 909
ttaagtgctg tgatgttagc tgctggtatt acgcgattag tccgttagcc cgatggtaa   59

<210> SEQ ID NO 910
<211> LENGTH: 51
<212> TYPE: DNA
<213> ORGANISM: Artificial
<220> FEATURE:
<223> OTHER INFORMATION: synthetic oligonucleotide primers or probes

<400> SEQUENCE: 910
ttattgcacg cgtcagccta tattacgctt tgcttctgtg gtctcgagta a         51

<210> SEQ ID NO 911
<211> LENGTH: 47
<212> TYPE: DNA
<213> ORGANISM: Artificial
<220> FEATURE:
<223> OTHER INFORMATION: synthetic oligonucleotide primers or probes

<400> SEQUENCE: 911
cagtgacgcc ttgggaatcc cattacatcc agtcgcaacg ctaaatg              47

<210> SEQ ID NO 912
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 912
ttattgcacg cgtcagccta tcacaaactc gtctcttcct tcccaa               46

<210> SEQ ID NO 913
<211> LENGTH: 48
<212> TYPE: DNA
<213> ORGANISM: Artificial
<220> FEATURE:
<223> OTHER INFORMATION: synthetic oligonucleotide primers or probes

<400> SEQUENCE: 913
ggtagaaggg ggacaaagtt ccctgattag cgccggtcaa tagagaaa             48
```

<210> SEQ ID NO 914
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 914
acacgaccgg taacgcttag aattacgcga ttacgcggac agccctggtt gtgagtgctt    60

<210> SEQ ID NO 915
<211> LENGTH: 59
<212> TYPE: DNA
<213> ORGANISM: Artificial
<220> FEATURE:
<223> OTHER INFORMATION: synthetic oligonucleotide primers or probes

<400> SEQUENCE: 915
ctaggactag ggtcttgcat agagccttca ttacgcgaaa atcacccgct ctagggaag    59

<210> SEQ ID NO 916
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 916
tgctaactag atcgcgggtt gattacgccc aatggttgca agaggttcc    49

<210> SEQ ID NO 917
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 917
tttgagactc ctgaagctga aacccattac gcgattacga gtccgttagc ccgatggtaa    60

<210> SEQ ID NO 918
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 918
tattcgctca taacgggttc gattacgcga ttacgtggca gctcggattc tgaaggtaat    60

<210> SEQ ID NO 919
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 919
ctctctcgag ctaacattgt ggagggatta catccagtcg caacgctaaa tg    52

<210> SEQ ID NO 920
<211> LENGTH: 47
<212> TYPE: DNA
<213> ORGANISM: Artificial
<220> FEATURE:

<223> OTHER INFORMATION: synthetic oligonucleotide primers or probes

<400> SEQUENCE: 920
acacgaccgg taacgcttag acactgtgat tcagcagtga agtcctg          47

<210> SEQ ID NO 921
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 921
cactgtcttg ccgtgatttc ccatatccag tcgcaacgct aaatg            45

<210> SEQ ID NO 922
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 922
tattcgctca taacgggttc gattacgcga ttcaggtgtt gactacatag tgccacacag    60

<210> SEQ ID NO 923
<211> LENGTH: 43
<212> TYPE: DNA
<213> ORGANISM: Artificial
<220> FEATURE:
<223> OTHER INFORMATION: synthetic oligonucleotide primers or probes

<400> SEQUENCE: 923
agtggtcagg tggcttccag caagtccgtt agcccgatgg taa              43

<210> SEQ ID NO 924
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 924
ttattgcacg cgtcagccta ttgttttgca ttcctcttcc tggc             44

<210> SEQ ID NO 925
<211> LENGTH: 41
<212> TYPE: DNA
<213> ORGANISM: Artificial
<220> FEATURE:
<223> OTHER INFORMATION: synthetic oligonucleotide primers or probes

<400> SEQUENCE: 925
agcctctggg ggcctcacaa aaatcacccg ctctagggaa g                41

<210> SEQ ID NO 926
<211> LENGTH: 46
<212> TYPE: DNA
<213> ORGANISM: Artificial
<220> FEATURE:
<223> OTHER INFORMATION: synthetic oligonucleotide primers or probes

<400> SEQUENCE: 926
acacgaccgg taacgcttag attttccctg ttacatagtg ctgggc           46

```
<210> SEQ ID NO 927
<211> LENGTH: 53
<212> TYPE: DNA
<213> ORGANISM: Artificial
<220> FEATURE:
<223> OTHER INFORMATION: synthetic oligonucleotide primers or probes

<400> SEQUENCE: 927
ttcttcccgg actagggtga attcaattac gcagtccgtt agcccgatgg taa        53

<210> SEQ ID NO 928
<211> LENGTH: 49
<212> TYPE: DNA
<213> ORGANISM: Artificial
<220> FEATURE:
<223> OTHER INFORMATION: synthetic oligonucleotide primers or probes

<400> SEQUENCE: 928
tgctaactag atcgcgggtt gattaccctg ctagttctga tccgaggca              49

<210> SEQ ID NO 929
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 929
agtcttttct gtgctttgcc ccaattacgc gattacgcgt agcgccggtc aatagagaaa  60

<210> SEQ ID NO 930
<211> LENGTH: 62
<212> TYPE: DNA
<213> ORGANISM: Artificial
<220> FEATURE:
<223> OTHER INFORMATION: synthetic oligonucleotide primers or probes

<400> SEQUENCE: 930
tattcgctca taacgggttc gattacgcga ttacgcctct agcatctgcc tttctgctga  60
ga                                                                 62

<210> SEQ ID NO 931
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 931
tatagaggct gctaaatcga cctgcgatta cgcgattaca tccagtcgca acgctaaatg  60

<210> SEQ ID NO 932
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 932
ttattgcacg cgtcagccta tattacgcga ttgggatgtg gtgtacacct accatcagtt  60

<210> SEQ ID NO 933
<211> LENGTH: 53
<212> TYPE: DNA
<213> ORGANISM: Artificial
<220> FEATURE:
```

<223> OTHER INFORMATION: synthetic oligonucleotide primers or probes

<400> SEQUENCE: 933
caggtgattg atggcttcca ttacaattac gcaaatcacc cgctctaggg aag         53

<210> SEQ ID NO 934
<211> LENGTH: 52
<212> TYPE: DNA
<213> ORGANISM: Artificial
<220> FEATURE:
<223> OTHER INFORMATION: synthetic oligonucleotide primers or probes

<400> SEQUENCE: 934
acacgaccgg taacgcttag aattacgctg gtgttatagc tggctctggc ag          52

<210> SEQ ID NO 935
<211> LENGTH: 40
<212> TYPE: DNA
<213> ORGANISM: Artificial
<220> FEATURE:
<223> OTHER INFORMATION: synthetic oligonucleotide primers or probes

<400> SEQUENCE: 935
tcagggtggg ggaagtggca aatcacccgc tctagggaag                         40

<210> SEQ ID NO 936
<211> LENGTH: 44
<212> TYPE: DNA
<213> ORGANISM: Artificial
<220> FEATURE:
<223> OTHER INFORMATION: synthetic oligonucleotide primers or probes

<400> SEQUENCE: 936
tgctaactag atcgcgggtt gagattattg aaggtggccc aggc                    44

<210> SEQ ID NO 937
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 937
cctattccca gccagatcgg atgaagtccg ttagcccgat ggtaa                   45

<210> SEQ ID NO 938
<211> LENGTH: 60
<212> TYPE: DNA
<213> ORGANISM: Artificial
<220> FEATURE:
<223> OTHER INFORMATION: synthetic oligonucleotide primers or probes

<400> SEQUENCE: 938
ttattgcacg cgtcagccta tattacgcga ttatccttttt gaacaattgt cttccactcc  60

<210> SEQ ID NO 939
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 939
tggaaaggga aggggaagtg gtagcgccgg tcaatagaga aa                      42

```
<210> SEQ ID NO 940
<211> LENGTH: 42
<212> TYPE: DNA
<213> ORGANISM: Artificial
<220> FEATURE:
<223> OTHER INFORMATION: synthetic oligonucleotide primers or probes

<400> SEQUENCE: 940
tgctaactag atcgcgggtt gacagcccac accatgagct ca                          42

<210> SEQ ID NO 941
<211> LENGTH: 54
<212> TYPE: DNA
<213> ORGANISM: Artificial
<220> FEATURE:
<223> OTHER INFORMATION: synthetic oligonucleotide primers or probes

<400> SEQUENCE: 941
tctagccctg cttttctct cccgattacg cgaatccagt cgcaacgcta aatg              54

<210> SEQ ID NO 942
<211> LENGTH: 45
<212> TYPE: DNA
<213> ORGANISM: Artificial
<220> FEATURE:
<223> OTHER INFORMATION: synthetic oligonucleotide primers or probes

<400> SEQUENCE: 942
tattcgctca taacgggttc ggtgccggag aagatgattc atgac                       45

<210> SEQ ID NO 943
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 943
acacgaccgg taacgcttag a                                                 21

<210> SEQ ID NO 944
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 944
tattcgctca taacgggttc g                                                 21

<210> SEQ ID NO 945
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 945
ttattgcacg cgtcagccta t                                                 21

<210> SEQ ID NO 946
<211> LENGTH: 21
<212> TYPE: DNA
<213> ORGANISM: Artificial
<220> FEATURE:
<223> OTHER INFORMATION: synthetic oligonucleotide primers or probes
```

<400> SEQUENCE: 946
tgctaactag atcgcgggtt g                                              21

<210> SEQ ID NO 947
<211> LENGTH: 29
<212> TYPE: DNA
<213> ORGANISM: Artificial
<220> FEATURE:
<223> OTHER INFORMATION: synthetic oligonucleotide primers or probes

<400> SEQUENCE: 947
gtttcttgct tccctagagc gggtgattt                                      29

<210> SEQ ID NO 948
<211> LENGTH: 67
<212> TYPE: DNA
<213> ORGANISM: Artificial
<220> FEATURE:
<223> OTHER INFORMATION: synthetic oligonucleotide primers or probes

<400> SEQUENCE: 948
gtttcttcga cgatacgacg atacgacgat acgacgatac gacgatcatt tagcgttgcg    60
actggat                                                              67

<210> SEQ ID NO 949
<211> LENGTH: 29
<212> TYPE: DNA
<213> ORGANISM: Artificial
<220> FEATURE:
<223> OTHER INFORMATION: synthetic oligonucleotide primers or probes

<400> SEQUENCE: 949
gtttcttgtt accatcgggc taacggact                                      29

<210> SEQ ID NO 950
<211> LENGTH: 67
<212> TYPE: DNA
<213> ORGANISM: Artificial
<220> FEATURE:
<223> OTHER INFORMATION: synthetic oligonucleotide primers or probes

<400> SEQUENCE: 950
gtttcttcga cgatacgacg atacgacgat acgacgatac gacgattttc tctattgacc    60
ggcgcta                                                              67

<210> SEQ ID NO 951
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 951
acacgaccgg taacgcttag a                                              21

<210> SEQ ID NO 952
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 952
tattcgctca taacgggttc g                                              21

<210> SEQ ID NO 953
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 953
ttattgcacg cgtcagccta t                                      21

<210> SEQ ID NO 954
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 954
tgctaactag atcgcgggtt g                                      21

<210> SEQ ID NO 955
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 955
aaatcacccg ctctagggaa g                                      21

<210> SEQ ID NO 956
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 956
atccagtcgc aacgctaaat g                                      21

<210> SEQ ID NO 957
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 957
agtccgttag cccgatggta a                                      21

<210> SEQ ID NO 958
<211> LENGTH: 21
<212> TYPE: DNA
<213> ORGANISM: Artificial
<220> FEATURE:
<223> OTHER INFORMATION: synthetic oligonucleotide primers or probes

<400> SEQUENCE: 958
tagcgccggt caatagagaa a                                      21

<210> SEQ ID NO 959
<211> LENGTH: 39
<212> TYPE: DNA
<213> ORGANISM: Artificial
<220> FEATURE:

```
<223> OTHER INFORMATION: synthetic oligonucleotide primers or probes

<400> SEQUENCE: 959
cgacgatacg acgatacgac gatacgacga tacgacgat                    39
```